(12) United States Patent
Kwon et al.

(10) Patent No.: US 10,665,788 B2
(45) Date of Patent: May 26, 2020

(54) AMINE-BASED COMPOUND, ORGANIC LIGHT-EMITTING DIODE INCLUDING THE SAME, AND ORGANIC LIGHT-EMITTING APPARATUS INCLUDING THE AMINE-BASED COMPOUND

(71) Applicant: Samsung Display Co. Ltd., Yongin-si, Gyeonggi-do (KR)

(72) Inventors: O-Hyun Kwon, Yongin-si (KR); Dong-Woo Shin, Yongin-si (KR); Kyul Han, Yongin-si (KR); Seul-Ong Kim, Yongin-si (KR); Byoung-Ki Choi, Yongin-si (KR)

(73) Assignee: Samsung Display Co., Ltd., Yongin-si (KR)

( * ) Notice: Subject to any disclaimer, the term of this patent is extended or adjusted under 35 U.S.C. 154(b) by 806 days.

(21) Appl. No.: 13/706,330

(22) Filed: Dec. 5, 2012

(65) Prior Publication Data

US 2013/0234118 A1 Sep. 12, 2013

(30) Foreign Application Priority Data

Mar. 6, 2012 (KR) ........................ 10-2012-0022878

(51) Int. Cl.
| | | |
|---|---|---|
| *H01L 51/00* | (2006.01) | |
| *H01L 51/50* | (2006.01) | |
| *C07D 251/22* | (2006.01) | |
| *C07D 213/38* | (2006.01) | |
| *C07D 241/44* | (2006.01) | |
| *C07C 255/58* | (2006.01) | |
| *C07D 217/22* | (2006.01) | |
| *C07D 239/94* | (2006.01) | |
| *C07D 213/74* | (2006.01) | |
| *C07C 211/61* | (2006.01) | |
| *C07D 209/86* | (2006.01) | |
| *C07D 239/42* | (2006.01) | |
| *C07D 307/91* | (2006.01) | |

(Continued)

(52) U.S. Cl.
CPC .......... *H01L 51/006* (2013.01); *C07C 211/61* (2013.01); *C07C 255/58* (2013.01); *C07D 209/86* (2013.01); *C07D 213/38* (2013.01); *C07D 213/74* (2013.01); *C07D 215/38* (2013.01); *C07D 217/22* (2013.01); *C07D 239/42* (2013.01); *C07D 239/84* (2013.01); *C07D 239/94* (2013.01); *C07D 241/44* (2013.01); *C07D 251/22* (2013.01); *C07D 307/91* (2013.01); *C07D 333/76* (2013.01); *C07D 409/12* (2013.01); *C07D 409/14* (2013.01); *C09B 1/00* (2013.01); *C09B 57/00* (2013.01); *C09B 57/001* (2013.01); *C09B 57/008* (2013.01); *H01L 51/0061* (2013.01); *H01L 51/5092* (2013.01); *C07C 2603/18* (2017.05); *C07C 2603/48* (2017.05); *C07C 2603/50* (2017.05); *C07C 2603/52* (2017.05); *C07C 2603/94* (2017.05); *H01L 51/0055* (2013.01); *H01L 51/0056* (2013.01); *H01L 51/0081* (2013.01); *H01L 51/5012* (2013.01); *H01L 2251/308* (2013.01)

(58) Field of Classification Search
CPC ............ C07C 2103/18; C07C 2103/48; C07C 2103/50; C07C 2103/52; C07C 2103/94; C07C 211/61; C07C 255/58; C07D 209/86; C07D 213/38; C07D 213/74; C07D 215/38; C07D 217/22; C07D 239/42; C07D 239/84; C07D 239/94; C07D 241/44; C07D 251/22; C07D 409/12; C07D 409/14; C09B 1/00; C09B 57/00; C09B 57/001; C09B 57/008; H01L 2251/308; H01L 51/0055; H01L 51/0056; H01L 51/006; H01L 51/0061; H01L 51/0081; H01L 51/5012; H01L 51/5092
See application file for complete search history.

(56) References Cited

U.S. PATENT DOCUMENTS

| | | | |
|---|---|---|---|
| 5,153,073 A | 10/1992 | Ohnuma et al. | |
| 7,507,485 B2 * | 3/2009 | Oh ...................... | H01L 51/0058 313/504 |

(Continued)

FOREIGN PATENT DOCUMENTS

| | | |
|---|---|---|
| CN | 1416301 A | 5/2003 |
| EP | 2 423 206 A1 | 2/2012 |

(Continued)

OTHER PUBLICATIONS

SIPO Office action dated Sep. 22, 2015, for corresponding Chinese Patent application 201310069133.X, (11 pages).

(Continued)

*Primary Examiner* — Dawn L Garrett
(74) *Attorney, Agent, or Firm* — Lewis Roca Rothgerber Christie LLP

(57) ABSTRACT

Embodiments of the present invention include an amine-based compound represented by Formula 1, an organic light-emitting diode including the amine-based compound, and an organic light-emitting apparatus including the amine-based compound.

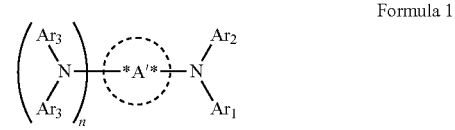

Formula 1

19 Claims, 1 Drawing Sheet

(51) Int. Cl.
*C07D 239/84* (2006.01)
*C07D 333/76* (2006.01)
*C07D 409/12* (2006.01)
*C07D 215/38* (2006.01)
*C07D 409/14* (2006.01)
*C09B 57/00* (2006.01)
*C09B 1/00* (2006.01)

(56) References Cited

U.S. PATENT DOCUMENTS

| | | | |
|---|---|---|---|
| 8,072,136 B2 | 12/2011 | Igawa et al. | |
| 8,691,398 B2* | 4/2014 | Yamada | C07C 211/61 |
| | | | 313/504 |
| 2002/0086180 A1* | 7/2002 | Seo | H01L 51/002 |
| | | | 428/690 |
| 2004/0137270 A1* | 7/2004 | Seo | C09K 11/06 |
| | | | 428/690 |
| 2005/0064233 A1* | 3/2005 | Matsuura | C07C 13/567 |
| | | | 428/690 |
| 2005/0238921 A1* | 10/2005 | Hosokawa | C09K 11/06 |
| | | | 428/690 |
| 2005/0249972 A1* | 11/2005 | Hatwar | H01L 51/5265 |
| | | | 428/690 |
| 2006/0152146 A1* | 7/2006 | Funahashi | C07C 211/61 |
| | | | 313/504 |
| 2009/0251049 A1 | 10/2009 | Kim et al. | |
| 2009/0256468 A1* | 10/2009 | Kim | C07D 213/74 |
| | | | 313/504 |
| 2010/0019663 A1 | 1/2010 | Shin et al. | |
| 2010/0038634 A1 | 2/2010 | Nagao et al. | |
| 2010/0052526 A1 | 3/2010 | Je et al. | |
| 2010/0314615 A1* | 12/2010 | Mizuki | C07D 307/91 |
| | | | 257/40 |
| 2011/0006669 A1* | 1/2011 | Lee | C09K 11/06 |
| | | | 313/504 |
| 2011/0042660 A1* | 2/2011 | Kawamura | C09K 11/06 |
| | | | 257/40 |
| 2011/0121268 A1 | 5/2011 | Nagao et al. | |
| 2011/0147732 A1 | 6/2011 | Mizuki | |
| 2011/0156016 A1* | 6/2011 | Kawamura | C07C 211/54 |
| | | | 257/40 |
| 2011/0248246 A1 | 10/2011 | Ogita et al. | |
| 2012/0091885 A1* | 4/2012 | Kim | C09K 11/06 |
| | | | 313/504 |
| 2012/0112169 A1 | 5/2012 | Mizuki et al. | |
| 2015/0255736 A1* | 9/2015 | Kim | H01L 51/0061 |
| | | | 257/40 |

FOREIGN PATENT DOCUMENTS

| | | |
|---|---|---|
| JP | 2011-23614 A | 2/2011 |
| KR | 10-2009-0005128 | 1/2009 |
| KR | 10-2009-0098585 | 9/2009 |
| KR | 10-2009-0128382 | 12/2009 |
| KR | 10-2010-0024894 | 3/2010 |
| KR | 10-2010-0075101 | 7/2010 |
| KR | 20100075101 A * | 7/2010 |
| KR | 10-2010-0097181 | 9/2010 |
| KR | 10-2011-0040874 | 4/2011 |
| KR | 10-2011-0043625 | 4/2011 |
| KR | 10-2011-0043658 | 4/2011 |
| KR | 10-2011-0071127 | 6/2011 |
| KR | 20140126108 A * | 10/2014 |
| TW | 200604319 A | 2/2006 |
| TW | 201012899 A | 4/2010 |
| WO | WO 2009/084512 A1 | 7/2009 |
| WO | WO 2010/122810 A1 | 10/2010 |

OTHER PUBLICATIONS

Chai, Sheng-yong, "Preparation of N, N, N'N'-Tetraphenylbiphenyldiamines for Organic Electroluminescent Device as Hole Transport Materials," 2001, vol. 16 (5 pages).

Yu, Ming-Xin, "Study on Synthesis of Organic Light Emitting Diode Materials of Aminoanthrancenes and Their Light Emitting Property," Chinese Journal of Organic Chemistry, 2005, vol. 25, No. 2 (4 pages).

* cited by examiner

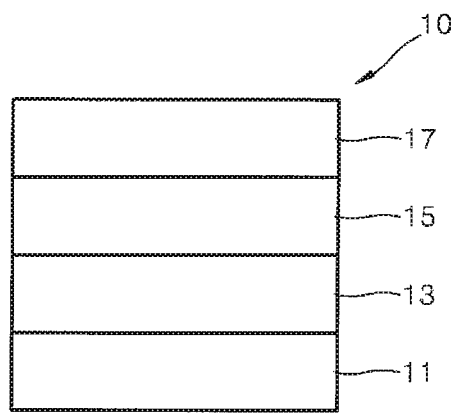

AMINE-BASED COMPOUND, ORGANIC LIGHT-EMITTING DIODE INCLUDING THE SAME, AND ORGANIC LIGHT-EMITTING APPARATUS INCLUDING THE AMINE-BASED COMPOUND

CROSS-REFERENCE TO RELATED PATENT APPLICATION

This application claims priority to and the benefit of Korean Patent Application No. 10-2012-0022878, filed on Mar. 6, 2012, in the Korean Intellectual Property Office, the entire content of which is incorporated herein by reference.

BACKGROUND

1. Technical Field

The present invention relates to a compound for an organic light-emitting diode, an organic light-emitting diode, and an organic light-emitting apparatus.

2. Description of the Related Art

Organic light emitting diodes are self-emission devices that have wide viewing angles, high contrast ratios, short response times, and good brightness, driving voltage, and response speed characteristics. Also, organic light emitting diodes can generate multi-colored images.

A typical organic light-emitting diode includes an anode disposed on a substrate, and a hole transport layer, an emitting layer, an electron transport layer, and a cathode (in that order) are disposed on the anode. In this regard, the hole transport layer, the emitting layer, and the electron transport layer are organic thin films formed of organic compounds.

The driving mechanism of an organic light-emitting diode having such a structure is described below.

Holes injected from the anode move to the emitting layer through the hole transport layer, and electrons injected from the cathode move to the emitting layer through the electron transport layer. The holes and electrons are recombined with each other in the emitting layer to generate excitons. Then, the excitons transition from an excited state to a ground state, thereby generating light.

SUMMARY OF THE INVENTION

Embodiments of the present invention provide an amine-based compound, an organic light-emitting diode including the same, and an organic light-emitting apparatus including the amine-based compound.

According to an aspect of the present invention, there is provided an amine-based compound represented by Formula 1 below:

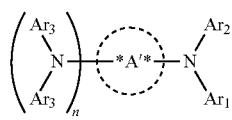

<Formula 1>

In Formula 1, a core A is a substituted or unsubstituted pyrene, a substituted or unsubstituted chrysene, or a substituted or unsubstituted diphenyl-benzofluoranthene. Also, n is 0 or 1. $Ar_1$ to $Ar_4$ are each independently a substituted or unsubstituted $C_6$-$C_{60}$ aryl group, a substituted or unsubstituted $C_2$-$C_{60}$ heteroaryl group, a substituent represented by Formula 2A below, or a substituent represented by Formula 2B below. In Formula 2A, $T_1$ is O, S, $N(R_{11})$, $C(R_{12})(R_{13})$, or $Si(R_{14})(R_{15})$. In Formula 2A and 2B, a is an integer of 0 to 3, b, c, and d are each independently an integer of 0 to 4, and * is a binding site to N of Formula 1. When n is 0, at least one of $Ar_1$ and $Ar_2$ (or when n is 1, at least one of $Ar_1$ to $Ar_4$) may be a substituent represented by Formula 2A below or a substituent represented by Formula 2B below:

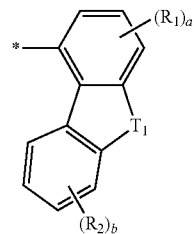

<Formula 2A>

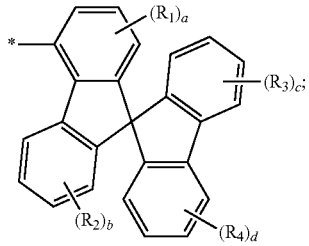

<Formula 2B>

At least one substituent of the substituted pyrene, the substituted chrysene, the substituted diphenyl-benzofluoranthene, the substituted $C_6$-$C_{60}$ aryl group, or the substituted $C_2$-$C_{60}$ heteroaryl group, $R_1$ to $R_4$, and $R_{11}$ to $R_{15}$ may be each independently one selected from deuterium; —F; —Cl; —Br; —I; —CN; a hydroxyl group; a —$NO_2$ group; an amino group; an amidino group; hydrazine; hydrazone; a carboxylic acid group or salt thereof; a sulfonic acid group or salt thereof; a phosphoric acid group or salt thereof; a $C_1$-$C_{60}$ alkyl group; a $C_1$-$C_{60}$ alkoxy group; a $C_2$-$C_{60}$ alkenyl group; a $C_2$-$C_{60}$ alkynyl group; a $C_1$-$C_{60}$ alkyl group, $C_1$-$C_{60}$ alkoxy group, $C_2$-$C_{60}$ alkenyl group, or $C_2$-$C_{60}$ alkynyl group substituted with at least one selected from deuterium, —F, —Cl, —Br, —I, —CN, a hydroxyl group, a —$NO_2$ group, an amino group, an amidino group, hydrazine, hydrazone, a carboxylic acid group or salt thereof, a sulfonic acid group or salt thereof, or a phosphoric acid group or salt thereof; a $C_3$-$C_{60}$ cycloalkyl group; a $C_3$-$C_{60}$ cycloalkenyl group; a $C_6$-$C_{60}$ aryl group; a $C_2$-$C_{60}$ heteroaryl group; a $C_6$-$C_{60}$ aralkyl group; a $C_6$-$C_{60}$ aryloxy group; a $C_6$-$C_{60}$ arylthio group; or a $C_3$-$C_{60}$ cycloalkyl group, $C_3$-$C_{60}$ cycloalkenyl group, $C_6$-$C_{60}$ aryl group, $C_2$-$C_{60}$ heteroaryl group, $C_6$-$C_{60}$ aralkyl group, $C_6$-$C_{60}$ aryloxy group, or $C_6$-$C_{60}$ arylthio group substituted with at least one selected from deuterium, —F, —Cl, —Br, —I, —CN, a hydroxyl group, a —$NO_2$ group, an amino group, an amidino group, hydrazine, hydrazone, a carboxylic acid group or salt thereof, a sulfonic acid group or salt thereof, a phosphoric acid group or salt thereof, a $C_1$-$C_{60}$ alkyl group, a $C_1$-$C_{60}$ alkyl group substituted with at least one —F, $C_1$-$C_{60}$ alkoxy group, $C_2$-$C_{60}$ alkenyl group, $C_2$-$C_{60}$ alkynyl group, $C_6$-$C_{60}$ aryl group, or $C_2$-$C_{60}$ heteroaryl group. Also, *' are binding sites with the core A.

According to another aspect of the present invention, there is provided an organic light-emitting diode including a first electrode; a second electrode facing the first electrode; and an organic layer between the first electrode and the second electrode, wherein the organic layer includes one or more amine-based compounds described above.

According to another aspect of the present invention, there is provided an organic light-emitting apparatus that includes a substrate including a first sub-pixel, a second sub-pixel, and a third sub-pixel; a first electrode formed in each of the first sub-pixel, the second sub-pixel, and the third sub-pixel; a second electrode that faces the first electrodes and is a common electrode that is shared by the first sub-pixel, the second sub-pixel, and the third sub-pixel; a first emission layer that is formed between the first electrode of the first sub-pixel and the second electrode and that emits a first color light; a second emission layer that is formed between the first electrode of the second sub-pixel and the second electrode and that emits a second color light; and a third emission layer that is formed between the first electrode of the third sub-pixel and the second electrode and that emits a third color light. The first emission layer includes one or more amine-based compounds described above. The first electrode is a transparent electrode or a semi-transparent electrode. The second electrode is a reflective electrode. A mixed light of the first color light, the second color light, and the third color light is white light, and the first color light is blue light.

BRIEF DESCRIPTION OF THE DRAWINGS

The above and other features and advantages of the present invention will become more apparent by reference to the following detailed description when considered in conjunction with the FIGURE, which is a schematic view of an organic light-emitting diode according to an embodiment of the present invention.

DETAILED DESCRIPTION OF THE INVENTION

Expressions, such as "at least one of" when preceding a list of elements, modify the entire list of elements and do not modify the individual elements of the list.

An amine-based compound according to an embodiment of the present invention is represented by Formula 1 below.

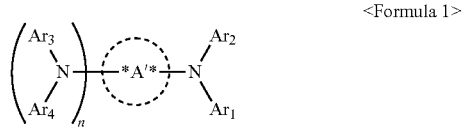

<Formula 1>

In Formula 1, the core A is a substituted or unsubstituted pyrene, a substituted or unsubstituted chrysene, or a substituted or unsubstituted diphenyl-benzofluoranthene.

In Formula 1, n is 0 or 1. That is, the amine-based compound represented by Formula 1 may include, when n is 0, as an amino group, only

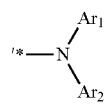

(hereinafter referred to as a "first diarylamino group"), and when n is 1, as an amino group, both the first diarylamino group and

(hereinafter referred to as a "second diarylamino group").

In Formula 1, $Ar_1$ to $Ar_4$ may each be independently a substituted or unsubstituted $C_6$-$C_{60}$ aryl group, a substituted or unsubstituted $C_2$-$C_{60}$ heteroaryl group, a substituent represented by Formula 2A below, or a substituent represented by Formula 2B below. When n is 0, at least one of $Ar_1$ and $Ar_2$ (or when n is 1, at least one of $Ar_1$ to $Ar_4$) may be a substituent represented by Formula 2A below or a substituent represented by Formula 2B below.

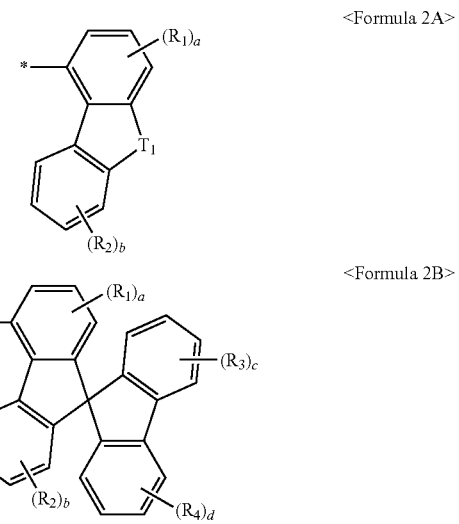

<Formula 2A>

<Formula 2B>

In Formula 2A above, $T_1$ is O, S, $N(R_{11})$, $C(R_{12})(R_{13})$, or $Si(R_{14})(R_{15})$. In Formulas 2A and 2B above, a is an integer of 0 to 3, b, c, and d are each independently an integer of 0 to 4, and * is a binding site with N of Formula 1.

In Formula 1, at least one substituent of the substituted pyrene, the substituted chrysene, the substituted diphenyl-benzofluoranthene (see the core A of Formula 1), the substituted $C_6$-$C_{60}$ aryl group, or the substituted $C_2$-$C_{60}$ heteroaryl group (see $Ar_1$ to $Ar_4$ of Formula 1), $R_1$ to $R_4$ (see Formulas 2A and 2B), and $R_{11}$ to $R_{15}$ (see $T_1$ of Formula 2A) may each be independently one selected from deuterium; —F; —Cl; —Br; —I; —CN; a hydroxyl group; a —$NO_2$ group; an amino group; an amidino group; hydrazine; hydrazone; a carboxylic acid group or salt thereof; a sulfonic acid group or salt thereof; a phosphoric acid group or salt thereof; a $C_1$-$C_{60}$ alkyl group; a $C_1$-$C_{60}$ alkoxy group; a $C_2$-$C_{60}$ alkenyl group; a $C_2$-$C_{60}$ alkynyl group; a $C_1$-$C_{60}$ alkyl group, $C_1$-$C_{60}$ alkoxy group, $C_2$-$C_{60}$ alkenyl group, or $C_2$-$C_{60}$ alkynyl group substituted with at least one selected from deuterium, —F, —Cl, —Br, —I, —CN, a hydroxyl group, a —$NO_2$ group, an amino group, an amidino group, hydrazine, hydrazone, a carboxylic acid group or salt thereof, a sulfonic acid group or salt thereof, or a phosphoric acid group or salt thereof; a $C_3$-$C_{60}$ cycloalkyl group; a a $C_3$-$C_{60}$ cycloalkenyl group; a $C_6$-$C_{60}$ aryl group; a $C_2$-$C_{60}$ heteroaryl group; a $C_6$-$C_{60}$ aralkyl group; a $C_6$-$C_{60}$ aryloxy group; a $C_6$-$C_{60}$ arylthio group, and a $C_3$-$C_{60}$ cycloalkyl group, $C_3$-$C_{60}$ cycloalkenyl group, $C_6$-$C_{60}$ aryl group, $C_2$-$C_{60}$ heteroaryl group, $C_6$-$C_{60}$ aralkyl group, $C_6$-$C_{60}$ aryloxy group, or $C_6$-$C_{60}$ arylthio group substituted with at least one selected from deuterium, —F, —Cl, —Br, —I, —CN, a hydroxyl group, a —$NO_2$ group, an amino group, an amidino group, hydrazine, hydrazone, a carboxylic acid group or salt thereof, a sulfonic acid group or salt thereof, a phosphoric acid group or salt thereof, a $C_1$-$C_{60}$ alkyl group, a $C_1$-$C_{60}$ alkyl group substituted with at least one —F, $C_1$-$C_{60}$ alkoxy group, $C_2$-$C_{60}$ alkenyl group, $C_2$-$C_{60}$ alkynyl group, $C_6$-$C_{60}$ aryl group, or $C_2$-$C_{60}$ heteroaryl group.

In Formula 1, * and *' are binding sites with the core A.

In Formula 2A, $T_1$ is O, S, $N(R_{11})$, or $C(R_{12})(R_{13})$, where $R_{11}$ is one selected from a $C_6$-$C_{20}$ aryl group; and a $C_6$-$C_{20}$ aryl group substituted with at least one selected from deuterium, —F, —Cl, —Br, —I, —CN, a hydroxyl group, a —$NO_2$ group, an amino group, an amidino group, hydrazine, hydrazone, a carboxylic acid group or salt thereof, a sulfonic acid group or salt thereof, a phosphoric acid group or salt thereof, a $C_1$-$C_{20}$ alkyl group, a $C_1$-$C_{20}$ alkyl group substituted with at least one —F, or a $C_1$-$C_{20}$ alkoxy group. $R_{12}$ and $R_{13}$ may each be independently one selected from a $C_1$-$C_{20}$ alkyl group; a $C_1$-$C_{20}$ alkyl group substituted with at least one selected from deuterium, —F, —Cl, —Br, —I, —CN, a hydroxyl group, a —$NO_2$ group, an amino group, an amidino group, hydrazine, hydrazone, a carboxylic acid group or salt thereof, a sulfonic acid group or salt thereof, a phosphoric acid group or salt thereof; a $C_6$-$C_{20}$ aryl group; or a $C_6$-$C_{20}$ aryl group substituted with at least one selected from deuterium, —F, —Cl, —Br, —I, —CN, a hydroxyl group, a —$NO_2$ group, an amino group, an amidino group, hydrazine, hydrazone, a carboxylic acid group or salt thereof, a sulfonic acid group or salt thereof, a phosphoric acid group or salt thereof, a $C_1$-$C_{20}$ alkyl group, or a $C_1$-$C_{20}$ alkyl group substituted with at least one —F, or $C_1$-$C_{20}$ alkoxy group.

For example, in Formula 2A, $T_1$ is O, S, $N(R_{11})$, or $C(R_{12})(R_{13})$, where $R_{11}$ is one selected from a phenyl group; a naphthyl group; or an anthryl group; or a phenyl group, naphthyl group, or anthryl group substituted with at least one selected from deuterium, —F, —Cl, —Br, —I, —CN, a hydroxyl group, a —$NO_2$ group, an amino group, an amidino group, hydrazine, hydrazone, a carboxylic acid group or salt thereof, a sulfonic acid group or salt thereof, a phosphoric acid group or salt thereof, a methyl group, an ethyl group, a propyl group, a butyl group, or a pentyl group. $R_{12}$ and $R_{13}$ may each be independently one selected from a methyl group; an ethyl group; a propyl group; a butyl group; a pentyl group; a methyl group, ethyl group, propyl group, butyl group, or pentyl group substituted with at least one selected from deuterium, —F, —Cl, —Br, —I, —CN, a hydroxyl group, a —$NO_2$ group, an amino group, an amidino group, hydrazine, hydrazone, a carboxylic acid group or salt thereof, a sulfonic acid group or salt thereof, or a phosphoric acid group or salt thereof; a phenyl group; a naphthyl group; or an anthryl group; or a phenyl group, naphthyl group, or anthryl group substituted with at least one selected from deuterium, —F, —Cl, —Br, —I, —CN, a hydroxyl group, a —$NO_2$ group, an amino group, an amidino group, hydrazine, hydrazone, a carboxylic acid group or salt thereof, a sulfonic acid group or salt thereof, a phosphoric acid group or salt thereof, a methyl group, an ethyl group, a propyl group, a butyl group, or a pentyl group.

Also, in Formula 2A, $R_1$ and $R_2$ are each independently one selected from deuterium; —F; —Cl; —Br; —I; —CN; a hydroxyl group; a —$NO_2$ group; an amino group; amidino group; a hydrazine; a hydrazone; a carboxylic acid group or salt thereof; a sulfonic acid group or salt thereof; a phosphoric acid group or salt thereof; a $C_1$-$C_{20}$ alkyl group; a $C_1$-$C_{20}$ alkoxy group; and a $C_1$-$C_{20}$ alkyl group or $C_1$-$C_{20}$ alkoxy group substituted with at least one selected from deuterium, —F, —Cl, —Br, —I, —CN, a hydroxyl group, —$NO_2$ group, an amino group, an amidino group, a hydrazine, a hydrazone, a carboxylic acid group or salt thereof, a sulfonic acid group or salt thereof, or a phosphoric acid group or salt thereof. Also, a and b may each be independently 0, 1, or 2.

For example, $R_1$ and $R_2$ in Formula 2A may each be independently one selected from deuterium; —F; —Cl; —Br; —I; —CN; a hydroxyl group; a —$NO_2$ group; an amino group; amidino group; a hydrazine; a hydrazone; a carboxylic acid group or salt thereof; a sulfonic acid group or salt thereof; a phosphoric acid group or salt thereof; a methyl group; an ethyl group; a propyl group; a butyl group; a pentyl group; or a methyl group, ethyl group, propyl group, butyl group, or pentyl group substituted with at least one selected from deuterium, —F, —Cl, —Br, —I, —CN, a hydroxyl group, a —$NO_2$ group, an amino group, an amidino group, a hydrazine, a hydrazone, a carboxylic acid group or salt thereof, a sulfonic acid group or salt thereof, or a phosphoric acid group or salt thereof. Also, a and b may each be independently 0 or 1, but are not limited thereto.

$R_1$ to $R_4$ in Formula 2B may each be independently one selected from deuterium; —F; —Cl; —Br; —I; —CN; a hydroxyl group; a —$NO_2$ group; an amino group; amidino group; a hydrazine; a hydrazone; a carboxylic acid group or salt thereof; a sulfonic acid group or salt thereof; a phosphoric acid group or salt thereof; a $C_1$-$C_{20}$ alkyl group; a $C_1$-$C_{20}$ alkoxy group; or a $C_1$-$C_{20}$ alkyl group or $C_1$-$C_{20}$ alkoxy group substituted with at least one selected from deuterium, —F, —Cl, —Br, —I, —CN, a hydroxyl group, a —$NO_2$ group, an amino group, an amidino group, a hydrazine, a hydrazone, a carboxylic acid group or salt thereof, a sulfonic acid group or salt thereof, or a phosphoric acid group or salt thereof. Also, a to d may each be independently 0, 1, or 2.

For example, $R_1$ to $R_4$ in Formula 2B may each be independently deuterium; —F; —Cl; —Br; —I; —CN; a hydroxyl group; —$NO_2$ group; an amino group; amidino group; a hydrazine; a hydrazone; a carboxylic acid group or salt thereof; a sulfonic acid group or salt thereof; a phosphoric acid group or salt thereof; a methyl group; an ethyl group; a propyl group; a butyl group; a pentyl group; or a methyl group, ethyl group, propyl group, a butyl group, or pentyl group substituted with at least one selected from deuterium, —F, —Cl, —Br, —I, —CN, a hydroxyl group, a —$NO_2$ group, an amino group, an amidino group, a hydrazine, a hydrazone, a carboxylic acid group or salt thereof, a sulfonic acid group or salt thereof, or a phosphoric acid group or salt thereof. Also, a to d may each be independently 0 or 1.

$Ar_1$ to $Ar_4$ in Formula 1 are each independently a substituted or unsubstituted phenyl group, a substituted or unsubstituted pentalenyl, a substituted or unsubstituted indenyl, a substituted or unsubstituted naphthyl group, a substituted or unsubstituted azulenyl, a substituted or unsubstituted heptalenyl, a substituted or unsubstituted indacenyl, a substituted or unsubstituted acenaphthyl group, a substituted or unsubstituted fluorenyl, a substituted or unsubstituted phenalenyl, a substituted or unsubstituted phenanthrenyl, a substituted or unsubstituted anthryl group, a substituted or unsubstituted fluoranthenyl group, a substituted or unsubstituted triphenylenyl group, a substituted or unsubstituted pyrenyl group, a substituted or unsubstituted chrysenyl group, a substituted or unsubstituted naphthacenyl group, a substituted or unsubstituted picenyl group, a substituted or unsubstituted perylenyl group, a substituted or unsubstituted pentaphenyl group, a substituted or unsubstituted hexacenyl group, a substituted or unsubstituted pyrrolyl group, a substituted or unsubstituted pyrazolyl group, a substituted or unsubstituted imidazolyl group, a substituted or unsubstituted imidazolinyl group, a substituted or unsubstituted imidazopyridinyl group, a substituted or unsubstituted imidazopyrimidinyl group, a substituted or unsubstituted pyridinyl group, a substituted or unsubstituted pyrazinyl, a substituted or unsubstituted pyrimidinyl group, a substituted or unsubstituted benzoimidazolyl group, a substituted or unsubstituted indolyl group, a substituted or unsubstituted purinyl group, a substituted or unsubstituted quinolinyl group, a substituted or unsubstituted isoquinolinyl group, a substituted or unsubstituted phthalazinyl group, a substituted or unsubstituted indolizinyl group, a substituted or unsubstituted naphthyridinyl group, a substituted or unsubstituted quinazolinyl group, a substituted or unsubstituted quinoxalinyl group, a substituted or unsubstituted cinnolinyl group, a substituted or unsubstituted indazolyl group, a substituted or unsubstituted carbazolyl group, a substituted or unsubstituted phenazinylene group, a substituted or unsubstituted phenanthridinyl group, a substituted or unsubstituted pyranyl group, a substituted or unsubstituted chromenyl group, a substituted or unsubstituted furanyl group, a substituted or unsubstituted benzofuranyl group, a substituted or unsubstituted thiophenyl group, a substituted or unsubstituted benzothiophenyl group, a substituted or unsubstituted isothiazolyl group, a substituted or unsubstituted benzoimidazolyl group, a substituted or unsubstituted isoxazolyl group, a substituted or unsubstituted dibenzothiophenyl group, a substituted or unsubstituted dibenzofuranyl group, a substituted or unsubstituted triazinyl group, a substituted or unsubstituted oxadiazolyl group, a substituted or unsubstituted pyridazinyl group, a substituted or unsubstituted triazolyl group, a substituted or unsubstituted tetrazolyl group, a substituted or unsubstituted phenanthrolinyl group, a substituent represented by Formula 2A, or a substituent represented by Formula 2B, where when n is 0, at least one of $Ar_1$ and $Ar_2$ (or when n is 1, at least one of $Ar_1$ to $Ar_4$) may be the substituent represented by Formula 2A.

For example, $Ar_1$ to $Ar_4$ in Formula 1 may each be independently a substituted or unsubstituted phenyl group, a substituted or unsubstituted naphthyl group, a substituted or unsubstituted fluorenyl group, a substituted or unsubstituted phenanthrenyl group, a substituted or unsubstituted anthryl group, a substituted or unsubstituted pyrenyl group, a substituted or unsubstituted chrysenyl group, a substituted or unsubstituted pyridinyl group, a substituted or unsubstituted pyrazinyl group, a substituted or unsubstituted pyrimidinyl group, a substituted or unsubstituted quinolinyl group, a substituted or unsubstituted isoquinolinyl group, a substituted or unsubstituted quinazolinyl group, a substituted or unsubstituted quinoxalinyl group, a substituted or unsubstituted carbazolyl group, a substituted or unsubstituted benzofuranyl group, a substituted or unsubstituted benzothiophenyl group, a substituted or unsubstituted dibenzothiophenyl group, a substituted or unsubstituted dibenzofuranyl group, a substituted or unsubstituted triazinyl group, the substituent represented by Formula 2A, or the substituent represented by Formula 2B, where when n is 0, at least one of $Ar_1$ and $Ar_2$ (or when n is 1, at least one of $Ar_1$ to $Ar_4$) may be a substituent represented by Formula 2A or a substituent represented by Formula 2B.

Also, for example, $Ar_1$ to $Ar_4$ in Formula 1 may each be independently a $C_6$-$C_{60}$ aryl group substituted with at least one selected from —F, —CN, —NO$_2$, or a $C_1$-$C_{20}$ alkyl group substituted with at least one —F (for example, a phenyl group, naphthyl group, or phenanthrenyl group substituted with at least one selected from —F, —CN, —NO$_2$, or a $C_1$-$C_{20}$ alkyl group substituted with at least one —F, etc.); a unsubstituted $C_2$-$C_{60}$ heteroaryl group (for example, a pyridinyl group, a pyrazinyl group, a pyrimidinyl group, a triazinyl group, etc.); a $C_2$-$C_{60}$ heteroaryl group substituted with at least one selected from —F, —CN, —NO$_2$, or a $C_1$-$C_{20}$ alkyl group substituted with at least one —F; a substituent represented by Formula 2A; or a substituent represented by Formula 2B, where when n is 0, at least one of $Ar_1$ and $Ar_2$ (or when n is 1, at least one of $Ar_1$ to $Ar_4$) may be a substituent represented by Formula 2A or a substituent represented by Formula 2B.

For example, $Ar_1$ to $Ar_4$ in Formula 1 may each be independently one selected from substituents represented by Formula 3(1) to Formula 3(25), the substituent represented by Formula 2A, or the substituent represented by Formula 2B, where when n is 0, at least one of $Ar_1$ and $Ar_2$ (or when n is 1, at least one of $Ar_1$ to $Ar_4$) may be a substituent represented by Formula 2A or a substituent represented by Formula 2B:

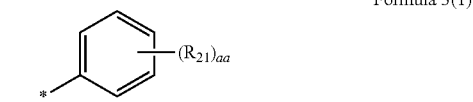

Formula 3(1)

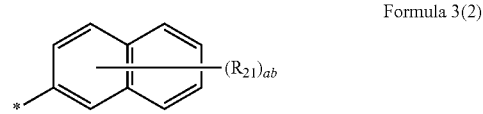

Formula 3(2)

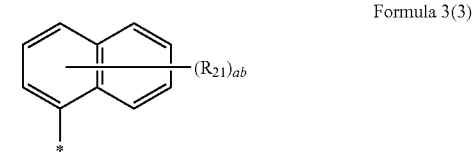

Formula 3(3)

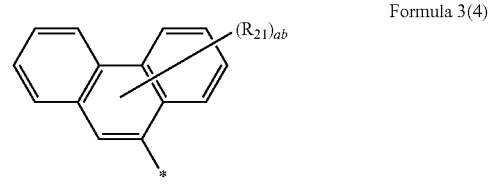

Formula 3(4)

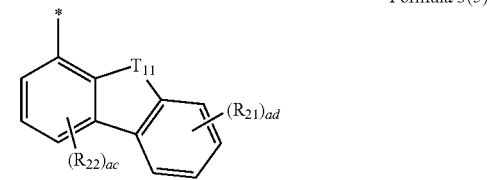

Formula 3(5)

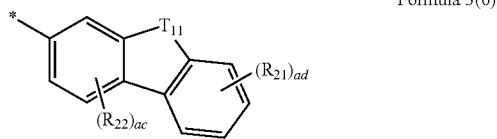

Formula 3(6)

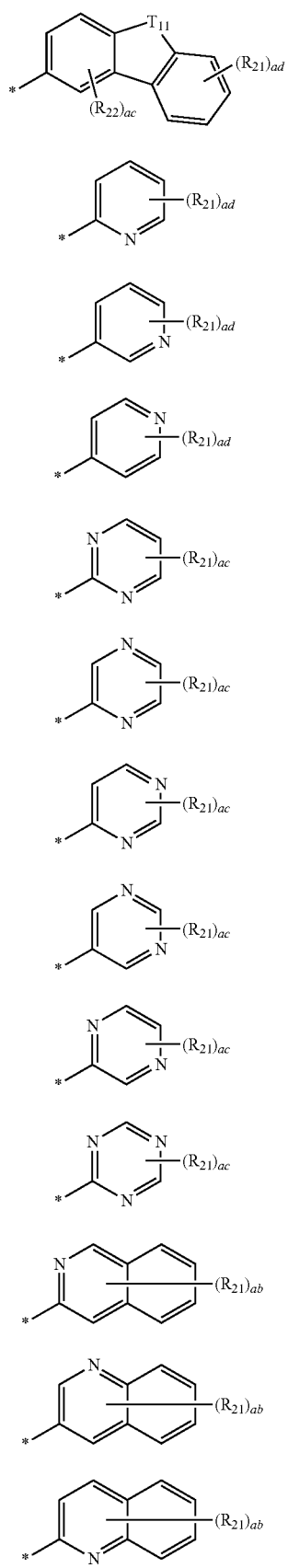

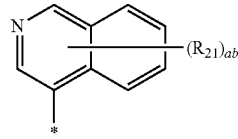
Formula 3(20)

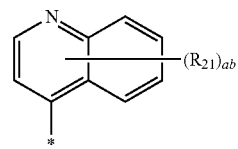
Formula 3(21)

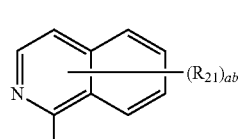
Formula 3(22)

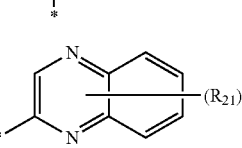
Formula 3(23)

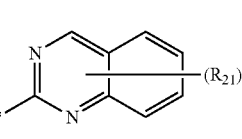
Formula 3(24)

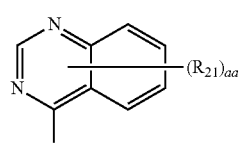
Formula 3(25)

In Formulae 3(1) to 3(25), $T_{11}$ is O, S, $N(R_{31})$, or $C(R_{32})(R_{33})$, where $R_{31}$ is understood by reference to the description of $R_{11}$, and $R_{32}$ and $R_{33}$ are understood by reference to the description of $R_{12}$ and $R_{13}$, respectively. $R_{21}$ and $R_{22}$ may each be independently one selected from deuterium; —F; —Cl; —Br; —I; —CN; a hydroxyl group; a —$NO_2$ group; an amino group; an amidino group; a hydrazine; a hydrazone; a carboxylic acid group or salt thereof; a sulfonic acid group or salt thereof; a phosphoric acid group or salt thereof; a $C_1$-$C_{20}$ alkyl group; a $C_1$-$C_{20}$ alkoxy group; a $C_1$-$C_{20}$ alkyl group or $C_1$-$C_{20}$ alkoxy group substituted with at least one selected from deuterium, —F, —Cl, —Br, —I, —CN, a hydroxyl group, a —$NO_2$ group, an amino group, an amidino group, a hydrazine, a hydrazone, a carboxylic acid group or salt thereof, a sulfonic acid group or salt thereof, or a phosphoric acid group or salt thereof; a $C_6$-$C_{20}$ aryl group; a $C_2$-$C_{20}$ heteroaryl group; or a $C_2$-$C_{60}$ aryl group and $C_2$-$C_{20}$ heteroaryl group substituted with at least one selected from deuterium, —F, —Cl, —Br, —I, —CN, a hydroxyl group, a —$NO_2$ group, an amino group, an amidino group, a hydrazine, a hydrazone, a carboxylic acid group or salt thereof, a sulfonic acid group or salt thereof, a phosphoric acid group or salt thereof, a $C_1$-$C_{20}$ alkyl group, a $C_1$-$C_{20}$ alkyl group substituted with at least one —F, or $C_1$-$C_{20}$ alkoxy group. Also, aa is an integer of 0 to 5 (for example, an integer of 0 to 3); ab is an integer of 0 to 6 (for example, an integer of 0 to 3); ac is an integer of 0 to 3; ad is an integer of 0 to 4 (for example, an integer of 0 to 3); ae is an integer of 0 to 2; and * is a binding site with N in Formula 1.

For example, $R_{21}$ and $R_{22}$ in Formulae 3(1) to 3(25) may be each independently one selected from deuterium; —F; —Cl; —Br; —I; —CN; a hydroxyl group; —$NO_2$ group; an amino group; an amidino group; a hydrazine; a hydrazone; a carboxylic acid group or salt thereof; a sulfonic acid group or salt thereof; a phosphoric acid group or salt thereof; a methyl group; an ethyl group; a propyl group; a butyl group; a pentyl group; a methyl group, ethyl group, propyl group, butyl group, or pentyl group substituted with at least one selected from deuterium, —F, —Cl, —Br, —I, —CN, a hydroxyl group, a —$NO_2$ group, an amino group, an amidino group, a hydrazine, a hydrazone, a carboxylic acid group or salt thereof, a sulfonic acid group or salt thereof, or a phosphoric acid group or salt thereof; a phenyl group; a naphthyl group; an anthryl group; or a phenyl group, naphthyl group, or anthryl group substituted with at least one selected from deuterium, —F, —Cl, —Br, —I, —CN, a hydroxyl group, a —$NO_2$ group, an amino group, an amidino group, a hydrazine, a hydrazone, a carboxylic acid group or salt thereof, a sulfonic acid group or salt thereof, a phosphoric acid group or salt thereof, a methyl group, an ethyl group, a propyl group, a butyl group, or a pentyl group, but are not limited thereto.

For example, $R_{21}$ and $R_{22}$ in Formulae 3(1) to 3(25) may each be independently one selected from —F; —CN; a —$NO_2$ group; a $C_1$-$C_{20}$ alkyl group or a $C_1$-$C_{20}$ alkoxy group substituted with at least one selected from —F, —CN, or a —$NO_2$ group; a phenyl group; a naphthyl group; a pyridinyl group; a pyrimidinyl group; a pyrazinyl group; a quinolinyl group; an isoquinolinyl group; a quinazolinyl group; a quinoxalinyl group; or a phenyl group, naphthyl group, pyridinyl group, pyrimidinyl group, pyrazinyl group, quinolinyl group, isoquinolinyl group, quinazolinyl group, or quinoxalinyl group substituted with at least one selected from —F, —CN, and —$NO_2$, but are not limited thereto.

The amine-based compound of Formula 1 above may be represented by any one of Formulae 1A to 1D below:

<Formula 1A>

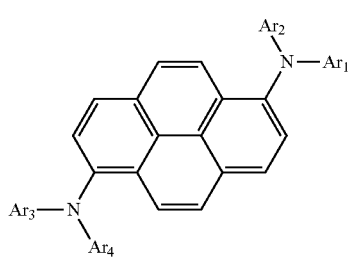

<Formula 1B>

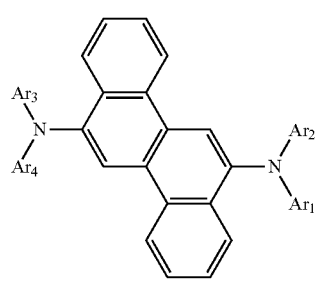

-continued

<Formula 1C>

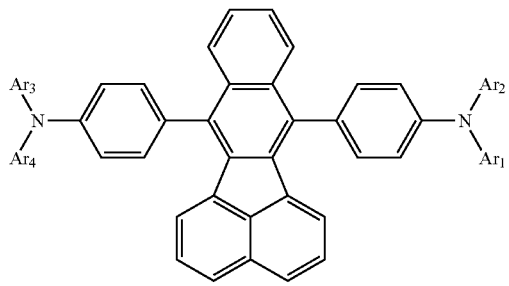

<Formula 1D>

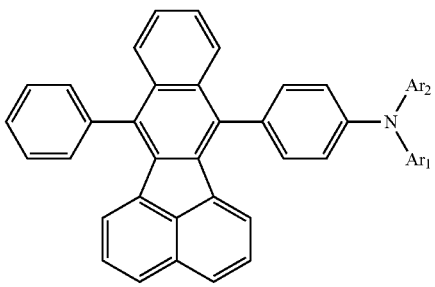

$Ar_1$ to $Ar_4$ in Formulae 1A to 1D may be understood by reference to the descriptions of $Ar_1$ to $Ar_4$.

For example, the amine-based compound may be represented by any one of Formulae 1A to 1C, and $Ar_1$ and $Ar_3$ in Formulae 1A to 1C may be identical to each other, and $Ar_2$ and $Ar_4$ in Formulae 1A to 1C may be identical to each other.

For example, the amine-based compound may be represented by any one of Formulae 1A to 1C, and $Ar_1$ and $Ar_3$ in Formulae 1A to 1C may be identical to each other, and $Ar_2$ and $Ar_4$ in Formulae 1A to 1C may be different from each other.

For example, the amine-based compound may be represented by any one of Formulae 1A to 1C, and $Ar_1$ to $Ar_4$ in Formulae 1A to 1C may be different from each other.

For example, the amine-based compound may be represented by Formula 1A, 1B or 10, and in the formulae, the first diarylamino group and the second diarylamino group may be identical to each other (for example, see Compounds 1 to 17, 28 to 43, and 45).

Alternatively, the amine-based compound may be represented by Formula 1A, 1B or 10, and in the formulae, the first diarylamino group and the second diarylamino group may be different from each other (for example, see Compounds 18 to 27, 44, and 46 to 48.)

According to an embodiment of the present invention, the amine-based compound of Formula 1 may be represented by Formula 1A, 1B, or 10. $Ar_1$ and $Ar_3$ in Formulae 1A to 1C may each be independently a substituent represented by Formula 2A or a substituent represented by Formula 2B. $Ar_2$ and $Ar_4$ in Formulae 1A to 1C may each be independently a substituent represented by one of Formula 3(1) to Formula 3(25). In this regard, $Ar_1$ and $Ar_3$ may be identical to each other, and $Ar_2$ and $Ar_4$ may be identical to each other; or $Ar_1$ and $Ar_3$ may be different from each other, and $Ar_2$ and $Ar_4$ may be identical to each other; or $Ar_1$ and $Ar_3$ may be identical to each other, and $Ar_2$ and $Ar_4$ may be different from each other; or $Ar_1$ to $Ar_4$ may be different from each other.

According to another embodiment of the present invention, the amine-based compound of Formula 1 is represented by Formula 1A, 1B, or 1C. $Ar_3$ in Formulae 1A to 10 may be a substituent represented by Formula 2A or a substituent represented by Formula 2B. $Ar_1$, $Ar_2$, and $Ar_4$ in Formulae 1A to 1C may each be independently a substituent represented by one of Formula 3(1) to Formula 3(25). In this regard, $Ar_2$ and $Ar_4$ may be identical to each other, or $Ar_2$ and $Ar_4$ may be different from each other.

According to another embodiment of the present embodiment, the amine-based compound of Formula 1 is represented by Formula 1 D. $Ar_3$ in Formula 1D may be a substituent represented by Formula 2A or a substituent represented by Formula 2B. $Ar_1$ in Formula 1D may be a substituent represented by Formula 3(1) to Formula 3(25).

The amine-based compound of Formula 1 may be represented by Formula 1A(1), 1A(2), 1A(3), 1A(4), 1A(5), 1B(1), 1B(2), 1B(3), 1C(1), 1C(2), or 1D(1) below, but may also be represented by other formulae.

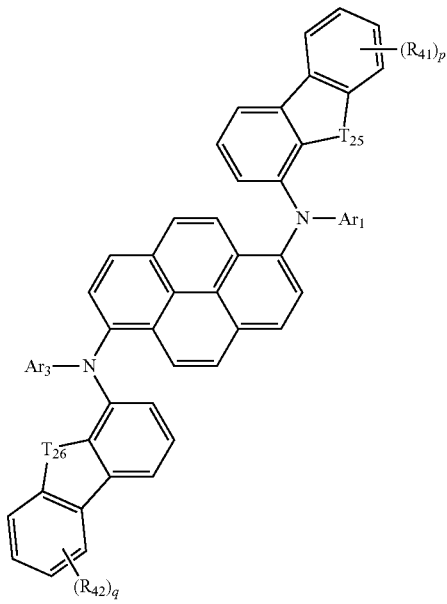
<Formula 1A(3)>

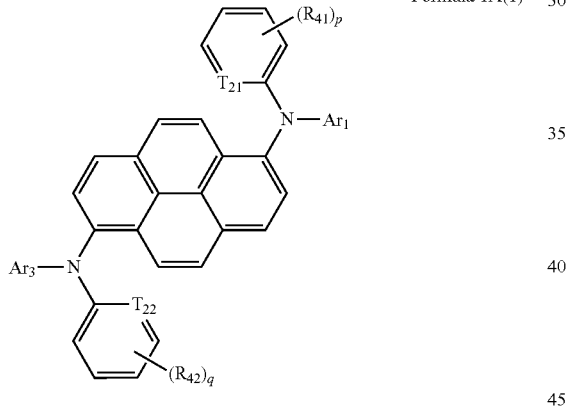
<Formula 1A(1)>

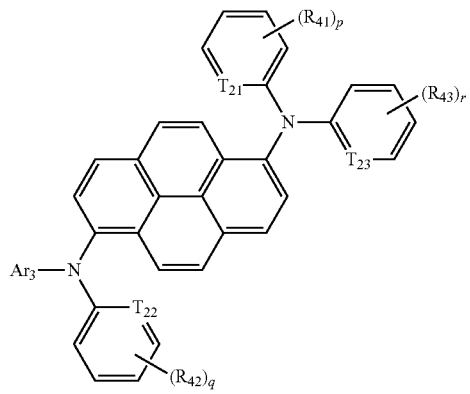
<Formula 1A(4)>

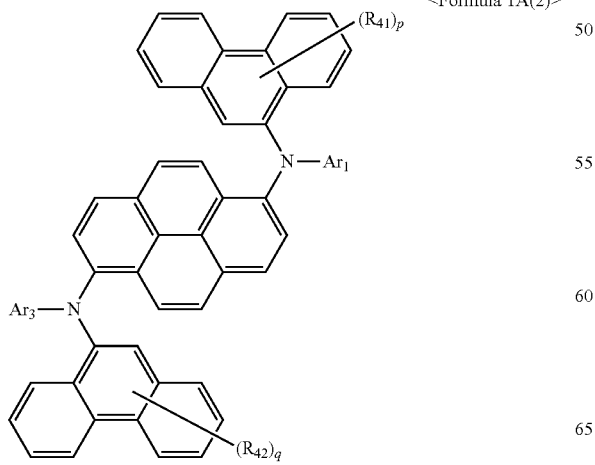
<Formula 1A(2)>

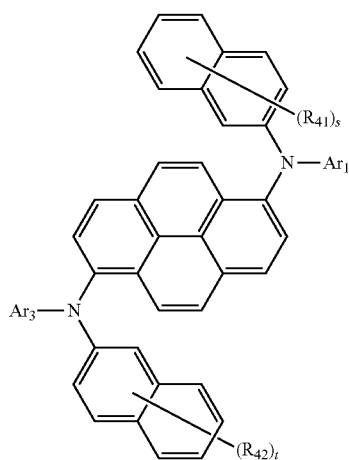
<Formula 1A(5)>

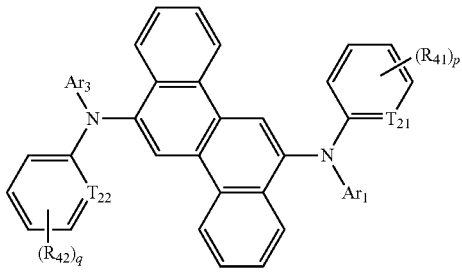
<Formula 1B(1)>

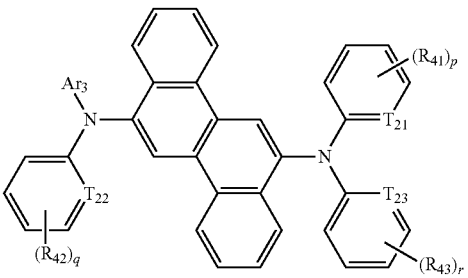
<Formula 1B(2)>

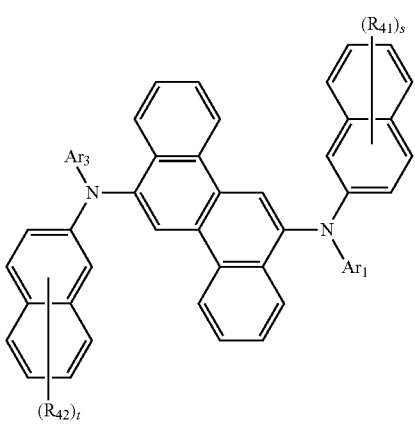
<Formula 1B(3)>

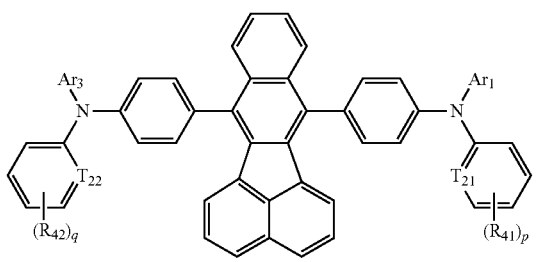
<Formula 1C(1)>

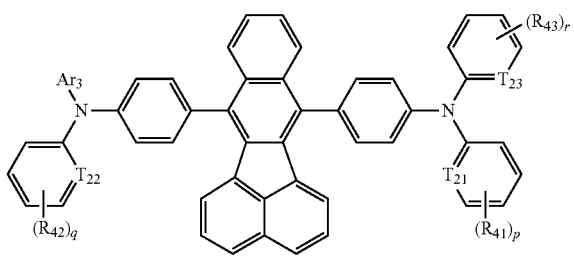
<Formula 1C(2)>

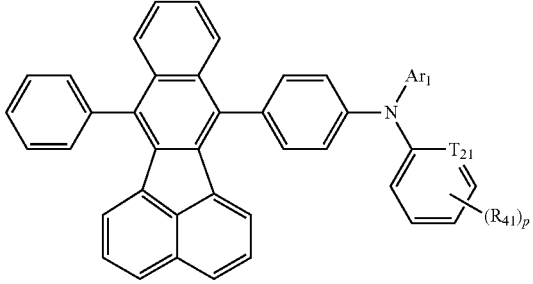
<Formula 1D(1)>

In Formulae 1A(1), 1A(2), 1A(3), 1A(4), 1A(5), 1B(1), 1B(2), 1B(3), 1C(1), 1C(2), and 1D(1), $T_{21}$ to $T_{23}$ may each be independently N or $C(R_{44})$. $T_{25}$ and $T_{26}$ may each be independently O or S. $R_{41}$ and $R_{44}$ may each be independently one selected from deuterium; —F; —Cl; —Br; —I; —CN; a hydroxyl group; —$NO_2$ group; an amino group; amidino group; a hydrazine; a hydrazone; a carboxylic acid group or salt thereof; a sulfonic acid group or salt thereof; a phosphoric acid group or salt thereof; a $C_1$-$C_{20}$ alkyl group; a $C_1$-$C_{20}$ alkoxy group; a $C_1$-$C_{20}$ alkyl group or $C_1$-$C_{20}$ alkoxy group substituted with at least one selected from deuterium, —F, —Cl, —Br, —I, —CN, a hydroxyl group, a —$NO_2$ group, an amino group, an amidino group, a hydrazine, a hydrazone, a carboxylic acid group or salt thereof, a sulfonic acid group or salt thereof, a phosphoric acid group or salt thereof; a $C_6$-$C_{20}$ aryl group; a $C_2$-$C_{20}$ heteroaryl group; or a $C_2$-$C_{60}$ aryl group or $C_2$-$C_{20}$ heteroaryl group substituted with at least one selected from deuterium, —F, —Cl, —Br, —I, —CN, a hydroxyl group, a —$NO_2$ group, an amino group, an amidino group, a hydrazine, a hydrazone, a carboxylic acid group or salt thereof, a sulfonic acid group or salt thereof, a phosphoric acid group or salt thereof, a $C_1$-$C_{20}$ alkyl group, a $C_1$-$C_{20}$ alkyl group substituted with at least one —F, or a $C_1$-$C_{20}$ alkoxy group. Also, p, q, and r may each be independently an integer of 0 to 4; s and t may each be independently an integer of 0 to 7. $Ar_1$ and $Ar_3$ may each be independently a substituent represented by Formula 2A or a substituent represented by Formula 2B.

The substituent represented by Formula 2A or the substituent represented by Formula 2B (which may be $Ar_1$ and/or $Ar_3$ in Formulae 1A(1), 1A(2), 1A(3), 1A(4), 1A(5), 1B(1), 1B(2), 1B(3), 1C(1), 1C(2) and 1D(1)) are described in detail above. Also, the p or s (i.e., the number of) $R_{41}$ groups may be identical to or different from each other, the q or t (i.e., the number of) $R_{42}$ groups may be identical to or different from each other, and the r (i.e. the number of) $R_{43}$ groups may be identical to or different from each other.

$R_{41}$ to $R_{44}$ in Formulae 1A(1), 1A(2), 1A(3), 1A(4), 1A(5), 1B(1), 1B(2), 1B(3), 1C(1), 1C(2) and 1D(1) may each be independently deuterium; —F; —Cl; —Br; —I; —CN; a hydroxyl group; —$NO^2$ group; an amino group; an amidino group; a hydrazine; a hydrazone; a carboxylic acid group or salt thereof; a sulfonic acid group or salt thereof; a phosphoric acid group or salt thereof; a methyl group; an ethyl group; a propyl group; a butyl group; a pentyl group; a methyl group, an ethyl group, a propyl group, a butyl group, or a pentyl group substituted with at least one selected from deuterium, —F, —Cl, —Br, —I, —CN, a hydroxyl group, a —$NO_2$ group, an amino group, an amidino group, a hydrazine, a hydrazone, a carboxylic acid group or salt thereof, a sulfonic acid group or salt thereof, or a phosphoric acid group or salt thereof; a phenyl group; a naphthyl group; an anthryl group; or a phenyl group, a naphthyl group, or an anthryl group substituted with at least one selected from deuterium, —F, —Cl, —Br, —I, —CN, a hydroxyl group, a —NO$_2$ group, an amino group, an amidino group, a hydrazine, a hydrazone, a carboxylic acid group or salt thereof, a sulfonic acid group or salt thereof, a phosphoric acid group or salt thereof, a methyl group, an ethyl group, a propyl group, a butyl group, or a pentyl group.

According to an embodiment of the present invention, the amine-based compound may be represented by Formula 1A(1), 1A(4), 1B(1), 1B(2), 1C(1), 1C(2), or 1D(1), where $T_{21}$ in Formulae 1A(1), 1A(4), 1B(1), 1B(2), 1C(1), 1C(2), and 1D(1) may be C($R_{44}$), and $R_{44}$ may be —F, —CN, —NO$_2$, or a $C_1$-$C_{10}$ alkyl group substituted with at least one —F.

According to another embodiment of the present invention, the amine-based compound may be represented by Formula 1A(1), 1A(4), 1B(1), 1B(2), 1C(1), 1C(2), or 1D(1), and $T_{21}$ in Formulae 1A(1), 1A(4), 1B(1), 1B(2), 1C(1), 1C(2), and 1D(1) may be N.

According to another embodiment of the present invention, the amine-based compound may be represented by Formula 1A(1), 1A(2), 1A(3), 1A(4), 1A(5), 1B(1), 1B(2), 1B(3), 1C(1), 1C(2), or 1D(1), and at least one of the p or s (i.e., the number of) $R_{41}$ groups in Formulae 1A(1), 1A(2), 1A(3), 1A(4), 1A(5), 1B(1), 1B(2), 1B(3), 1C(1), 1C(2), and 1D(1) may be —F, —CN, —NO$_2$, or a $C_1$-$C_{10}$ alkyl group substituted with at least one —F.

According to another embodiment of the present invention, the amine-based compound may be represented by Formula 1A(1), 1A(2), 1A(3), 1A(4), 1A(5), 1B(1), 1B(2), 1B(3), 1C(1), or 1C(2), and the first diarylamino group and the second diarylamino group in Formula 1A(1), 1A(2), 1A(3), 1A(4), 1A(5), 1B(1), 1B(2), 1B(3), 1C(1), or 1C(2) may be identical to each other.

According to another embodiment of the present invention, the amine-based compound may be represented by Formula 1A(1), 1A(2), 1A(3), 1A(4), 1A(5), 1B(1), 1B(2), 1B(3), 1C(1), or 1C(2), and the first diarylamino group and the second diarylamino group in Formula 1A(1), 1A(2), 1A(3), 1A(4), 1A(5), 1B(1), 1B(2), 1B(3), 1C(1), and 1C(2) may be different from each other.

$Ar_1$ in Formula 1A(1), 1A(2), 1A(3), 1A(4), 1A(5), 1B(1), 1B(2), 1B(3), 1C(1), 1C(2), and 1D(1) may be a substituent represented by Formula 2A or a substituent represented by Formula 2B, and $T_1$ in Formula 2A may be C($R_{12}$)($R_{13}$) where $R_{12}$ and $R_{13}$ may each be independently one selected from a methyl group; an ethyl group; a propyl group; a butyl group; a pentyl group; or a methyl group, an ethyl group, a propyl group, a butyl group, or a pentyl group substituted with at least one selected from deuterium, —F, —Cl, —Br, —I, —CN, a hydroxyl group, a —NO$_2$ group, an amino group, an amidino group, a hydrazine, a hydrazone, a carboxylic acid group or salt thereof, a sulfonic acid group or salt thereof, or a phosphoric acid group or salt thereof; a phenyl group; a naphthyl group; an anthryl group; or a phenyl group, a naphthyl group, or an anthryl group substituted with at least one selected from deuterium, —F, —Cl, —Br, —I, —CN, a hydroxyl group, —NO$_2$ group, an amino group, an amidino group, a hydrazine, a hydrazone, a carboxylic acid group or salt thereof, a sulfonic acid group or salt thereof, a phosphoric acid group or salt thereof, a $C_1$-$C_{20}$ alkyl group, a $C_1$-$C_{20}$ alkyl group substituted with at least one —F, or $C_1$-$C_{20}$ alkoxy group. $R_1$ to $R_4$ in Formulae 2A and 2B may each be independently one selected from deuterium; —F; —Cl; —Br; —I; —CN; a hydroxyl group; —NO$_2$ group; an amino group; an amidino group; a hydrazine; a hydrazone; a carboxylic acid group or salt thereof; a sulfonic acid group or salt thereof; a phosphoric acid group or salt thereof; a methyl group; an ethyl group; a propyl group; a butyl group; or a pentyl group; or a methyl group, an ethyl group, a propyl group, a butyl group, or a pentyl group substituted with at least one selected from deuterium, —F, —Cl, —Br, —I, —CN, a hydroxyl group, a —NO$_2$ group, an amino group, an amidino group, a hydrazine, a hydrazone, a carboxylic acid group or salt thereof, a sulfonic acid group or salt thereof, or a phosphoric acid group or salt thereof. Also, a and b may each be independently 0 or 1.

The amine-based compound of Formula 1 may be, for example, one of Compounds 1 to 222, but are not limited thereto.

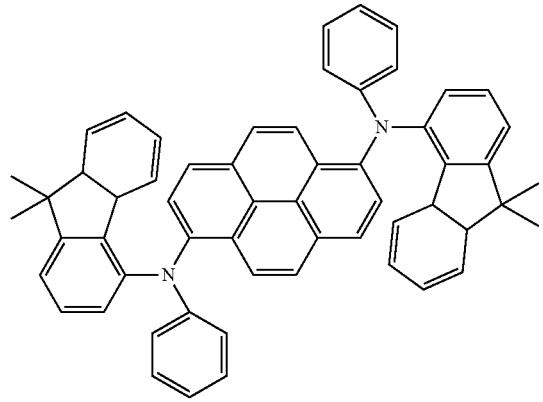

1

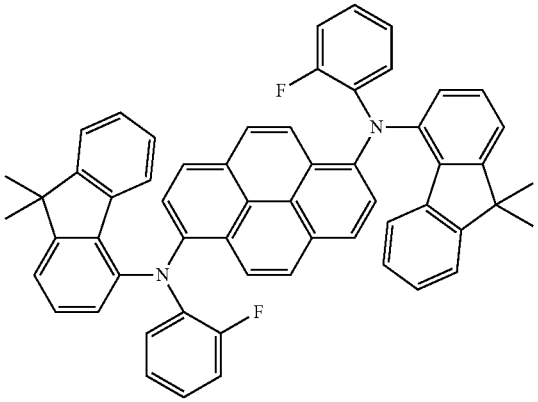

2

-continued
3
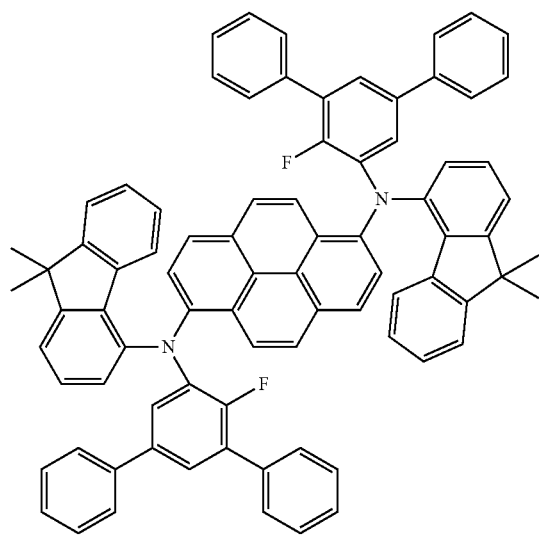
4
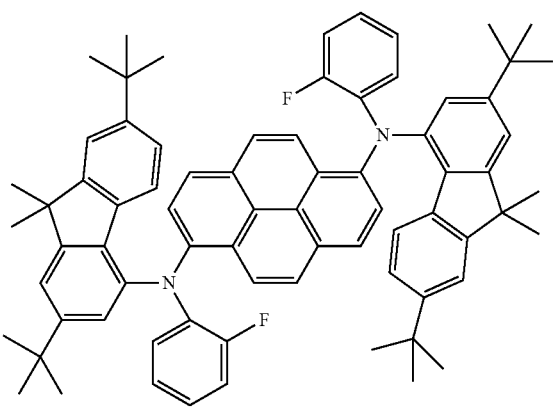
5
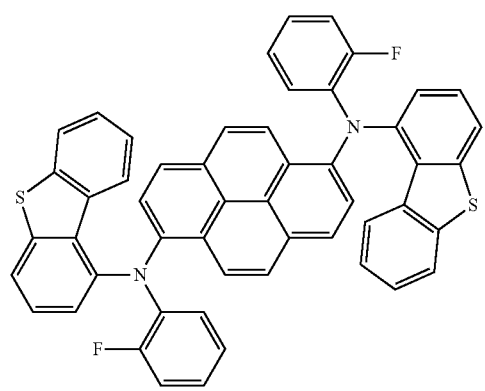
6
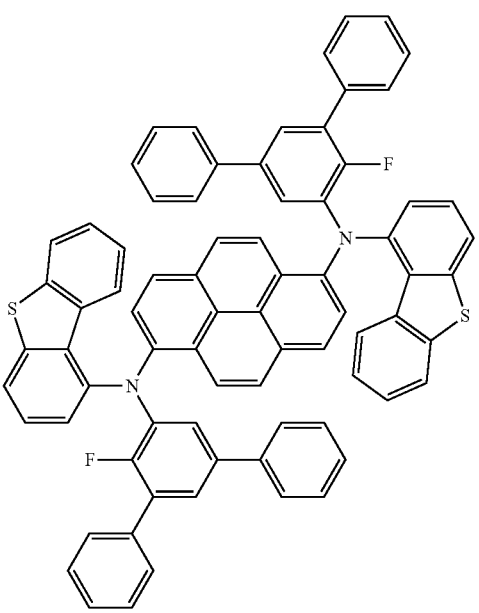
7
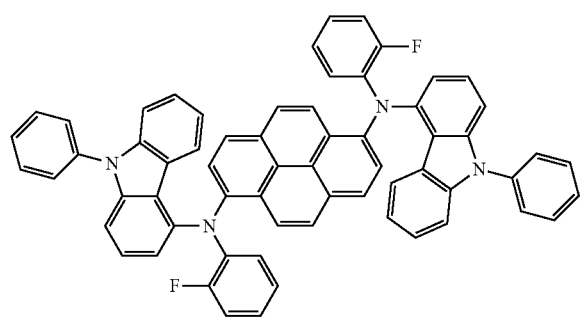
8
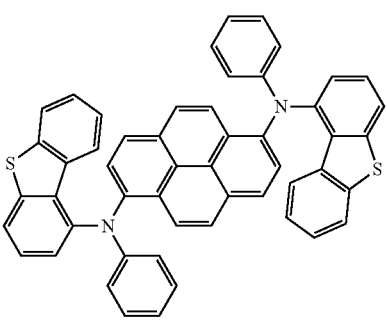

9
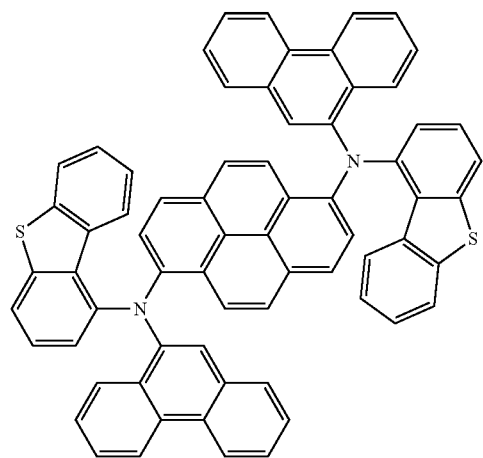
10
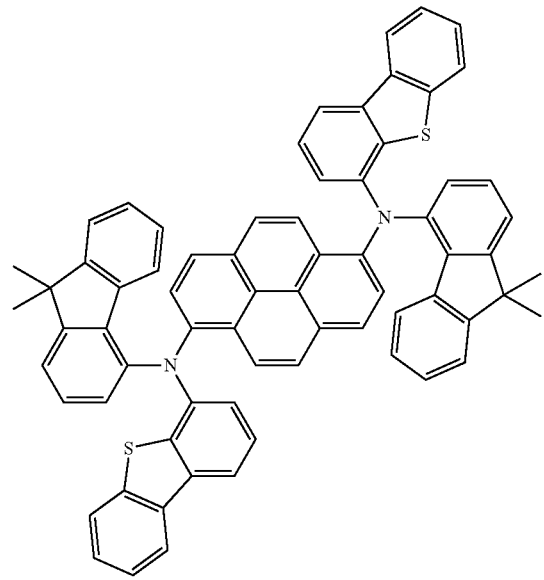
11
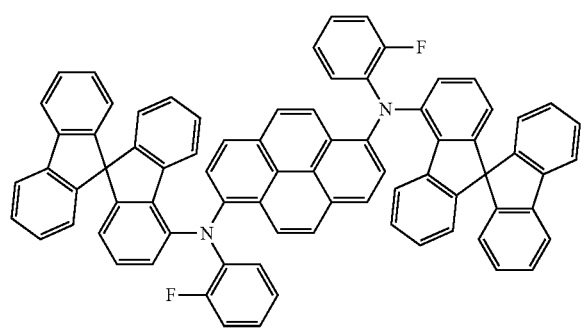
12
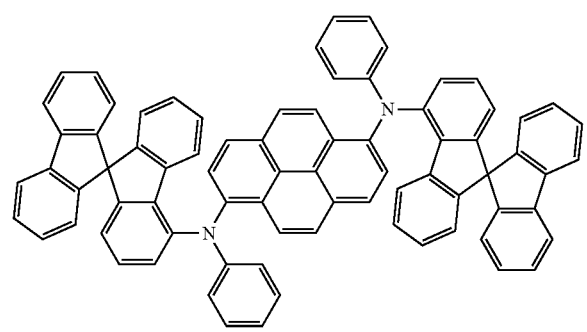
13
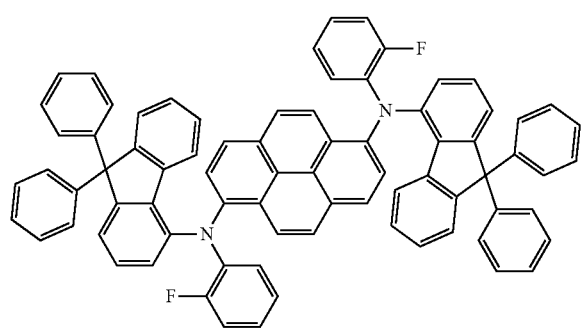
14
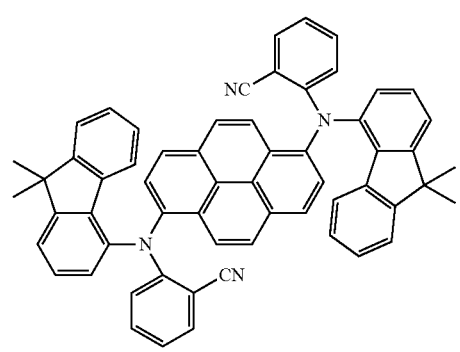

-continued
15
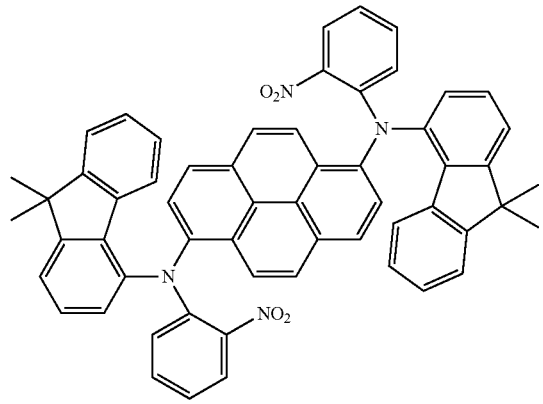
16
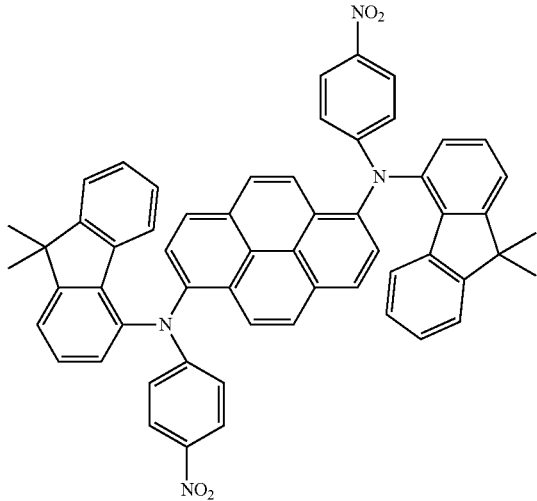
17
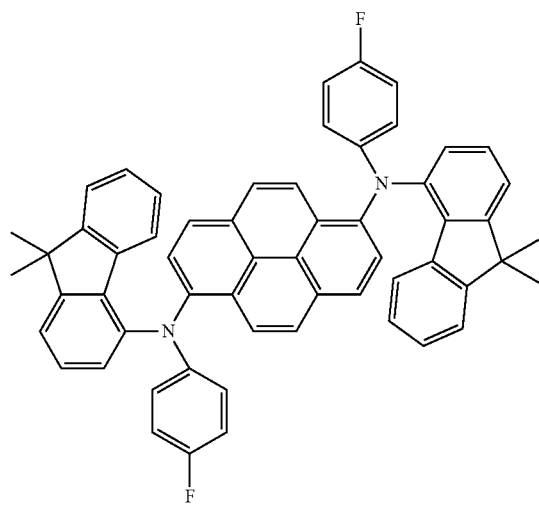
18
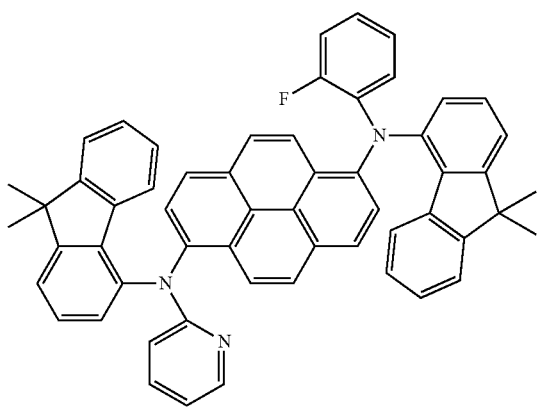
19
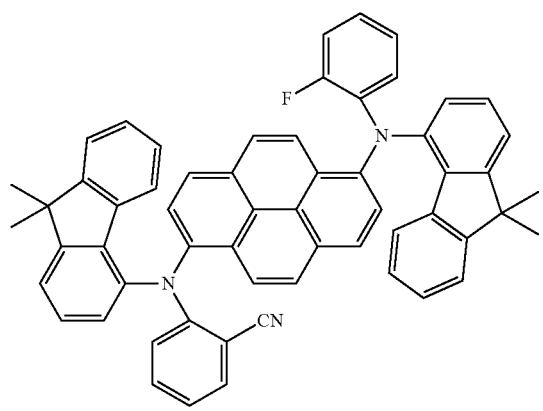
20
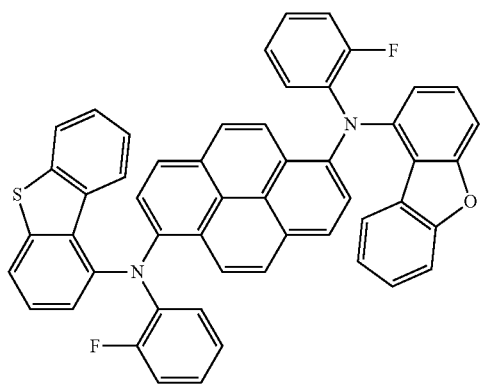

-continued
21
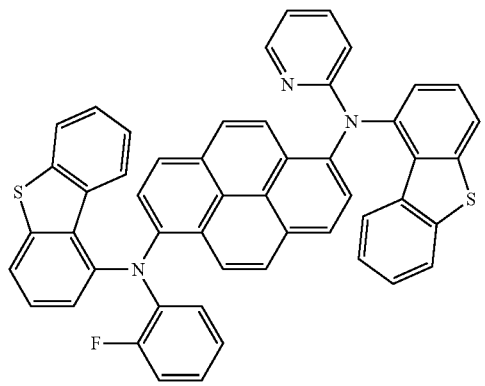
22
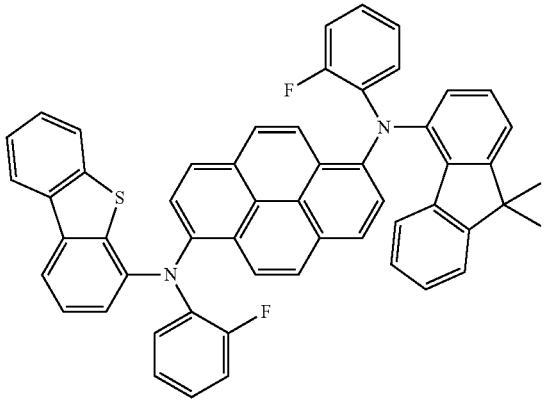
23
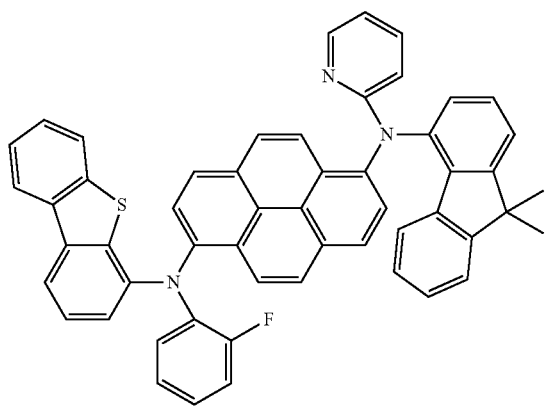
24
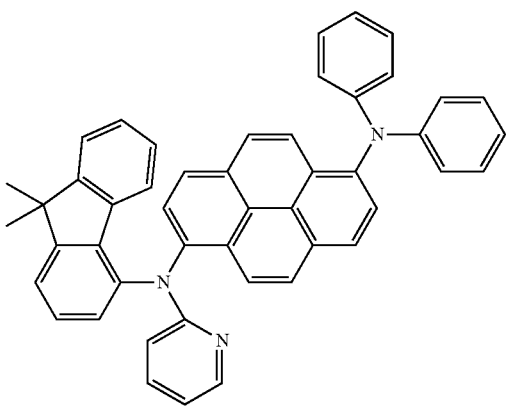
25
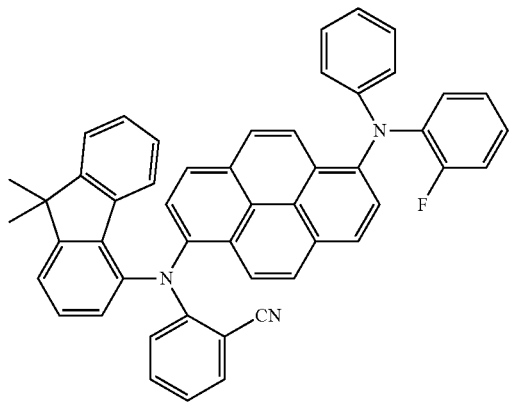
26
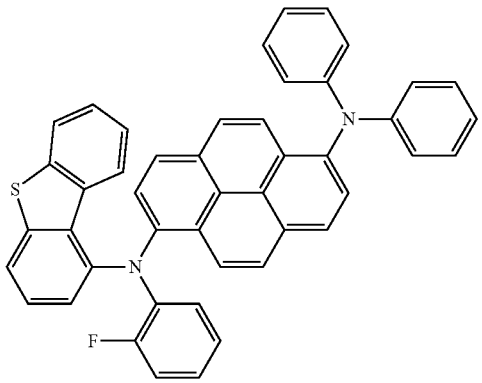
27
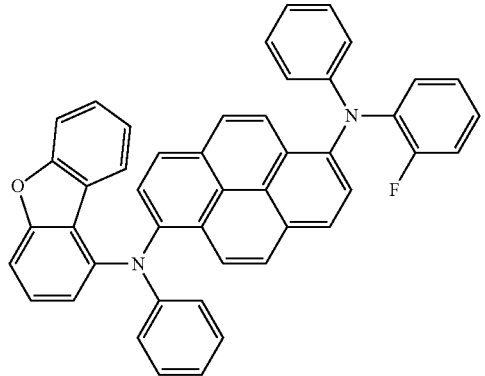
28
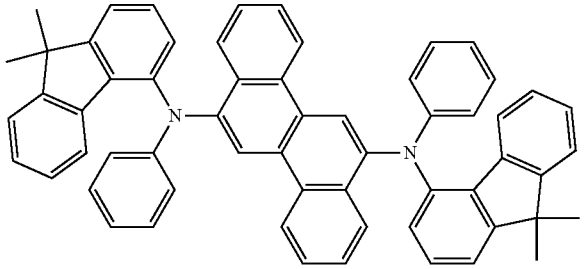

-continued
| 29 | 30 |
|---|---|
| 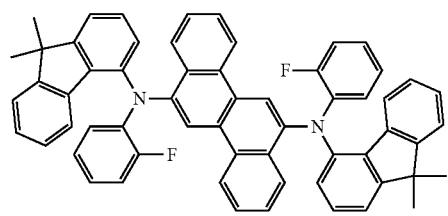 | 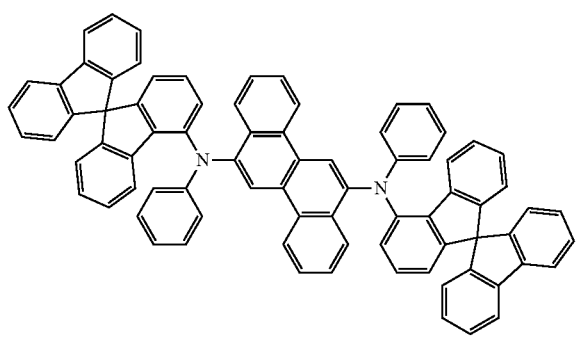 |
| 31 | 32 |
|---|---|
| 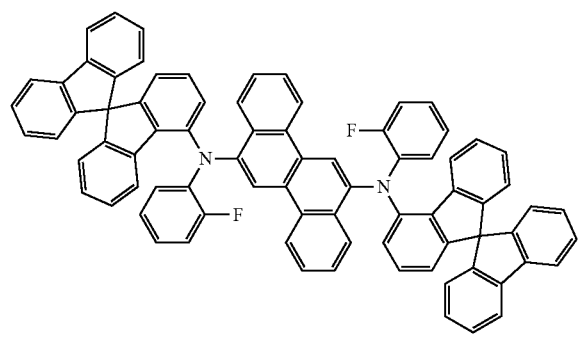 | 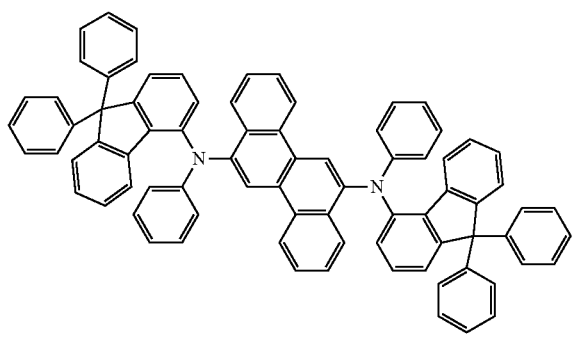 |
| 33 | 34 |
|---|---|
| 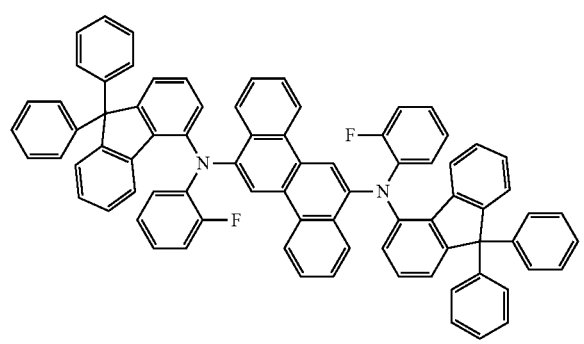 | 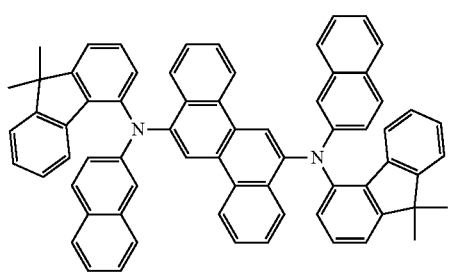 |
| 35 | 36 |
|---|---|
| 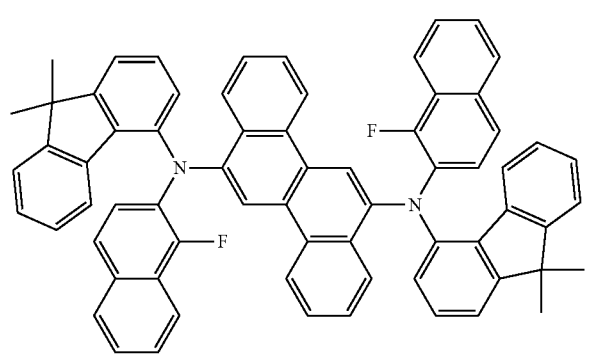 | 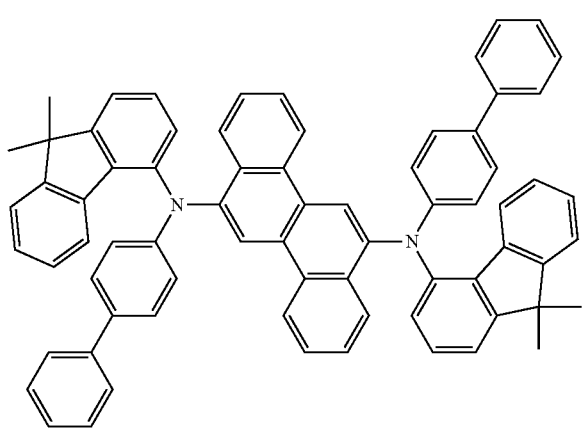 |

-continued
37
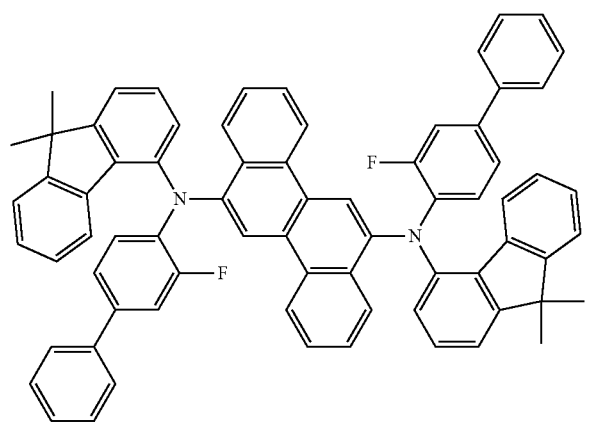
38
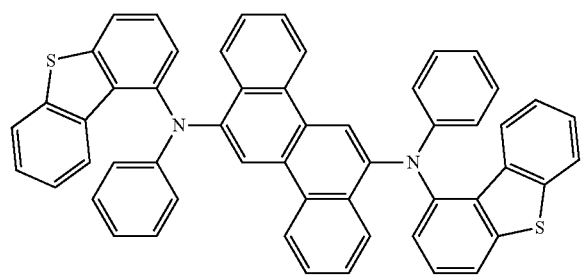
39
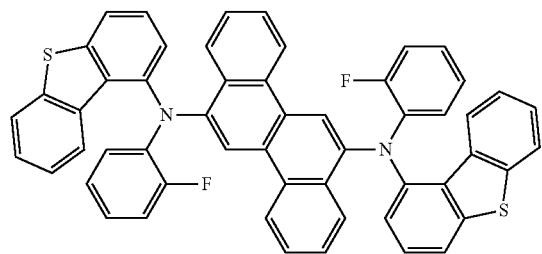
40
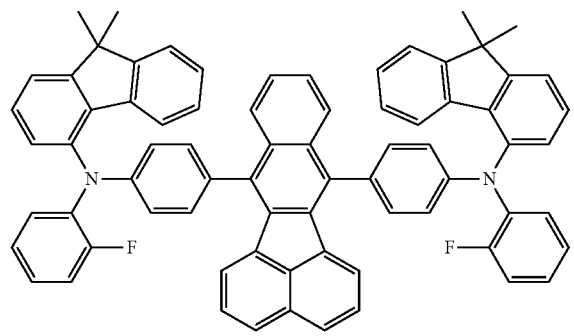
41
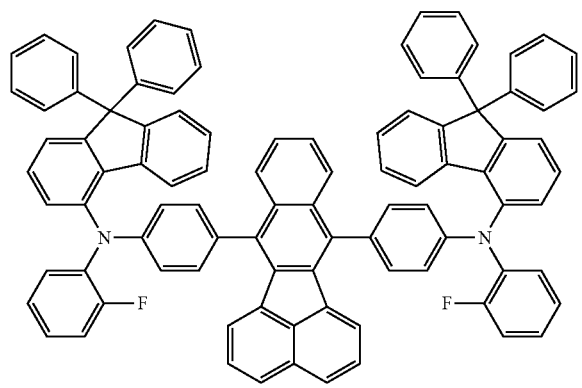
42
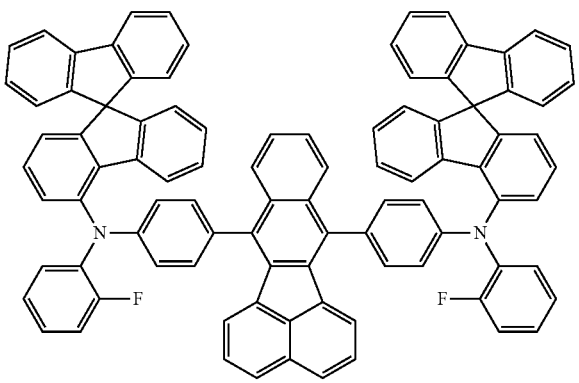
43
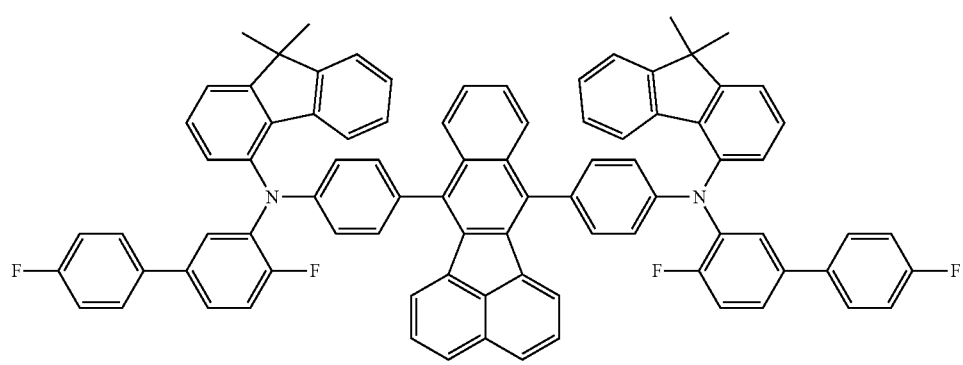

-continued
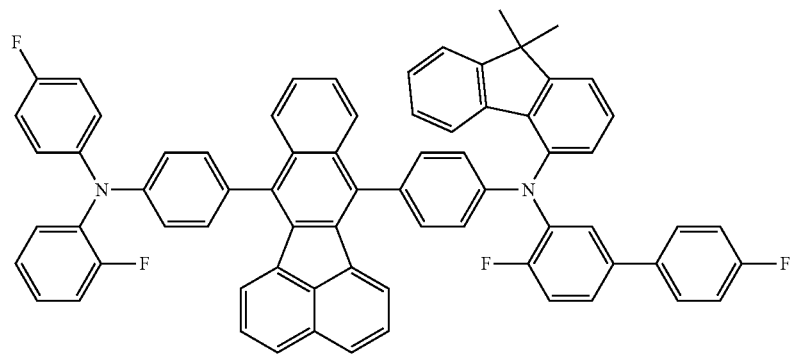
44
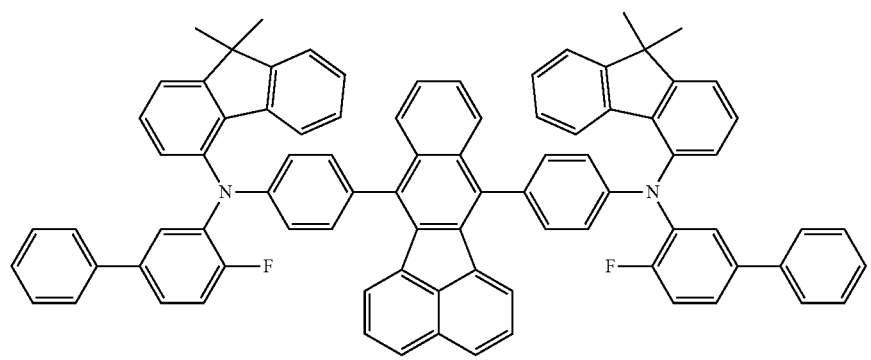
45
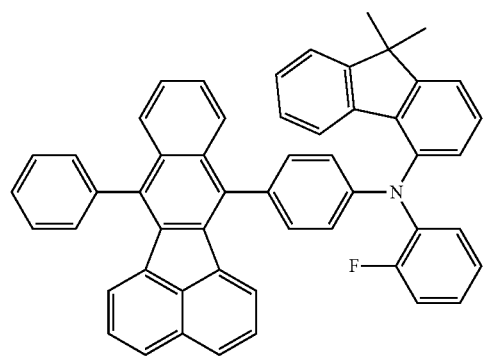
46
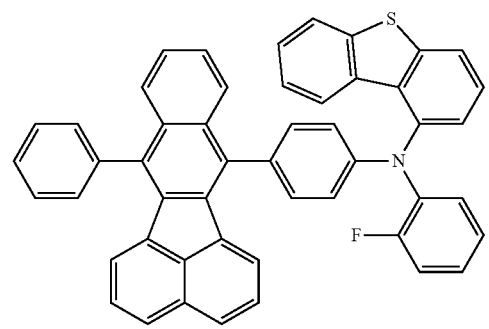
47
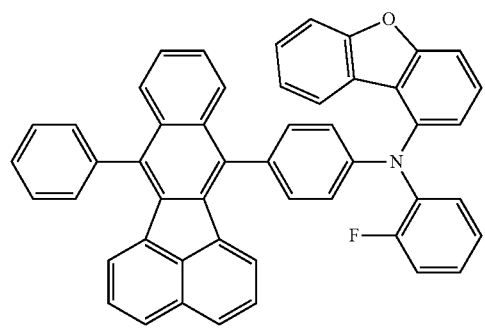
48
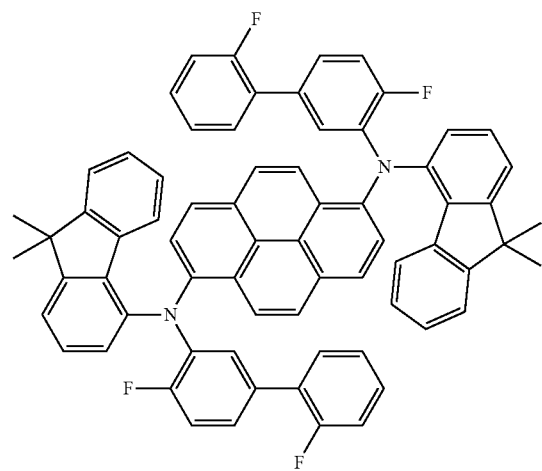
49

50
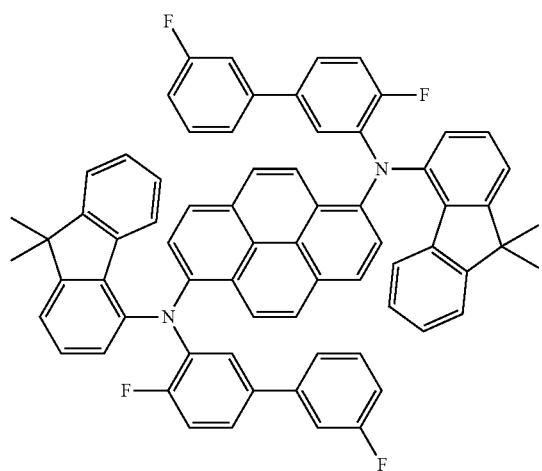
51
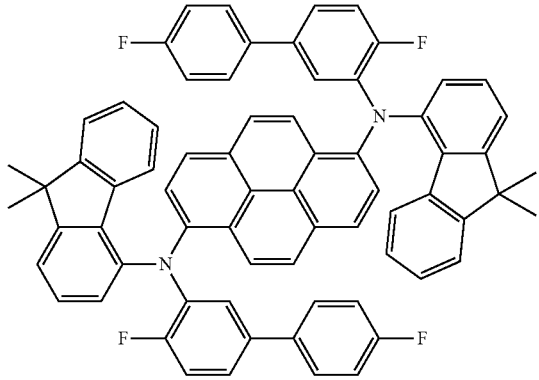
52
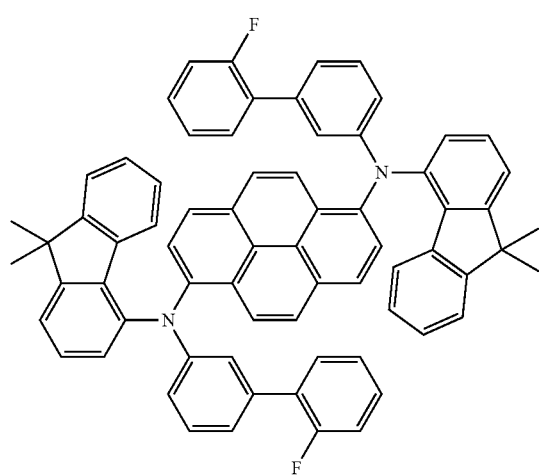
53
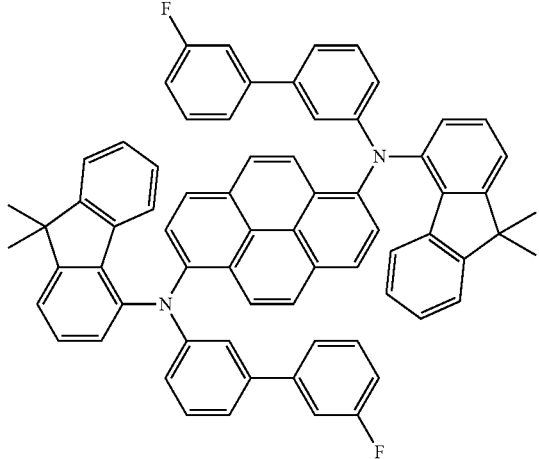
54
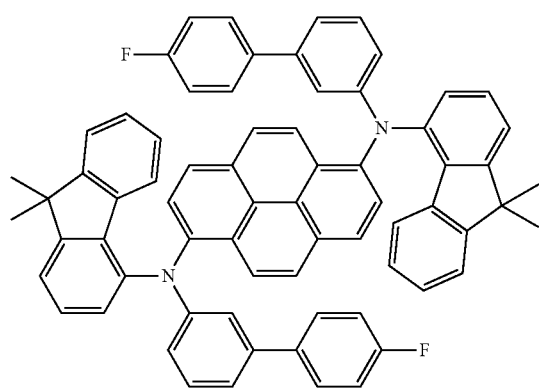
55
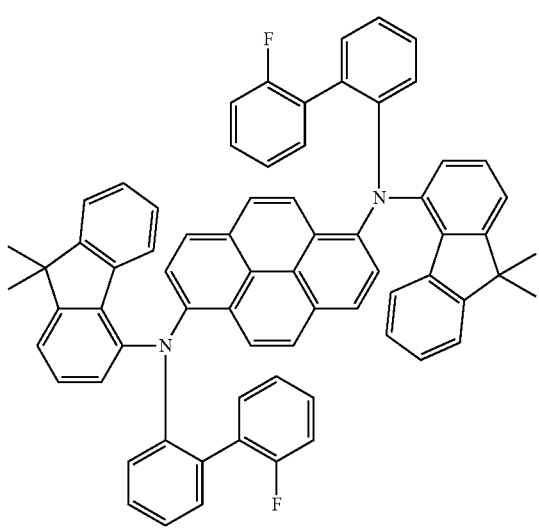

-continued
56
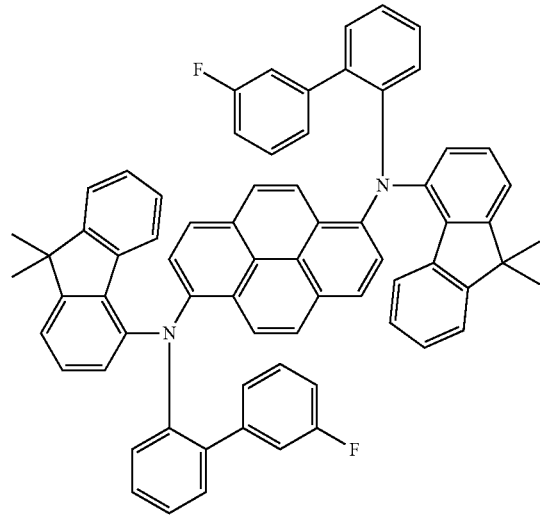
57
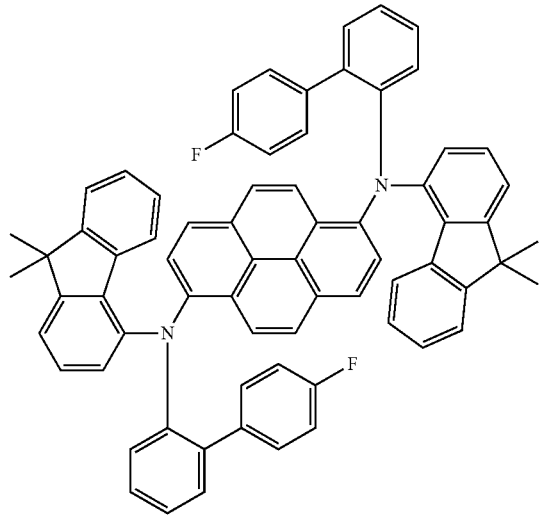
58
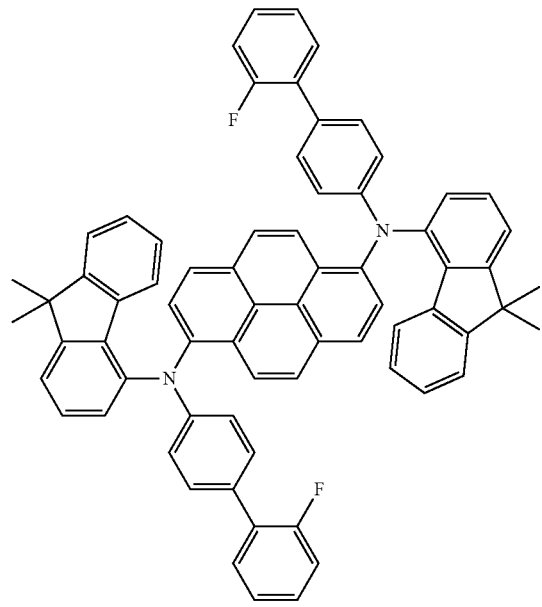
59
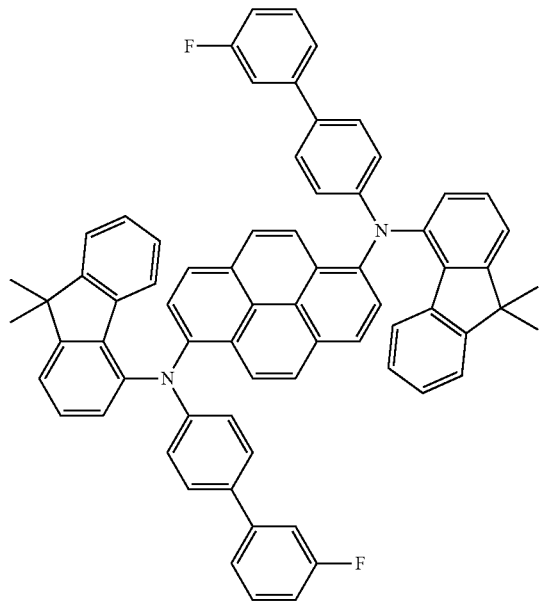

-continued
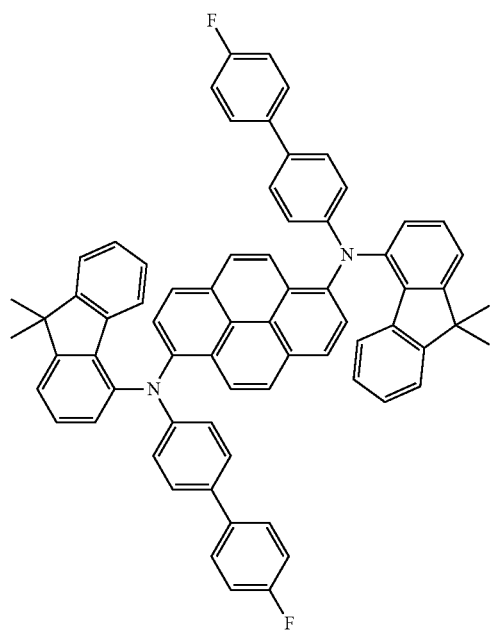
60
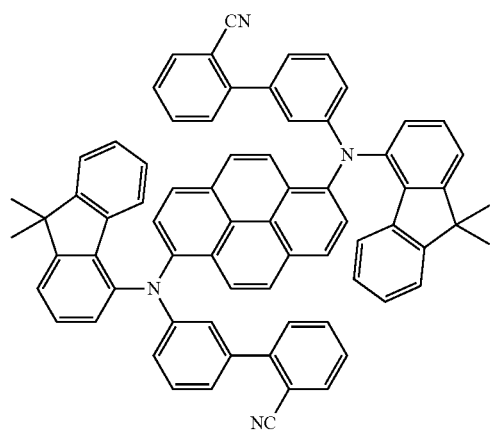
61
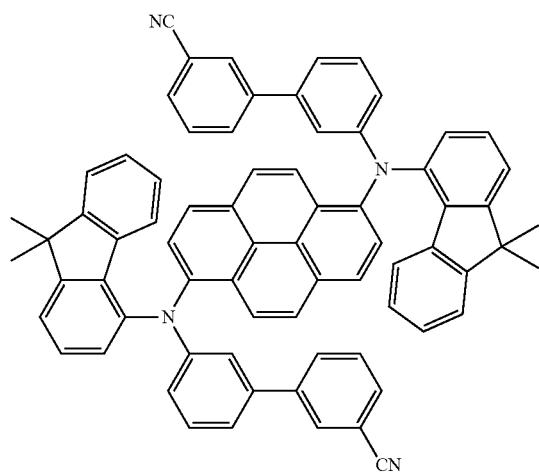
62
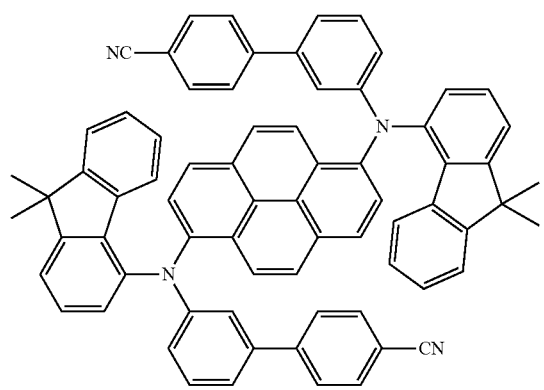
63
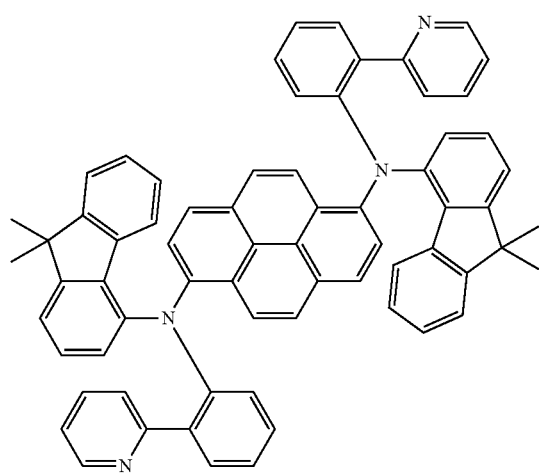
64
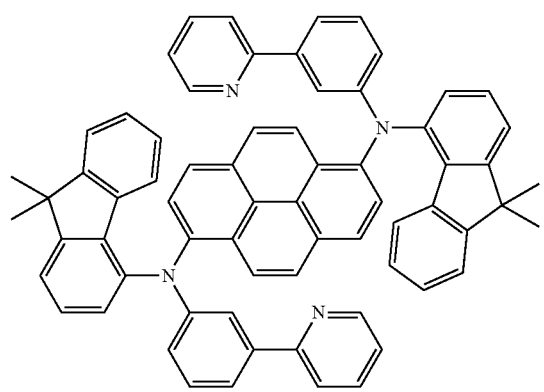
65

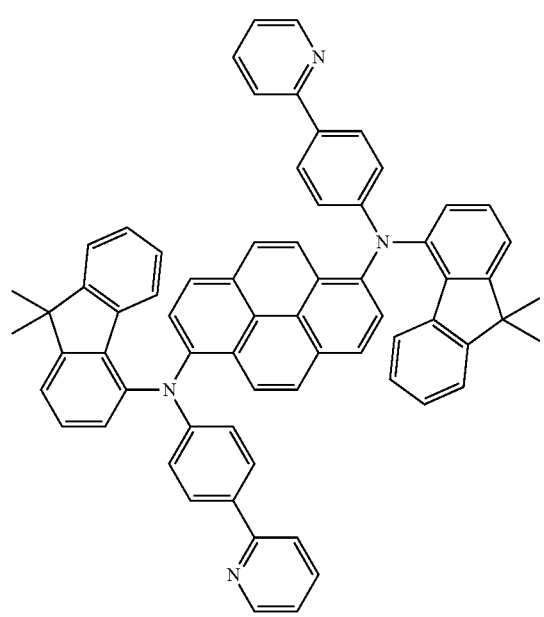
66
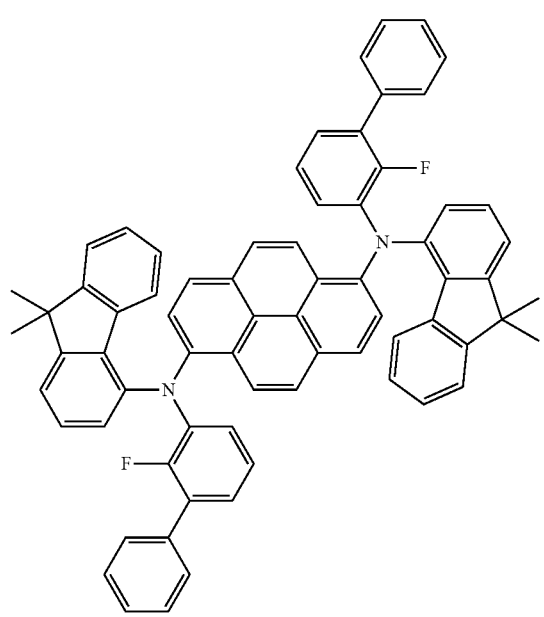
67
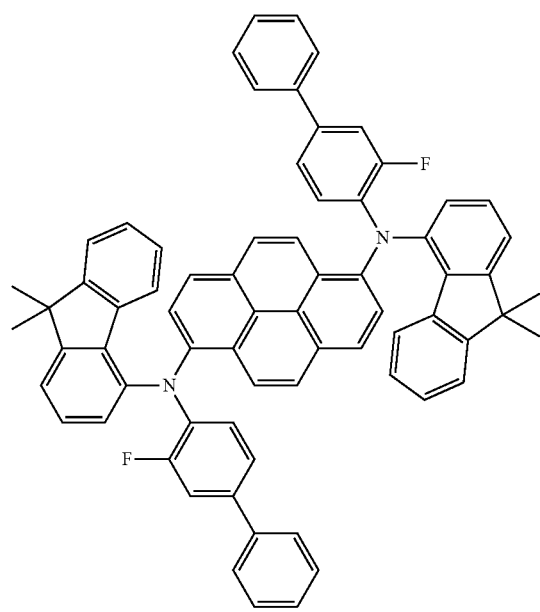
68
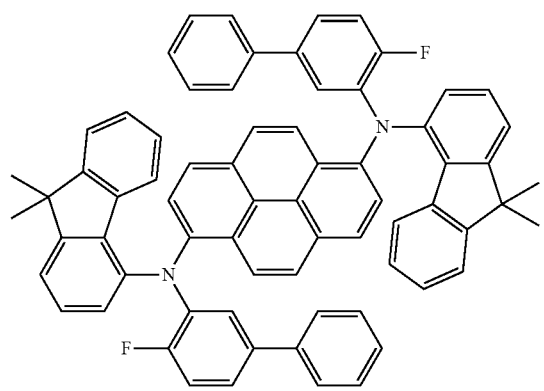
69

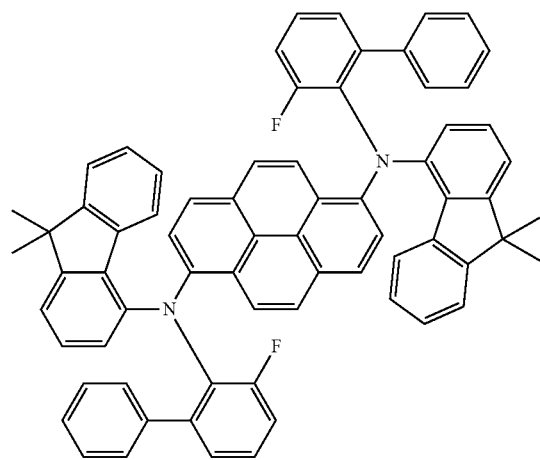
70
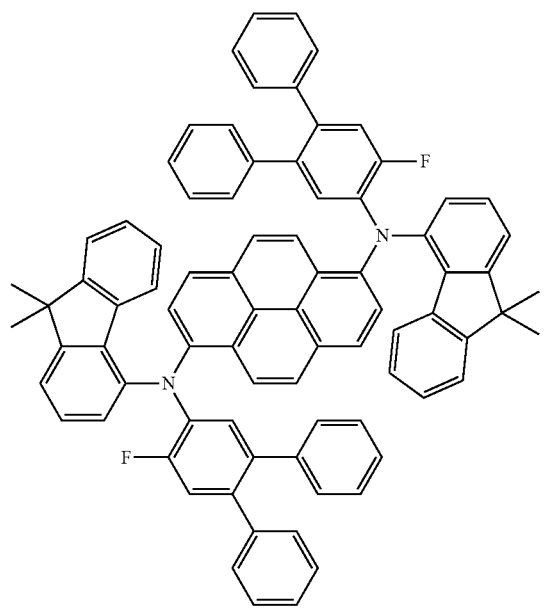
71
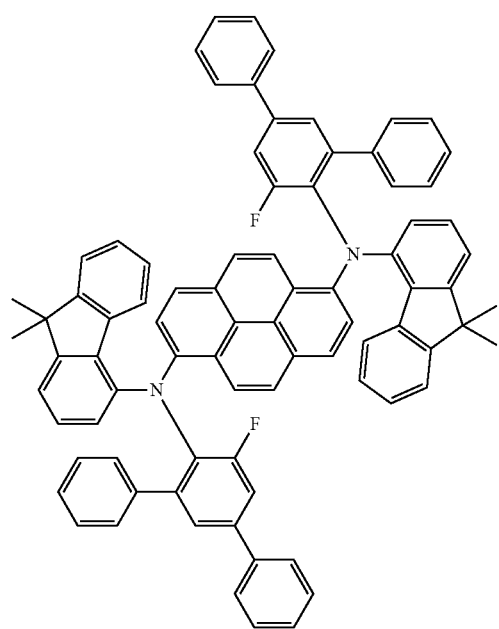
72
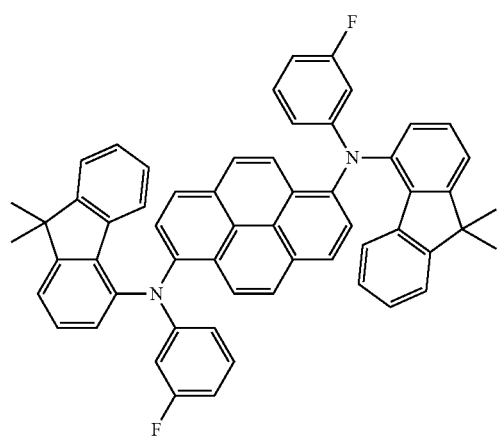
73

-continued
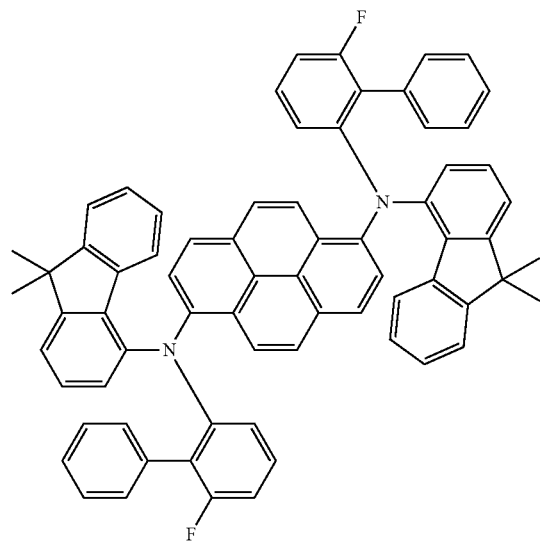
74
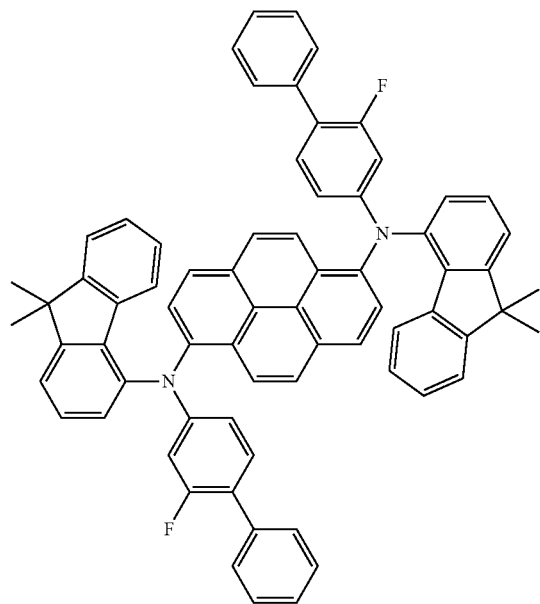
75
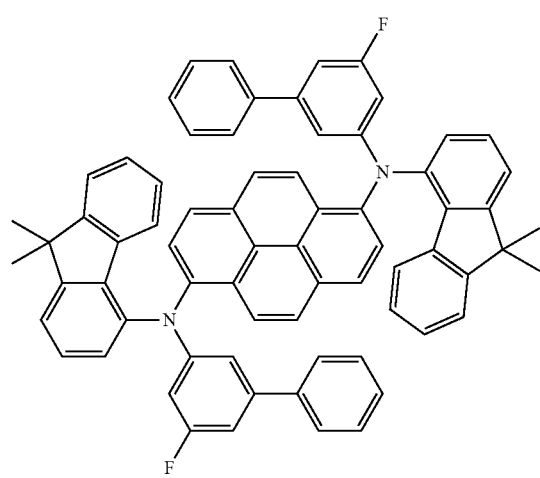
76
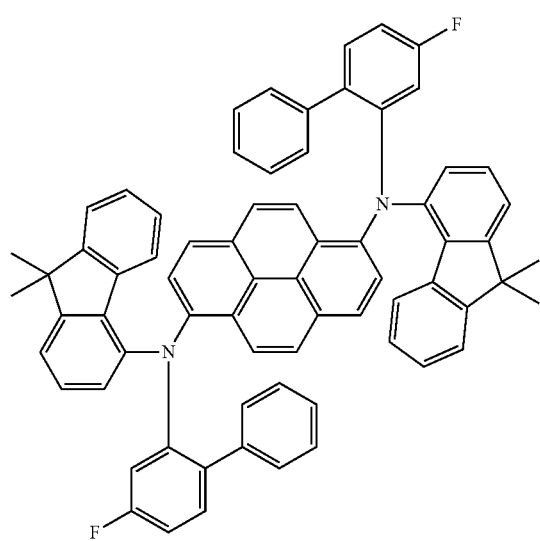
77

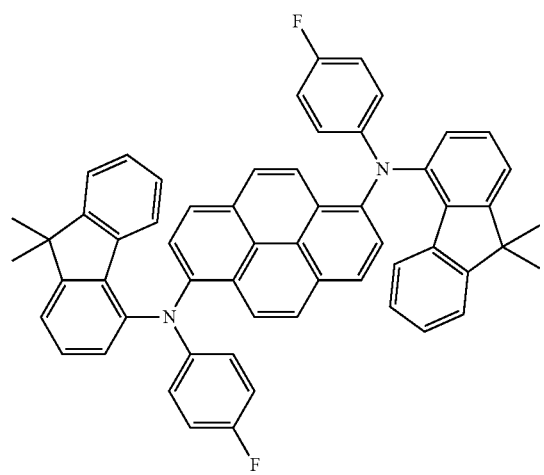
78
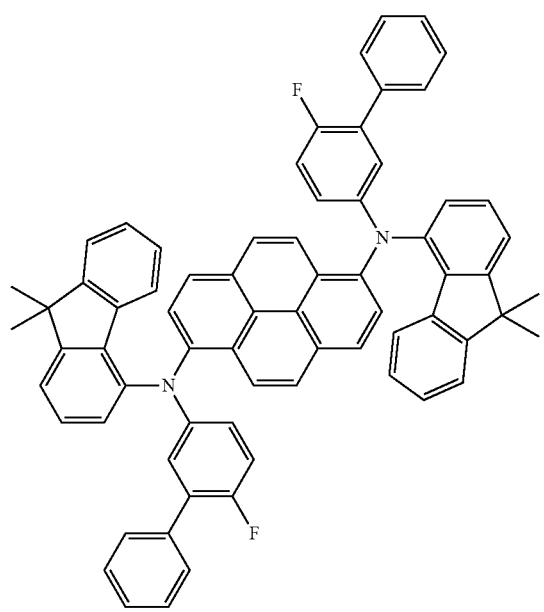
79
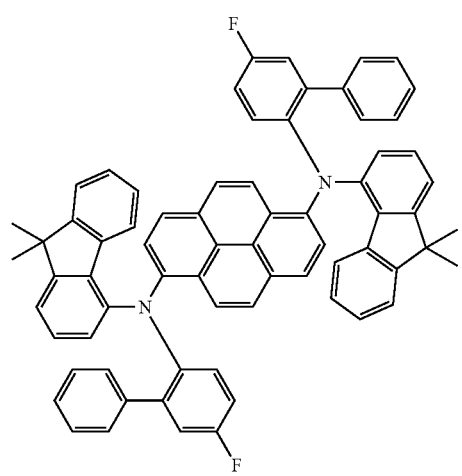
80
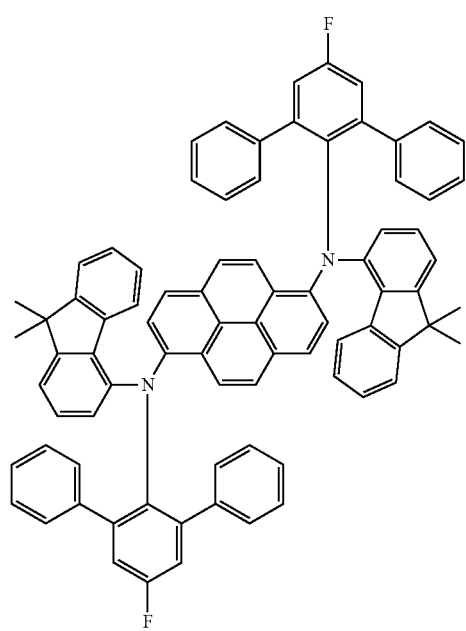
81

82
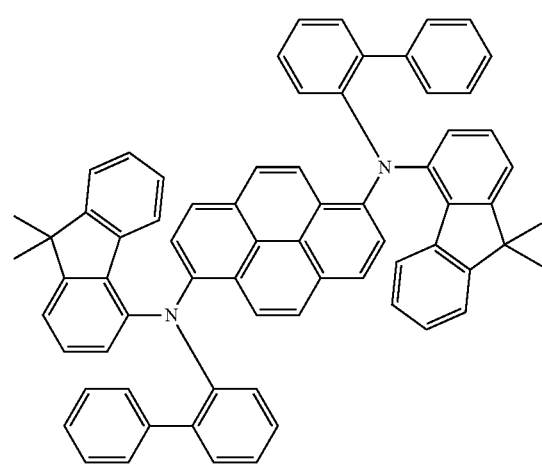
83
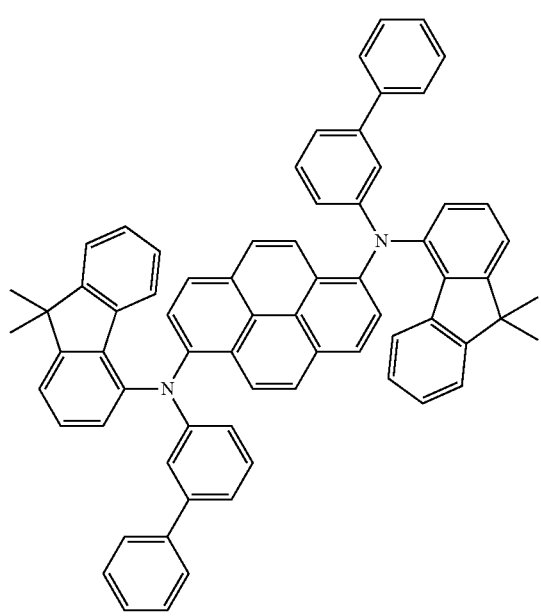
84
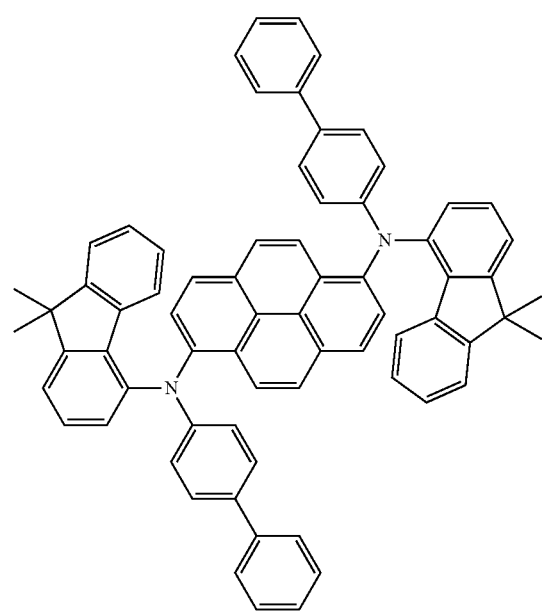
85
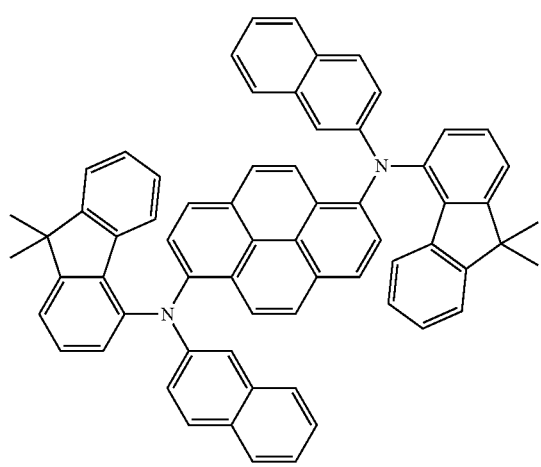

-continued
86
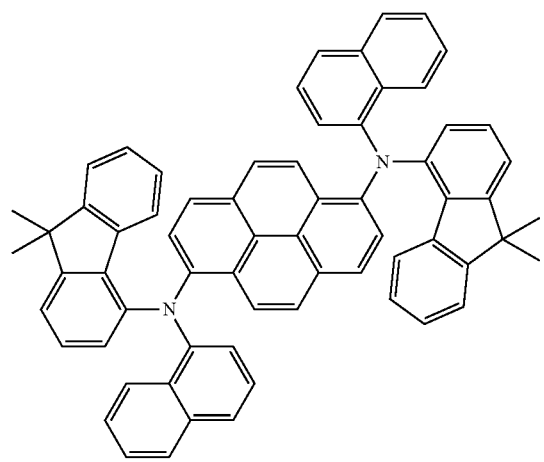
87
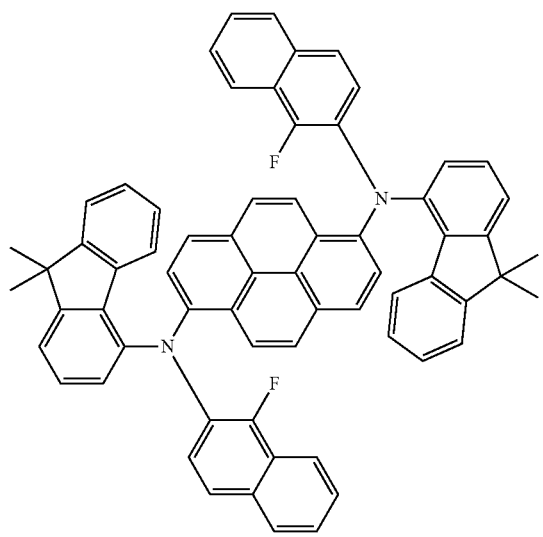
88
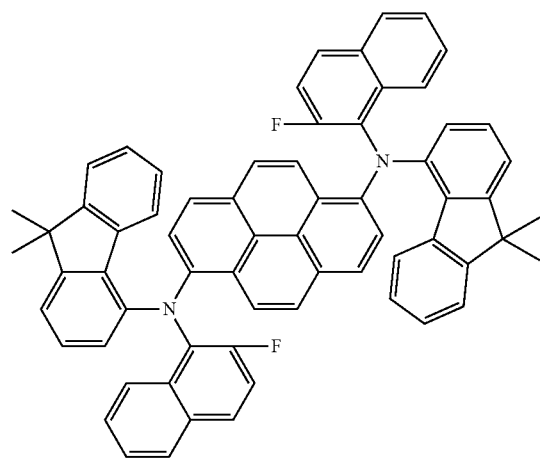
89
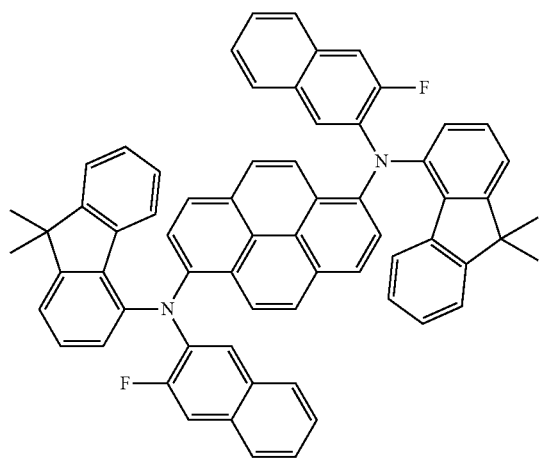
90
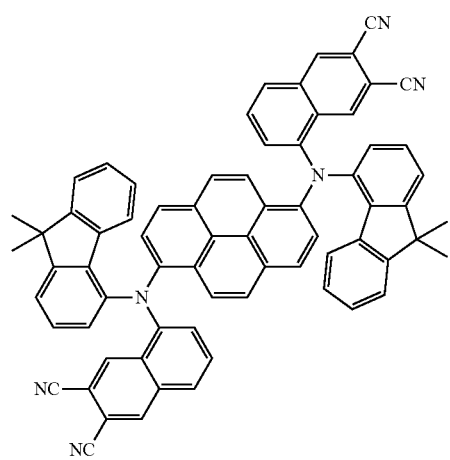
91
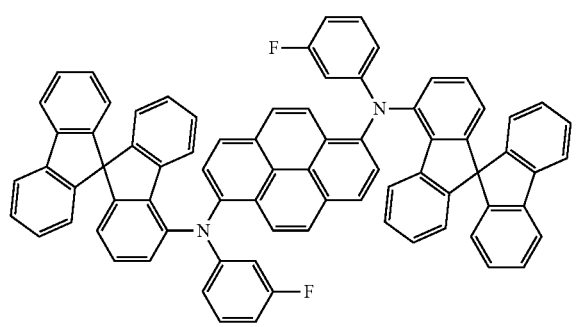

-continued
92
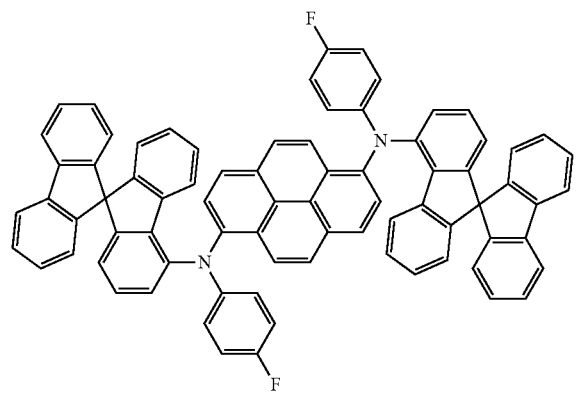
93
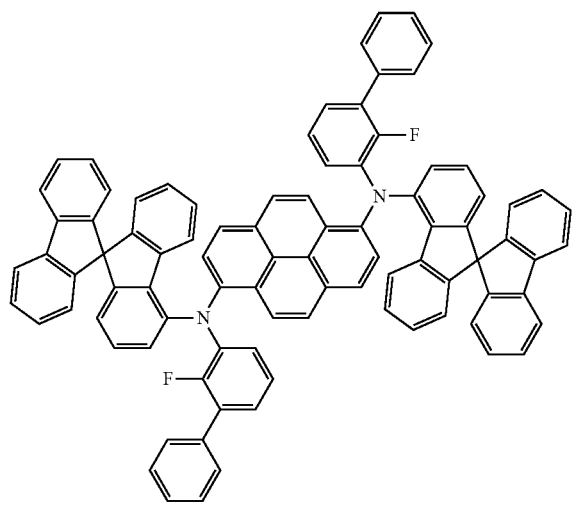
94
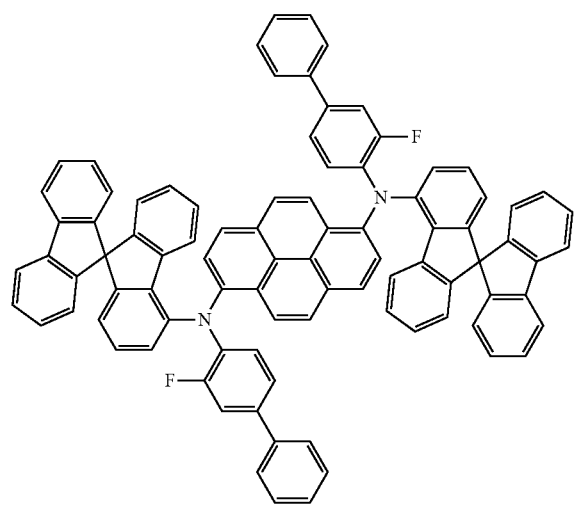
95
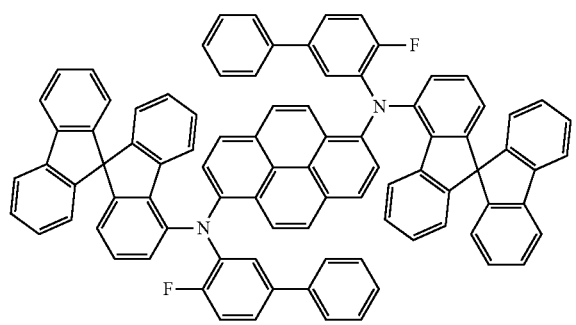
96
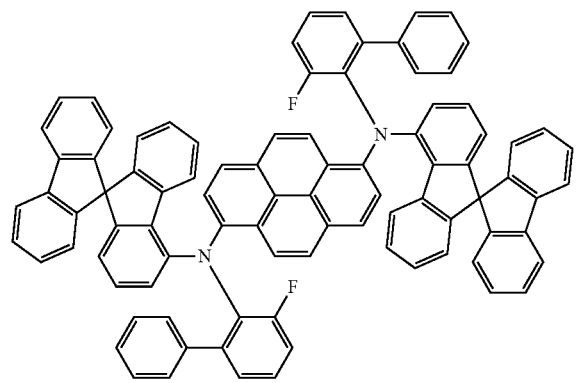
97
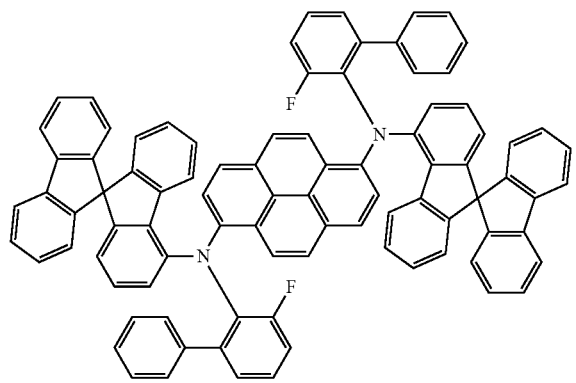

-continued
98
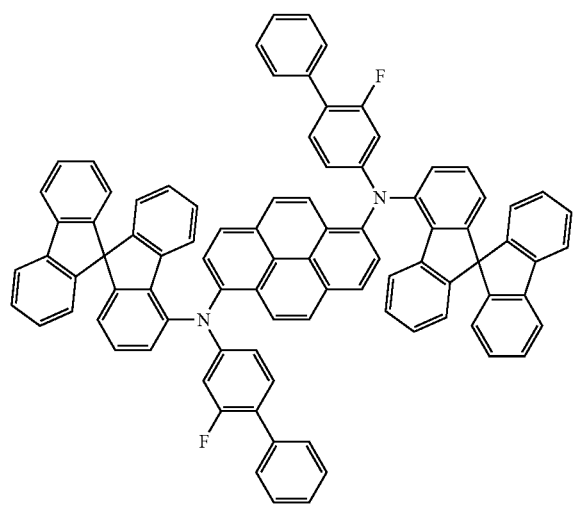
99
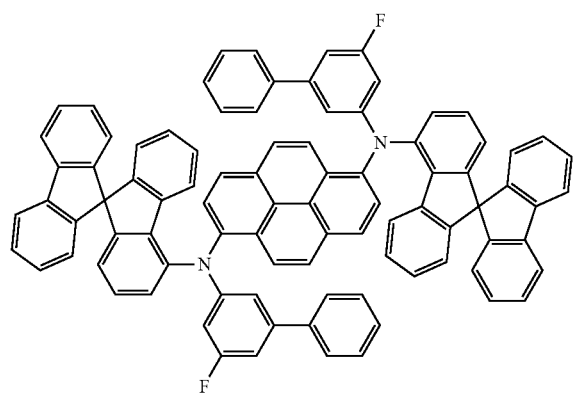
100
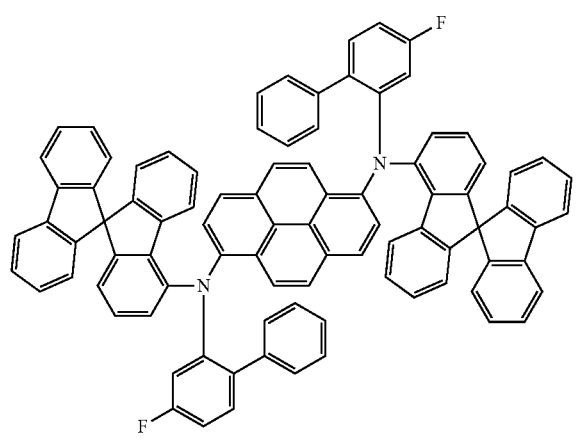
101
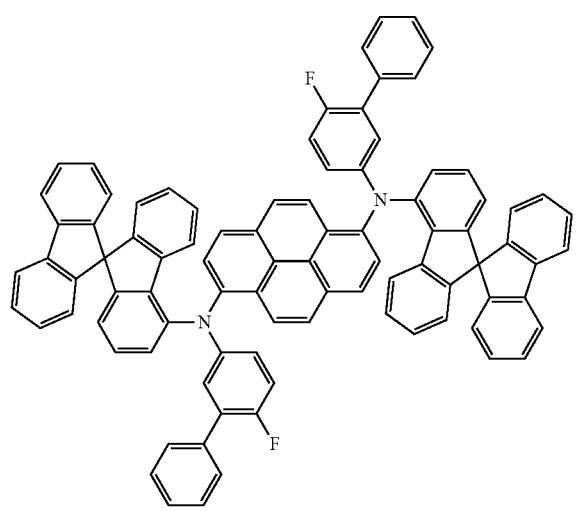
102
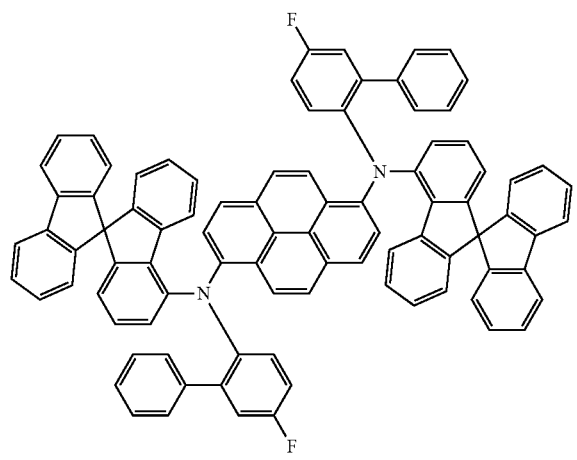
103
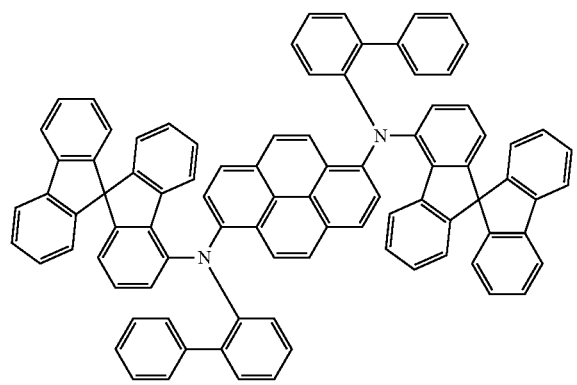

-continued
104
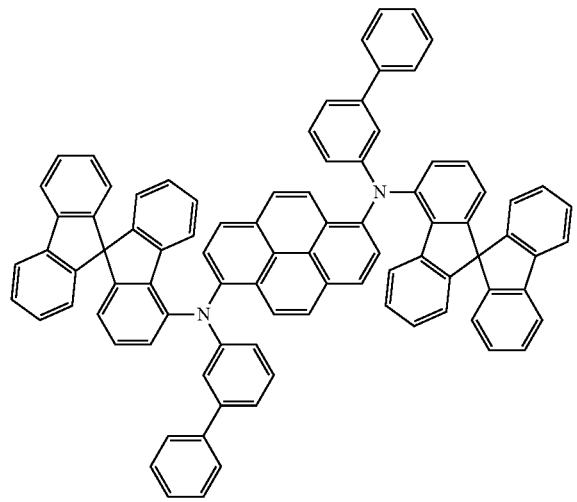
105
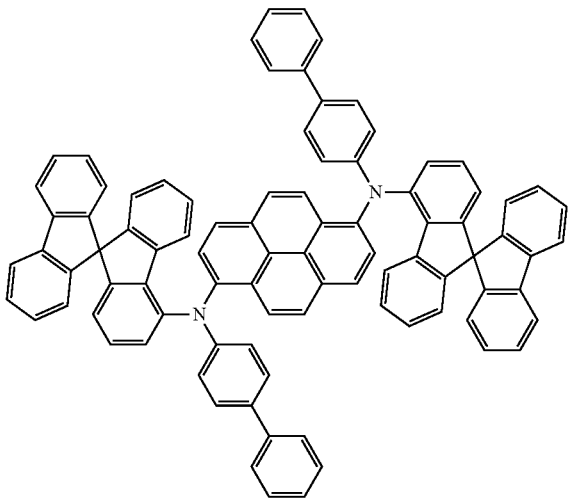
106
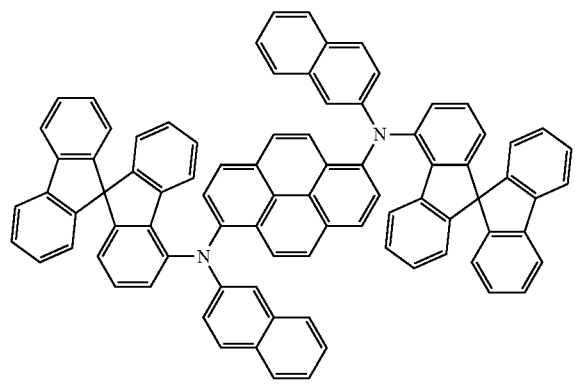
107
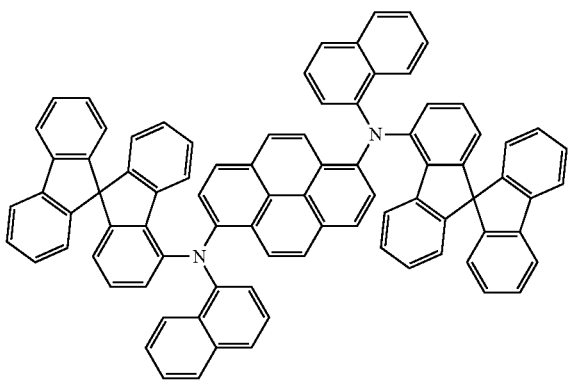
108
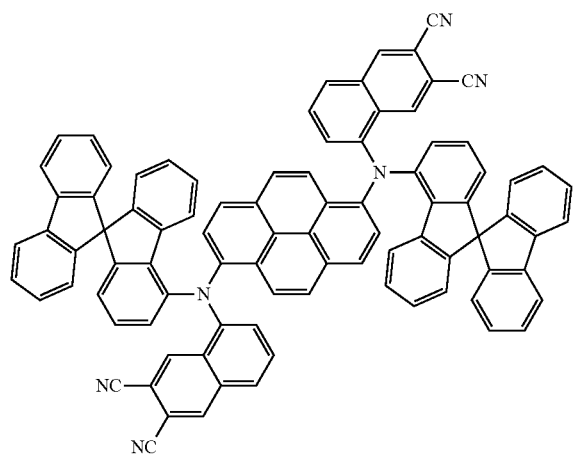
109
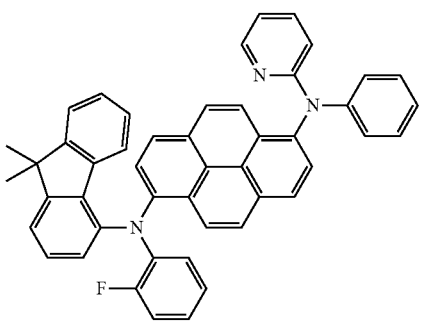

-continued
110
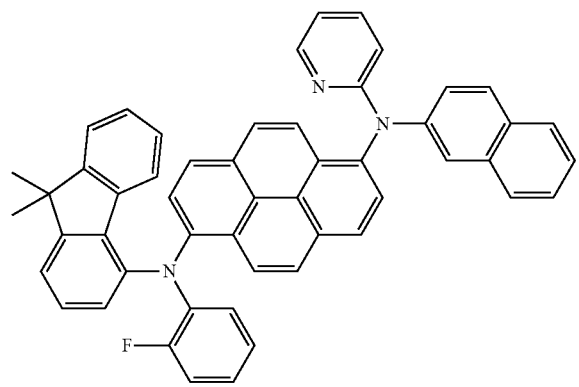
111
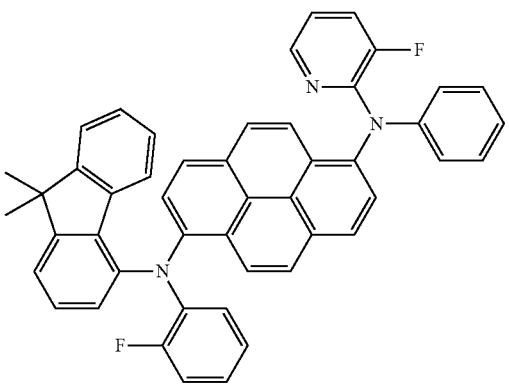
112
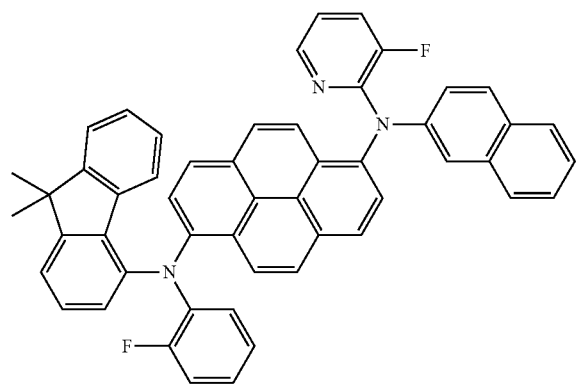
113
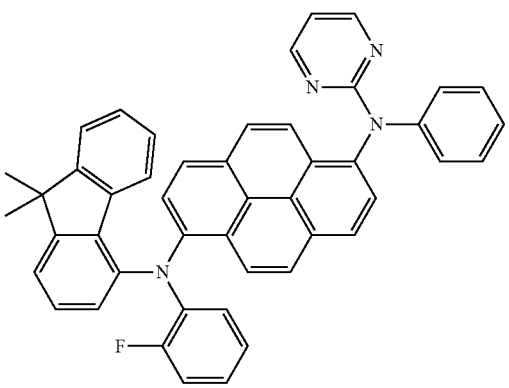
114
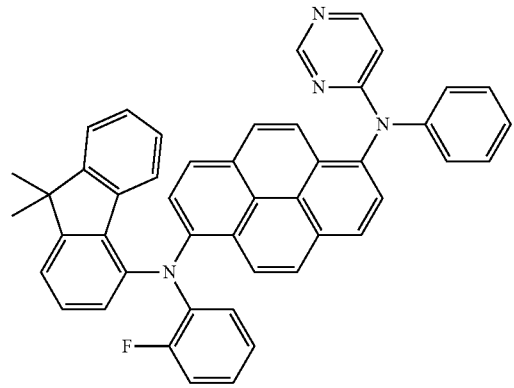
115
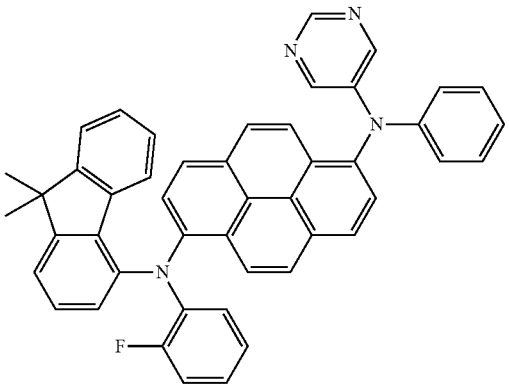
116
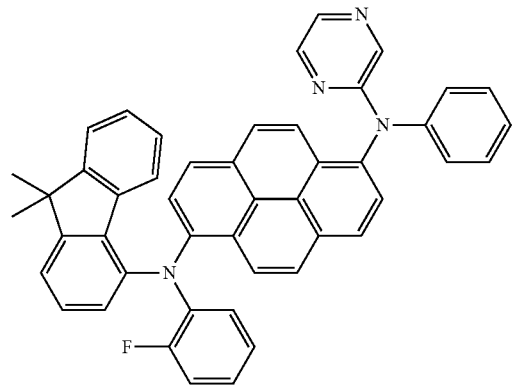
117
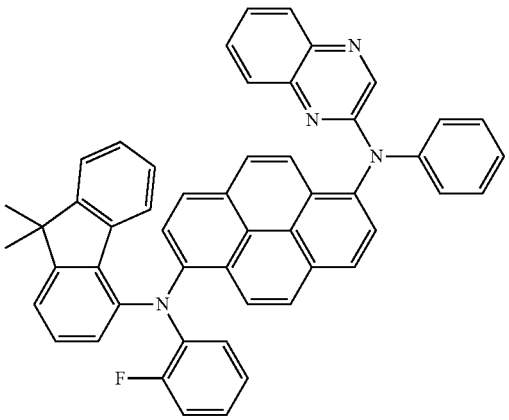

-continued
118
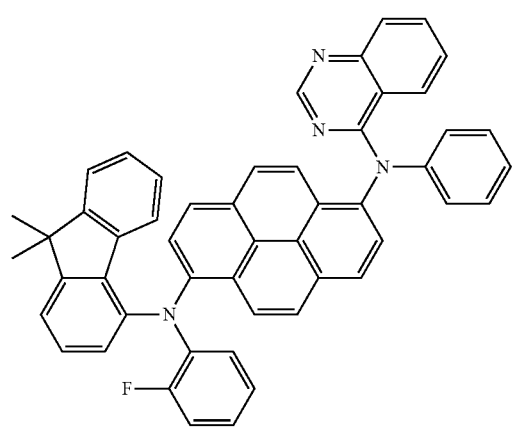
119
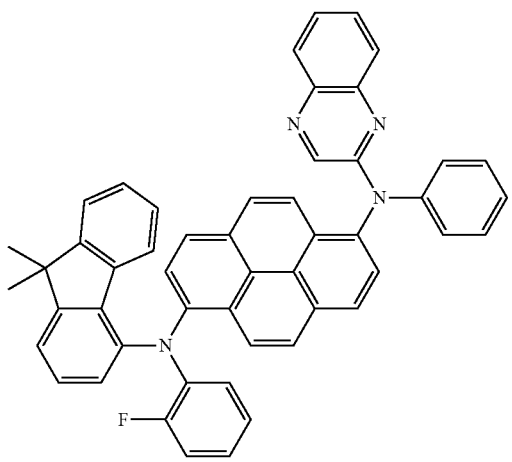
120
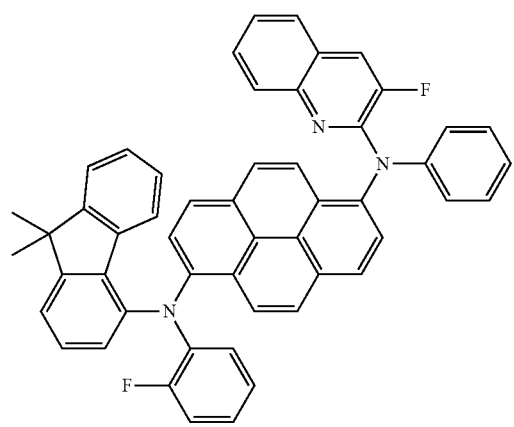
121
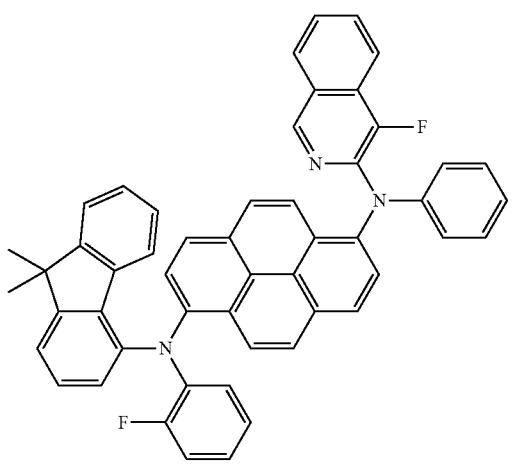
122
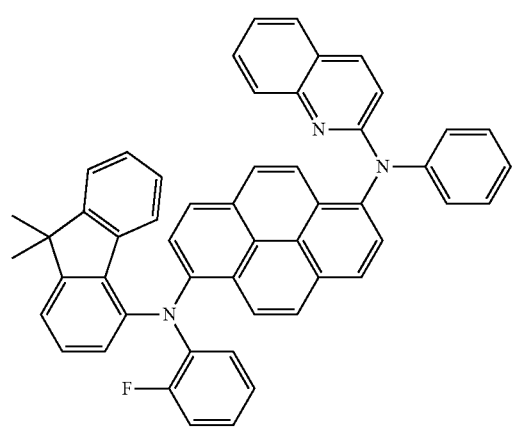
123
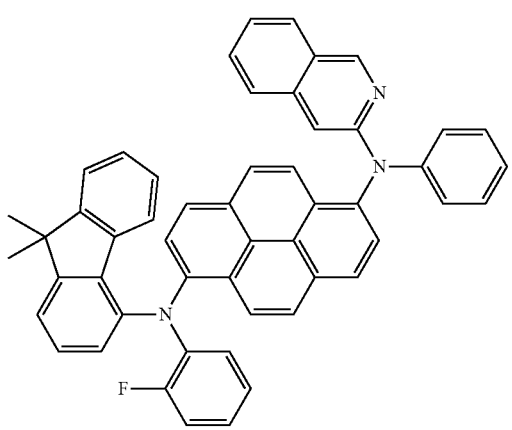

124
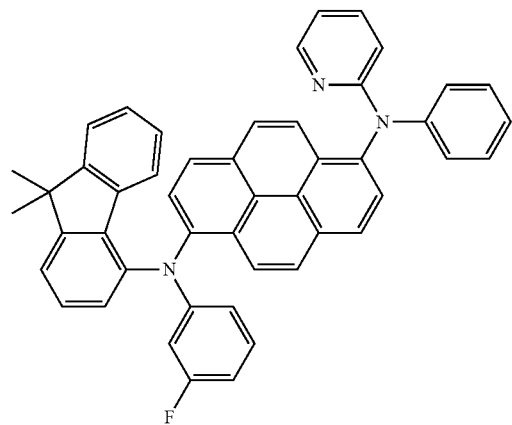
125
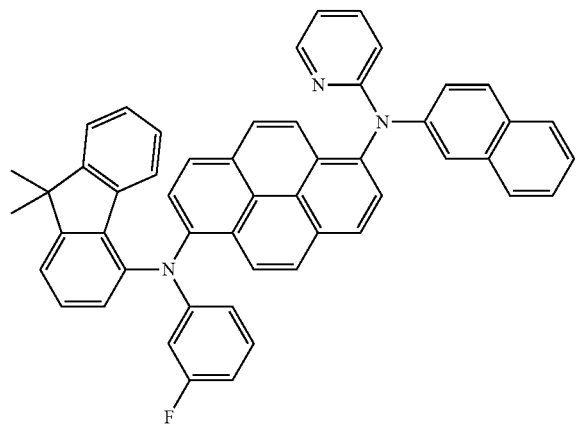
126
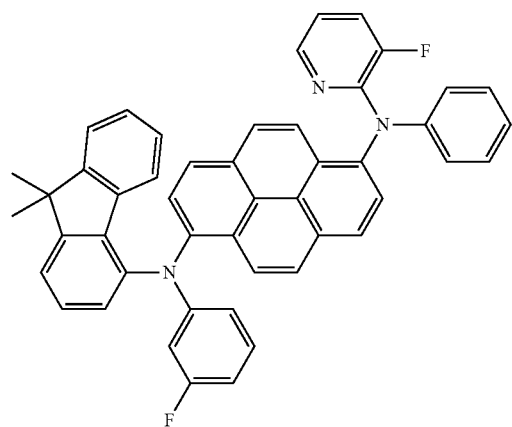
127
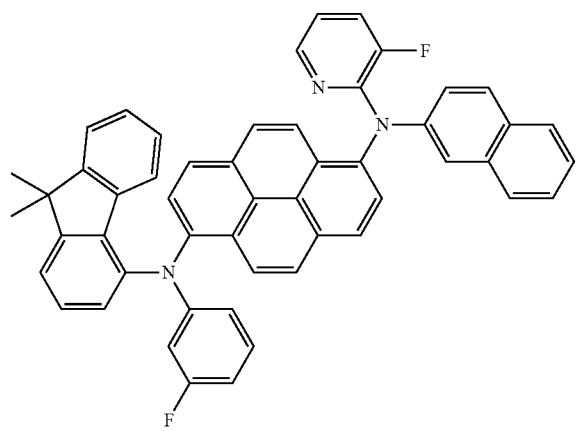
128
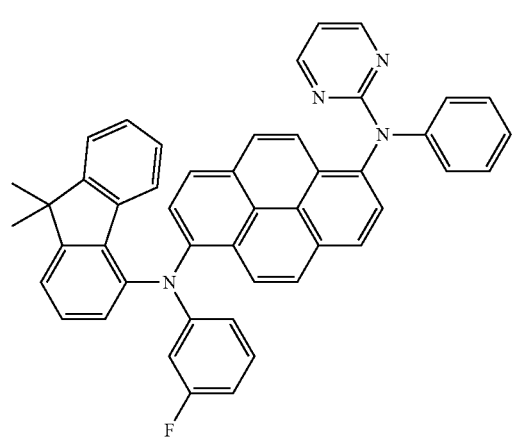
129
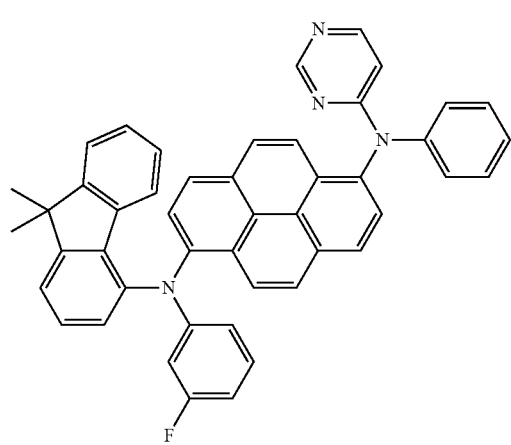

-continued
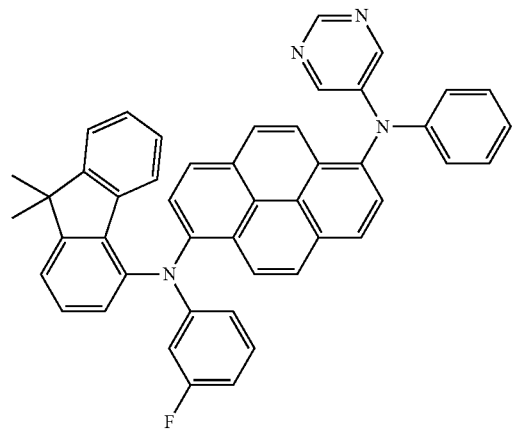
130
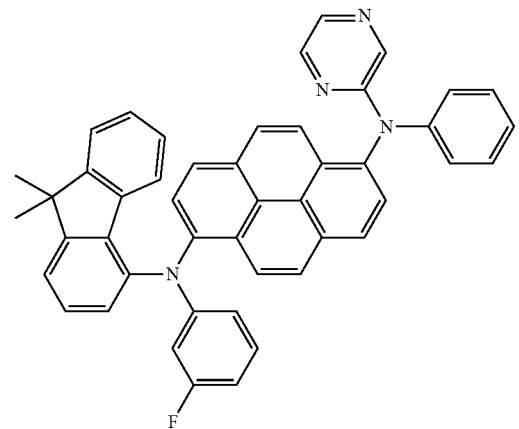
131
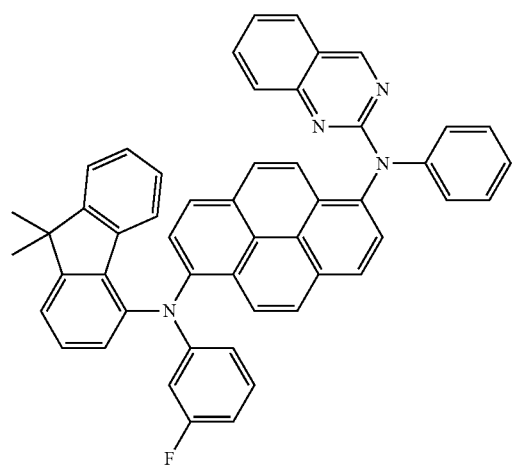
132
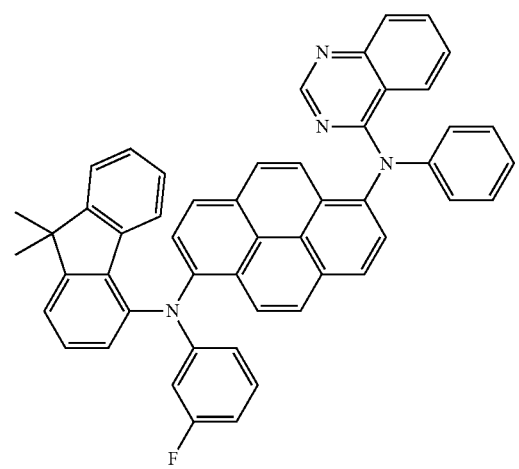
133
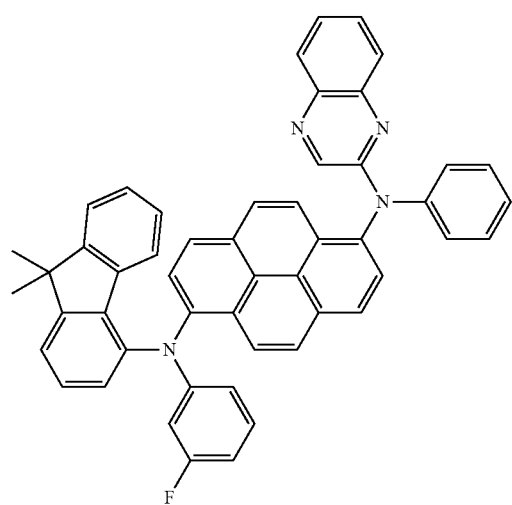
134
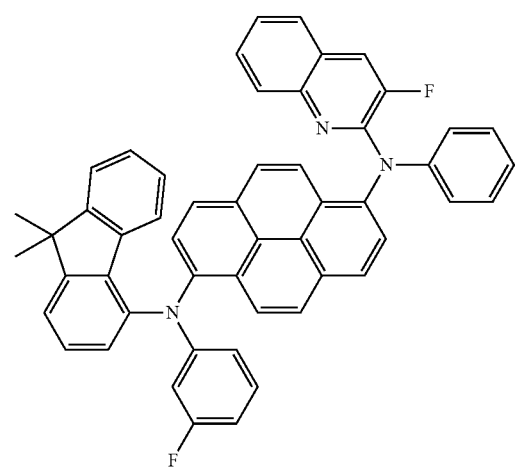
135

-continued
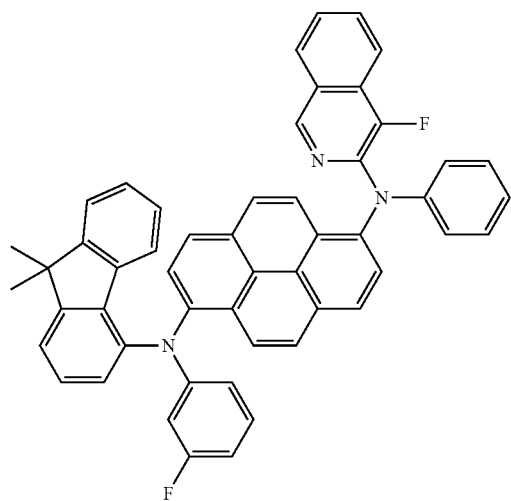
136
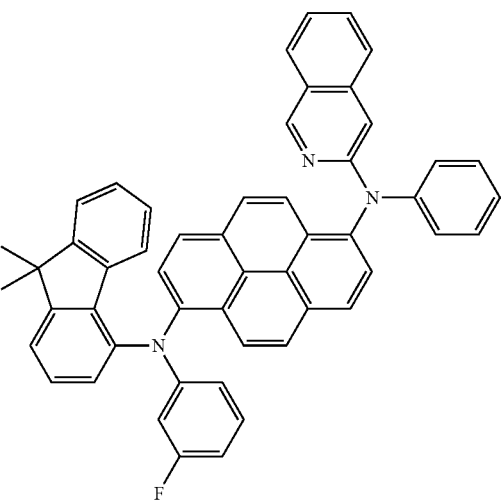
137
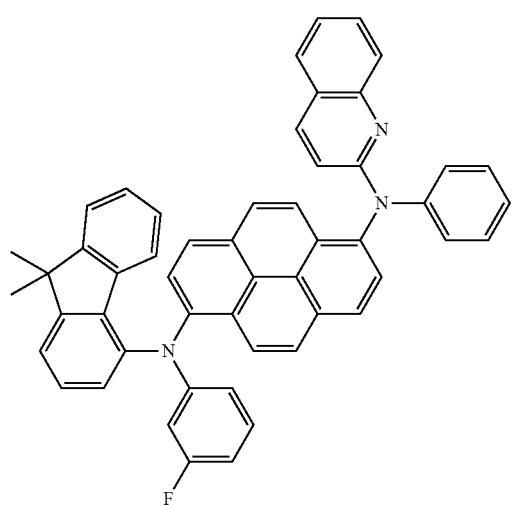
138
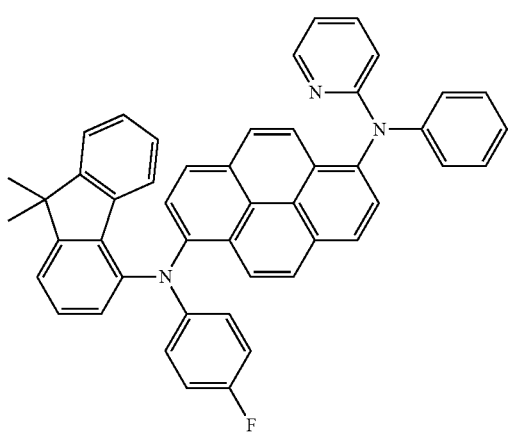
139
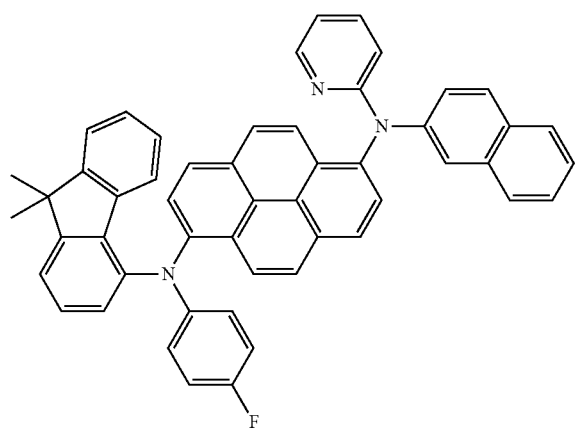
140
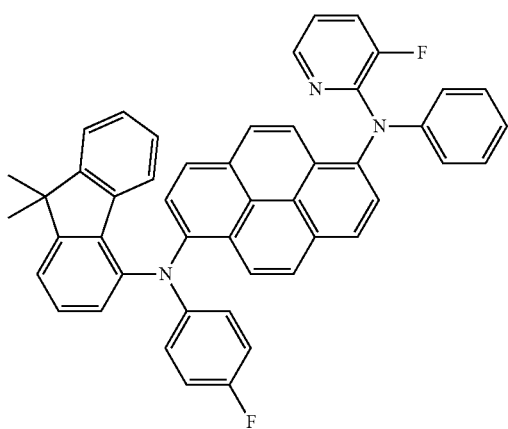
141

142
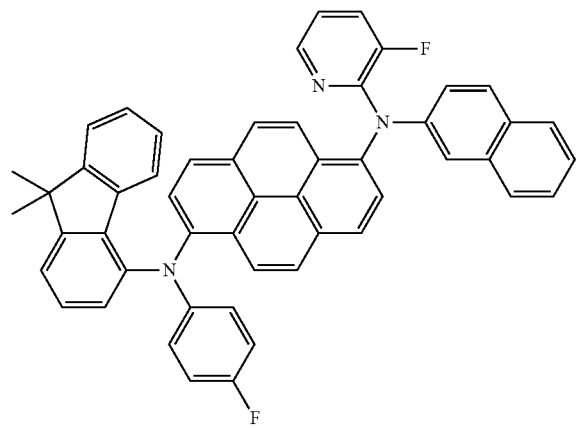
143
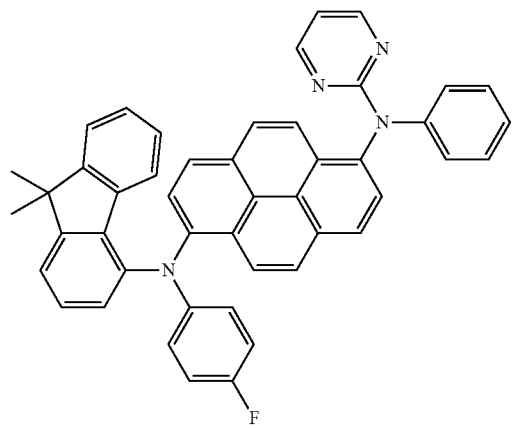
144
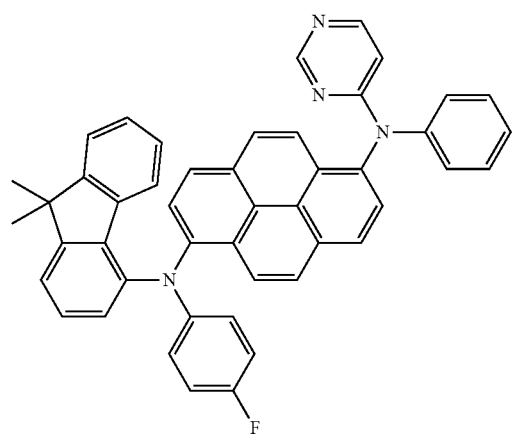
145
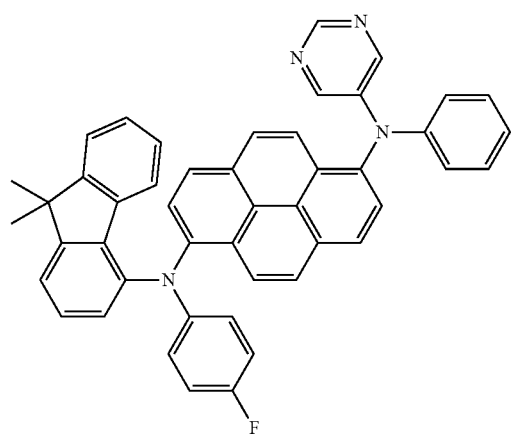
146
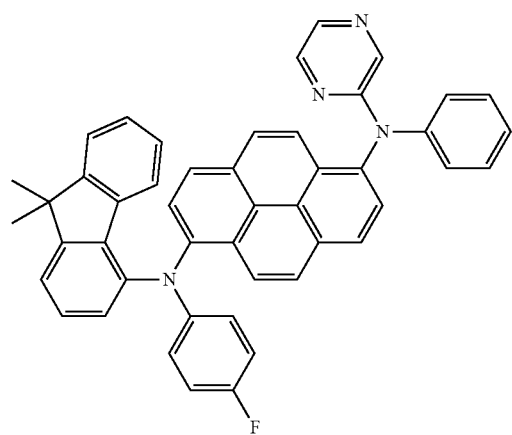
147
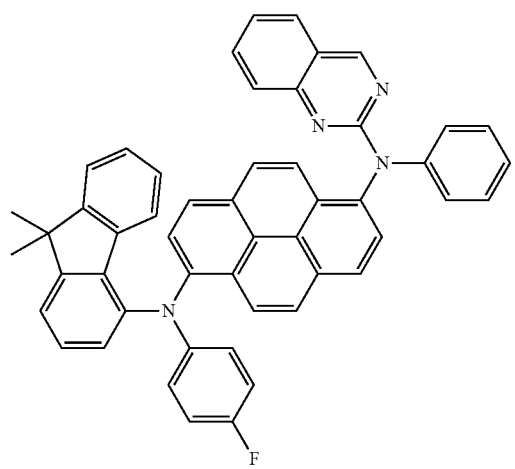

-continued
148 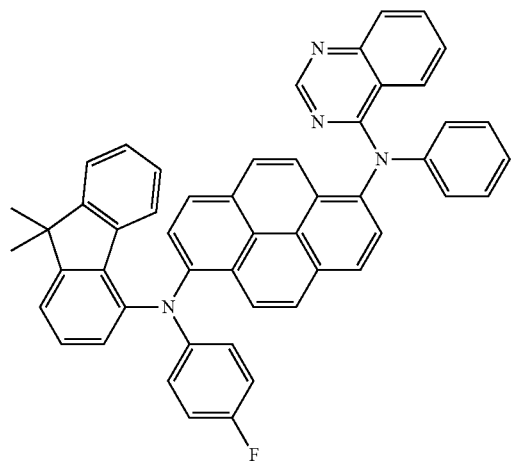
149 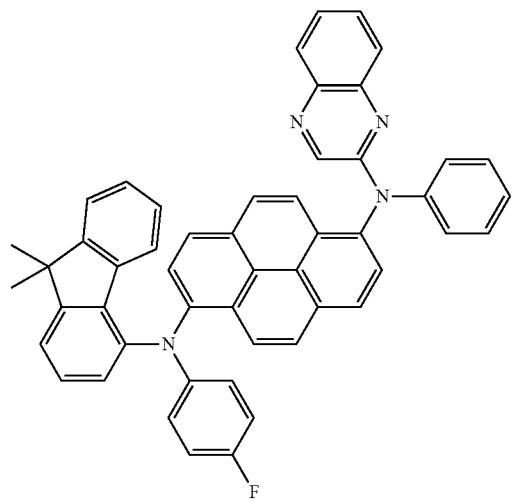
150 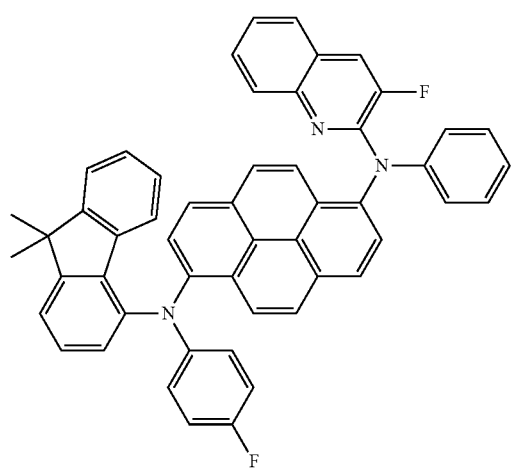
151 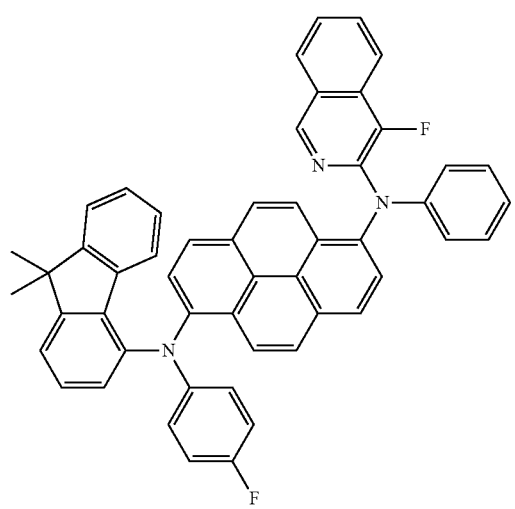
152 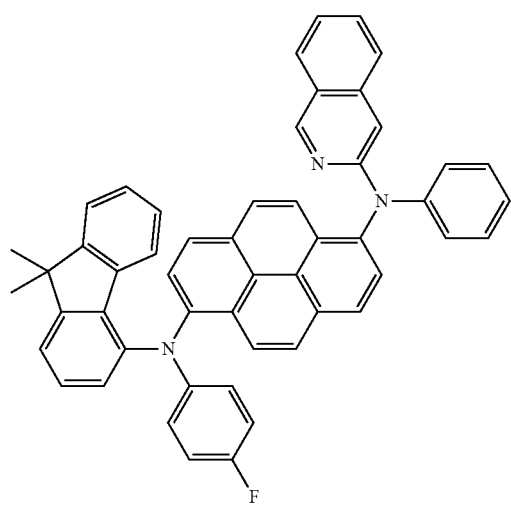
153 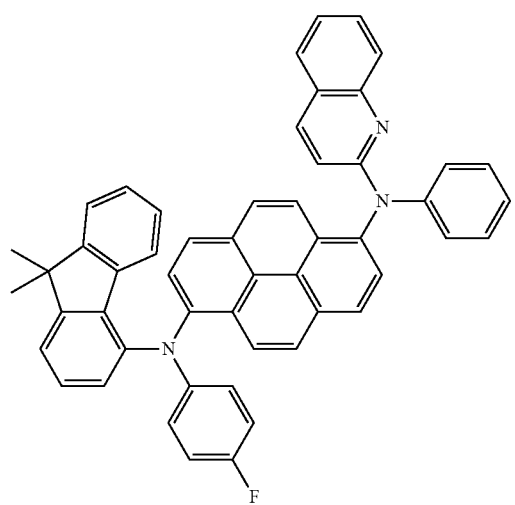

-continued
154
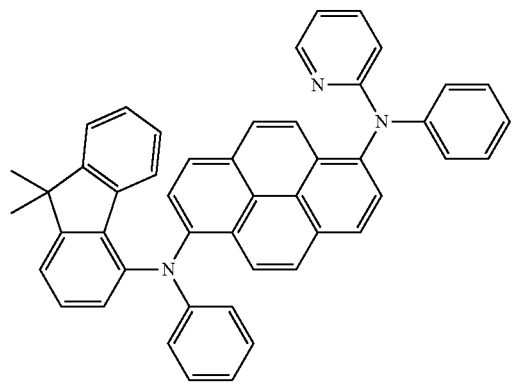
155
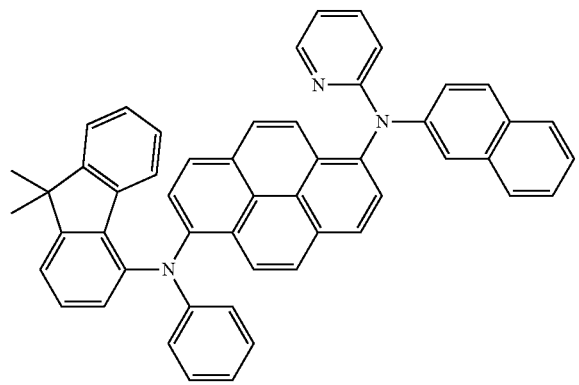
156
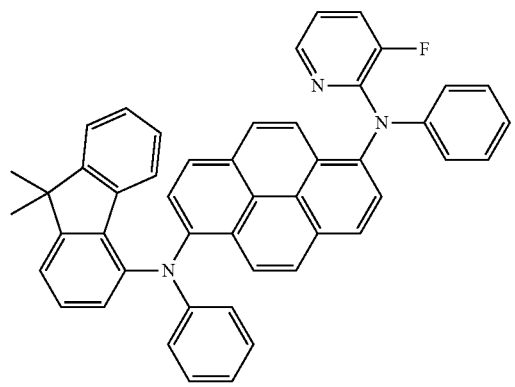
157
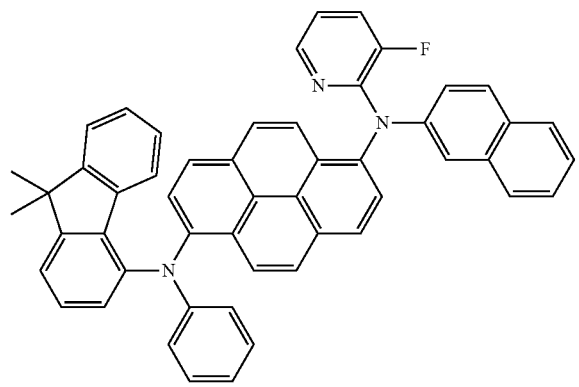
158
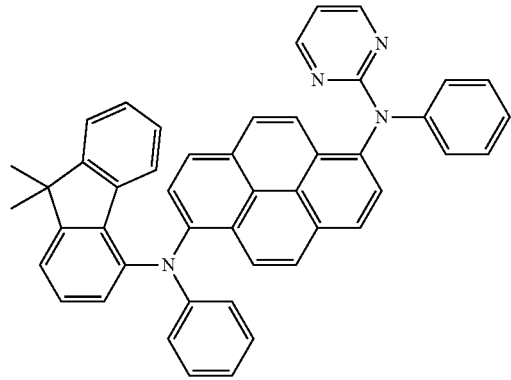
159
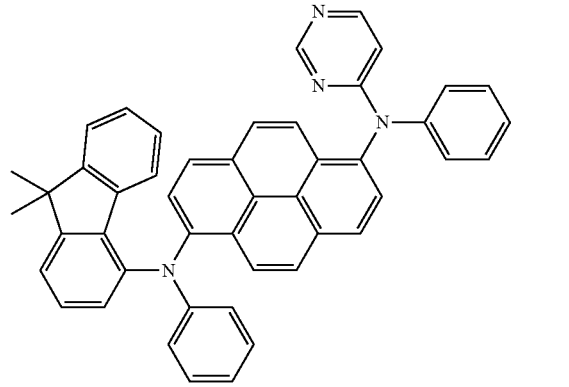
160
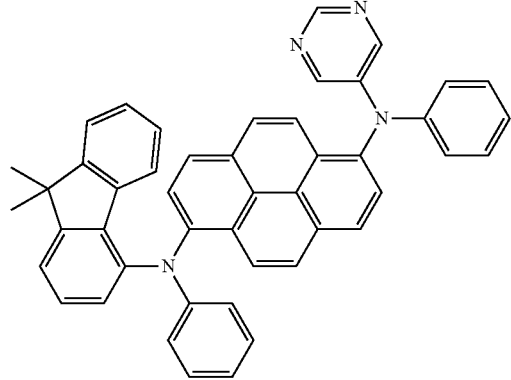
161
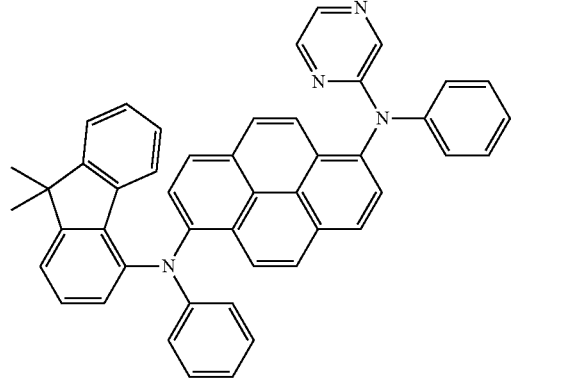

-continued
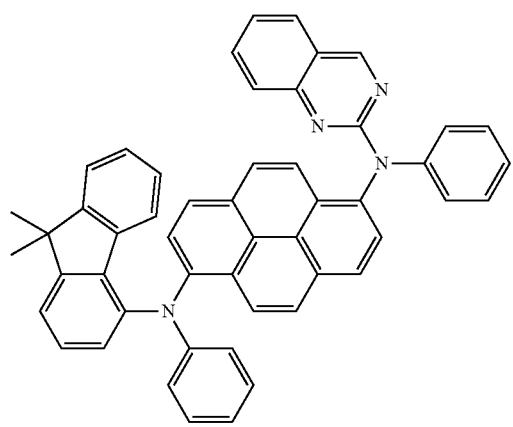
162
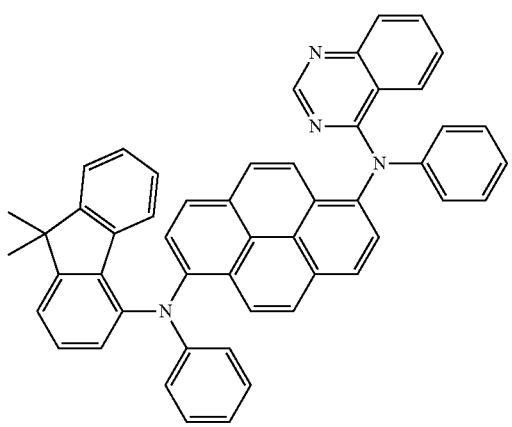
163
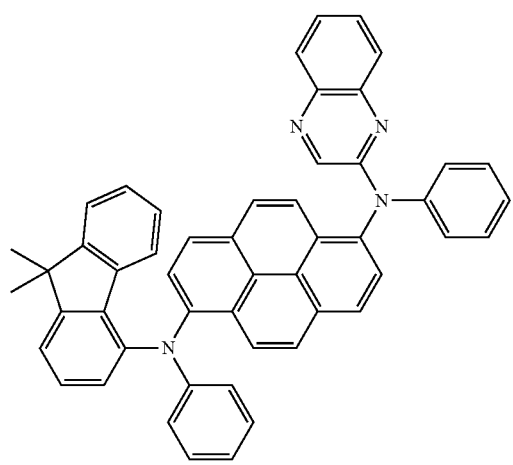
164
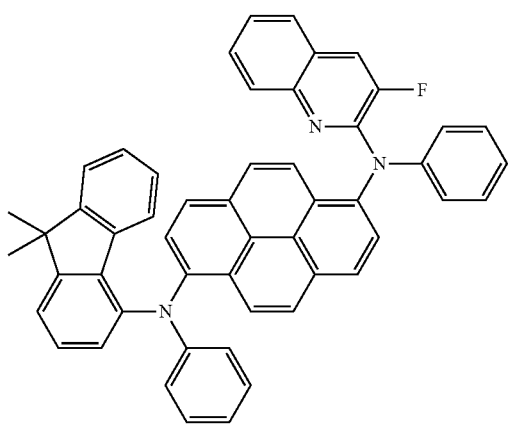
165
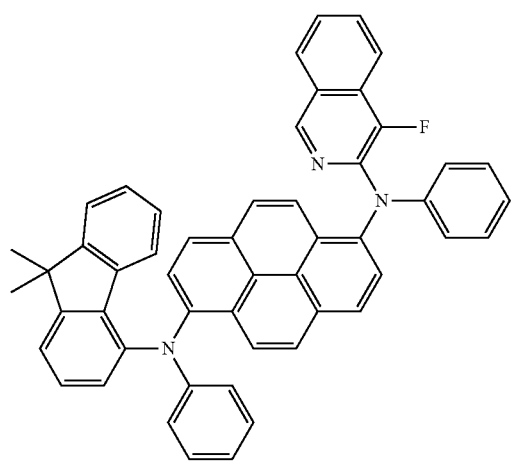
166
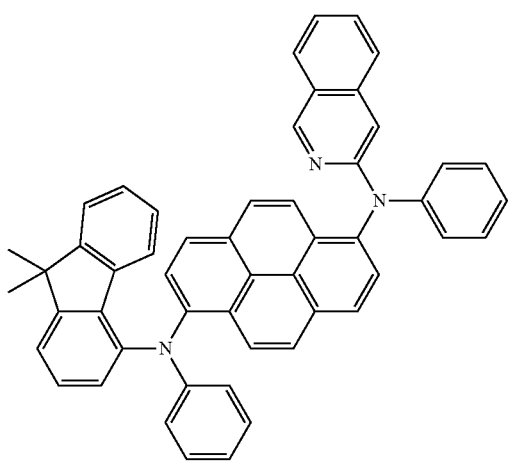
167

-continued
168
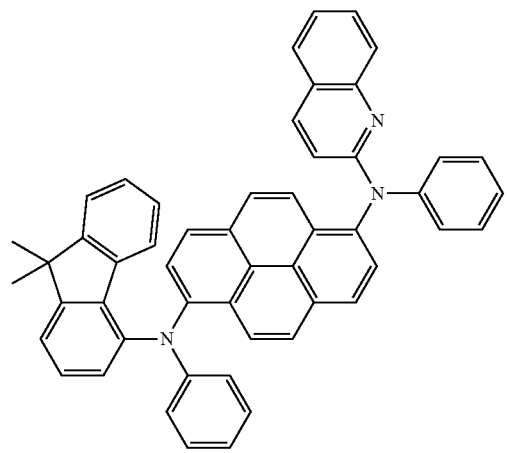
169
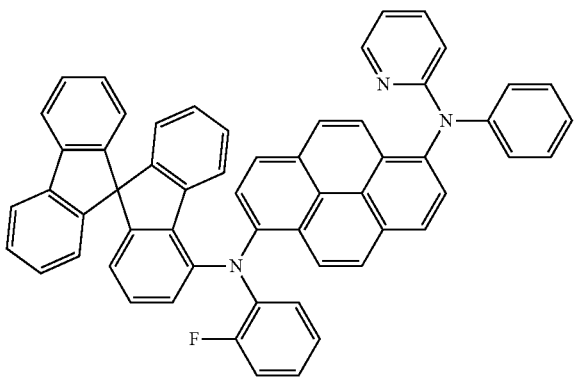
170
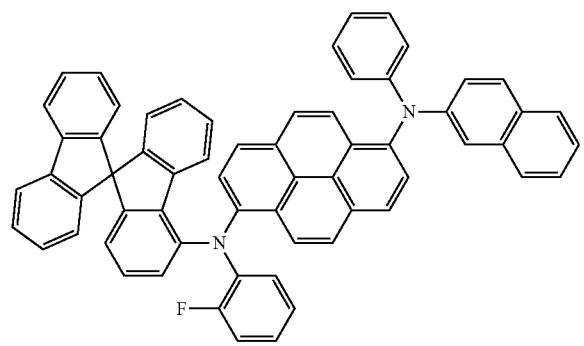
171
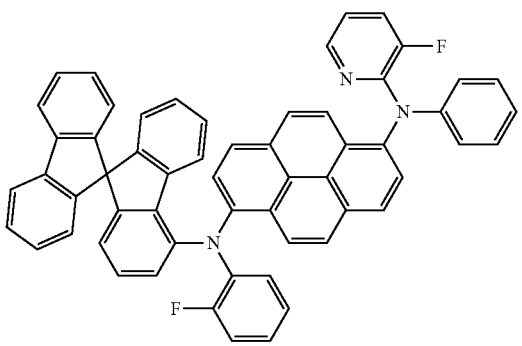
172
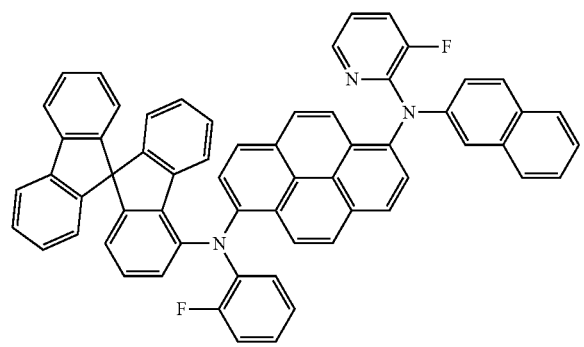
173
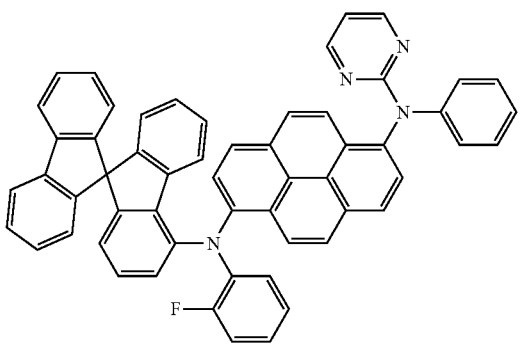
174
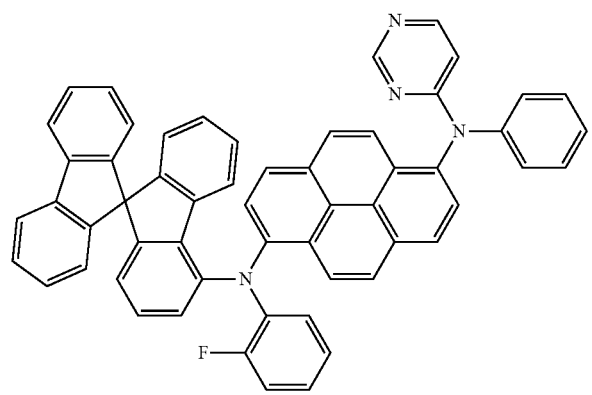
175
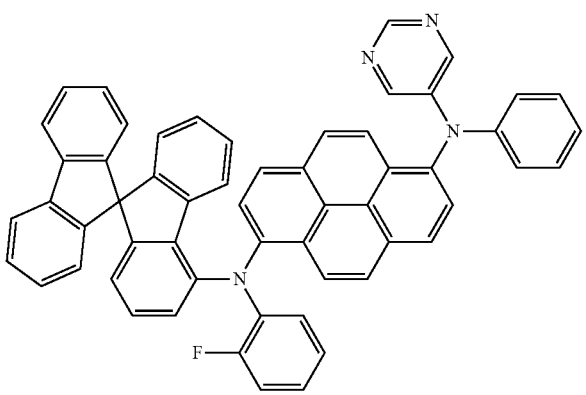

-continued
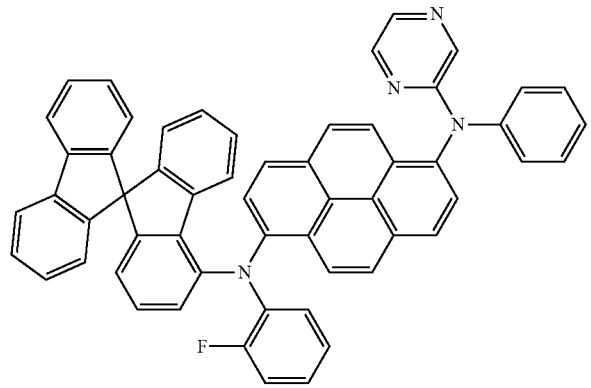
176
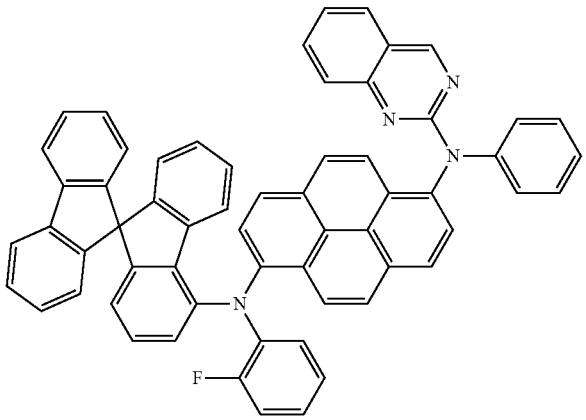
177
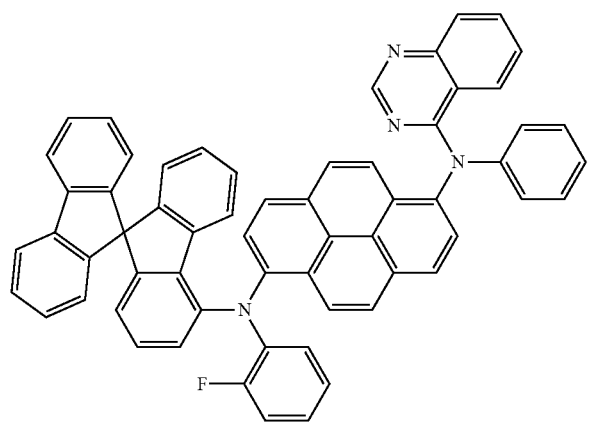
178
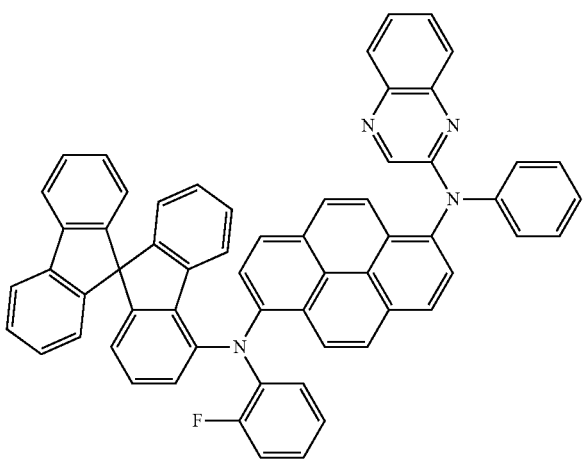
179
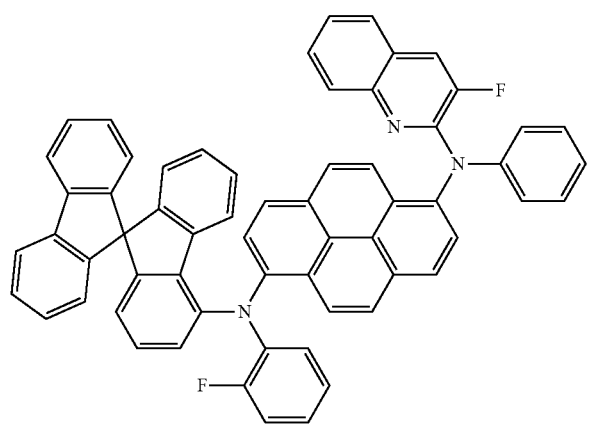
180
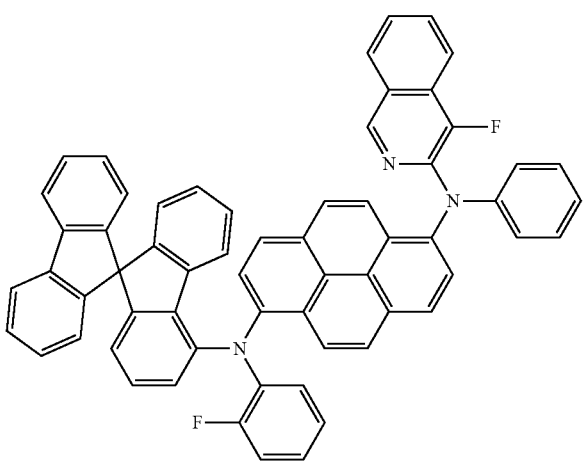
181

-continued
182
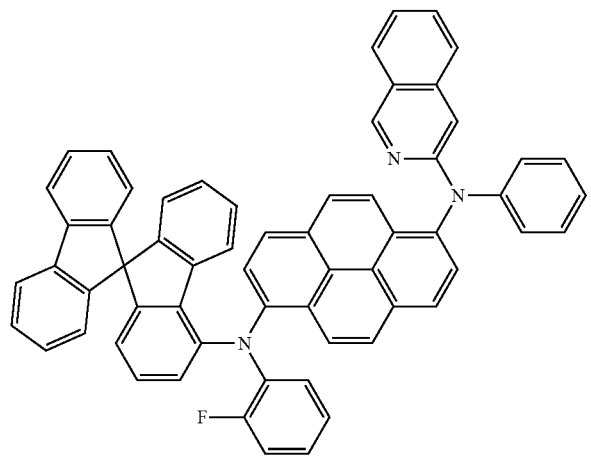
183
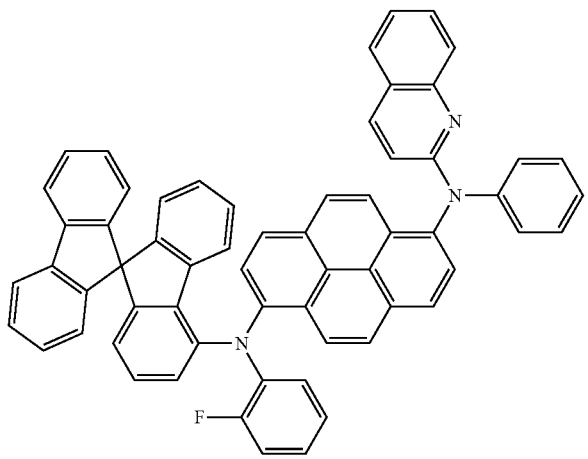
184
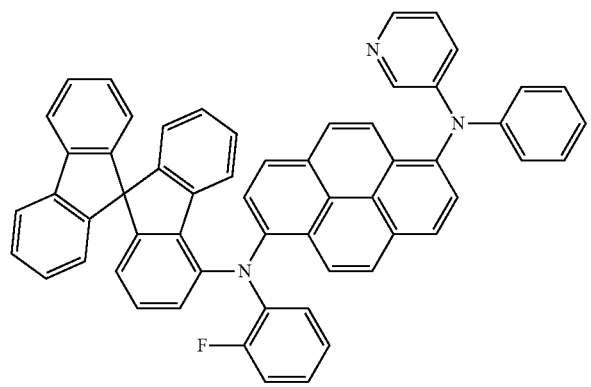
185
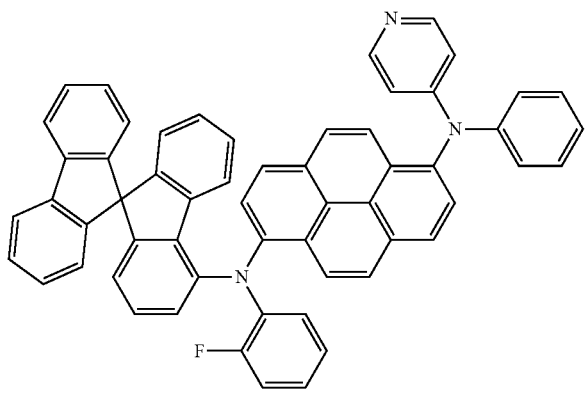
186
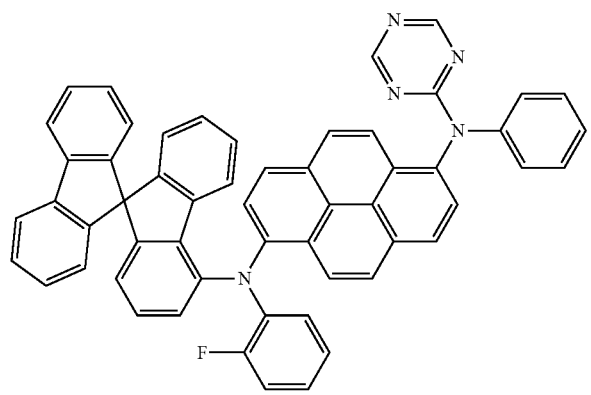
187
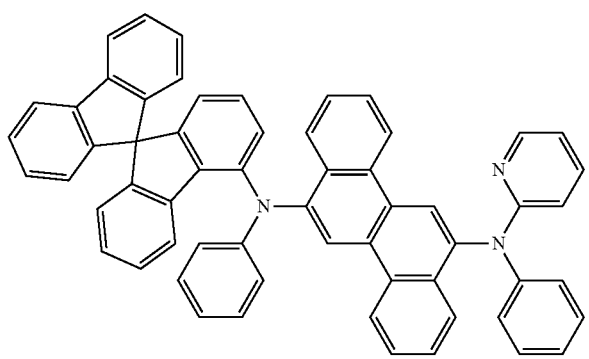

-continued
188
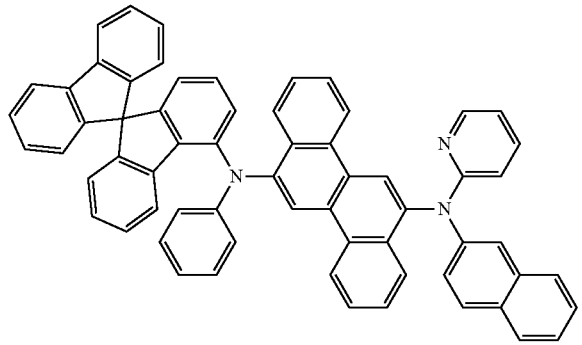
189
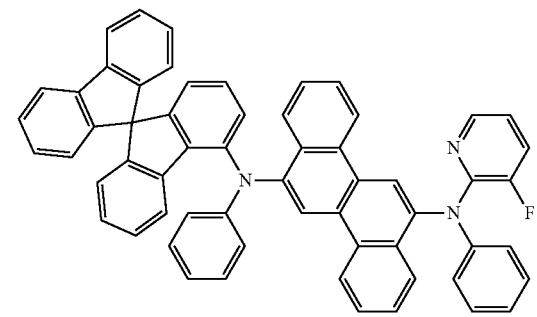
190
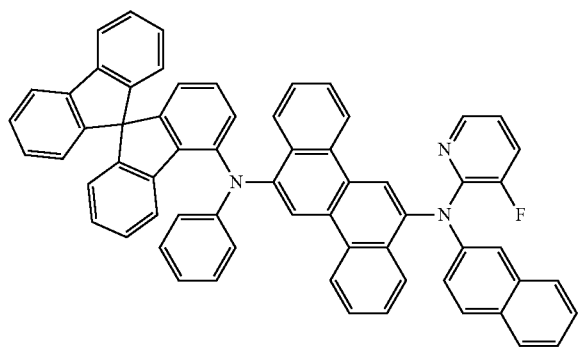
191
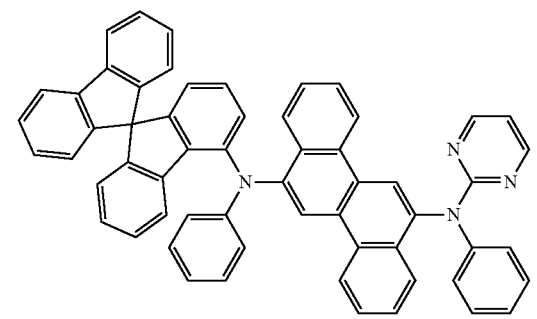
192
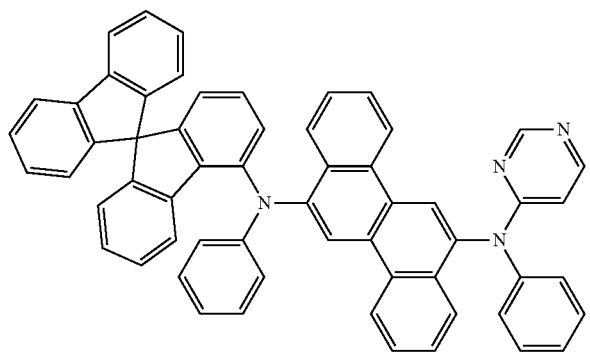
193
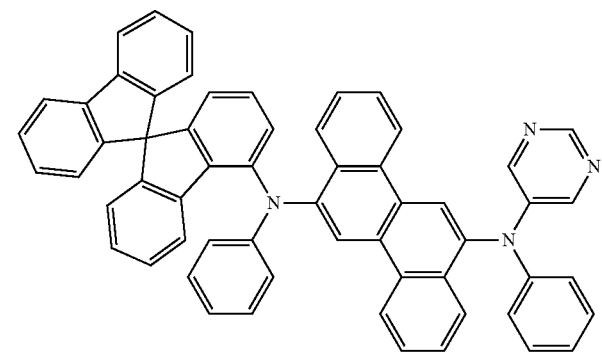
194
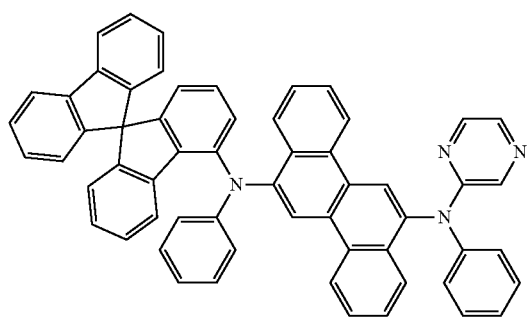
195
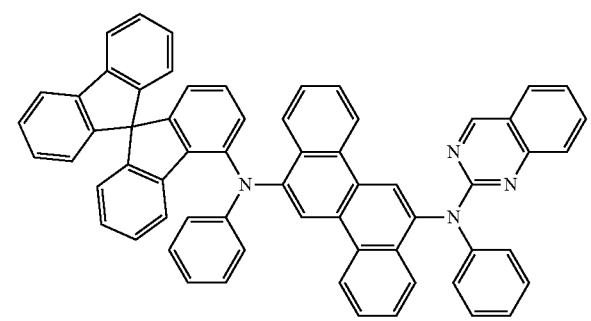

196 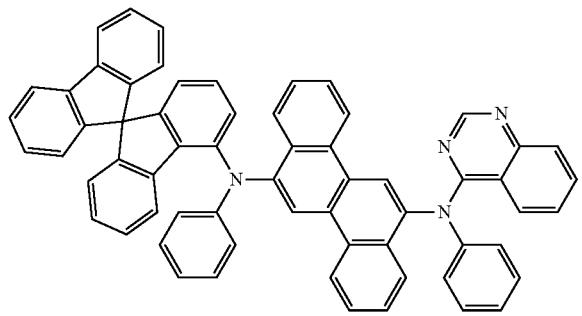
197 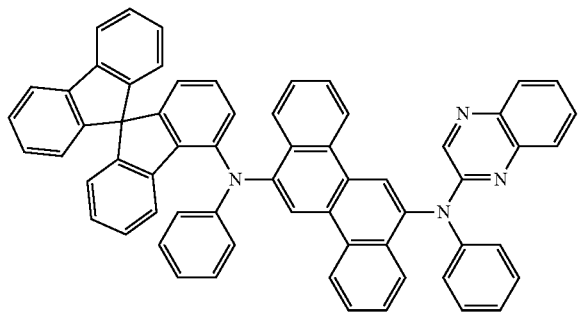
198 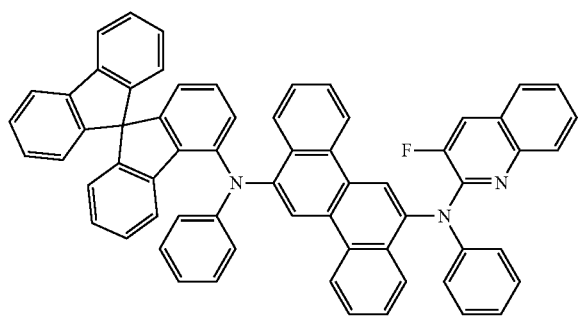
199 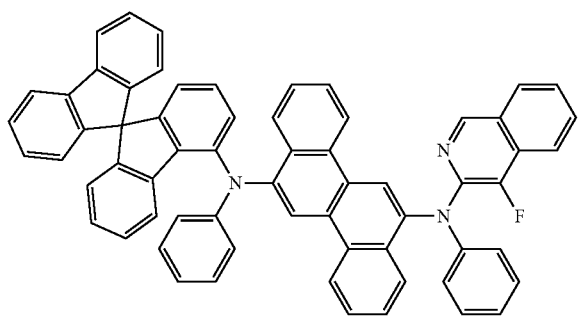
200 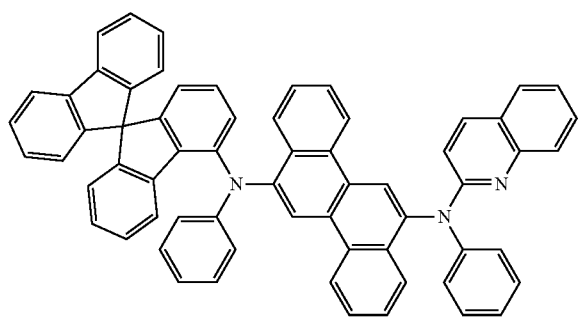
201 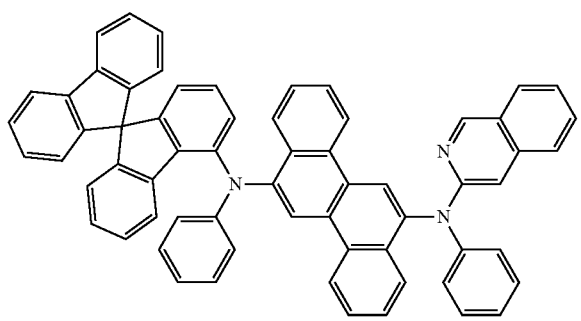
202 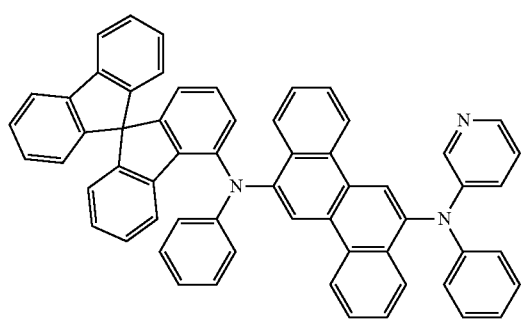
203 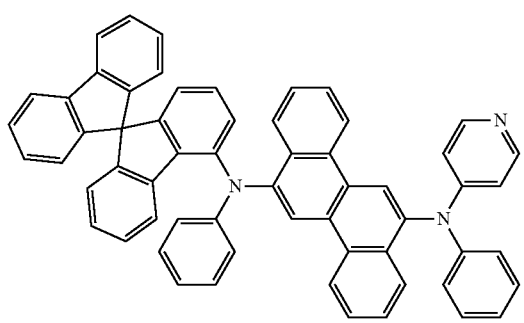

-continued
204
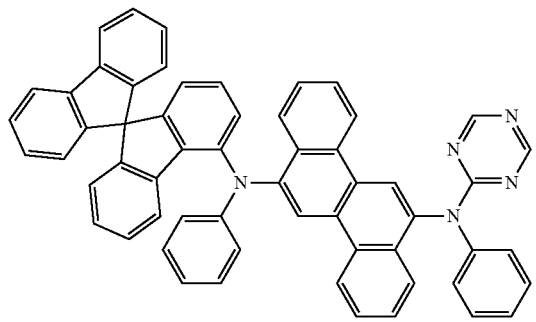
205
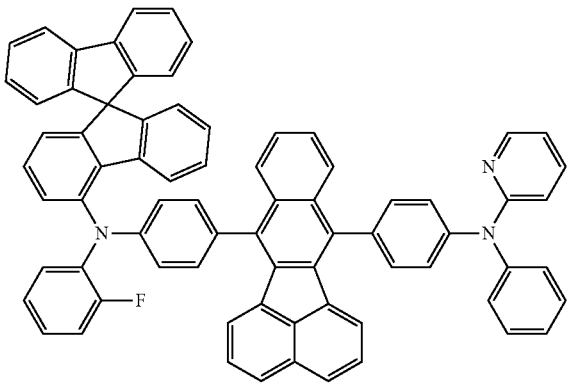
206
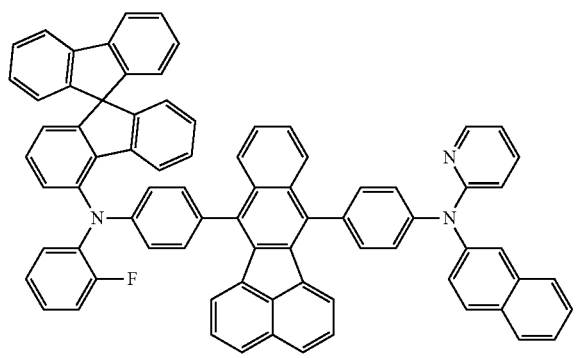
207
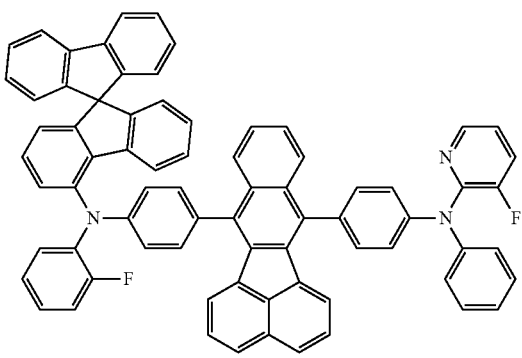
208
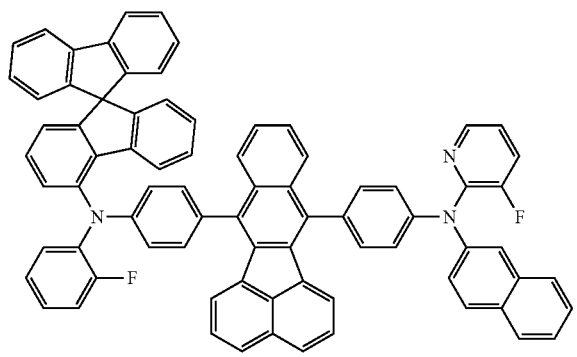
209
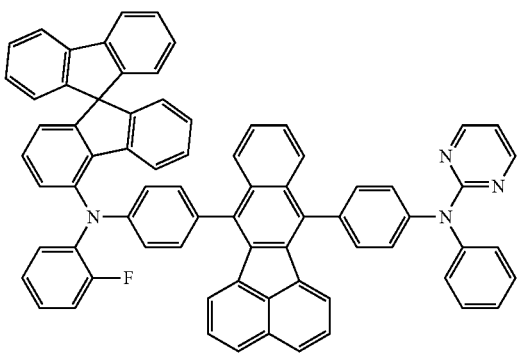
210
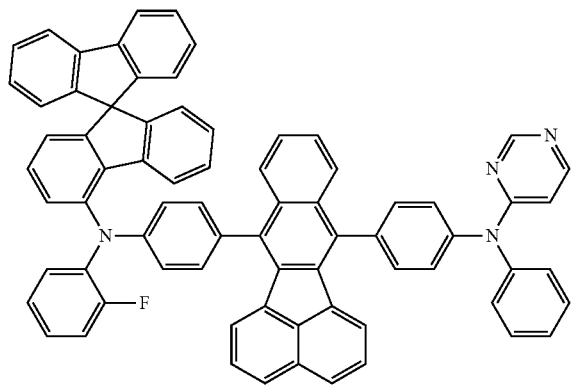
211
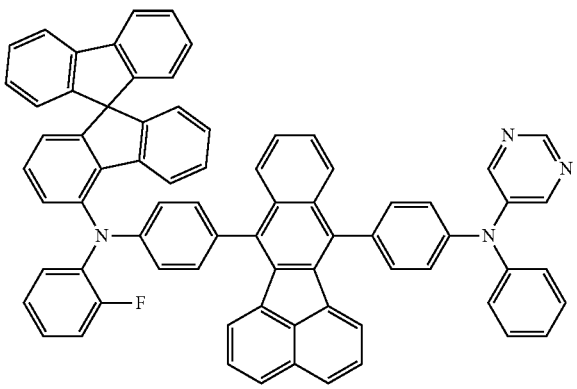

-continued
212
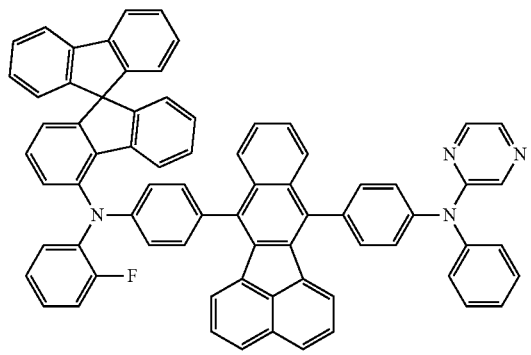
213
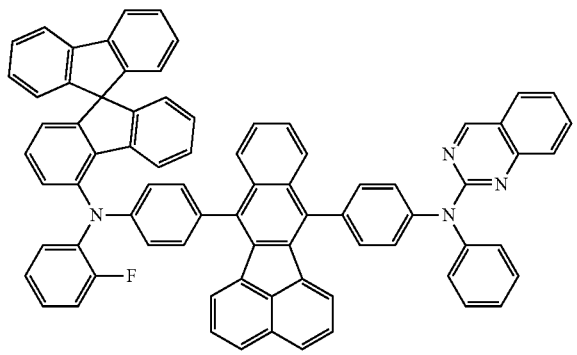
214
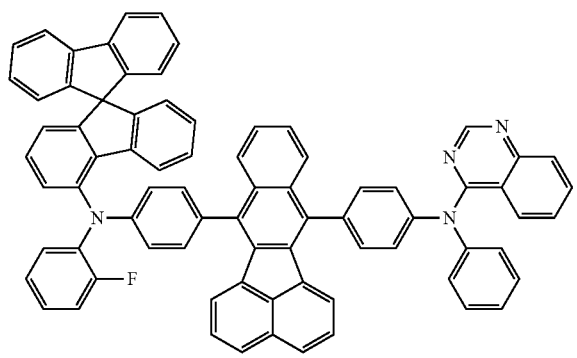
215
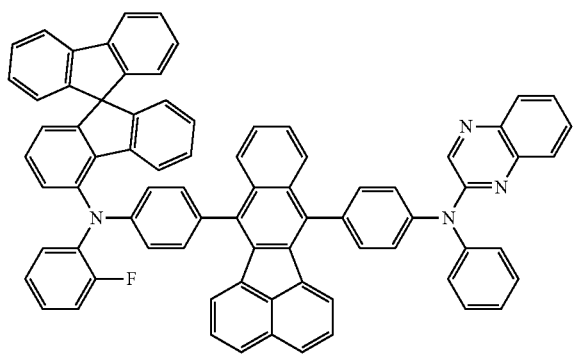
216
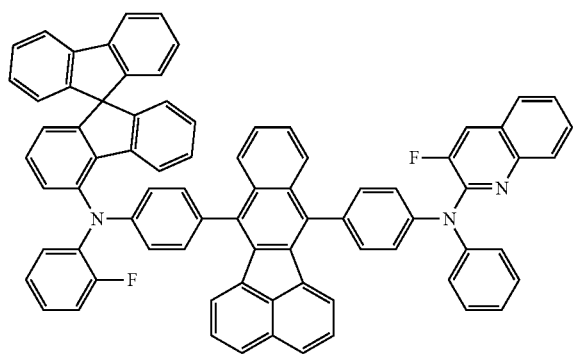
217
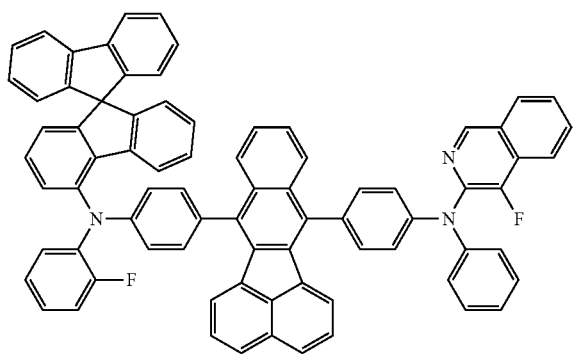
218
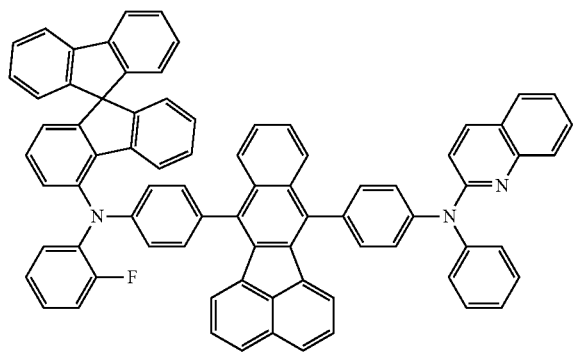
219
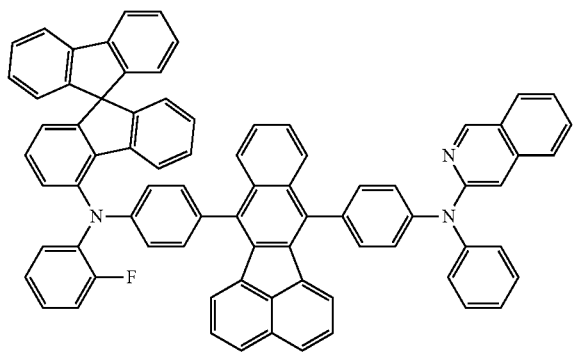

-continued

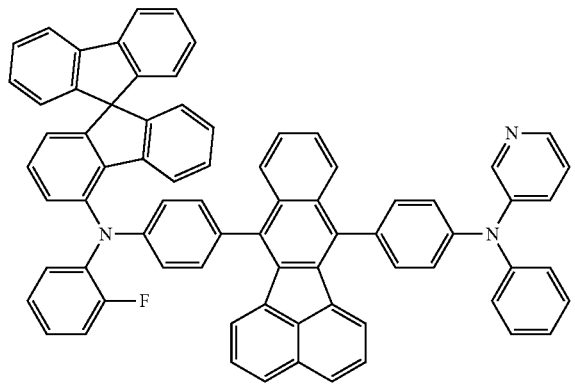
220

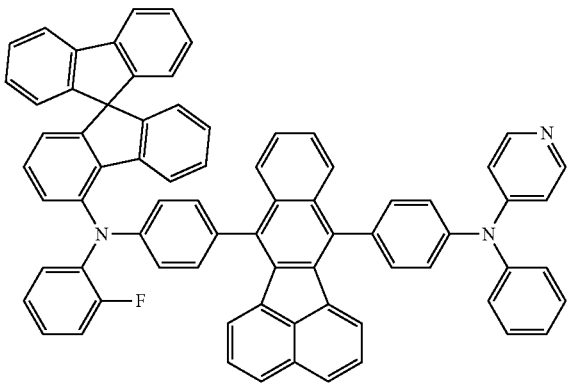
221

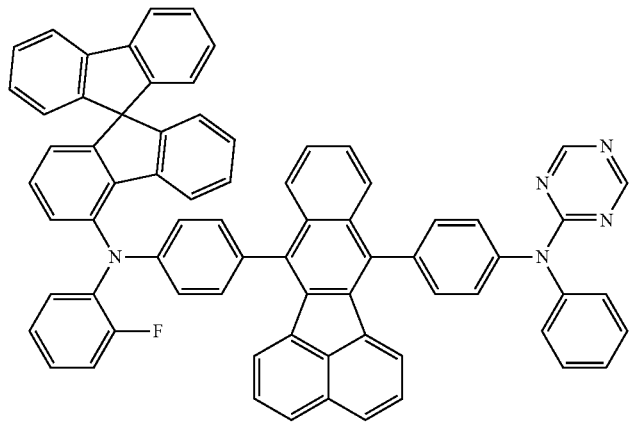
222

Because when n in Formula 1 is 0, at least one of $Ar_1$ and $Ar_2$ (or when n in Formula 1 is 1, at least one of $Ar_1$ to $Ar_4$) may be a substituent represented by Formula 2A or a substituent represented by Formula 2B, coordination with the core A may be weak. Accordingly, the amine-based compound of Formula 1 may emit blue light having a relatively short wavelength.

Furthermore, when $Ar_1$ to $Ar_4$ are each independently a $C_6$-$C_{60}$ aryl group substituted with at least one electron withdrawing group selected from —F, —CN, —$NO_2$, or a $C_1$-$C_{20}$ alkyl group substituted with at least one —F; a unsubstituted $C_2$-$C_{60}$ heteroaryl group; the substituent represented by Formula 2A; or the substituent represented by Formula 2B, and when n in Formula 1 is 0, at least one of $Ar_1$ and $Ar_2$ (or when n in Formula 1 is 1, at least one of $Ar_1$ to $Ar_4$) is a substituent represented by Formula 2A or a substituent represented by Formula 2B, the amine-based compound of Formula 1 may efficiently emit a relatively short wavelength of blue light.

For example, in a photoluminescence (PL) spectrum of the amine-based compound of Formula 1 in toluene, a maximum peak may be 465 nm or less. Accordingly, the amine-based compound of Formula 1 may emit blue light having good color purity. For example, an organic light-emitting diode employing the amine-based compound of Formula 1 may provide blue light having color purity characteristics such that the y coordinate is 0.1 or less, for example, 0.09 or less. Thus, the organic light-emitting diode may emit blue light that is close to the NTSC or sRGB standard.

Accordingly, an organic light-emitting diode employing the amine-based compound of Formula 1 may provide good electric characteristics (e.g., a low driving voltage, a high current density, a long lifespan, and the like) and good color purity characteristics.

The amine-based compound of Formula 1 may be synthesized using known organic synthesis methods. Methods of synthesizing the amine-based compound would be known to those of ordinary skill in the art, especially with reference to the following examples.

One or more of the amine-based compounds of Formula 1 may be used between a pair of electrodes of an organic light-emitting diode. For example, one or more of the amine-based compounds may be used in an emission layer.

Accordingly, an organic light-emitting diode according to an embodiment of the present invention includes: a first electrode; a second electrode facing the first electrode; and an organic layer between the first electrode and the second electrode, wherein the organic layer includes one or more of the amine-based compounds described above.

The expression "(an organic layer) includes one or more amine-based compounds," as used herein, may include cases in which an organic layer includes one amine-based compound of Formula 1 and cases in which an organic layer includes two or more different amine-based compounds of Formula 1.

For example, the organic layer may include as the amine-based compound, only Compound 1. In this regard, Compound 1 may exist in an emission layer of an organic light-emitting device. Alternatively, the organic layer may include, as the amine-based compound, Compound 2 and Compound 3. In this regard, Compound 2 and Compound 3 may exist in the same layer (for example, Compound 2 and Compound 3 may exist in an emission layer) or in different layers (for example, Compound 2 may exist in an emission layer and Compound 3 may exist in a hole transport layer).

The organic layer may include at least one layer selected from a hole injection layer, a hole transport layer, a functional layer having hole injection and hole transport functions (hereinafter referred to as an "H-functional layer"), a buffer layer, an electron blocking layer, an emission layer, a hole blocking layer, an electron transport layer, an electron injection layer, and a functional layer having electron transport and electron injection functions (hereinafter referred to as an "E-functional layer").

The term "organic layer," as used herein, refers to a single layer and/or a plurality of layers between the first electrode and the second electrode of an organic light-emitting diode.

The organic layer may include an emission layer, and the emission layer may include one or more of the amine-based compounds described above.

The amine-based compound included in the emission layer may function as a dopant. For example, the amine-based compound may function as a fluorescent dopant. An emission layer including the amine-based compound may emit blue light. In this regard, the emission layer may further include a host.

The host may include at least one compound selected from an anthracene-based compound represented by Formula 400 below and an anthracene-based compound represented by Formula 401 below.

<Formula 400>

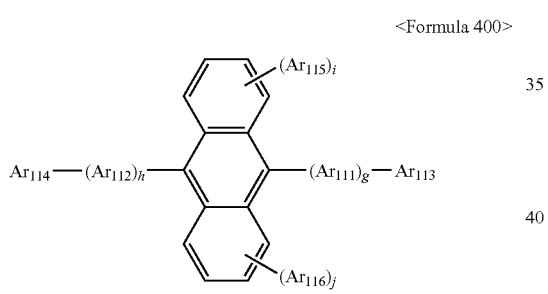

In Formula 400, $Ar_{111}$ and $Ar_{112}$ may each be independently a substituted or unsubstituted $C_6$-$C_{60}$ arylene group. $Ar_{113}$ to $Ar_{116}$ may each be independently a substituted or unsubstituted $C_1$-$C_{10}$ alkyl group or a substituted or unsubstituted $C_6$-$C_{60}$ aryl group. Also, g, h, i, and j may each be independently an integer of 0 to 4.

For example, $Ar_{111}$ and $Ar_{112}$ in Formula 400 may be each independently one selected from a phenylene group; a naphthylene group; a phenanthrenylene group; a pyrenylene group; or a phenylene group, a naphthylene group, a phenanthrenylene group, a fluorenyl group, or a pyrenylene group substituted with at least one selected from a phenyl group, a naphthyl group, or an anthryl group, but are not limited thereto.

Also, g, h, i, and j in Formula 400 may each be independently 0, 1, or 2.

$Ar_{113}$ to $Ar_{116}$ in Formula 400 may be each independently one selected from a $C_1$-$C_{10}$ alkyl group substituted with at least one selected from a phenyl group, a naphthyl group, or an anthryl group; a phenyl group; a naphthyl group; an anthryl group; a pyrenyl group; a phenanthrenyl group; a fluorenyl group; a phenyl group, a naphthyl group, a anthryl group, a pyrenyl group, a phenanthrenyl group, or a fluorenyl group substituted with at least one selected from deuterium, a halogen atom, a hydroxyl group, a cyano group, a nitro group, an amino group, an amidino group, a hydrazine, a hydrazone, a carboxylic acid group or salt thereof, a sulfonic acid group or salt thereof, a phosphoric acid group or salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a phenyl group, a naphthyl group, an anthryl group, a pyrenyl group, a phenanthrenyl group, or a fluorenyl group; or

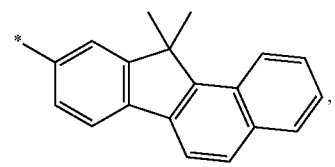 [SMILES: *c1ccc2c(c1)C(C)(C)c1c-2ccc2ccccc12]

but are not limited thereto.

For example, the anthracene-based compound represented by Formula 400 may be one of the following compounds, but is not limited thereto.

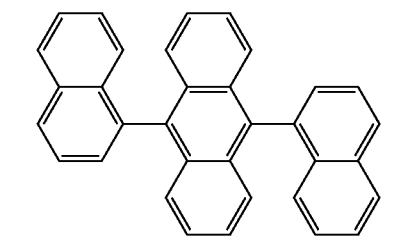

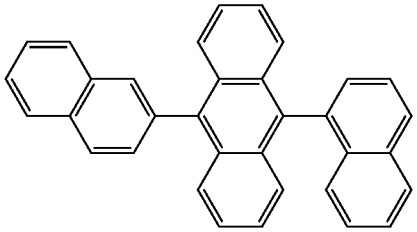

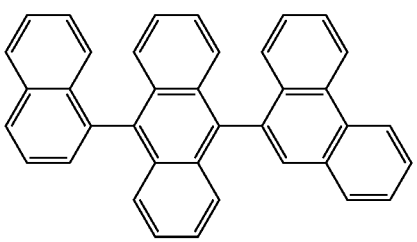

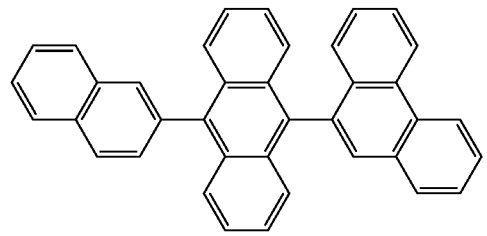

93
-continued
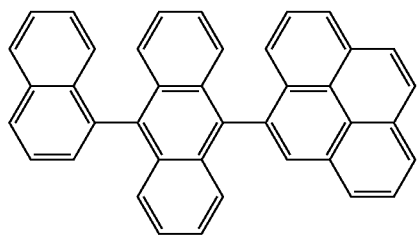
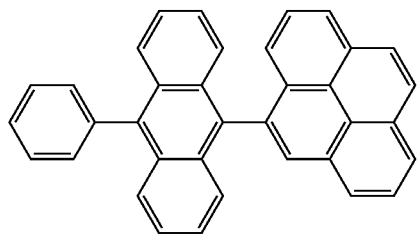
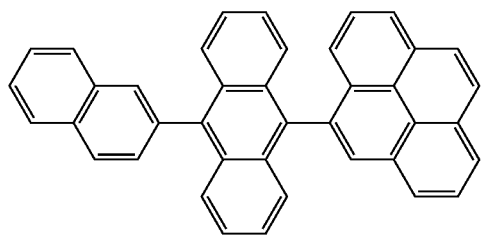
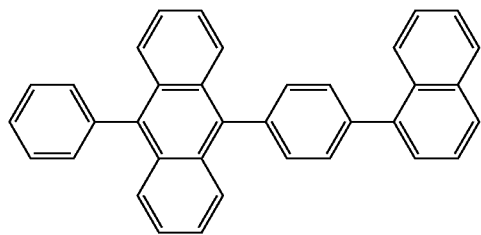
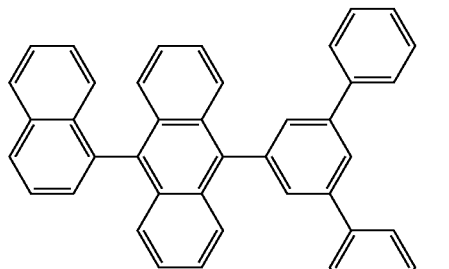
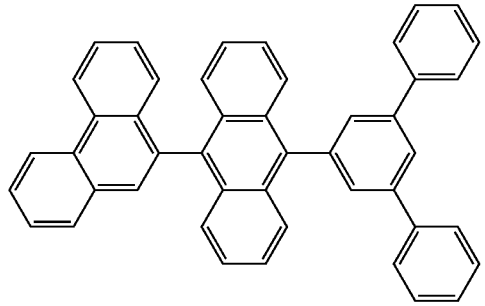
94
-continued
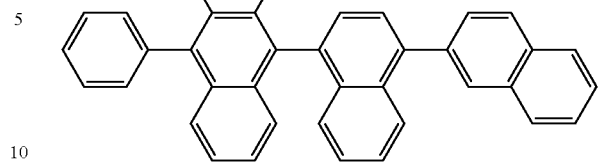
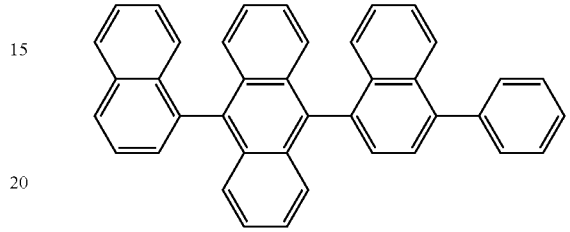
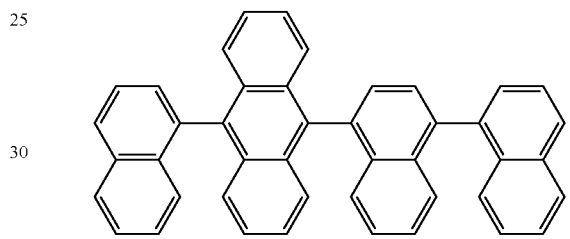
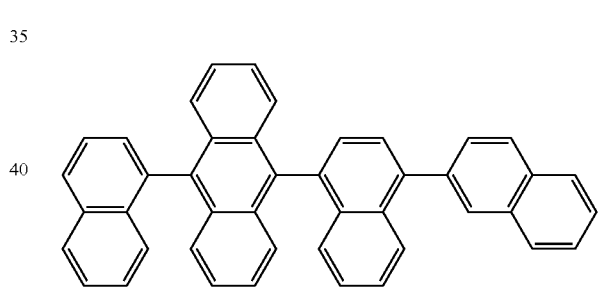
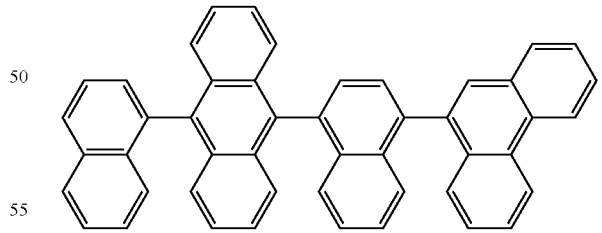
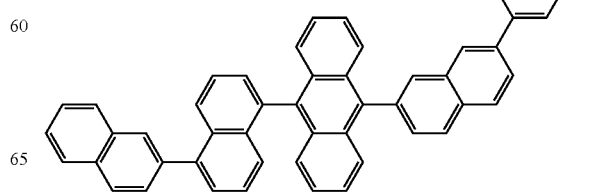

-continued
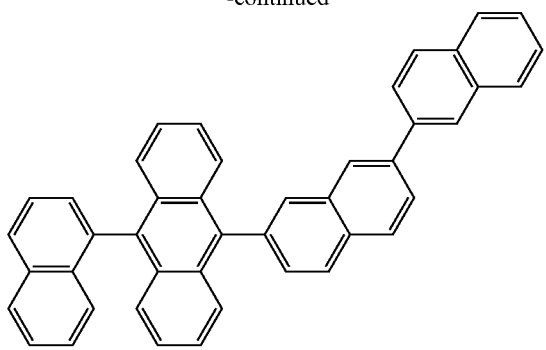
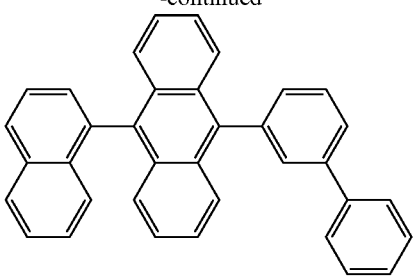

97
-continued
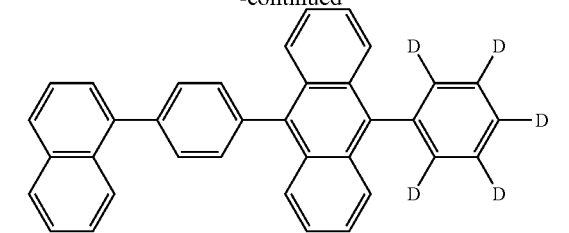
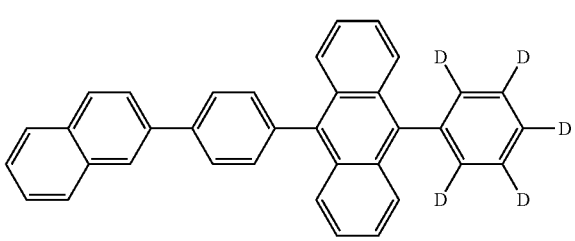
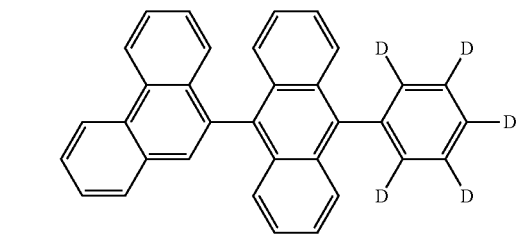
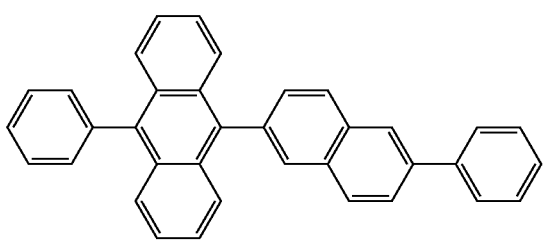
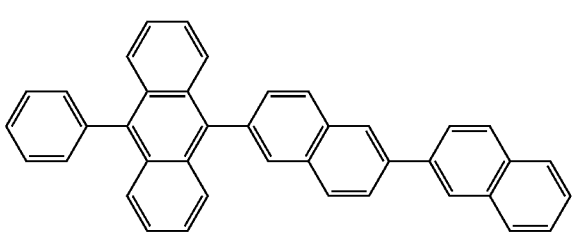
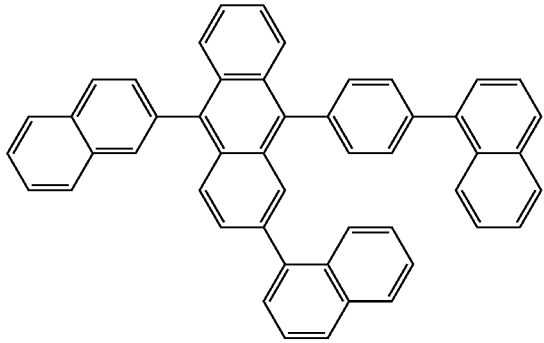
98
-continued
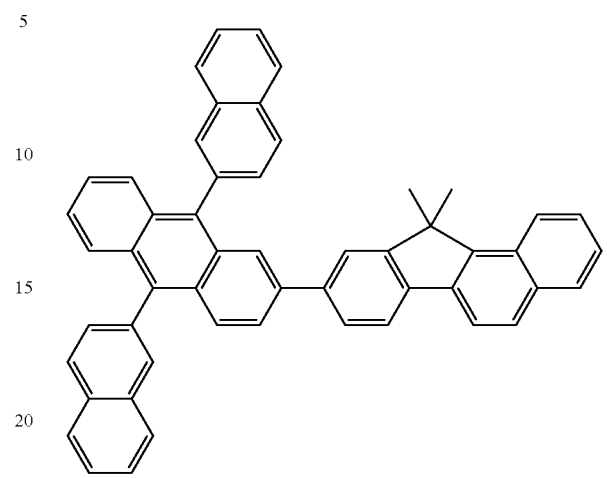
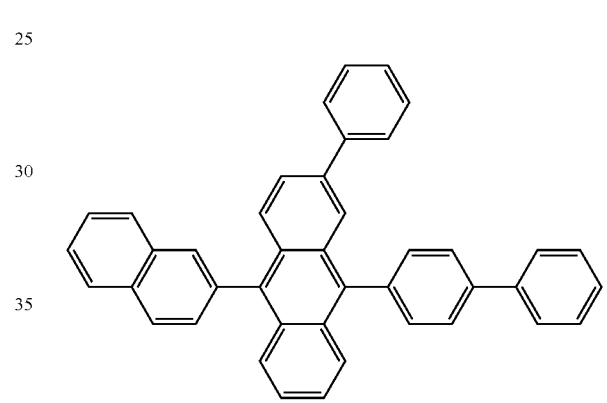
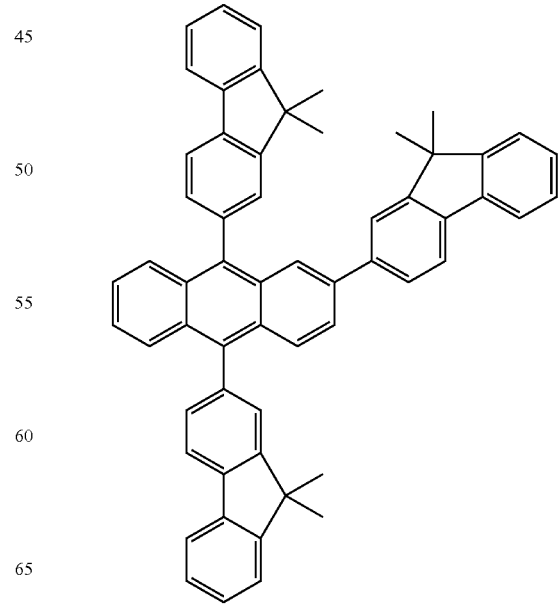

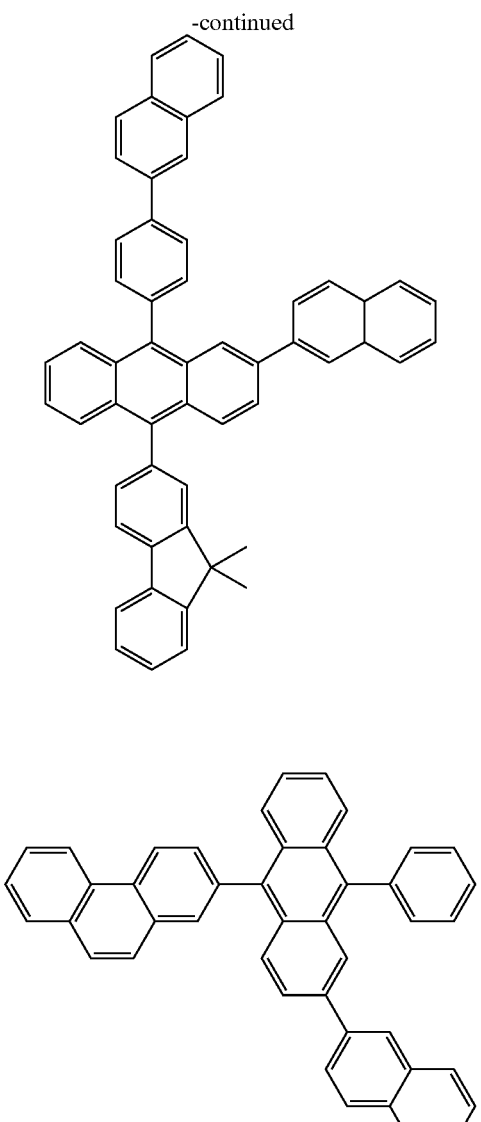

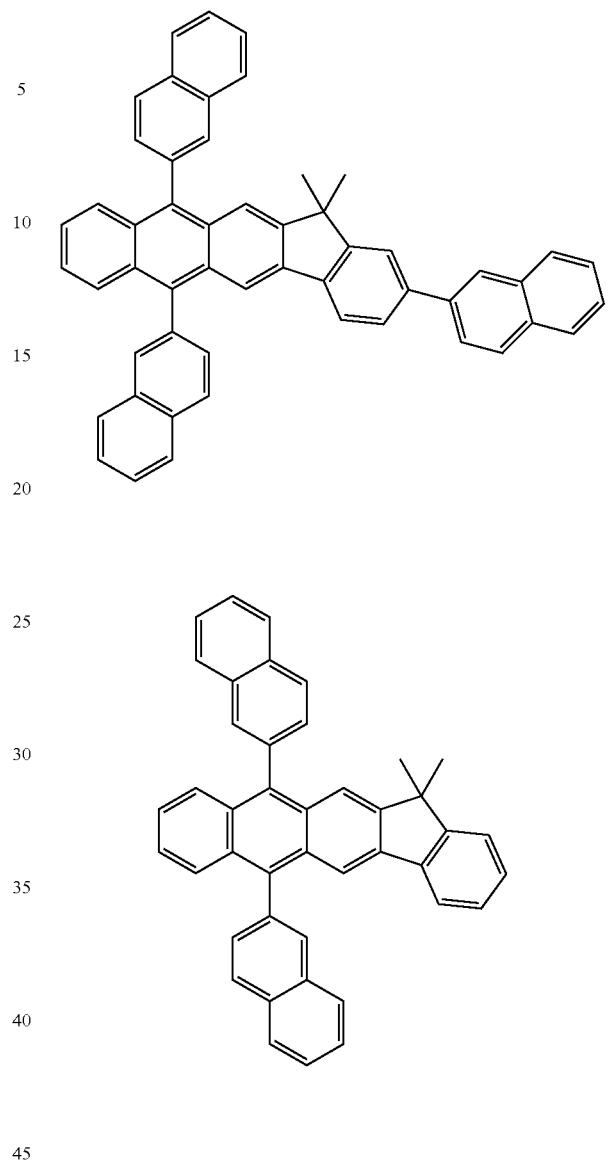

<Formula 401>

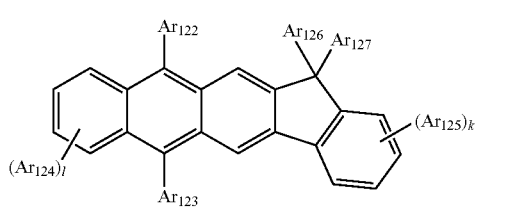

Ar$_{122}$ to Ar$_{125}$ in Formula 401 may be understood by reference to the description of Ar$_{113}$ in Formula 400.

Ar$_{126}$ and Ar$_{127}$ in Formula 401 may each be independently a $C_1$-$C_{10}$ alkyl group (for example, a methyl group, an ethyl group, or a propyl group).

Also, k and l in Formula 401 may each be independently an integer of 0 to 4. For example, k and l may be 0, 1, or 2.

For example, the anthracene-based compound represented by Formula 401 may be one of the following compounds, but is not limited thereto.

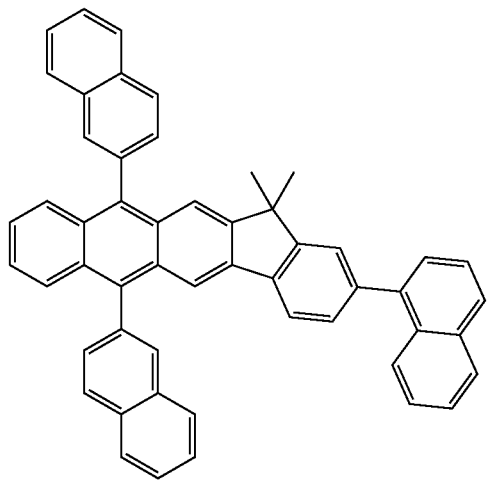

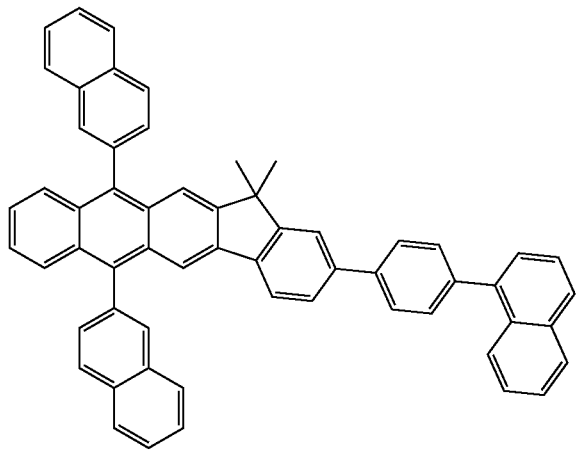 [SMILES: CC1(C)c2cc(-c3ccc(-c4cccc5ccccc45)cc3)ccc2-c2cc3c(-c4ccc5ccccc5c4)c4ccccc4c(-c4ccc5ccccc5c4)c3cc21]

An organic light-emitting diode employing the amine-based compound of Formula 1 may emit blue light that satisfies the sRGB standard. Accordingly, the organic light-emitting diode may be used in a large full-color display device (for example, an organic light-emitting display (OLED) television (TV), etc.). The FIGURE is a schematic cross-sectional view of an organic light-emitting diode 10 according to an embodiment of the present invention. Hereinafter, with reference to the FIGURE, the structure of an organic light-emitting diode according to an embodiment of the present invention, and a method of manufacturing the organic light-emitting diode, according to another embodiment of the present invention, will be described in detail.

The substrate 11 may be any one of various substrates that are used in known organic light-emitting devices, and may be a glass substrate or a transparent plastic substrate with good mechanical strength, thermal stability, transparency, surface smoothness, ease of handling, and water repellency.

A first electrode 13 may be formed by depositing or sputtering a material for forming the first electrode on the substrate 11. When the first electrode 13 is an anode, the material for forming the first electrode may be chosen from materials having a high work function to allow holes to be easily injected. The first electrode 13 may be a reflective electrode, a semi-transparent electrode, or a transparent electrode. For example, when the organic light-emitting diode is used in a large display device, the first electrode 13 may be a semi-transparent electrode or a transparent electrode. Examples of the first electrode material are indium tin oxide (ITO), indium zinc oxide (IZO), tin oxide ($SnO_2$), and zinc oxide (ZnO), which have transparency and high conductivity. Alternatively, when magnesium (Mg), aluminum (Al), aluminum-lithium (Al—Li), calcium (Ca), magnesium-indium (Mg—In), magnesium-silver (Mg—Ag), or the like is used, the first electrode 13 may be formed as a reflective electrode.

The first electrode 13 may be a single-layered structure or a multi-layered structure including two or more layers. For example, the first electrode 13 may have a three-layered structure of ITO/Ag/ITO, but the structure of the first electrode 13 is not limited thereto.

An organic layer 15 is disposed on first electrode 13. The organic layer 15 may include a hole injection layer, a hole transport layer, a buffer layer, an emission layer, an electron transport layer, and an electron injection layer.

A hole injection layer (HIL) may be formed on the first electrode 13 using any one of various methods, for example, vacuum deposition, spin coating, casting, or Langmuir-Blodgett (LB) deposition.

When a hole injection layer is formed by vacuum deposition, the deposition conditions may vary according to the material used to form the hole injection layer, and the desired structural and thermal characteristics of the hole injection layer. For example, the deposition conditions may include a deposition temperature of about 100 to about 500° C., a vacuum pressure of about $10^{-8}$ to about $10^{-3}$ torr, and a deposition rate of about 0.01 to about 100 Å/sec. However, the deposition conditions are not limited thereto.

When the hole injection layer is formed using spin coating, the coating conditions may vary according to the material used to form the hole injection layer, and the desired structural and thermal properties of the hole injection layer. For example, a coating speed may be from about 2000 rpm to about 5000 rpm, and a temperature at which heat treatment is performed (to remove solvent after coating) may be from about 80° C. to about 200° C. However, the coating conditions are not limited thereto.

The material used to form the hole injection layer may be any known hole injecting material. Nonlimiting examples of the hole injecting material include a phthalocyanine compound, such as copperphthalocyanine, N,N'-diphenyl-N,N'-bis-[4-(phenyl-m-tolyl-amino)-phenyl]-biphenyl-4,4'-diamine (DNTPD); 4,4',4"-tris(3-methylphenylphenylamino)triphenylamine (m-MTDATA); TDATA; 2T-NATA; polyaniline/dodecylbenzenesulfonic acid (Pani/DBSA); poly(3,4-ethylenedioxythiophene)/poly(4-styrenesulfonate) (PEDOT/PSS); polyaniline/camphor sulfonic acid (Pani/CSA); and polyaniline)/poly(4-styrenesulfonate)(PANI/PSS).

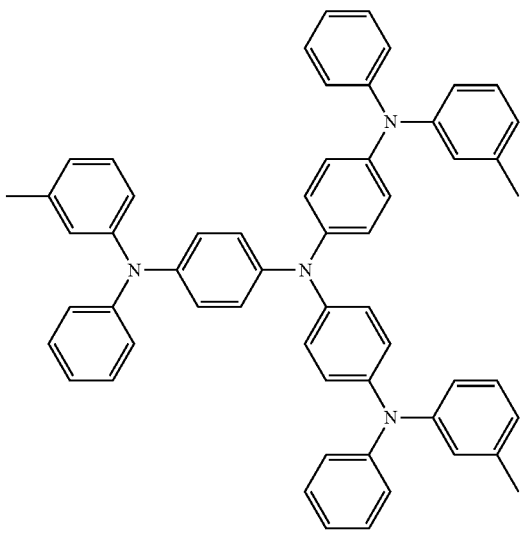

m-MTDATA

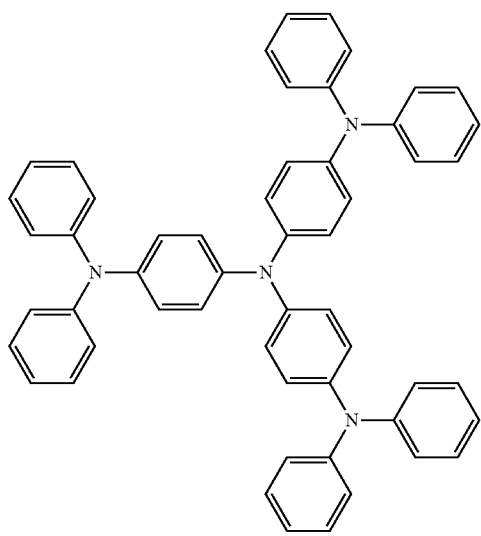

TDATA

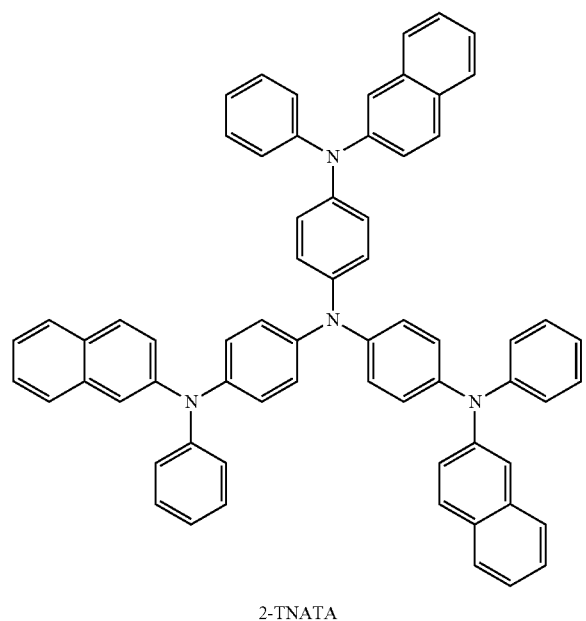

2-TNATA

The hole injection layer may have a thickness of about 100 Å to about 10000 Å, for example, a thickness of about 100 Å to about 1000 Å. When the thickness of the hole injection layer is within these ranges, the hole injection layer may have good hole injection characteristics without an increase in driving voltage.

A hole transport layer (HTL) may be formed on the hole injection layer by vacuum deposition, spin coating, casting, LB deposition, etc. When the hole transport layer is formed by vacuum deposition or spin coating, the deposition or coating conditions may be similar to those described above with respect to the formation of the hole injection layer, although the deposition or coating conditions may vary according to the material that is used to form the hole transport layer.

The material used to form the hole transport layer may be any known hole transport material. Nonlimiting examples of the material used to form the hole transport layer include a carbazole derivative, such as N-phenylcarbazole or polyvinylcarbazole; N,N'-bis(3-methylphenyl)-N,N'-diphenyl-[1,1-biphenyl]-4,4'-diamine (TPD); 4,4',4''-tris(N-carbazolyl)triphenylamine (TCTA), and alpha ($\alpha$)-NPD.

TPD alpha ($\alpha$)-NPD

The hole transport layer may have a thickness of about 50 Å to about 2000 Å, for example, a thickness of about 100 Å to about 1500 Å. When the thickness of the hole transport layer is within the above ranges, the hole transport layer may have satisfactory hole transport characteristics without a substantial increase in driving voltage.

An H-functional layer (having hole injection and hole transport functions) may include at least one material selected from hole injection layer materials and hole transport layer materials, and a thickness of the H-functional layer may be in a range of about 500 Å to about 10000 Å, for example, about 100 Å to about 1000 Å. When the thickness of the H-functional layer is within the above ranges, the H-functional layer may have satisfactory hole injection and hole transport characteristics without a substantial increase in driving voltage.

Also, at least one layer selected from the hole injection layer, the hole transport layer, and the H-functional layer may include at least one selected from a compound represented by Formula 300 below and a compound represented by Formula 350 below:

<Formula 300>

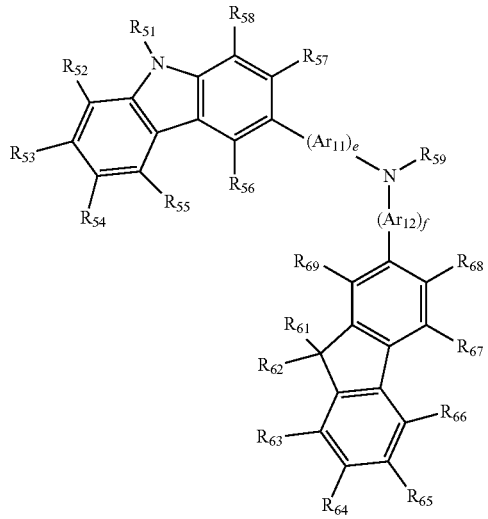

<Formula 350>

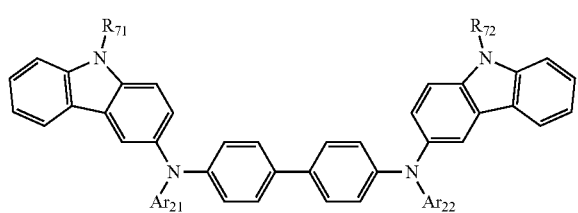

In Formula 300, $Ar_{11}$ and $Ar_{12}$ are each independently a substituted or unsubstituted $C_6$-$C_{60}$ arylene group. When $Ar_{11}$ and $Ar_{12}$ are each independently a substituted $C_6$-$C_{60}$ arylene group, at least one substituent of the substituted $C_6$-$C_{60}$ arylene group may be selected from deuterium; a halogen; a hydroxyl group; a cyano group; a nitro group; an amino group; an amidino group; hydrazine; hydrazone; a carboxyl group or a salt thereof; a sulfonic acid group or a salt thereof; a phosphoric acid group or a salt thereof; a $C_1$-$C_{10}$ alkyl group; a $C_1$-$C_{10}$ alkoxy group; a phenyl group, a naphthyl group, a fluorenyl group, a phenanthrenyl group, an anthryl group, a triphenylenyl group, a pyrenyl group, a chrysenyl group, an imidazolyl group, an imidazolynyl group, an imidazopyridinyl group, an imidazopyrimidinyl group, a pyridinyl group, a pyrizinyl group, a pyrimidinyl group, or an indolyl group; or a phenyl group, a naphthyl group, a fluorenyl group, a phenanthrenyl group, an anthryl group, a triphenylenyl group, a pyrenyl group, a chrysenyl group, an imidazolyl group, an imidazolynyl group, an imidazopyridinyl group, an imidazopyrimidinyl group, a pyridinyl group, a pyrizinyl group, a pyrimidinyl group, or an indolyl group substituted with at least one of deuterium, a halogen, a hydroxyl group, a cyano group, a nitro group, an amino group, an amidino group, hydrazine, hydrazone, a carboxyl group or a salt thereof, a sulfonic acid group or a salt thereof, a phosphoric acid group or a salt thereof, a $C_1$-$C_{10}$ alkyl group, or a $C_1$-$C_{10}$ alkoxy group.

$Ar_{11}$ and $Ar_{12}$ may be each independently a substituted or unsubstituted phenylene group, a substituted or unsubstituted pentalenylene group, a substituted or unsubstituted indenylene group, a substituted or unsubstituted naphthylene group, a substituted or unsubstituted azulenylene group, a substituted or unsubstituted heptalenylene group, a substituted or unsubstituted indacenylene group, a substituted or unsubstituted acenaphthylene group, a substituted or unsubstituted fluorenylene group, a substituted or unsubstituted phenalenylene group, a substituted or unsubstituted phenanthrenylene group, a substituted or unsubstituted anthrylene group, a substituted or unsubstituted fluoranthenylene group, a substituted or unsubstituted triphenylenylene group, a substituted or unsubstituted pyrenylene group, a substituted or unsubstituted chrysenylene group, a substituted or unsubstituted naphthacenylene group, a substituted or unsubstituted pycenylene group, a substituted or unsubstituted perylenylene group, a substituted or unsubstituted pentacenylene group, or a substituted or unsubstituted hexacenylene group.

For example, $Ar_{11}$ and $Ar_{12}$ may be each independently a substituted or unsubstituted phenylene group, a substituted or unsubstituted naphthylene group, a substituted or unsubstituted fluorenylene group, or a substituted or unsubstituted phenanthrenylene group, but are not limited thereto.

In Formula 350 above, $Ar_{21}$ and $Ar_{22}$ may be each independently a substituted or unsubstituted $C_6$-$C_{60}$ aryl group or a substituted or unsubstituted $C_2$-$C_{60}$ heteroaryl group. For example, $Ar_{21}$ and $Ar_{22}$ may be each independently a substituted or unsubstituted phenyl group, a substituted or unsubstituted naphthyl group, a substituted or unsubstituted phenanthrenyl group, a substituted or unsubstituted anthryl group, a substituted or unsubstituted pyrenyl group, a substituted or unsubstituted chrysenyl group, a substituted or unsubstituted fluorenyl group, a substituted or unsubstituted carbazolyl group, a substituted or unsubstituted dibenzofuranyl group, or a substituted or unsubstituted dibenzothiophenyl group. In this case, at least one of the substituents of the substituted phenyl group, the substituted naphthyl group, the substituted phenanthrenyl group, the substituted anthryl group, the substituted pyrenyl group, the substituted chrysenyl group, the substituted fluorenyl group, the substituted carbazolyl group, the substituted dibenzofuranyl group, or the substituted dibenzothiophenyl group may be selected from deuterium; a halogen atom; a hydroxyl group; a cyano group; a nitro group; an amino group; an amidino group; hydrazine; hydrazone; a carboxyl group or a salt thereof; a sulfonic acid group or a salt thereof; a phosphoric acid or a salt thereof; a $C_1$-$C_{10}$ alkyl group; a $C_1$-$C_{10}$ alkoxy group; a phenyl group, a naphthyl group, a fluorenyl group, a phenanthrenyl group, an anthryl group, an triphenylenyl group, a pyrenyl group, a chrysenyl group, an imidazolyl group, an imidazolinyl group, an imidazopyridinyl group, an imidazopyrimidinyl group, a pyridinyl group, a pyrazinyl group, a pyrimidinyl group, or an indolyl group; or a phenyl group, a naphthyl group, a fluorenyl group, a phenanthrenyl group, an anthryl group, a triphenylenyl group, a pyrenyl group, a chrysenyl group, an imidazolyl group, an imidazolinyl group, an imidazopyridinyl group, an imidazopyrimidinyl group, a pyridinyl group, a pyrazinyl group, a pyrimidinyl group, or an indolyl group substituted with at least one of deuterium, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid or a salt thereof, a $C_1$-$C_{10}$ alkyl group, or a $C_1$-$C_{10}$ alkoxy group.

In Formula 300, e and f may each be independently an integer of 0 to 5, or 0, 1, or 2. For example, e is 1 and f is 0, but e and f are not limited thereto.

$R_{51}$ to $R_{58}$, $R_{61}$ to $R_{69}$ and $R_{71}$, and $R_{72}$ in Formulae 300 and 350 may each be independently hydrogen, deuterium, a halogen atom, a hydroxyl group, a cyano group, a nitro group, an amino group, an amidino group, a hydrazine, a hydrazone, a carboxylic acid group or salt thereof, a sulfonic acid group or salt thereof, a phosphoric acid group or salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{60}$ cycloalkyl group, a substituted or unsubstituted $C_6$-$C_{60}$ aryl group, a substituted or unsubstituted $C_6$-$C_{60}$ aryloxy group, or a substituted or unsubstituted $C_6$-$C_{60}$ arylthio group. For example, $R_{51}$ to $R_{58}$, $R_{61}$ to $R_{69}$ and $R_{71}$ and $R_{72}$ may each be independently hydrogen; deuterium; a halogen atom; a hydroxyl group; a cyano group; a nitro group; an amino group; an amidino group; a hydrazine; a hydrazone; a carboxylic acid group or salt thereof; a sulfonic acid group or salt thereof; a phosphoric acid group or salt thereof; a $C_1$-$C_{10}$ alkyl group (for example, a methyl group, an ethyl group, a propyl group, a butyl group, a pentyl group, a hexyl group, or the like); a $C_1$-$C_{10}$ alkoxy group (for example, a methoxy group, an ethoxy group, a propoxy group, a butoxy group, a pentoxy, or the like); a $C_1$-$C_{10}$ alkyl group or $C_1$-$C_{10}$ alkoxy group substituted with at least one selected from deuterium, a halogen atom, a hydroxyl group, a cyano group, a nitro group, an amino group, an amidino group, a hydrazine, a hydrazone, a carboxylic acid group or salt thereof, a sulfonic acid group or salt thereof, and a phosphoric acid group or salt thereof; a phenyl group; a naphthyl group; an anthryl group; a fluorenyl group; a pyrenyl group; or a phenyl group, a naphthyl group, an anthryl group, a fluorenyl group, or a pyrenyl group substituted with at least one selected from deuterium, a halogen atom, a hydroxyl group, a cyano group, a nitro group, an amino group, an amidino group, a hydrazine, a hydrazone, a carboxylic acid group or salt thereof, a sulfonic acid group or salt thereof, a phosphoric acid group or salt thereof, a $C_1$-$C_{10}$ alkyl group, or a $C_1$-$C_{10}$ alkoxy group, but are not limited thereto.

$R_{59}$ in Formula 300 may be one selected from a phenyl group; a naphthyl group; an anthryl group; a biphenyl group; a pyridyl group; or a phenyl group, naphthyl group, anthryl group, biphenyl group, or pyridyl group substituted with at least one selected from deuterium, a halogen atom, a hydroxyl group, a cyano group, a nitro group, an amino group, an amidino group, a hydrazine, a hydrazone, a carboxylic acid group or salt thereof, a sulfonic acid group or salt thereof, a phosphoric acid group or salt thereof, a substituted or unsubstituted $C_1$-$C_{20}$ alkyl group, or a substituted or unsubstituted $C_1$-$C_{20}$ alkoxy group.

According to an embodiment of the present invention, the compound represented by Formula 300 may be represented by Formula 300A below, but is not limited thereto.

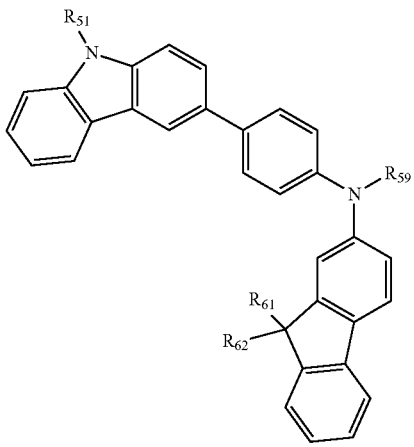

<Formula 300A>

$R_{51}$, $R_{60}$, $R_{61}$, and $R_{59}$ in Formula 300A are described above.

For example, at least one layer selected from the hole injection layer, the hole transport layer, and the H-functional layer may include at least one selected from Compounds 301 to 320, but these layers may instead include other compounds.

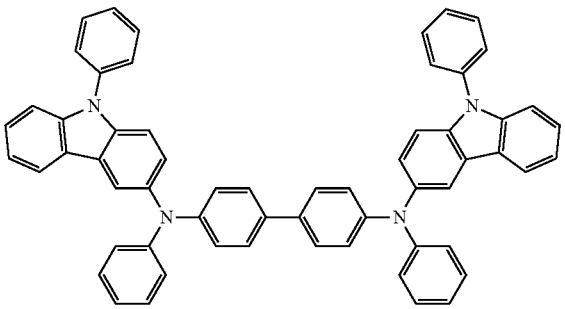

301

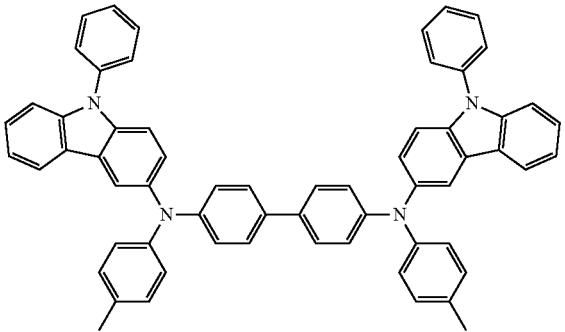

302

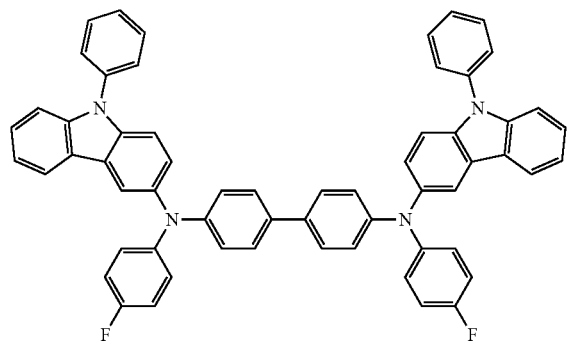
303
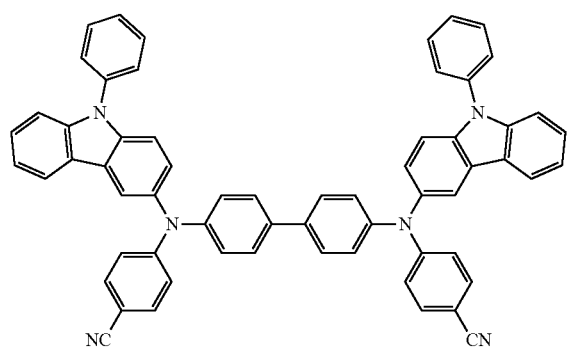
304
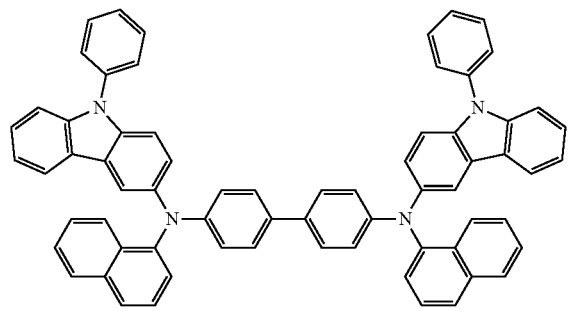
305
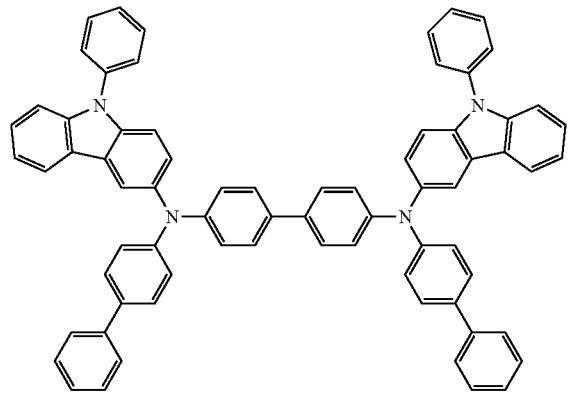
306
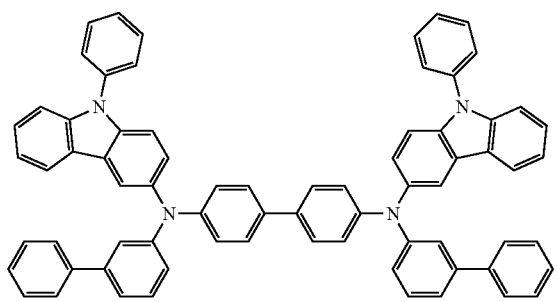
307
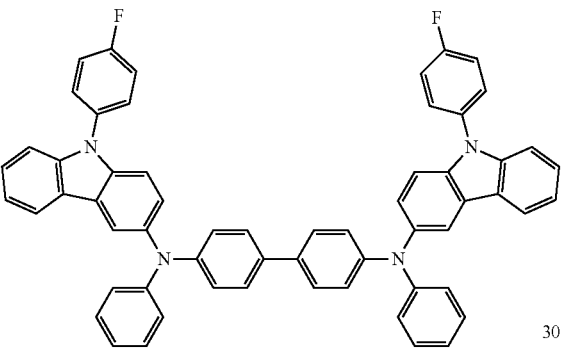
308
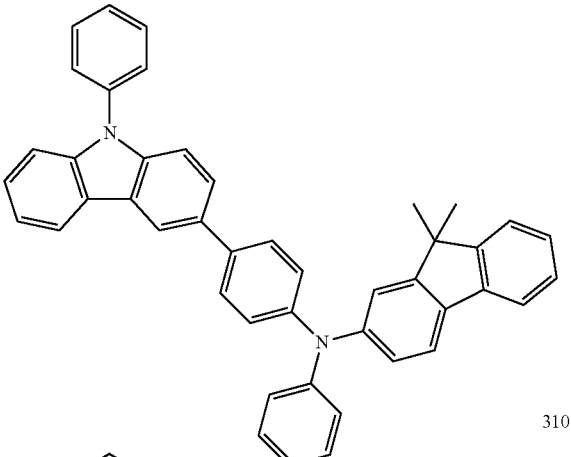
309
310

111
-continued
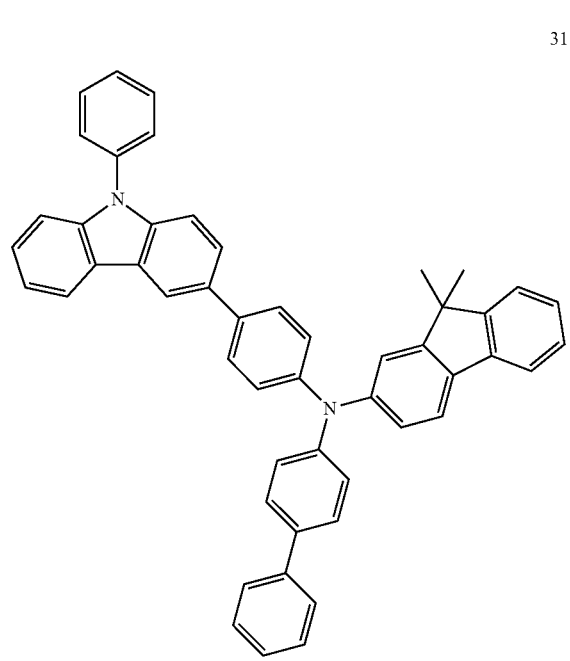
311
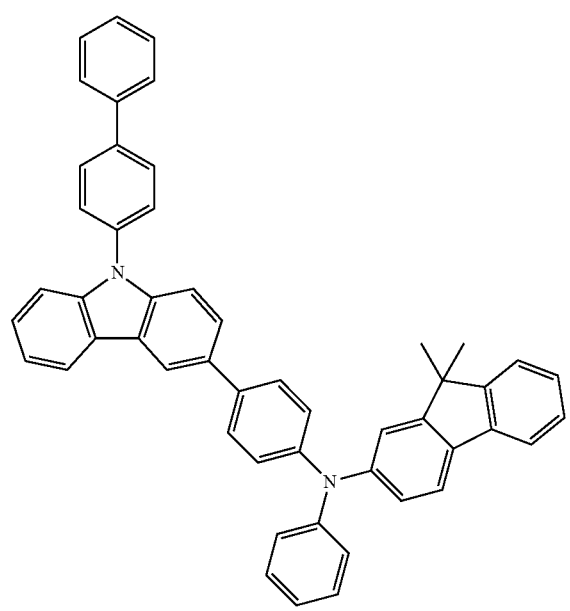
312
112
-continued
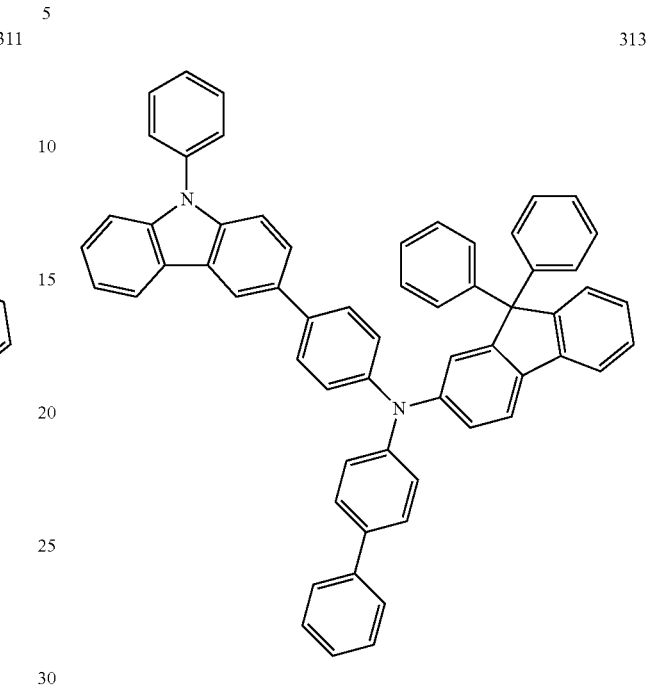
313
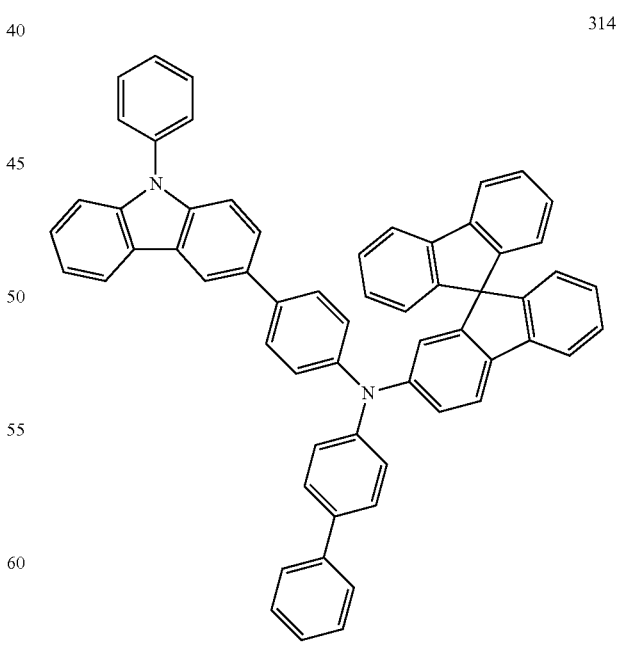
314

315
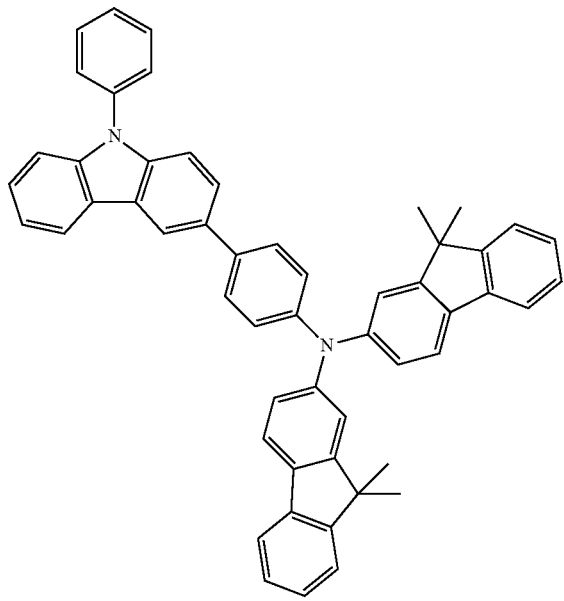
316
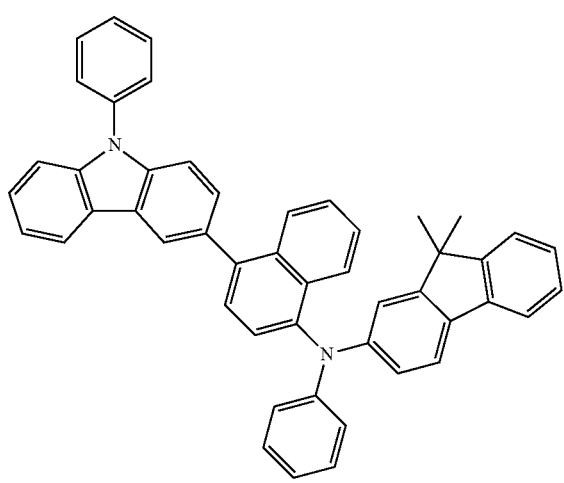
317
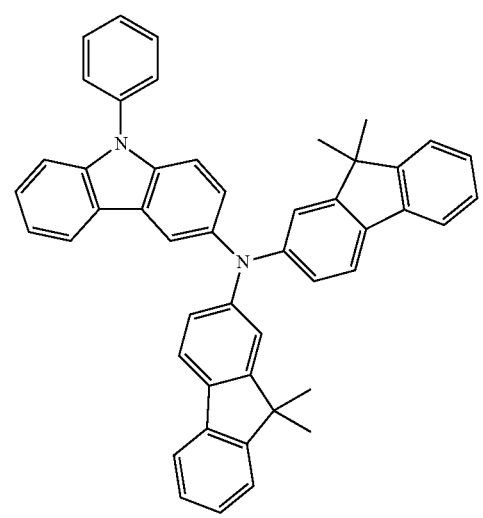
318
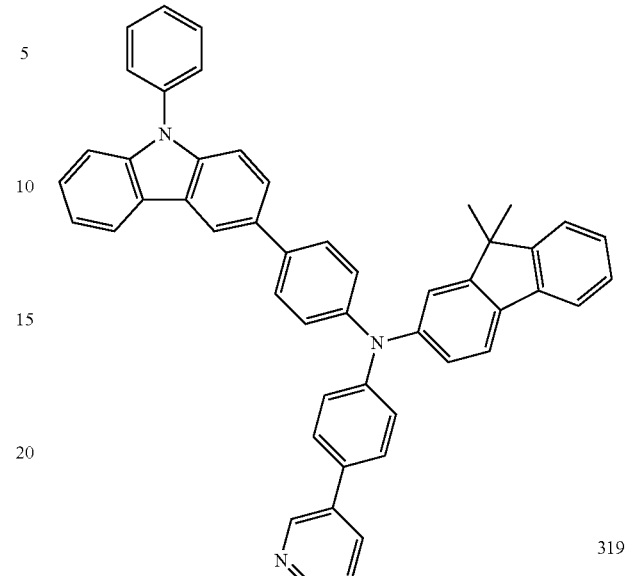
319
320
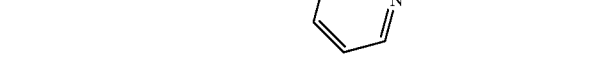
At least one layer selected from the hole injection layer, the hole transport layer, and the H-functional layer may further include, in addition to known hole injection materials, known hole transport materials, and/or materials having hole injection and hole transport functions, a charge-generating material to increase conductivity of the corresponding layer.

The charge-generating material may be, for example, a p-dopant. The p-dopant may be a quinone derivative, a metal oxide, or a cyano group-containing compound, but is not limited thereto. For example, nonlimiting examples of the p-dopant are a quinone derivative, such as tetracyanoquinonedimethane (TCNQ) and 2,3,5,6-tetrafluoro-tetracyano-1,4-benzoquinonedimethane (F4-TCNQ), or the like; a metal oxide, such as a tungsten oxide and a molybdenum oxide; and a cyano group-containing compound, such as Compound 200 below, but are not limited thereto.

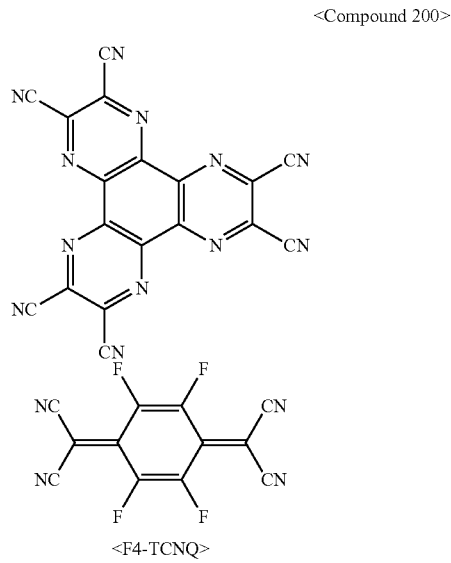

<Compound 200>

<F4-TCNQ>

When the hole injection layer, the hole transport layer, or the H-functional layer further include the charge-generating material, the charge-generating material may be, for example, homogeneously or non-homogeneously distributed in the hole injection layer, the hole transport layer, or the H-functional layer.

A buffer layer may be disposed between at least one of the hole injection layer, the hole transport layer, and the H-functional layer and the emission layer. The buffer layer may compensate for an optical resonance distance according to the wavelength of light emitted from the emission layer to increase efficiency. The buffer layer may include a known hole injection material and a known hole transport material. Alternatively, the buffer layer may include one of materials included in the hole injection layer, the hole transport layer, and the H-functional layer formed under the buffer layer.

An emission layer (EML) may be formed on the hole transport layer, the H-functional layer, or the buffer layer by vacuum deposition, spin coating, casting, LB deposition, etc. When the emission layer is formed by vacuum deposition or spin coating, the deposition or coating conditions may be similar to those described above with respect to the formation of the hole injection layer, although the deposition or coating conditions may vary according to the material used to form the emission layer.

The emission layer may include one or more of the amine-based compounds described above. The amine-based compound included in the emission layer may function as a dopant (for example, a blue fluorescent dopant). For example, the emission layer may further include, in addition to the amine-based compound, a host.

As the host, Alq$_3$, 4,4'-N,N'-dicarbazole-biphenyl(CBP), poly(n-vinylcarbazole)(PVK), 9,10-di(naphthalene-2-yl)anthracene (ADN), TCTA, 1,3,5-tris(N-phenylbenzimidazole-2-yl)benzene (TPBI), 3-tert-butyl-9,10-di(naphth-2-yl) anthracene (TBADN), E3, distyrylarylene (DSA), dmCBP (see the following chemical structure), Compounds 501 to 509 illustrated below, or the like may be used, but other materials may instead be used as the host.

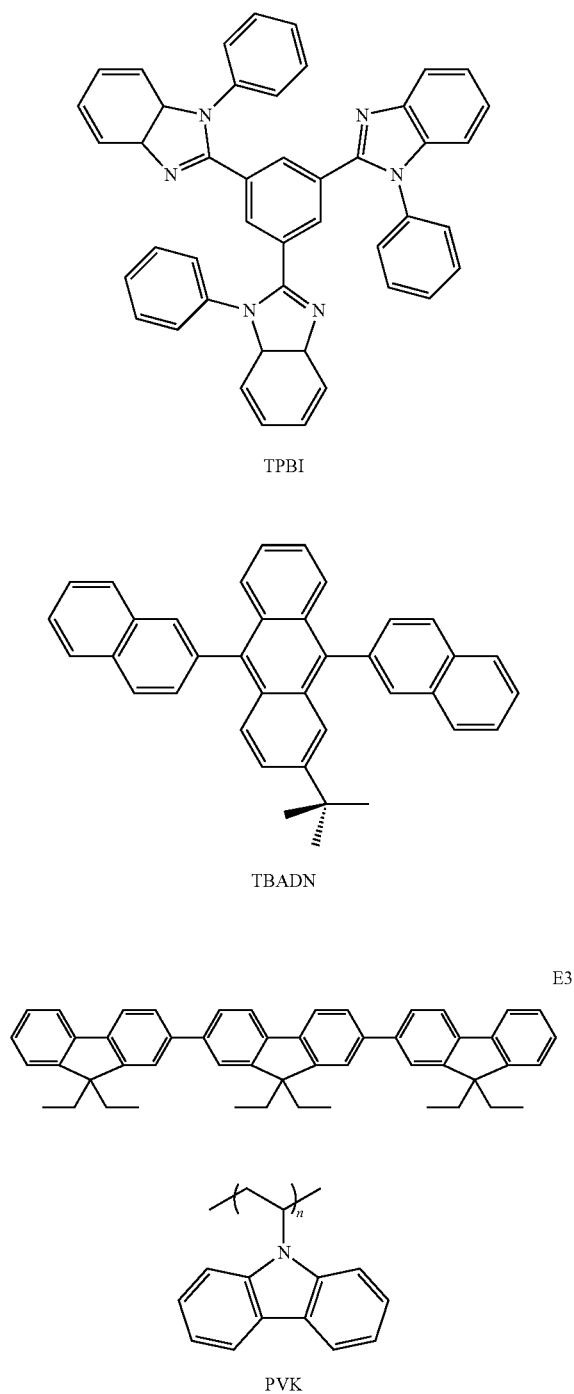

TPBI

TBADN

E3

PVK

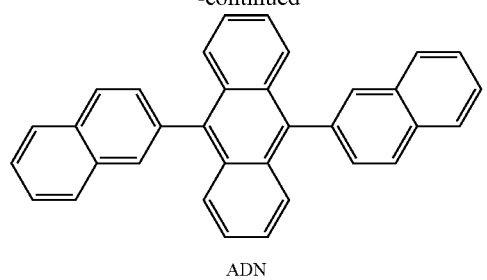
ADN
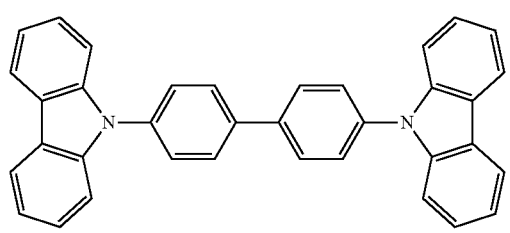
CBP
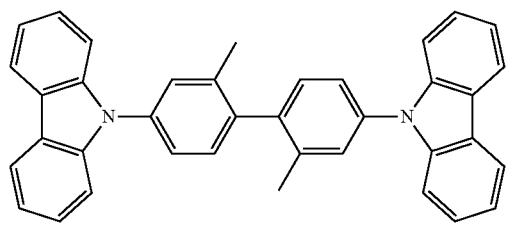
dmCBP
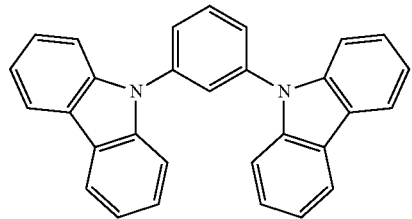
501
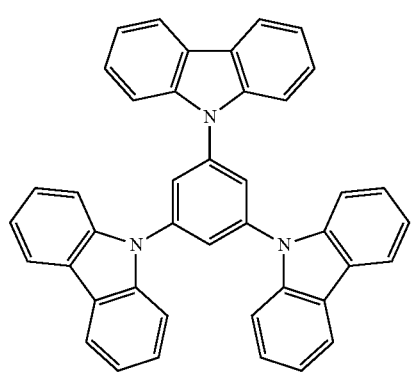
502
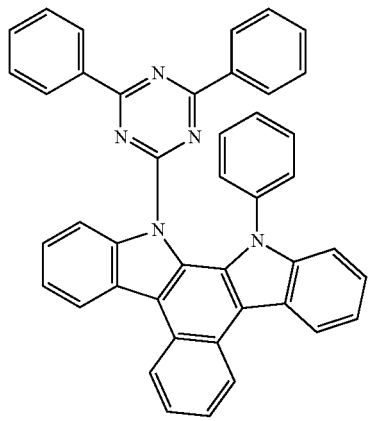
503
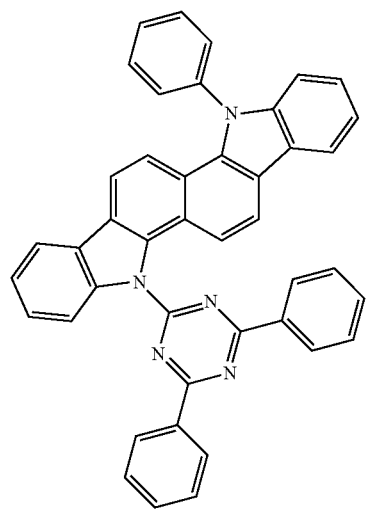
504
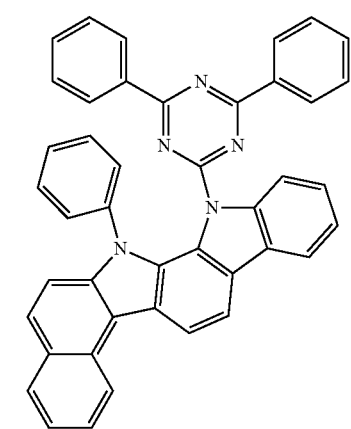
505

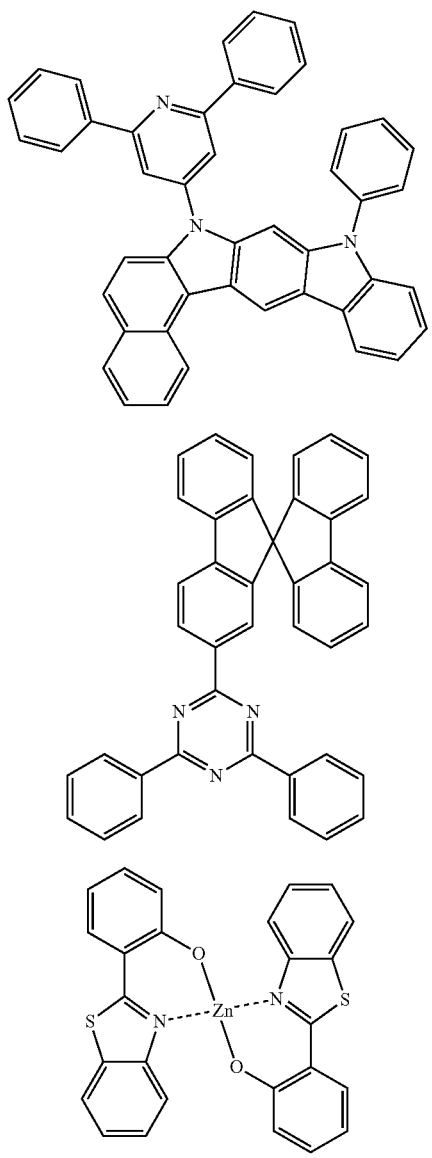

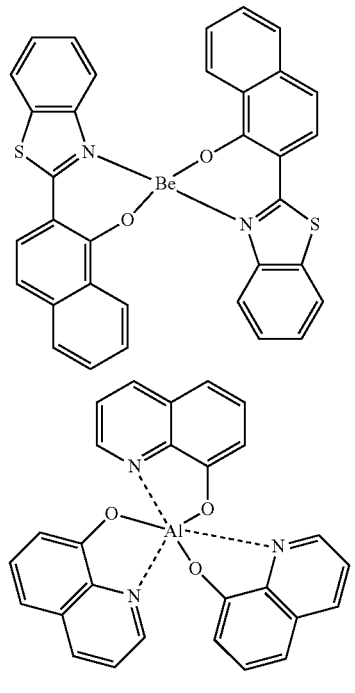

Alq3

Alternatively, the host may include at least one compound selected from an anthracene-based compound represented by Formula 400 and an anthracene-based compound represented by Formula 401.

The organic light-emitting diode may include a blue sub-pixel that emits blue light, a green sub-pixel that emits green light, and a red sub-pixel that emits red light. The blue sub-pixel may include a blue emission layer that emits blue light, and the blue emission layer may include the amine-based compound represented by Formula 1.

Also, the blue emission layer may further include one or more of the compounds illustrated below as the blue dopant, but other materials may further be included in the blue emission layer.

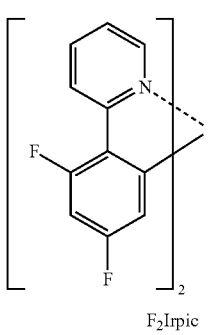

F₂Irpic

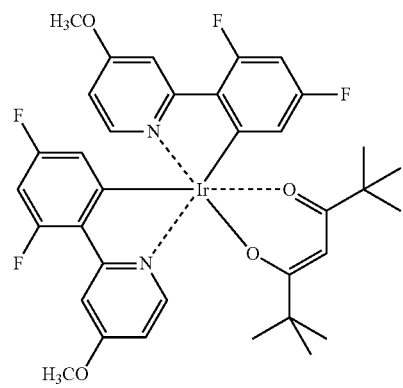

(F₂ppy)₂Ir(tmd)

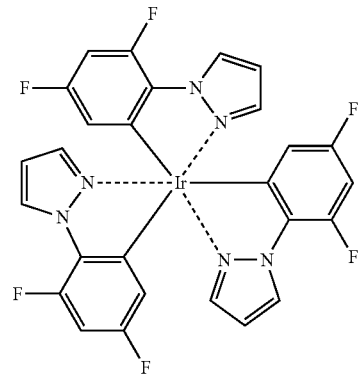

Ir(dfppz)₃

121 122
-continued
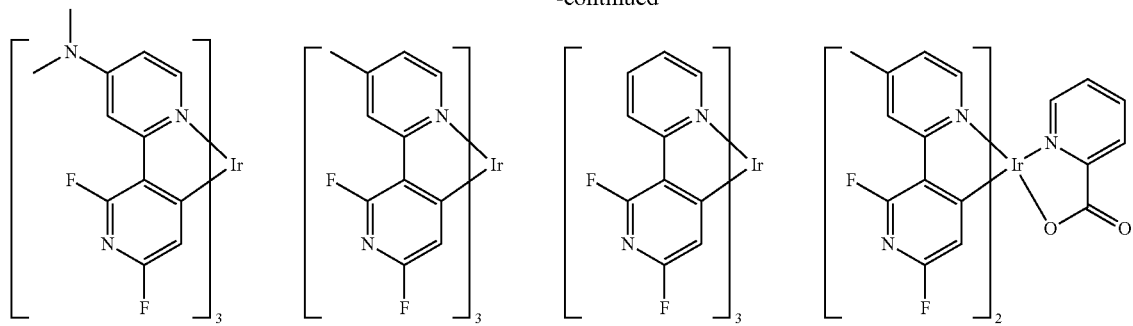
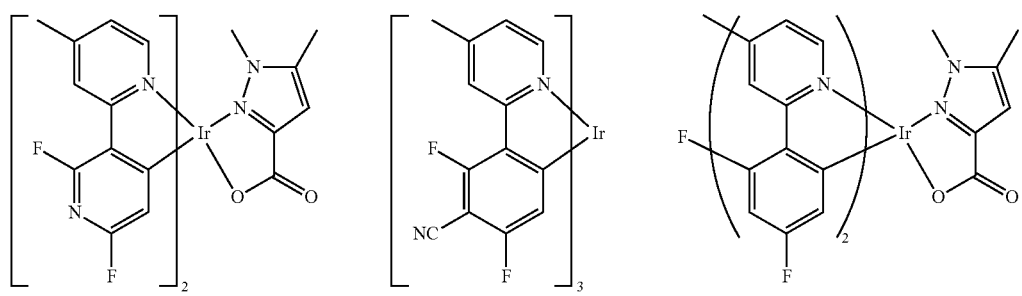
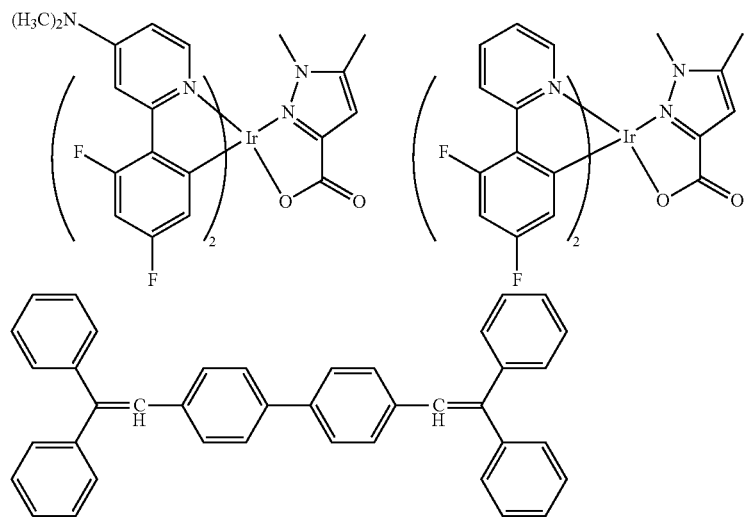
DPVBi
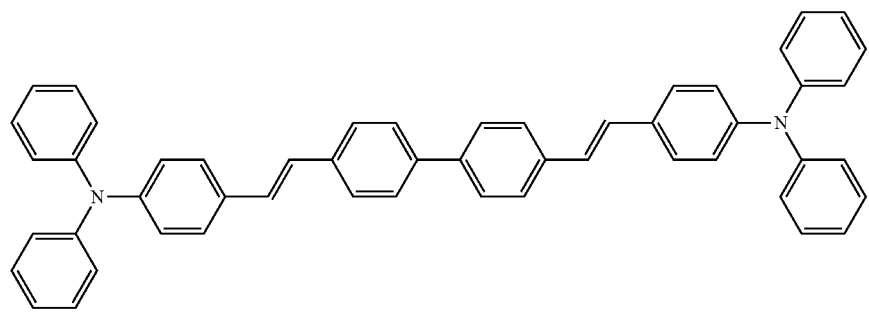
DPAVBi

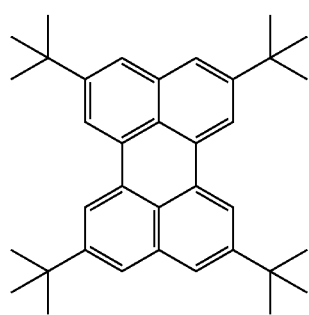
TBPe
For example, the red sub-pixel may include a red emission layer, and the red emission layer may include as a red dopant, one or more of the compounds illustrated below, but other materials may instead be included in the red emission layer. Also, as the red dopant, DCM or DCJTB may be used.
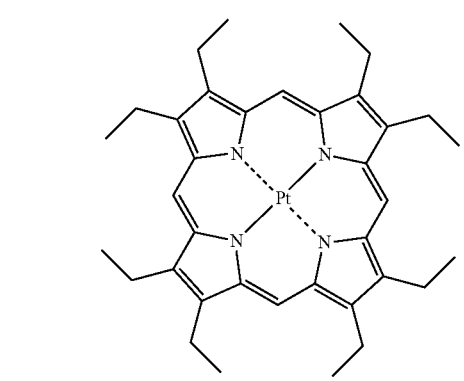
PtOEP
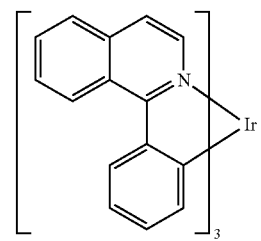
Ir(piq)₃
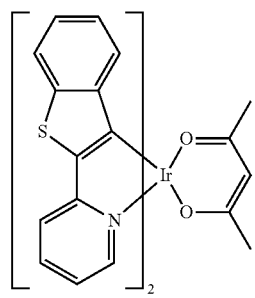
Btp₂Ir(acac)
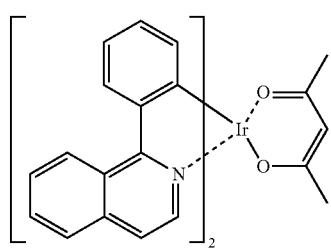
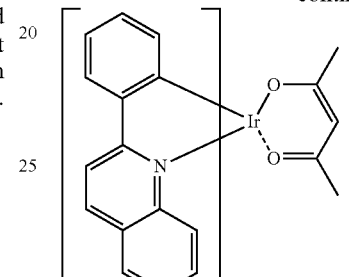
Ir(pq)₂(acac)
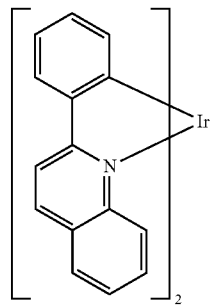
Ir(2-phq)₃
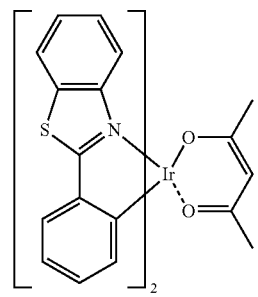
Ir(BT)₂(acac)
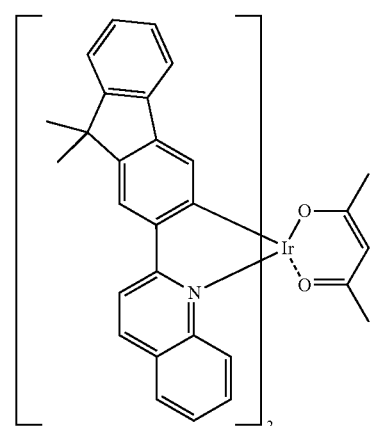
Ir(flq)₂(acac)

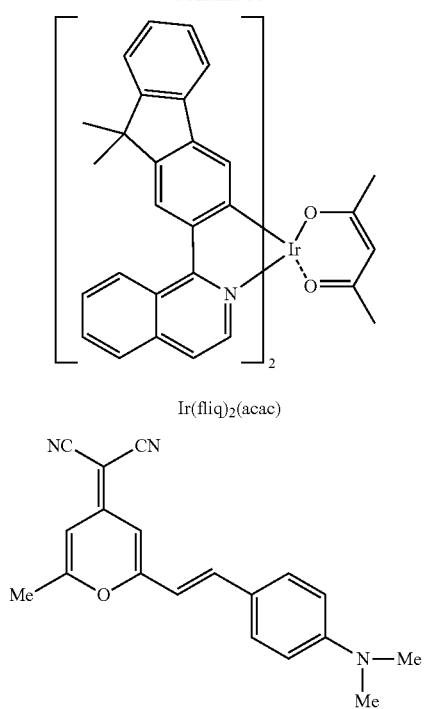

Ir(fliq)₂(acac)

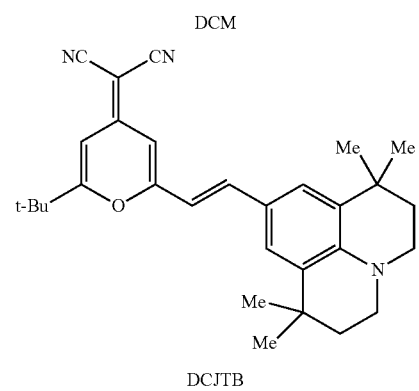

DCM

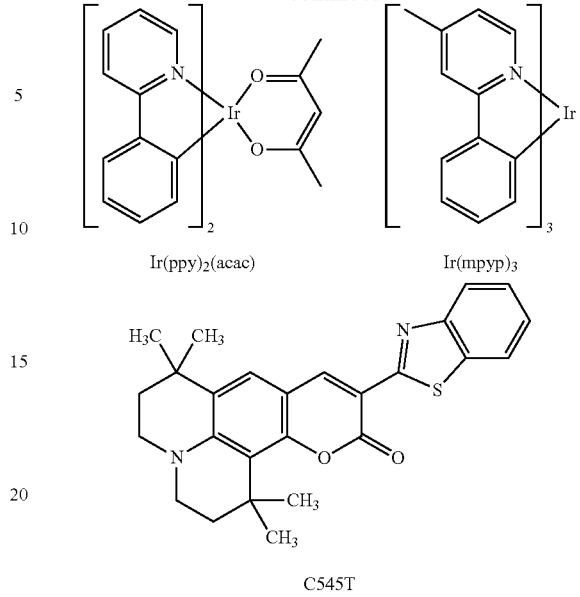

Ir(ppy)₂(acac)        Ir(mpyp)₃

C545T

Also, other examples of dopants that may be included in the emission layer include the Pt-complexes depicted below, but the dopant is not limited thereto.

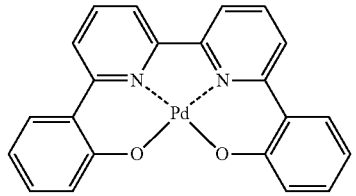

D1

DCJTB

Also, the green sub-pixel may include a green emission layer, and the green emission layer may include as a green dopant, one or more of the compounds illustrated below, but other materials may instead be included in the green emission layer. Also, as the green dopant, C545T below may be used.

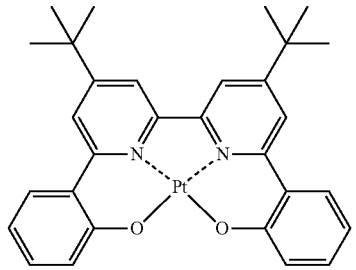

D2

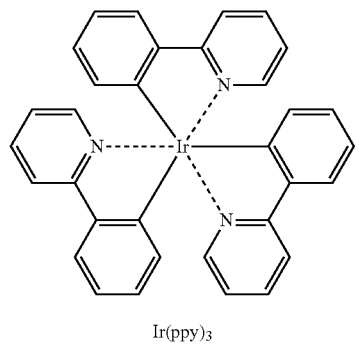

Ir(ppy)₃

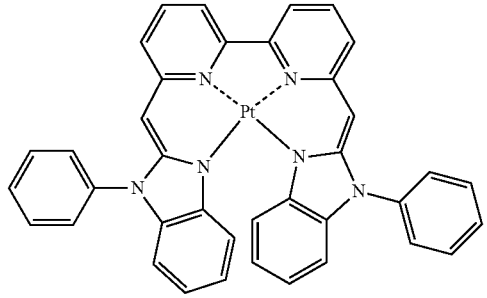

D3

D4 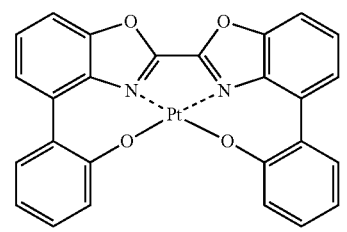
D5 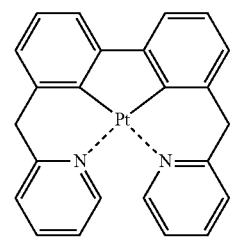
D6 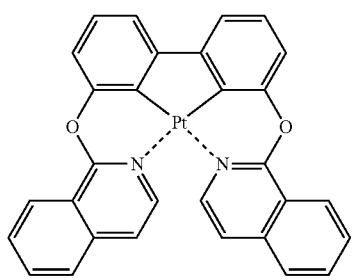
D7 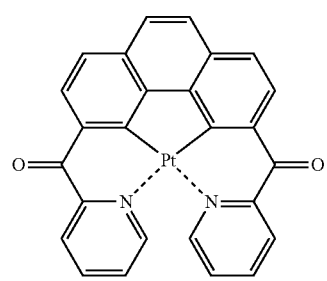
D8 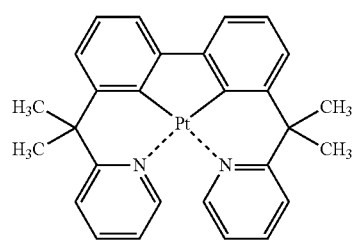
D9 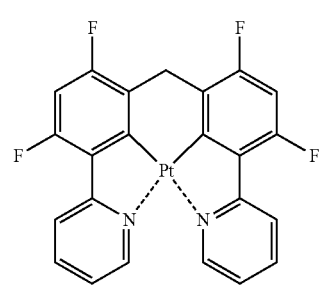
D10 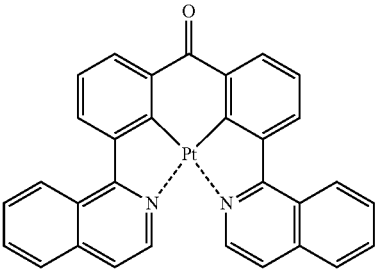
D11 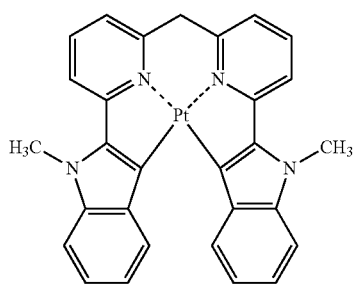
D12 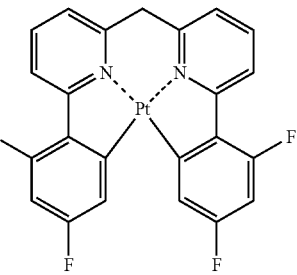
D13 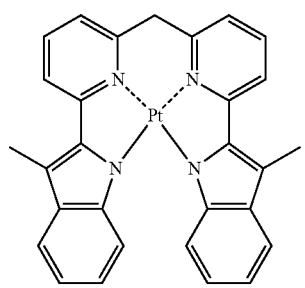
D14 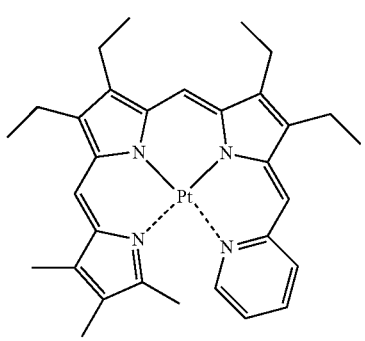

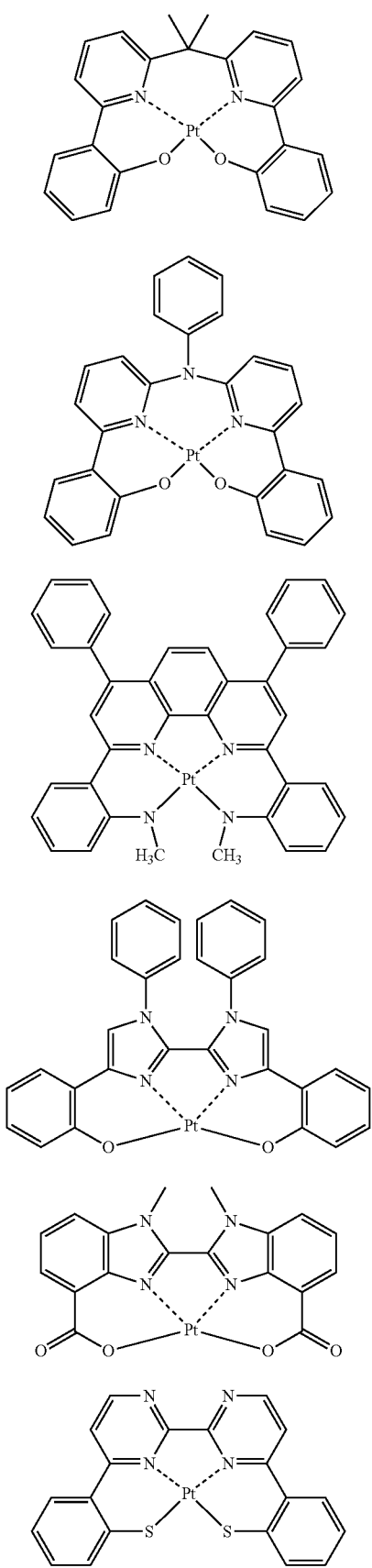
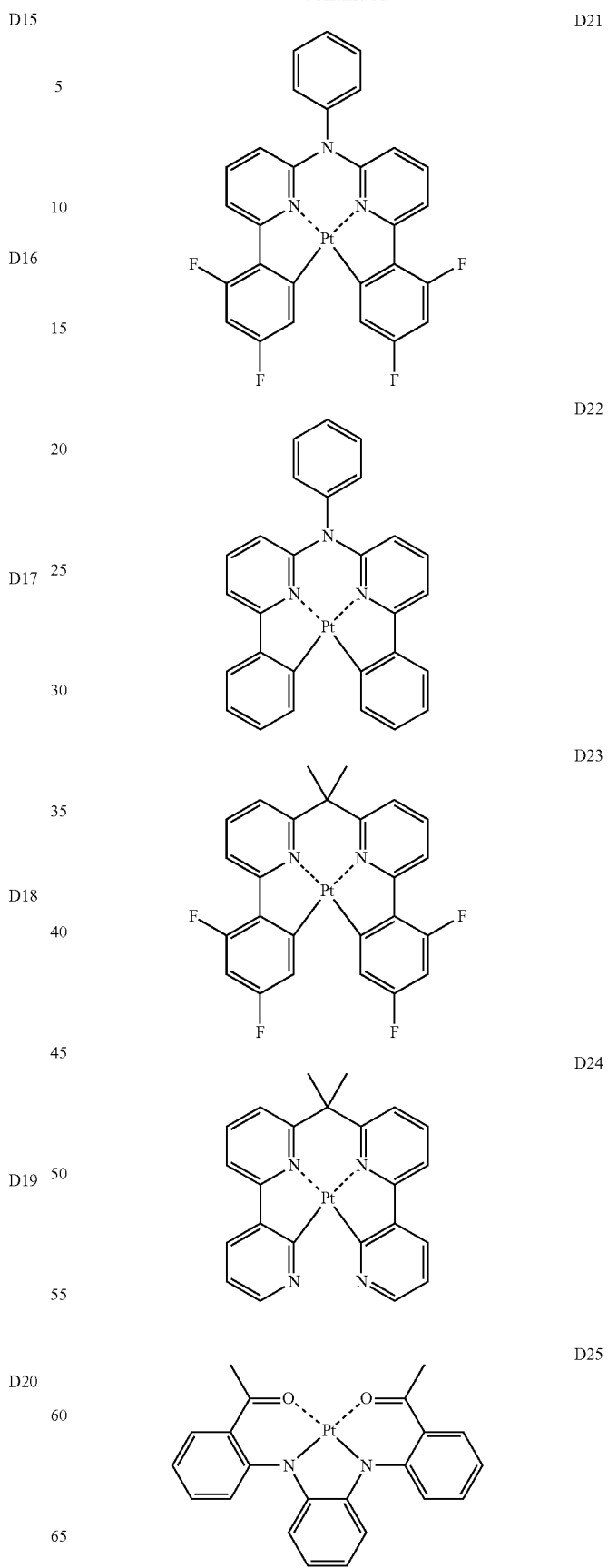

D26 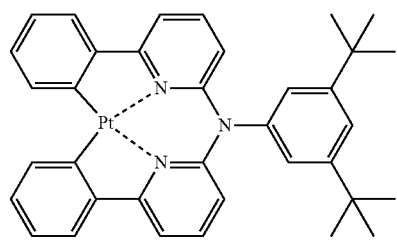
D27 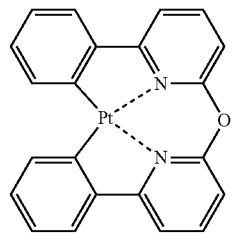
D28 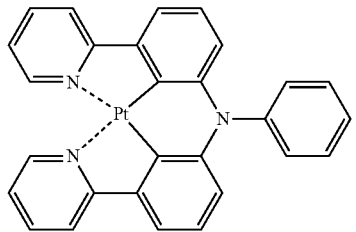
D29 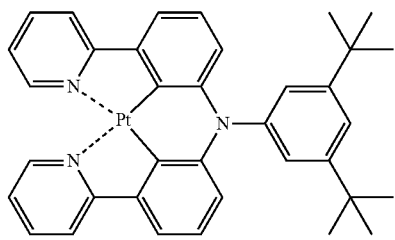
D30 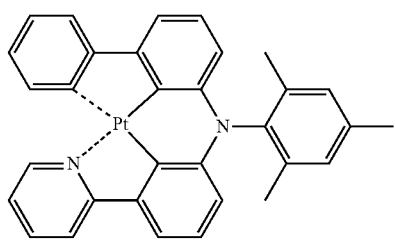
D31 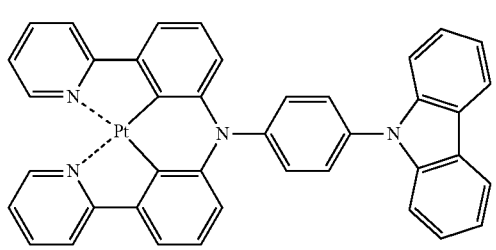
D32 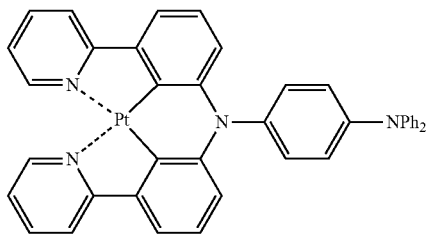
D33 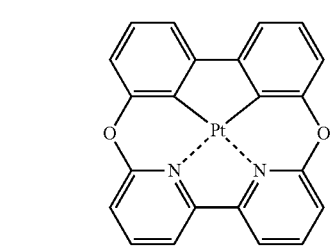
D34 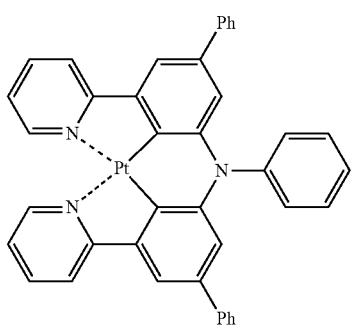
D35 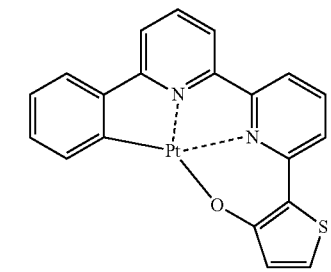
D36 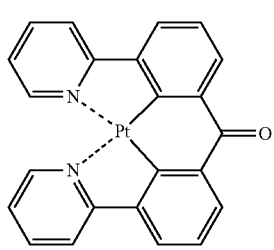

D37 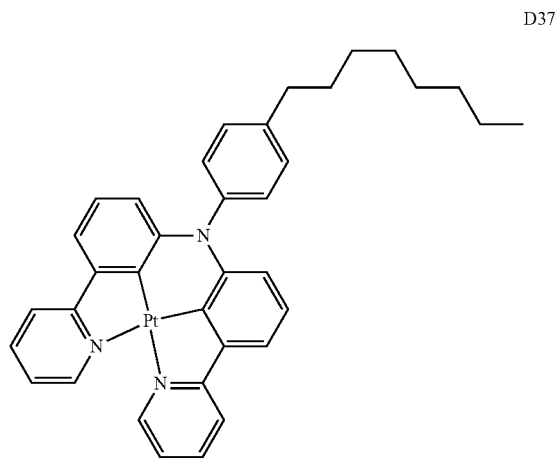
D38 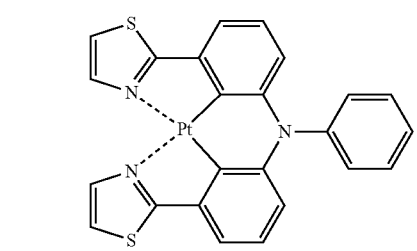
D39 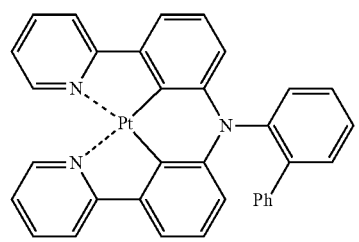
D40 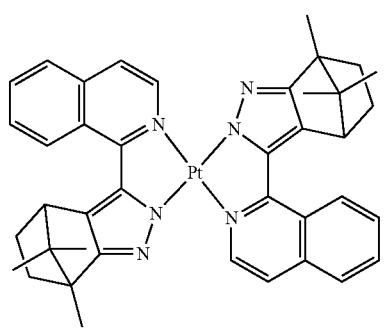
D41 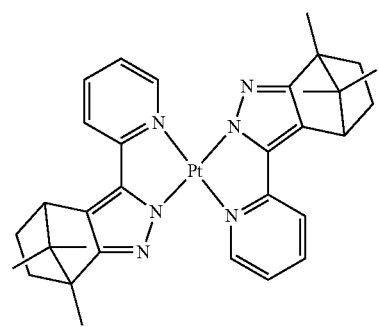
D42 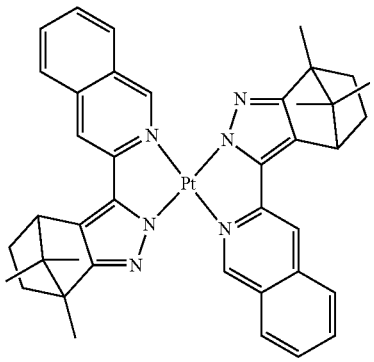
D43 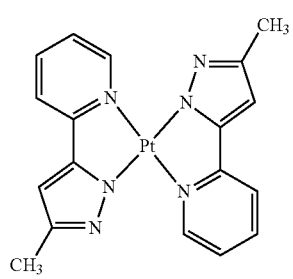
D44 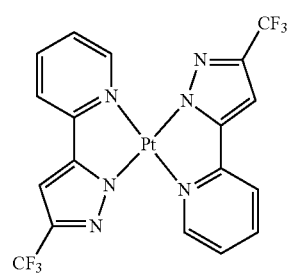
D45 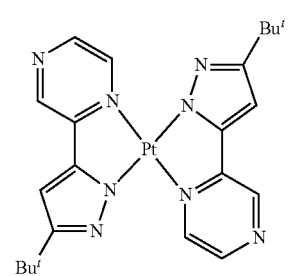
D46 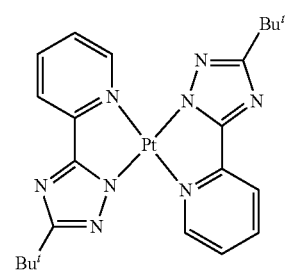

-continued

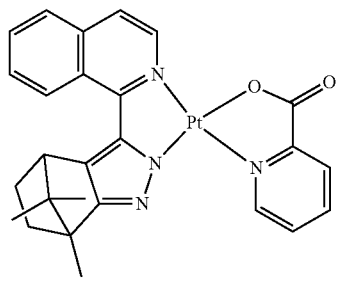
D47

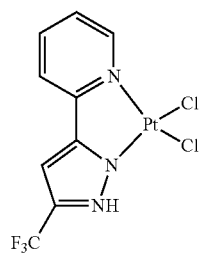
D48

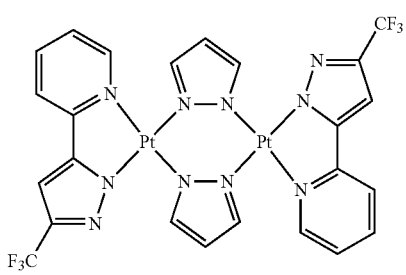
D49

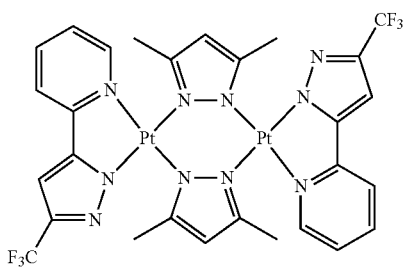
D50

Also, other examples of the dopant included in the emission layer include the Os-complexes depicted below, but the dopant is not limited thereto:

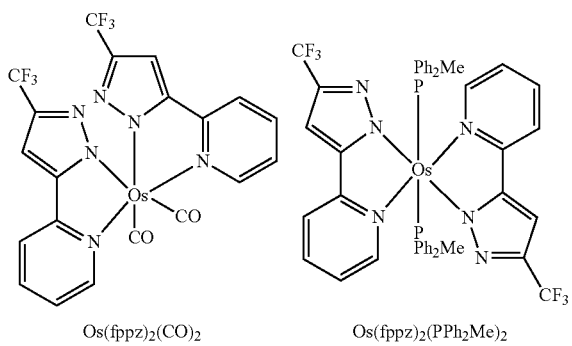

Os(fppz)₂(CO)₂    Os(fppz)₂(PPh₂Me)₂

-continued

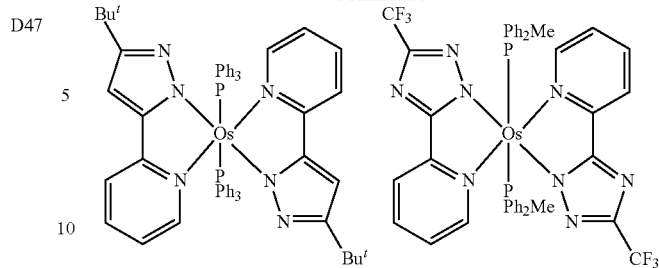

Os(bppz)₂(PPh₃)₂    Os(fptz)₂(PPh₂Me)₂

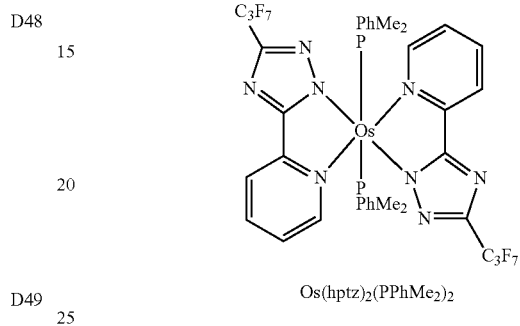

Os(hptz)₂(PPhMe₂)₂

When the emission layer includes a host and a dopant, the amount of the dopant may be from about 0.01 to about 15 parts by weight based on 100 parts by weight of the host. However, the amount of the dopant is not limited thereto.

The emission layer may have a thickness of about 100 Å to about 1000 Å, for example, a thickness of about 100 Å to about 600 Å. When the thickness of the emission layer is within these ranges, the emission layer may have good luminescence characteristics without a substantial increase in driving voltage.

Then, an electron transport layer (ETL) may be formed on the emission layer by any one of various methods, such as vacuum deposition, spin coating, casting, etc. When the electron transport layer is formed by vacuum deposition or spin coating, the deposition or coating conditions may be similar to those described above with respect to the formation of the hole injection layer, although the deposition or coating conditions may vary according to the material used to form the emission layer.

The material for forming the electron transport layer may be any material that stably transports electrons injected from an electron injection electrode (e.g., cathode), and such a material may be chosen from known electron transport materials. Examples of electron transport materials include a quinoline derivative, such as tris(8-quinolinolate)aluminum ($Alq_3$), TAZ, BAlq, beryllium bis(benzoquinolin-10-olate) ($Bebq_2$), ADN, Compound 201, and Compound 202, but are not limited thereto.

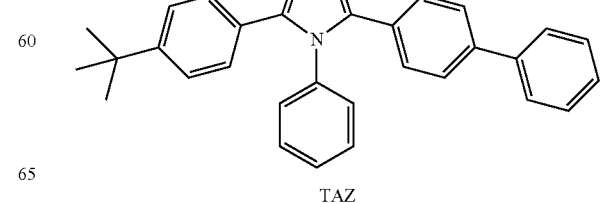

TAZ

<Compound 201>

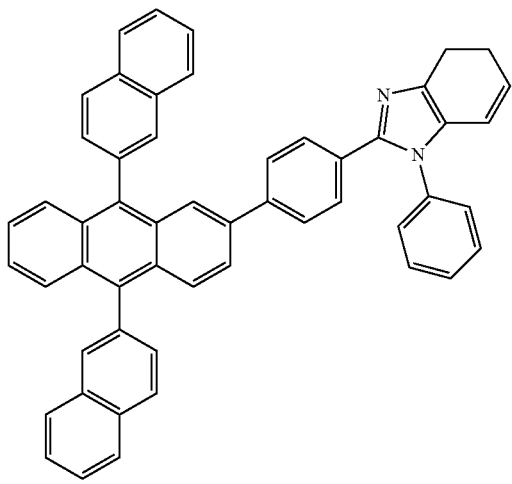

<Compound 202>

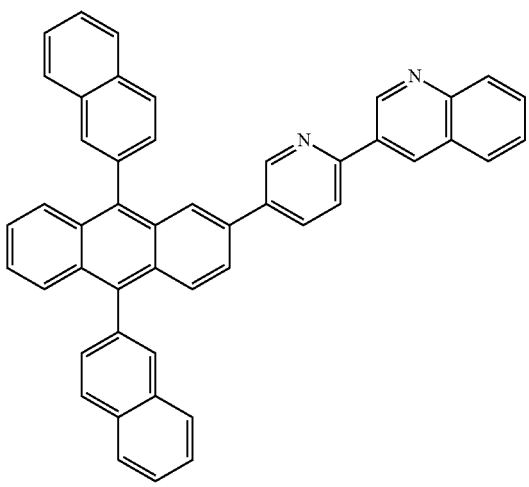

BCP

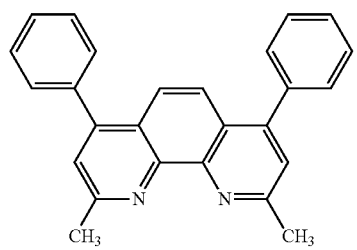

<Compound 203>

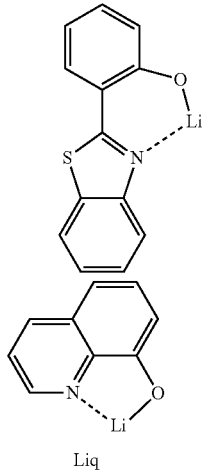

Liq

The electron transport layer may have a thickness of about 100 Å to about 1000 Å, for example, a thickness of about 150 Å to about 500 Å. When the thickness of the electron transport layer is within the above ranges, the electron transport layer may have satisfactory hole transport characteristics without a substantial increase in driving voltage.

Also, the electron transport layer may include, in addition to a known electron transport organic compound, a metal-containing material.

The metal-containing material may include a Li complex. Nonlimiting examples of the Li complex are lithium quinolate (Liq) and Compound 203 below.

Also, a material that allows electron to be easily injected from an anode may be deposited on the electron transport layer to form an electron injection layer (EIL), and the material is not particularly limited.

The material used to form the electron injection layer may be any one of various materials, such as LiF, NaCl, CsF, $Li_2O$, BaO, or the like. Deposition conditions for forming the electron injection layer may be similar to those described above with respect to formation of the hole injection layer, although the deposition or coating conditions may vary according to the material used to form the emission layer.

The electron injection layer may have a thickness of about 1 Å to about 100 Å, for example, a thickness of about 3 Å to about 90 Å. When the thickness of the electron injection layer is within the above ranges, the electron injection layer may have satisfactory hole injection characteristics without a substantial increase in driving voltage.

A second electrode 17 is formed on the organic layer 15. The second electrode may be a cathode (i.e., an electron injection electrode). In this case, as a metal for forming the second electrode, a metal, alloy, electrically conductive compound, or mixture thereof that has a low work function may be used. For example, lithium (Li), magnesium (Mg), aluminum (Al), aluminum-lithium (Al—Li), calcium (Ca), magnesium-indium (Mg—In), magnesium-silver (Mg—Ag), or the like may be used to form a thin film for use as a reflective electrode, a semi-transparent electrode, or a transparent electrode. Also, to form a top emission type light-emitting diode, ITO or IZO may be used to form a transparent electrode. When the organic light-emitting diode is used for a large full-color display, the second electrode 17 (cathode) of the organic light-emitting diode may be a reflective electrode, but is not limited thereto.

Above, the organic light-emitting diode has been described with reference to the FIGURE, but is not limited thereto.

Also, when the emission layer includes a phosphorescent dopant, a hole blocking layer (HBL) may be formed between the hole transport layer and the emission layer, or between the H-functional layer and the emission layer, by vacuum deposition, spin coating, casting, LB deposition, etc. so as to prevent diffusion of triplet excitons or holes into the electron transport layer. When the hole blocking layer is formed by vacuum deposition or spin coating, the deposition or coating conditions may be similar to those described above with respect to the formation of the hole injection layer, although the deposition or coating conditions may vary according to the material that is used to form the HBL. In this regard, a known hole blocking material may be used, and examples thereof include an oxadiazole derivative, a triazole derivative, a phenanthroline derivative, or the like. For example, BCP (below) may be used to form the hole blocking layer.

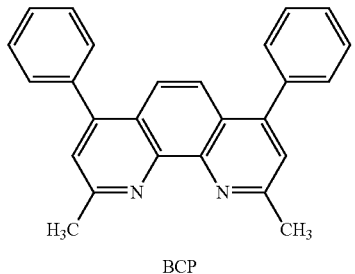 [SMILES: Cc1cc(-c2ccccc2)c2ccc3c(-c4ccccc4)cc(C)nc3c2n1 ; "BCP"]

BCP

The hole blocking layer may have a thickness of about 20 Å to about 1000 Å, for example, a thickness of about 30 Å to about 300 Å. When the thickness of the hole blocking layer is within these ranges, the hole blocking layer may have good hole blocking characteristics without a substantial increase in driving voltage.

The organic light-emitting diode may be used in a full color display apparatus, lamp, etc. For example, the organic light-emitting diode may be a full color display apparatus.

Accordingly, an organic light-emitting apparatus according to an embodiment of the present invention includes: a substrate including a first sub-pixel, a second sub-pixel, and a third sub-pixel; a first electrode formed in each of the first sub-pixel, second sub-pixel and third sub-pixel of the substrate; a second electrode that faces the first electrodes and is a common electrode shared by the first sub-pixel, the second sub-pixel, and the third sub-pixel; a first emission layer that is formed between the first electrode of the first sub-pixel and the second electrode and that emits a first color light; a second emission layer that is formed between the first electrode of the second sub-pixel and the second electrode and that emits a second color light; and a third emission layer that is formed between the first electrode of the third sub-pixel and the second electrode and that emits a third color light. The first emission layer includes one or more of the amine-based compounds described above. The first electrode is a transparent electrode or a semi-transparent electrode, and the second electrode is a reflective electrode.

A mixed light of the first color light, the second color light, and the third color light of the organic light-emitting apparatus may be white light. Accordingly, the organic light-emitting apparatus may be a full color display apparatus. The first color light may be blue light. Also, the second color light may be green light, and the third color light may be red light.

The first emission layer of the organic light-emitting apparatus includes the amine-based compound of Formula 1. Due to the inclusion of the amine-based compound, the emitted first color light (blue light) may have good color purity characteristics (for example, a y color coordinate of 1.0 or less) that satisfies the NTSC or sRGB standards. Accordingly, the organic light-emitting apparatus may be used as a large high-quality TV.

The organic light-emitting apparatus may be a bottom emission type organic light-emitting apparatus in which the first electrode is a transparent electrode or a semi-transparent electrode, and the second electrode is a reflective electrode.

The organic light-emitting apparatus may be a top emission type organic light-emitting apparatus in which the first electrode is a reflective electrode, and the second electrode is a transparent electrode or a semi-transparent electrode.

The organic light-emitting apparatus includes the amine-based compound of Formula 1. Due to the inclusion of the amine-based compound, blue light having good color purity characteristics (for example, a y color coordinate of 1.0 or less) that satisfies the sRGB standard may be emitted. Accordingly, a complicated resonance structure that compensates for color purity, such as blue light, is not needed, and thus, manufacturing costs may be reduced.

The full color display may be used in a television (TV), a personal computer monitor, a mobile communication terminal, an MP3 player, a navigation device for use in vehicles, or the like.

The unsubstituted $C_1$-$C_{60}$ alkyl group (or $C_1$-$C_{60}$ alkyl group) used herein may be, for example, a linear or branched alkyl group having 1 to 60 carbon atoms, and examples thereof include methyl, ethyl, propyl, isobutyl, sec-butyl, pentyl, iso-amyl, and hexyl. The substituted $C_1$-$C_{60}$ alkyl group refers to a case in which one or more hydrogen atoms of the unsubstituted $C_1$-$C_{60}$ alkyl group are substituted with one selected from deuterium; —F; —Cl; —Br; —I; —CN; a hydroxyl group; a nitro group; an amino group; an amidino group; a hydrazine; a hydrazone; a carboxylic acid group or salt thereof; a sulfonic acid group or salt thereof; a phosphoric acid group or salt thereof; a $C_1$-$C_{60}$ alkyl group; a $C_1$-$C_{60}$ alkoxy group; a $C_2$-$C_{60}$ alkenyl group; a $C_2$-$C_{60}$ alkynyl group; a $C_1$-$C_{60}$ alkyl group, $C_1$-$C_{60}$ alkoxy group, $C_2$-$C_{60}$ alkenyl group, or $C_2$-$C_{60}$ alkynyl group substituted with at least one selected from deuterium, —F, —Cl, —Br, —I, —CN, a hydroxyl group, a nitro group, an amino group, an amidino group, a hydrazine, a hydrazone, a carboxylic acid group or salt thereof, a sulfonic acid group or salt thereof, or a phosphoric acid group or salt thereof; a $C_3$-$C_{60}$ cycloalkyl group; a $C_5$-$C_{60}$ aryl group; a $C_2$-$C_{60}$ heteroaryl group; a $C_5$-$C_{60}$ aralkyl group; a $C_5$-$C_{60}$ aryloxy group; or a $C_3$-$C_{60}$ cycloalkyl group, $C_5$-$C_{60}$ aryl group, $C_2$-$C_{60}$ heteroaryl group, $C_5$-$C_{60}$ aralkyl group, or $C_5$-$C_{60}$ aryloxy group substituted with at least one selected from deuterium, —F, —Cl, —Br, —I, —CN, a hydroxyl group, a nitro group, an amino group, an amidino group, a hydrazine, a hydrazone, a carboxylic acid group or salt thereof, a sulfonic acid group or salt thereof, a phosphoric acid group or salt thereof, a $C_1$-$C_{60}$ alkyl group, a $C_1$-$C_{60}$ alkoxy group, a $C_2$-$C_{60}$ alkenyl group, a $C_2$-$C_{60}$ alkynyl group, a $C_5$-$C_{60}$ aryl group, or a $C_2$-$C_{60}$ heteroaryl group.

The unsubstituted $C_1$-$C_{60}$ alkoxy group (or $C_1$-$C_{60}$ alkoxy group) used herein may have a chemical structure of —OA (where A is an unsubstituted $C_1$-$C_{60}$ alkyl group as described above), and examples thereof include methoxy, ethoxy, and isopropyloxy. One or more hydrogen atoms of the alkoxy groups may be substituted with any one of the substituents discussed above with respect to the substituted $C_1$-$C_{60}$ alkyl group.

The unsubstituted $C_2$-$C_{60}$ alkenyl group (or $C_2$-$C_{60}$ alkenyl group) used herein refers to a case in which at least one carbon-carbon double blond exists at the center or at a terminal end of the unsubstituted $C_2$-$C_{60}$ alkyl group. Examples thereof include an ethenyl group, a propenyl group, and a butenyl group. One or more hydrogen atoms of the unsubstituted $C_2$-$C_{60}$ alkenyl group may be substituted with any one of the substituents discussed above with respect to the substituted $C_1$-$C_{60}$ alkyl group.

The unsubstituted $C_2$-$C_{60}$ alkynyl group (or $C_2$-$C_{60}$ alkynyl group), as used herein, refers to a case in which at least one carbon-carbon triple blond exists at the center or at a terminal end of the unsubstituted $C_2$-$C_{60}$ alkyl group. Examples thereof include ethynyl, and propynyl. One or more hydrogen atoms of the alkynyl groups may be substituted with any one of the substituents discussed above with respect to the substituted $C_1$-$C_{60}$ alkyl group.

The unsubstituted $C_5$-$C_{60}$ aryl group used herein refers to a monovalent group that includes one or more aromatic rings and has 5 to 60 carbon atoms, and the unsubstituted $C_5$-$C_{60}$ arylene group refers to a divalent group that includes one or more aromatic rings and has 5 to 60 carbon atoms. When the aryl group or the arylene group includes two or more rings, the two or more rings may be fused with each other. One or more hydrogen atoms of the aryl group or arylene group may be substituted with any one of the substituents discussed above with respect to the substituted $C_1$-$C_{60}$ alkyl group.

Examples of the substituted or unsubstituted $C_5$-$C_{60}$ aryl group include a phenyl group, a $C_1$-$C_{10}$alkylphenyl group (for example, ethylphenyl group), a $C_1$-$C_{10}$alkylbiphenyl group (for example, ethylbiphenyl group), a halophenyl group (for example, o-, m- and p-fluorophenyl group, a dichlorophenyl group), a dicyanophenyl group, a trifluoromethoxyphenyl group, an o-, m-, and p-toryl group, an o-, m- and p-cumenyl group, a mesityl group, a phenoxy phenyl group, a (α,α-dimethylbenzene)phenyl group, (N,N'-dimethyl)aminophenyl group, (N,N'-diphenyl)aminophenyl group, pentalenyl group, indenyl group, naphthyl group, halonaphthyl group (for example, fluoronaphthyl group), a $C_1$-$C_{10}$alkylnaphthyl group (for example, methylnaphthyl group), a $C_1$-$C_{10}$ alkoxynaphthyl group (for example, a methoxynaphthyl group), an anthracenyl group, an azulenyl group, a heptalenyl group, an acenaphthalenyl group, a phenalenyl group, a fluorenyl group, an anthraquinolyl group, a methylanthryl group, a phenanthryl group, a triphenylenyl group, a pyrenyl group, a chrysenyl group, ethylchrysenyl group, a pycenyl group, a perylenyl group, a chloroperylenyl group, a pentaphenyl group, a pentacenyl group, a tetraphenylenyl group, a hexaphenyl group, a hexacenyl group, a rubicenyl group, a coronenyl group, a trinaphthylenyl group, a heptaphenyl group, a heptacenyl group, a pyranthrenyl group, and an ovalenyl group. Examples of the substituted $C_5$-$C_{60}$ aryl group may be easily understood by reference to the examples of the unsubstituted $C_5$-$C_{60}$ aryl group and the substituents of the substituted $C_1$-$C_{60}$ alkyl group described above. Examples of the substituted or unsubstituted $C_5$-$C_{60}$ arylene group may be easily understood by reference to the examples of the substituted or unsubstituted $C_5$-$C_{60}$ aryl group.

The unsubstituted $C_2$-$C_{60}$ heteroaryl group, as used herein, refers to a monovalent group having a system including at least one aromatic ring having one or more hetero atoms selected from nitrogen (N), oxygen (O), phosphorous (P), and sulfur (S) with the residual ring atoms being carbon atoms. The unsubstituted $C_2$-$C_{60}$ heteroarylene group refers to a divalent group having a system including at least one aromatic ring having one or more hetero atoms selected from nitrogen (N), oxygen (O), phosphorous (P), and sulfur (S) with the residual ring atoms being carbon atoms. In this regard, when the heteroaryl group or heteroarylene group each include two or more rings, the two or more rings may be fused with each other. One or more hydrogen atoms of the heteroaryl group or the heteroarylene group may be substituted with any one of the substituents discussed above with respect to the substituted $C_1$-$C_{60}$ alkyl group.

Examples of the unsubstituted $C_2$-$C_{60}$ heteroaryl group include a pyrazolyl group, an imidazolyl group, an oxazolyl group, a thiazolyl group, a triazolyl group, a tetrazolyl group, an oxadiazolyl group, a pyridinyl group, a pyridazinyl group, a pyrimidinyl group, a triazinyl group, a carbazolyl group, an indolyl group, a quinolinyl group, an isoquinolinyl group, a benzoimidazolyl group, an imidazopyridinyl group, and an imidazopyrimidinyl group. Examples of the unsubstituted $C_2$-$C_{60}$heteroarylene group may be easily understood by reference to the examples of the substituted or unsubstituted $C_2$-$C_{60}$arylene group.

The substituted or unsubstituted $C_5$-$C_{60}$ aryloxy group, as used herein, refers to —$OA_2$ (where $A_2$ is a substituted or unsubstituted $C_5$-$C_{60}$ aryl group, as defined above). The substituted or unsubstituted $C_5$-$C_{60}$ arylthio group is —$SA_3$ (where $A_3$ is an substituted or unsubstituted $C_5$-$C_{60}$ aryl group as defined above).

Hereinafter, an organic light-emitting diode according to an embodiment of the present invention is described with reference to Synthesis Examples and Examples. However, the organic light-emitting diode is not limited thereto.

Synthesis Example 1: Synthesis of Compound 2

Synthesis of Intermediate 2A

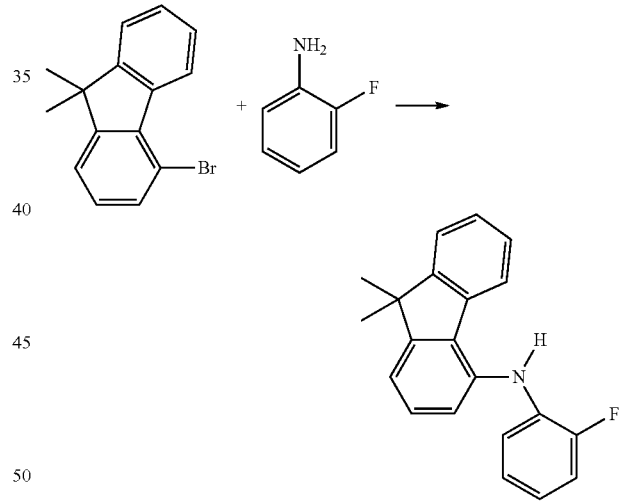

Intermediate 2A

Under a nitrogen atmosphere, 2.9 g (10.8 mmol) of 4-bromo-9,9-dimethyl-9H-fluorene, 1.2 g (10.8 mmol) of 1-fluoro-aniline, 120 mg (0.54 mol) of palladium acetate (Pd(OAc)$_2$), 432 mg (2.62 mmol) of tri-tert-butylphosphine (P(t-Bu)$_3$), and 3.0 g (33 mmol) of sodium t-butoxide were added to 200 ml of toluene, followed by refluxing for 12 hours. After the reaction was completed, the solvent was removed by evaporation, and then 1000 ml of methylene chloride and 1000 ml of water were separately added thereto for washing, and then an organic layer was collected, followed by drying with magnesium sulfate anhydride. Subsequently, recrystallization and silicagel chromatography were performed thereon to obtain 2.4 g of Intermediate 2A (Yield: 75%).

143
Synthesis of Compound 2

144
Synthesis Example 2: Synthesis of Compound 3

Synthesis of Intermediate 3A

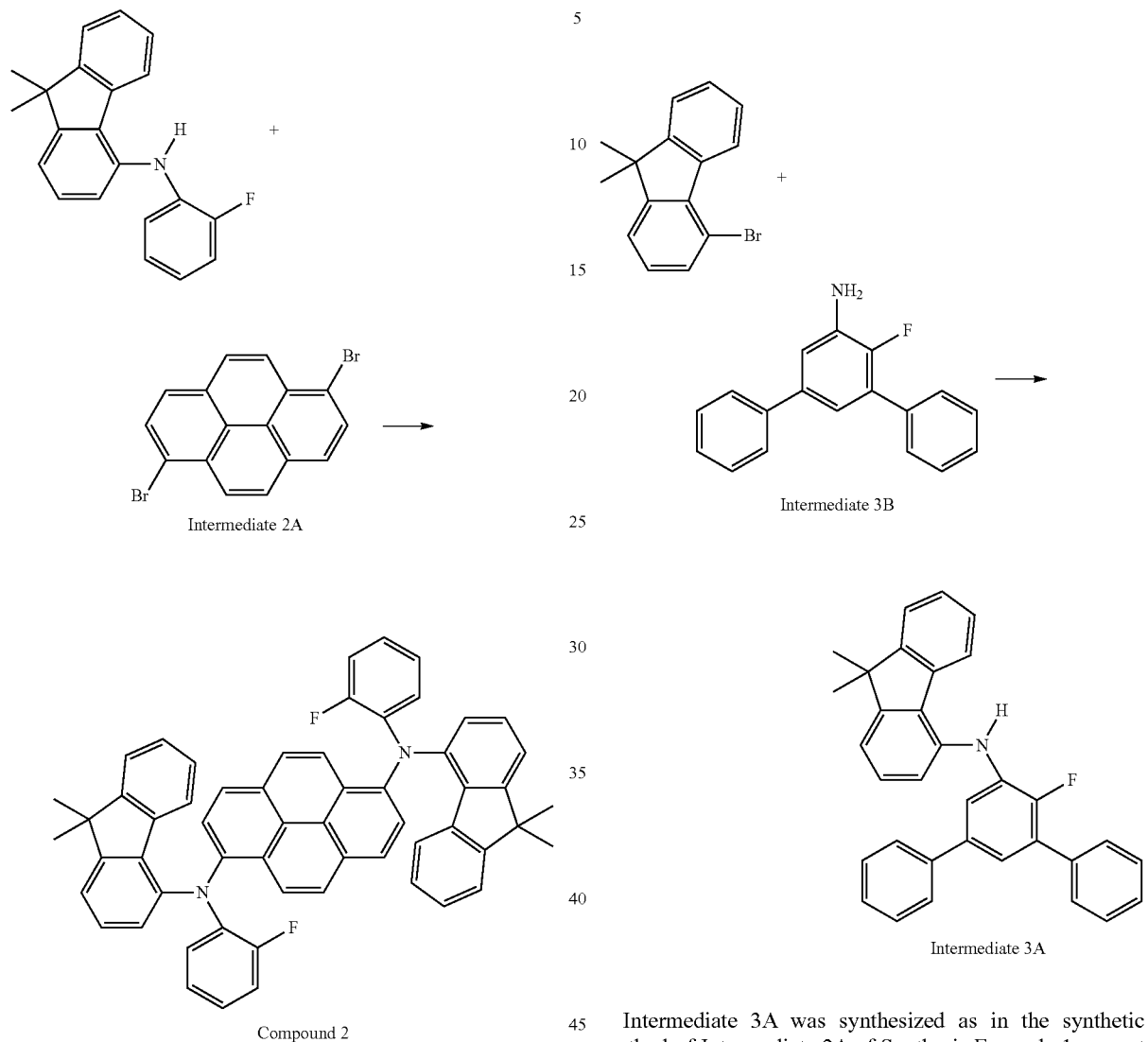

Intermediate 2A

Compound 2

Intermediate 3B

Intermediate 3A

Intermediate 3A was synthesized as in the synthetic method of Intermediate 2A of Synthesis Example 1, except that Intermediate 3B was used instead of 1-fluoro-aniline Under a nitrogen atmosphere, 2.1 g (7.2 mmol) of Intermediate 2A, 1.3 g (3.6 mmol) of 1,6-dibromopyrene, 40 mg (0.18 mol) of $Pd(OAc)_2$, 108 mg (0.54. mmol) of $P(t-Bu)_3$, and 1.0 g (10.9 mmol) of sodium t-butoxide were added to 100 ml of toluene, followed by refluxing for 12 hours. After the reaction was completed, the solvent was removed by evaporation, and then 1000 ml of methylene chloride and 1000 ml of water were separately added thereto for washing, and then an organic layer was collected, followed by drying with magnesium sulfate anhydride. Subsequently, recrystallization and silicagel chromatography were performed thereon to obtain 1.5 g of Compound 2 (Yield: 50%). The obtained compound was identified by NMR and MS.

H-NMR ($CDCl_3$, 300 MHz, ppm): 7.9 (m, 2H), 7.8-7.7 (m, 6H), 7.6-7.3 (m, 6H), 7.0-6.9 (m, 10H), 6.7-6.6 (m, 6H), 1.7 (s, 12H).

MS (MALDI-TOF) m/z: 804 [M]+.

Synthesis of Compound 3

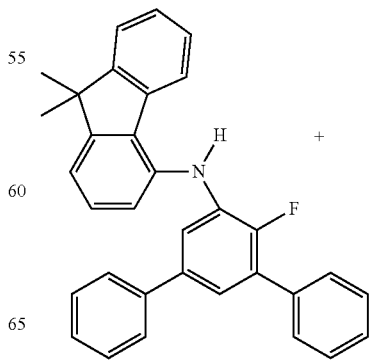

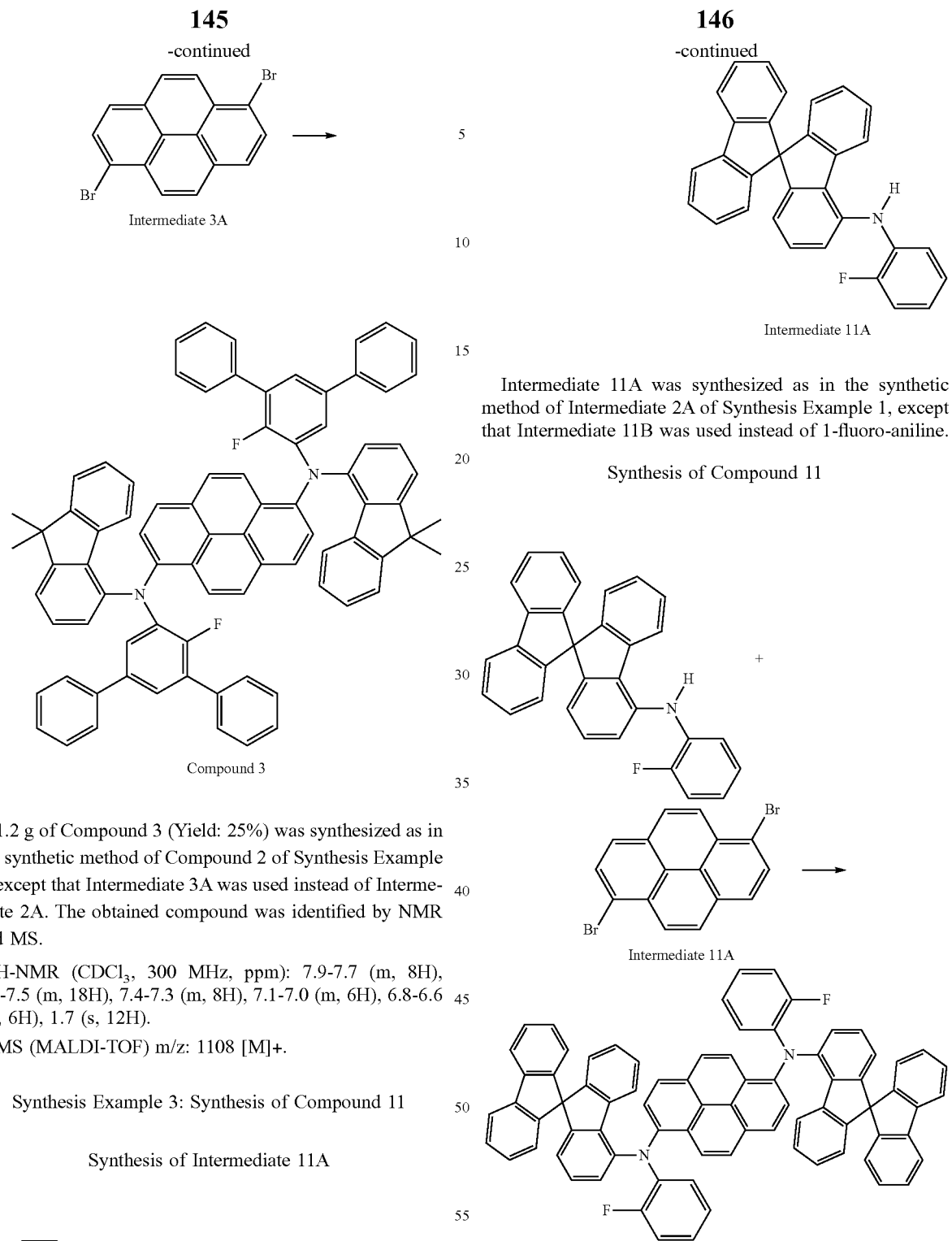

Compound 3

1.2 g of Compound 3 (Yield: 25%) was synthesized as in the synthetic method of Compound 2 of Synthesis Example 1, except that Intermediate 3A was used instead of Intermediate 2A. The obtained compound was identified by NMR and MS.

H-NMR (CDCl₃, 300 MHz, ppm): 7.9-7.7 (m, 8H), 7.6-7.5 (m, 18H), 7.4-7.3 (m, 8H), 7.1-7.0 (m, 6H), 6.8-6.6 (m, 6H), 1.7 (s, 12H).

MS (MALDI-TOF) m/z: 1108 [M]+.

Synthesis Example 3: Synthesis of Compound 11

Synthesis of Intermediate 11A

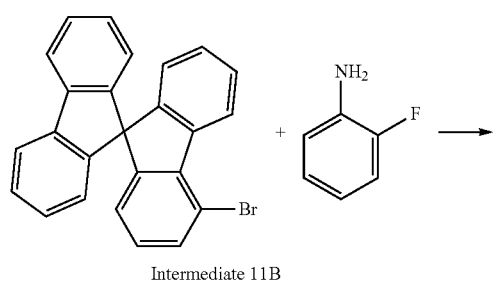

Intermediate 11B

Intermediate 11A was synthesized as in the synthetic method of Intermediate 2A of Synthesis Example 1, except that Intermediate 11B was used instead of 1-fluoro-aniline.

Synthesis of Compound 11

5 g of Compound 11 (Yield: 51%) was synthesized as in the synthetic method of Compound 2 of Synthesis Example 1, except that Intermediate 11A was used instead of Intermediate 2A. The obtained compound was identified by NMR and MS.

H-NMR (CDCl₃, 300 MHz, ppm): 7.9-7.8 (m, 12H), 7.5-7.2 (m, 18H), 7.0-6.9 (m, 10H), 6.6-6.5 (m, 6H).

MS (MALDI-TOF) m/z: 1048 [M]+.

Synthesis Example 4: Synthesis of Compound 18

Synthesis of Intermediate 18B

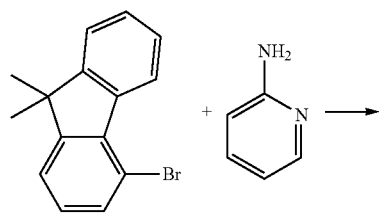

Intermediate 18B

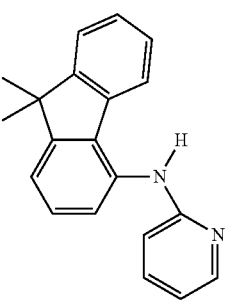

Intermediate 18B was synthesized as in the synthetic method of Intermediate 2A of Synthesis Example 1, except that 1-aminopyridine was used instead of 1-fluoro-aniline.

Synthesis of Intermediate 18A

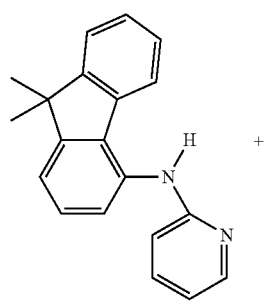

+

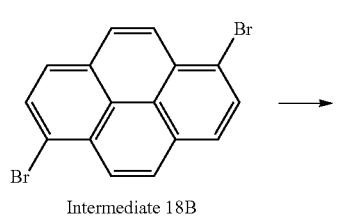

Intermediate 18B

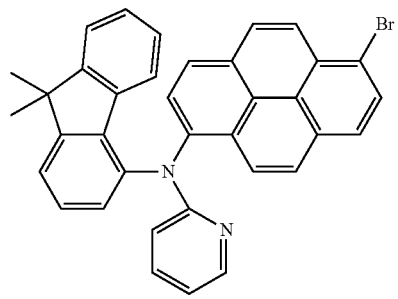

Intermediate 18A

Under a nitrogen atmosphere, 1.0 g (3.6 mmol) of Intermediate 18B, 1.3 g (3.6 mmol) of 1,6-dibromopyrene, 40 mg (0.18 mol) of Pd(OAc)$_2$, 108 mg (0.54. mmol) of P(t-Bu)$_3$, and 1.0 g (10.9 mmol) of sodium t-butoxide were added to 100 ml of toluene, followed by refluxing for 12 hours. After the reaction was completed, the solvent was removed by evaporation, and then 1000 ml of methylene chloride and 1000 ml of water were separately added thereto for washing, and then an organic layer was collected, followed by drying with magnesium sulfate. Subsequently, recrystallization and silicagel chromatography were performed thereon to obtain 1.0 g of Intermediate 18A (Yield: 50%).

Synthesis of Compound 18

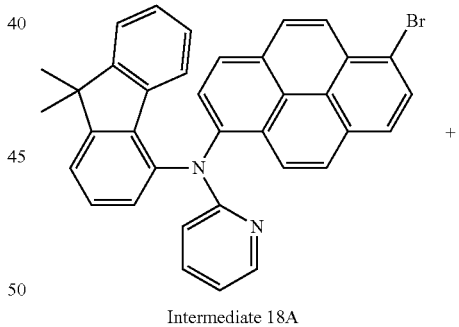

Intermediate 18A

+

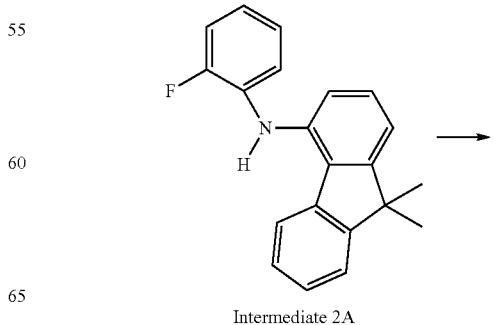

Intermediate 2A

-continued

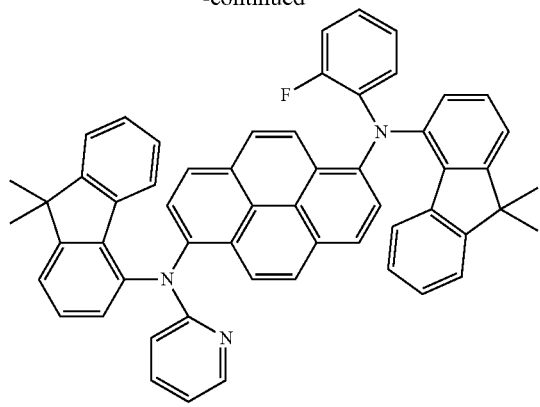

Compound 18

1.1 g of Compound 18 (Yield: 10%) was synthesized as in the synthetic method of Intermediate 18A, except that Intermediate 2A was used instead of Intermediate 18B and Intermediate 18A was used instead of 1,6-dibromopyrene. The obtained compound was identified by NMR and MS.

H-NMR (CDCl$_3$, 300 MHz, ppm): 8.1-7.9 (m, 4H), 7.7-7.6 (m, 8H), 7.4-7.3 (m, 4H), 7.0-6.9 (m, 8H), 6.7-6.6 (m, 6H), 1.7 (s, 12H).

MS (MALDI-TOF) m/z: 787 [M]+.

Synthesis Example 5: Synthesis of Compound 22

Synthesis of Intermediate 22B

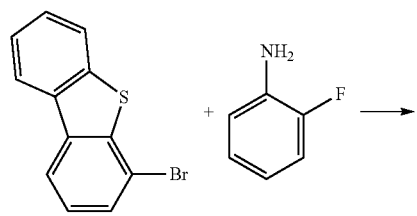

Intermediate 22B

Intermediate 22B was synthesized as in the synthetic method of Intermediate 2A of Synthesis Example 1, except that 4-bromodibenzo[b,d]thiophene was used instead of 4-bromo-9,9-dimethyl-9H-fluorene.

Synthesis of Intermediate 22A

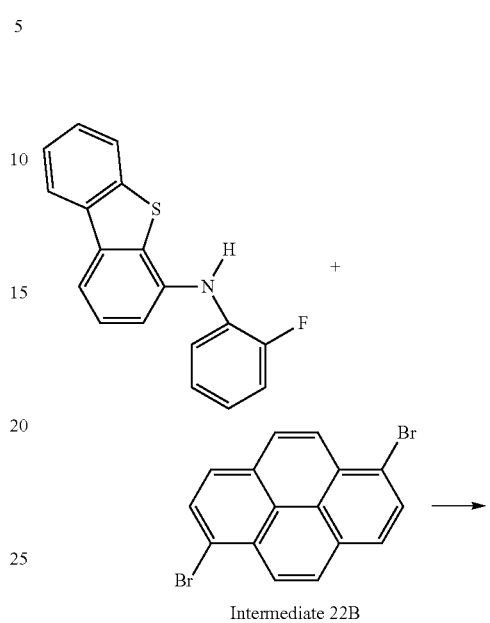

Intermediate 22B

Intermediate 22A

Intermediate 22A was synthesized as in the synthetic method of Intermediate 18A of Synthesis Example 4, except that Intermediate 22B was used instead of Intermediate 18B.

Synthesis of Compound 22

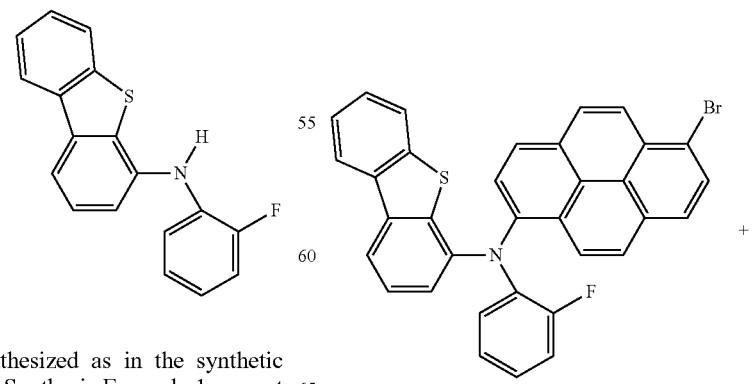

Intermediate 22A

-continued

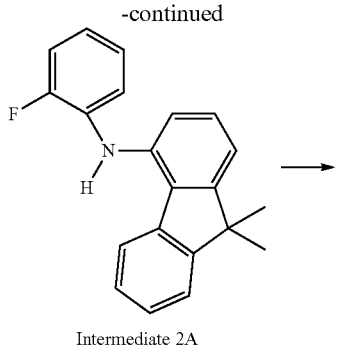

Intermediate 2A

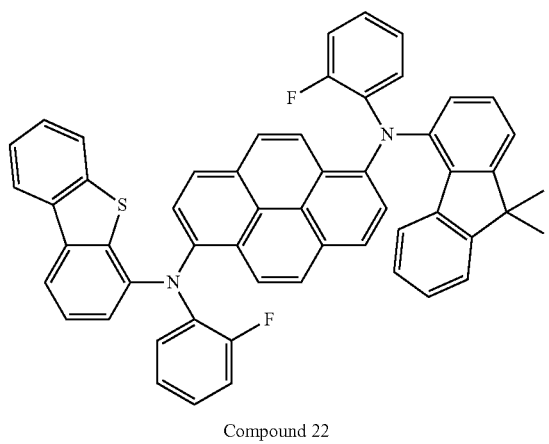

Compound 22

1.4 g of Compound 22 (Yield: 41%) was synthesized as in the synthetic method of Intermediate 18A of Synthesis Example 4, except that Intermediate 2A was used instead of Intermediate 18B, and Intermediate 22A was used instead of 1,6-dibromopyrene. The obtained compound was identified by NMR and MS.

H-NMR (CDCl$_3$, 300 MHz, ppm): 8.5 (m, 1H), 8.0-7.9 (m, 4H), 7.7-7.3 (m, 1H), 7.0-6.9 (m, 9H), 6.6-6.5 (m, 5H), 1.7 (s, 6H).

MS (MALDI-TOF) m/z: 794 [M]+.

Synthesis Example 6: Synthesis of Compound 25

Synthesis of Intermediate 25B

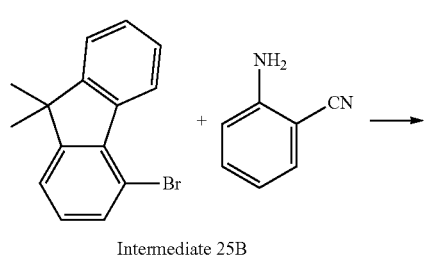

Intermediate 25B

-continued

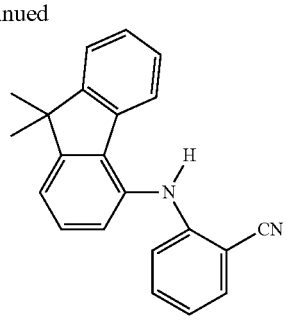

Intermediate 25B was synthesized as in the synthetic method of Intermediate 2A of Synthesis Example 1, except that 2-aminobenzonitrile was used instead of 1-fluoro-aniline.

Synthesis of Intermediate 25A

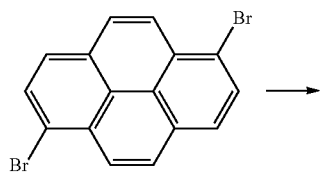

+

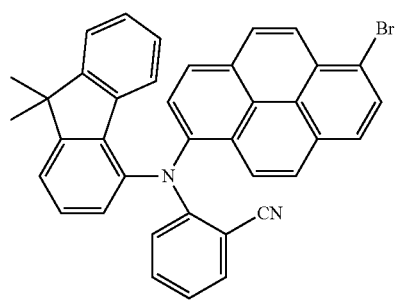

Intermediate 25A

Intermediate 25A was synthesized as in the synthetic method of Intermediate 18A of Synthesis Example 4, except that Intermediate 25B was used instead of Intermediate 18B.

Synthesis of Compound 25

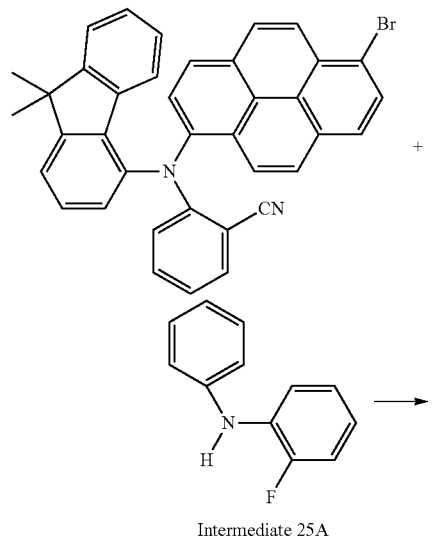

Intermediate 25A

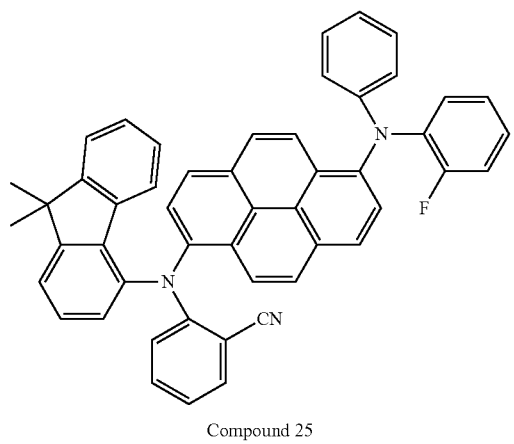

Compound 25

1.1 g of Compound 25 (Yield: 15%) was synthesized as in the synthetic method of Intermediate 18A of Synthesis Example 4, except that Intermediate 25A was used instead of Intermediate 18B, and 2-fluoro-N-phenylaniline was used instead of 1,6-dibromopyrene. The obtained compound was identified by NMR and MS.

H-NMR (CDCl$_3$, 300 MHz, ppm): 7.9-7.7 (m, 6H), 7.6-7.2 (m, 8H), 7.0-6.9 (m, 9H), 6.6-6.5 (m, 5H), 1.7 (s, 6H).

MS (MALDI-TOF) m/z: 695 [M]+.

Synthesis Example 7: Synthesis of Compound 49

Synthesis of Intermediate 49A

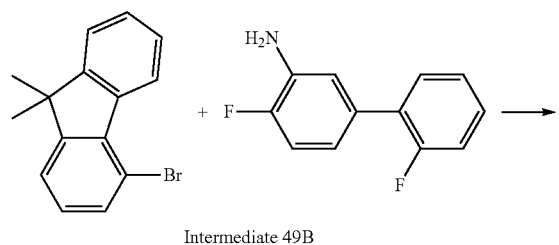

Intermediate 49B

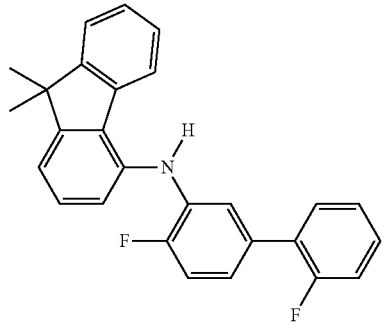

Intermediate 49A

Intermediate 49A was synthesized as in the synthetic method of Intermediate 2A of Synthesis Example 1, except that Intermediate 49B was used instead of 1-fluoro-aniline.

Synthesis of Compound 49

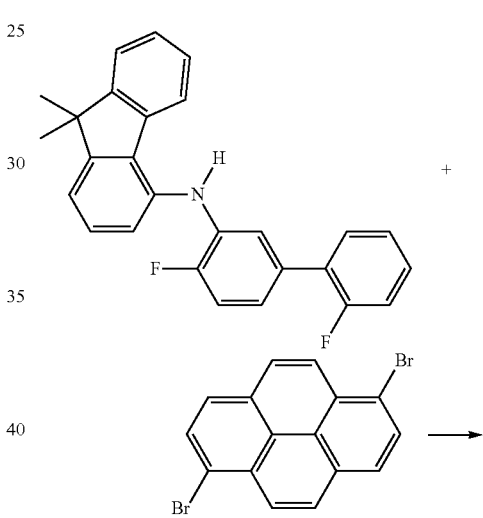

Intermediate 49A

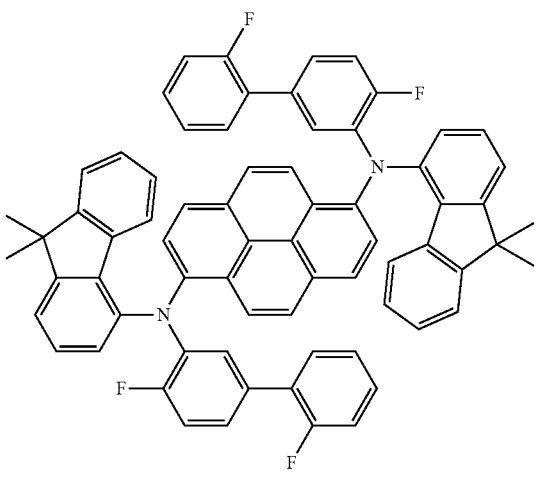

Compound 49

5 g of Compound 49 (Yield: 48%) was synthesized as in the synthetic method of Compound 2 of Synthesis Example 1, except that Intermediate 49A was used instead of Intermediate 2A. The obtained compound was identified by NMR and MS.

H-NMR (CDCl₃, 300 MHz, ppm): 7.9-7.5 (m, 16H), 7.4-7.3 (m, 6H), 7.0-6.9 (m, 10H), 6.8-6.6 (m, 4H), 1.7 (s, 12H).

MS (MALDI-TOF) m/z: 992 [M]+.

Synthesis Example 8: Synthesis of Compound 50

Synthesis of Intermediate 50A

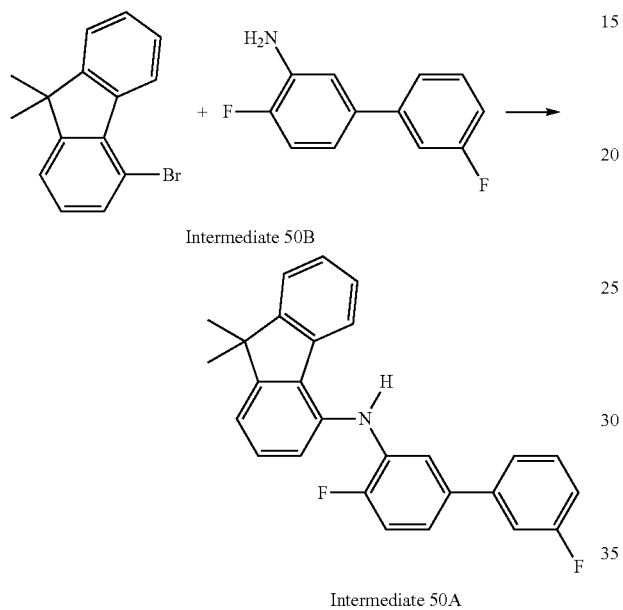

Intermediate 50A was synthesized as in the synthetic method of Intermediate 2A of Synthesis Example 1, except that Intermediate 50B was used instead of 1-fluoro-aniline.

Synthesis of Compound 50

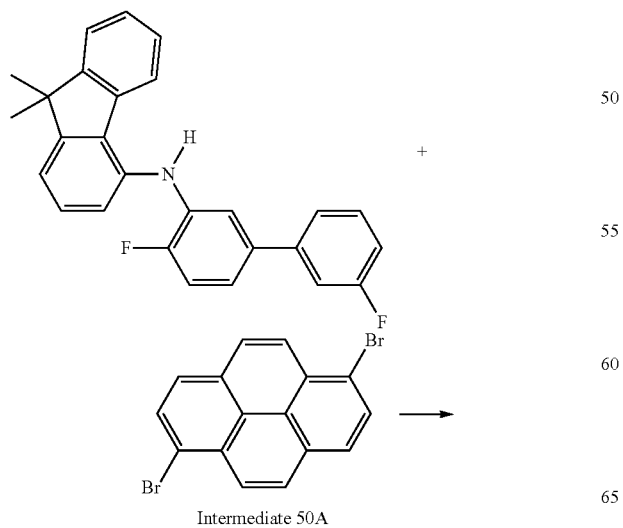

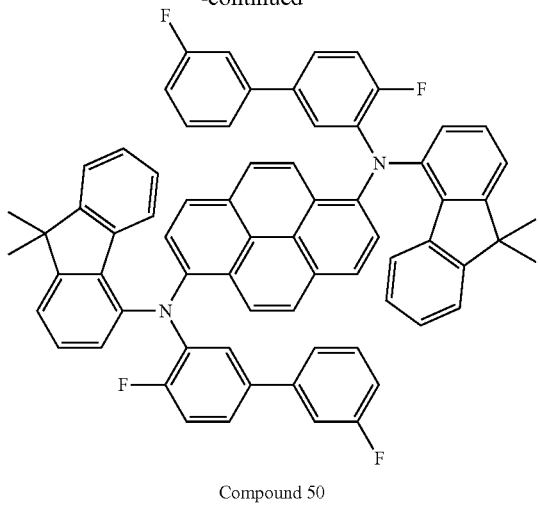

Compound 50

5.2 g of Compound 50 (Yield: 45%) was synthesized as in the synthetic method of Compound 2 of Synthesis Example 1, except that Intermediate 50A was used instead of Intermediate 2A. The obtained compound was identified by NMR and MS.

H-NMR (CDCl₃, 300 MHz, ppm): 7.9-7.7 (m, 8H), 7.6-7.5 (m, 6H), 7.4-7.2 (m, 8H), 7.1-7.0 (m, 6H), 6.9-6.6 (m, 8H), 1.7 (s, 12H).

MS (MALDI-TOF) m/z: 992 [M]+.

Synthesis Example 9: Synthesis of Compound 51

Synthesis of Intermediate 51A

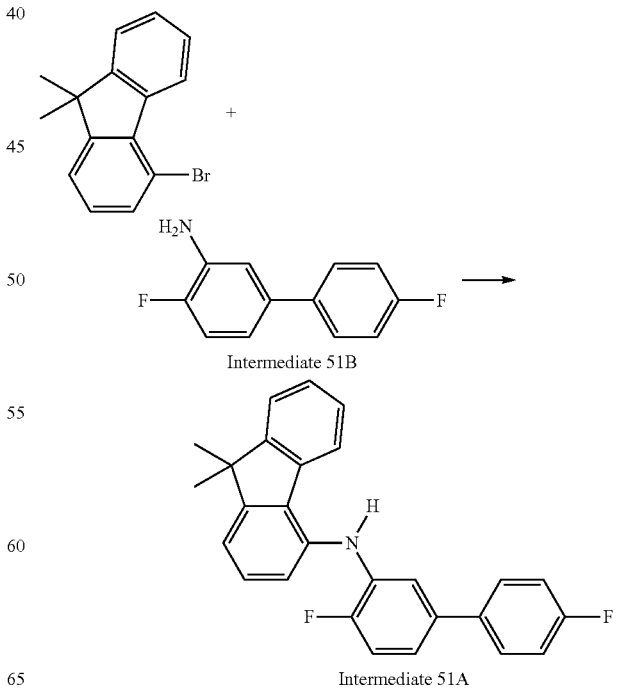

Intermediate 51A was synthesized as in the synthetic method of Intermediate 2A, except that Intermediate 51B was used instead of 1-fluoro-aniline.

Synthesis of Compound 51

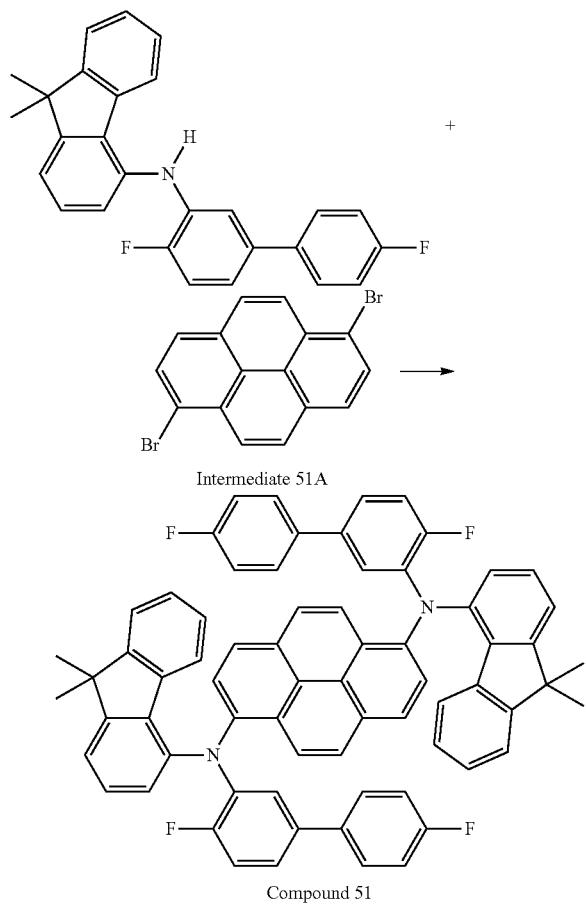

Intermediate 51A

Compound 51

5.6 g of Compound 51 (Yield: 51%) was synthesized as in the synthetic method of Compound 2 of Synthesis Example 1, except that Intermediate 51A was used instead of Intermediate 2A. The obtained compound was identified by NMR and MS.

H-NMR (CDCl₃, 300 MHz, ppm): 7.9-7.7 (m, 8H), 7.6-7.3 (m, 14H), 7.1-7.0 (m, 6H), 6.9-6.6 (m, 8H), 1.7 (s, 12H).

MS (MALDI-TOF) m/z: 992 [M]+.

Synthesis Example 10: Synthesis of Compound 53

Synthesis of Intermediate 53A

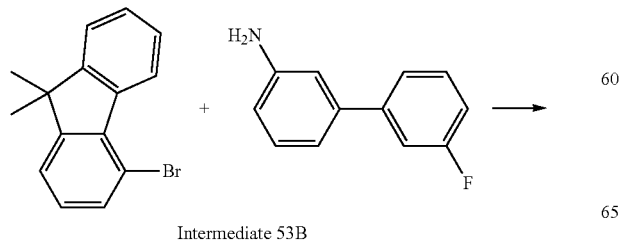

Intermediate 53B

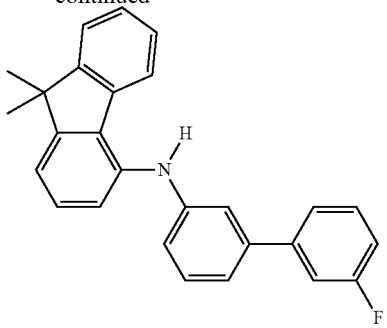

Intermediate 53A

Intermediate 53A was synthesized as in the synthetic method of Intermediate 2A of Synthesis Example 1, except that Intermediate 53B was used instead of 1-fluoro-aniline.

Synthesis of Compound 53

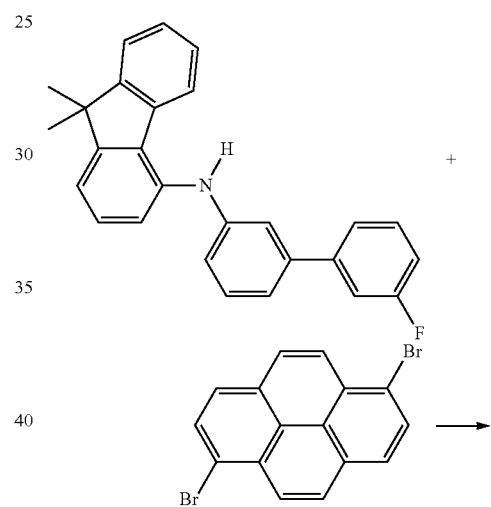

Intermediate 53A

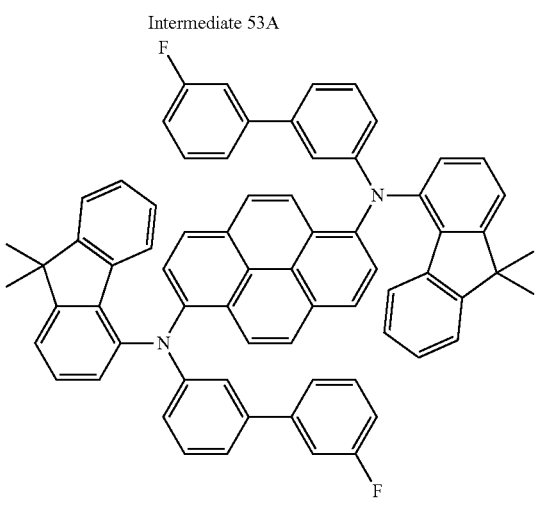

Compound 53

3.2 g of Compound 53 (Yield: 49%) was synthesized as in the synthetic method of Compound 2 of Synthesis Example 1, except that Intermediate 53A was used instead of Intermediate 2A. The obtained compound was identified by NMR and MS.

H-NMR (CDCl₃, 300 MHz, ppm): 7.9-7.7 (m, 8H), 7.6-7.2 (m, 16H), 7.0-6.9 (m, 10H), 6.6-6.5 (m, 4H), 1.7 (s, 12H).

MS (MALDI-TOF) m/z: 956 [M]+.

Synthesis Example 11: Synthesis of Compound 62

Synthesis of Intermediate 62A

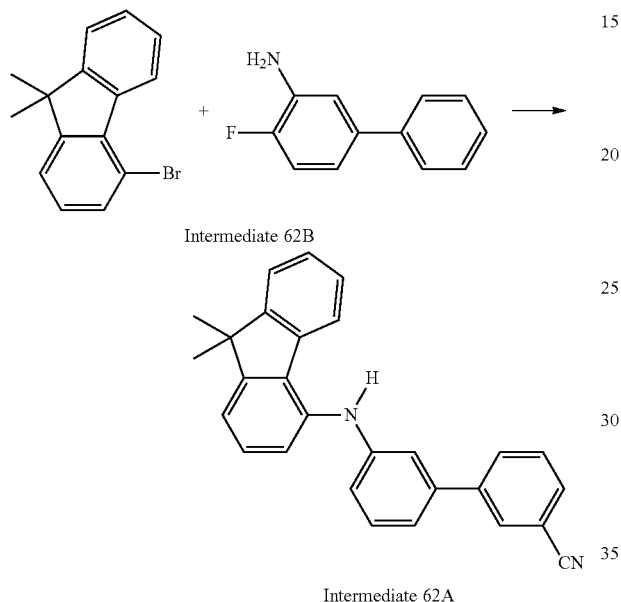

Intermediate 62A

Intermediate 62A was synthesized as in the synthetic method of Intermediate 2A, except that Intermediate 62B was used instead of 1-fluoro-aniline.

Synthesis of Compound 62

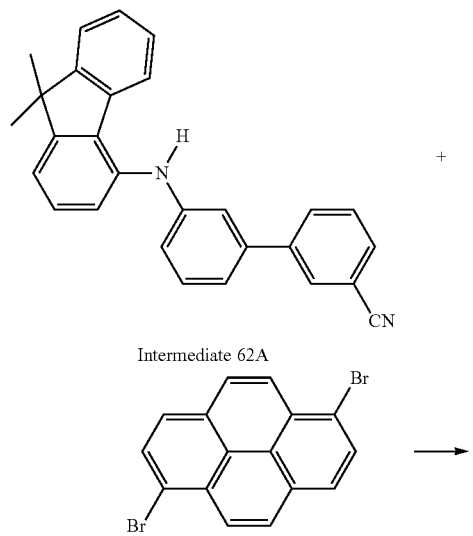

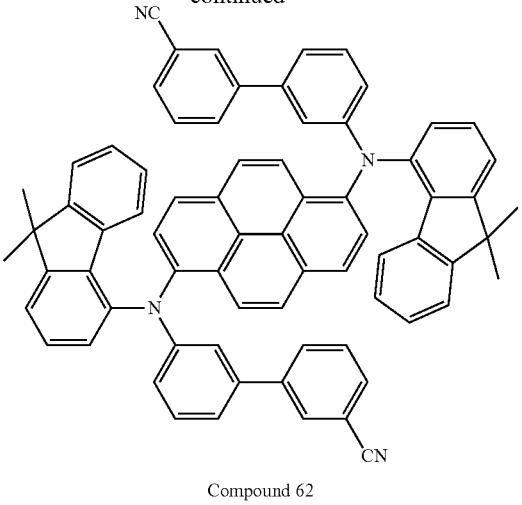

Compound 62

3.5 g of Compound 62 (Yield: 43%) was synthesized as in the synthetic method of Compound 2 of Synthesis Example 1, except that Intermediate 62A was used instead of Intermediate 2A.

H-NMR (CDCl₃, 300 MHz, ppm): 7.9-7.7 (m, 16H), 7.6-7.3 (m, 8H), 7.0-6.9 (m, 10H), 6.6-6.5 (m, 4H), 1.7 (s, 12H).

MS (MALDI-TOF) m/z: 970 [M]+.

Synthesis Example 12: Synthesis of Compound 63

Synthesis of Intermediate 63A

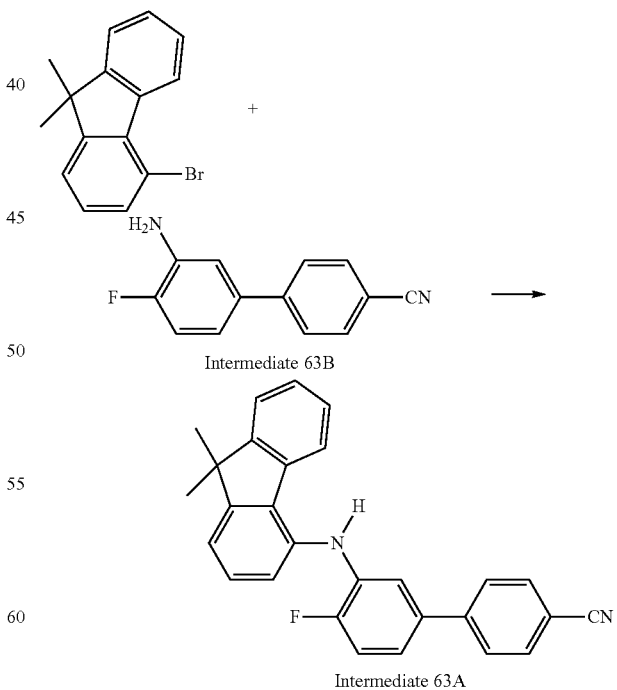

Intermediate 63A

Intermediate 63A was synthesized as in the synthetic method of Intermediate 2A of Synthesis Example 1, except that Intermediate 63B was used instead of 1-fluoro-aniline.

Synthesis of Compound 63

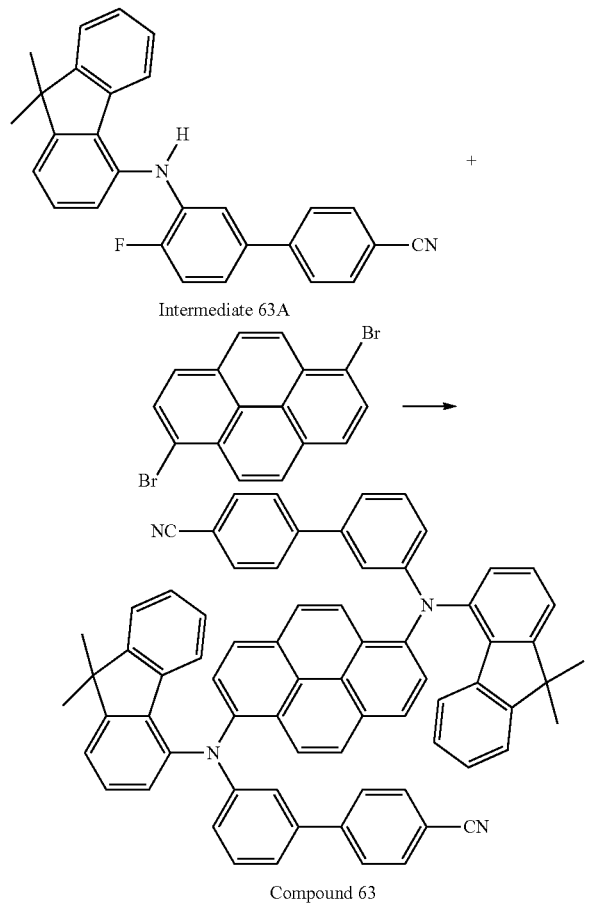

1.3 g of Compound 63 (Yield: 25%) was synthesized as in the synthetic method of Compound 2 of Synthesis Example 1, except that Intermediate 63A was used instead of Intermediate 2A. The obtained compound was identified by NMR and MS.

H-NMR (CDCl$_3$, 300 MHz, ppm): 7.9-7.7 (m, 16H), 7.6-7.3 (m, 8H), 7.1-6.8 (m, 10H), 6.6-6.5 (m, 4H), 1.7 (s, 12H).

MS (MALDI-TOF) m/z: 970 [M]+.

Synthesis Example 13: Synthesis of Compound 67

Synthesis of Intermediate 67A

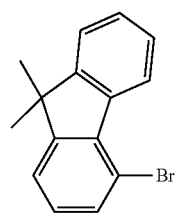

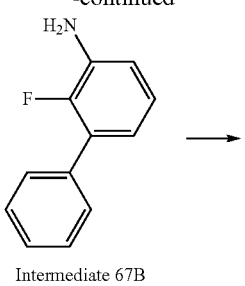

Intermediate 67B

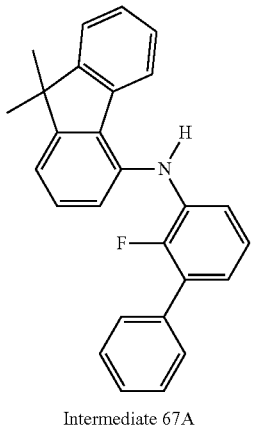

Intermediate 67A

Intermediate 67A was synthesized as in the synthetic method of Intermediate 2A of Synthesis Example 1, except that Intermediate 67B was used instead of 1-fluoro-aniline.

Synthesis of Compound 67

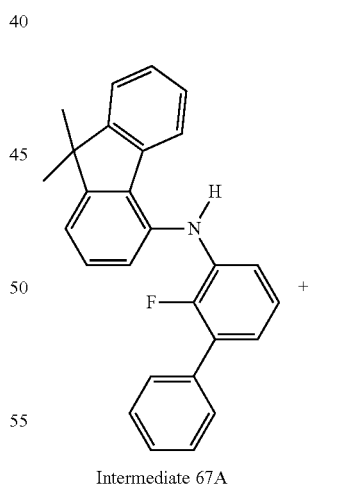

Intermediate 67A

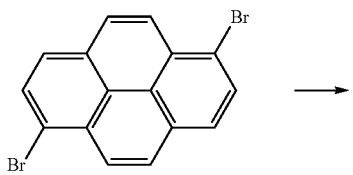

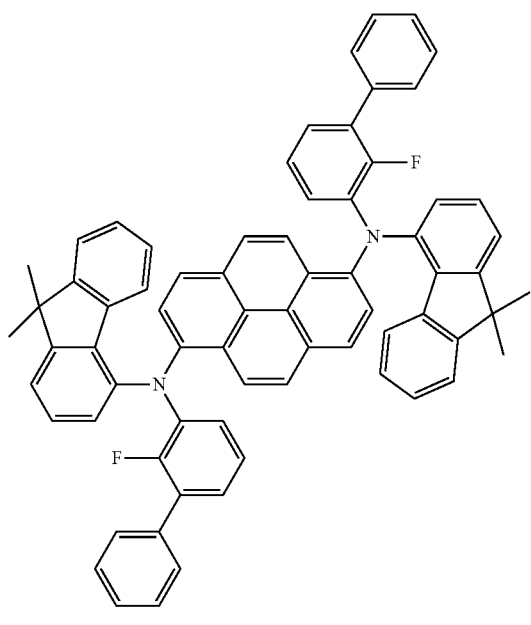

Compound 67

5.3 g of Compound 67 (Yield: 52%) was synthesized as in the synthetic method of Compound 2 of Synthesis Example 1, except that Intermediate 67A was used instead of Intermediate 2A. The obtained compound was identified by NMR and MS.

H-NMR (CDCl$_3$, 300 MHz, ppm): 7.9-7.7 (m, 8H), 7.6-7.5 (m, 10H), 7.4-7.1 (m, 10H), 7.0-6.9 (m, 6H), 6.6-6.5 (m, 4H), 1.7 (s, 12H).

MS (MALDI-TOF) m/z: 956 [M]+.

Synthesis Example 14: Synthesis of Compound 69

Synthesis of Intermediate 69A

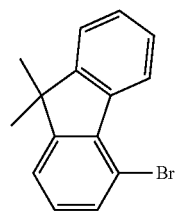

+

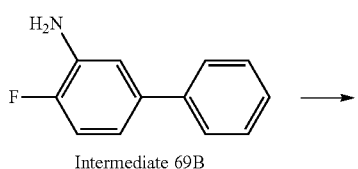

Intermediate 69B

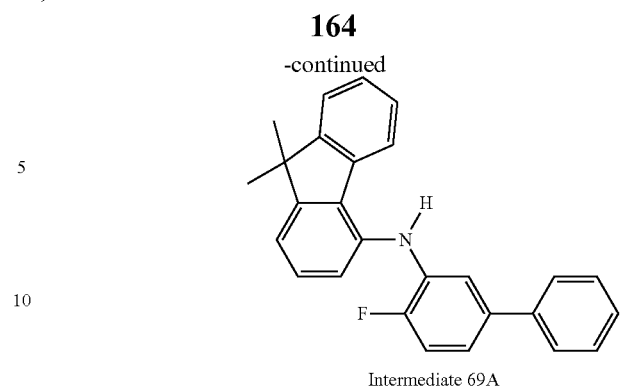

Intermediate 69A

Intermediate 69A was synthesized as in the synthetic method of Intermediate 2A of Synthesis Example 1, except that Intermediate 69B was used instead of 1-fluoro-aniline.

Synthesis of Compound 69

6.1 g of Compound 69 (Yield: 52%) was synthesized as in the synthetic method of Compound 2 of Synthesis Example 1, except that Intermediate 69A was used instead of Intermediate 2A. The obtained compound was confirmed by NMR and MS.

H-NMR (CDCl$_3$, 300 MHz, ppm): 7.9-7.7 (m, 8H), 7.6-7.3 (m, 16H), 7.1-7.0 (m, 6H), 6.9-6.6 (m, 8H), 1.7 (s, 12H).

MS (MALDI-TOF) m/z: 956 [M]+.

Synthesis Example 15: Synthesis of Compound 75

Synthesis of Intermediate 75A

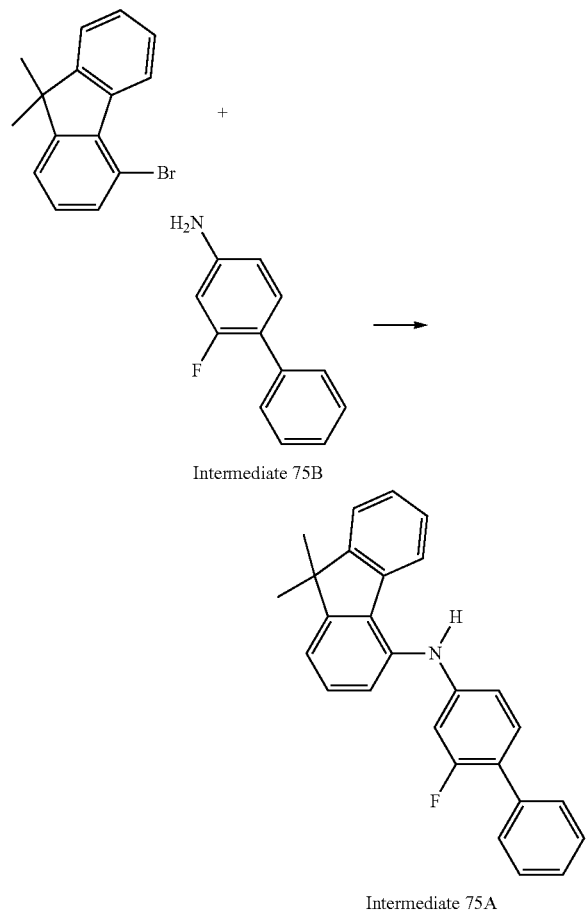

Intermediate 75A

Intermediate 75A was synthesized as in the synthetic method of Intermediate 2A of Synthesis Example 1, except that Intermediate 75B was used instead of 1-fluoro-aniline.

Synthesis of Compound 75

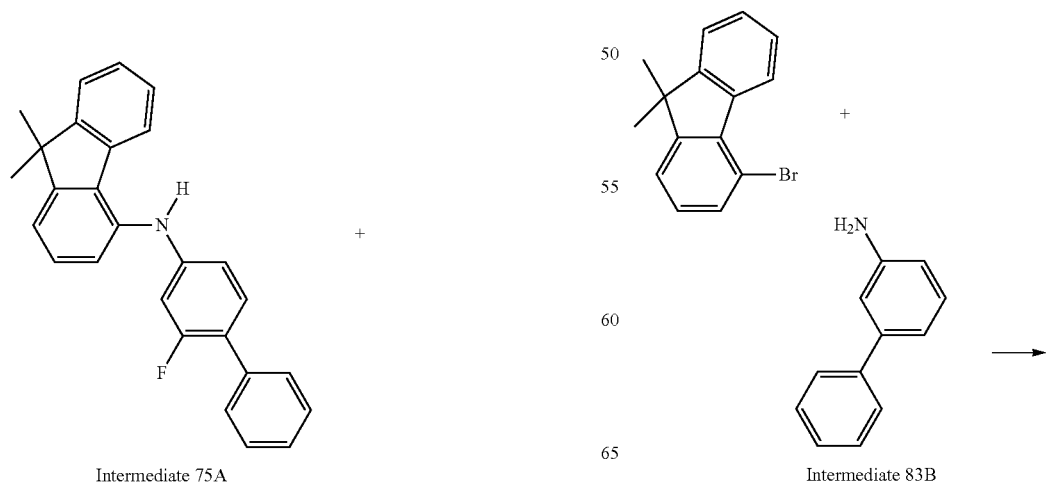

Compound 75

4.8 g of Compound 75 (Yield: 42%) was synthesized as in the synthetic method of Compound 2 of Synthesis Example 1, except that Intermediate 75A was used instead of Intermediate 2A. The obtained compound was confirmed by NMR and MS.

H-NMR (CDCl$_3$, 300 MHz, ppm): 7.9-7.7 (m, 8H), 7.6-7.3 (m, 18H), 7.0-6.9 (m, 6H), 6.6-6.5 (m, 6H), 1.7 (s, 12H).

MS (MALDI-TOF) m/z: 956 [M]+.

Synthesis Example 16: Synthesis of Compound 83

Synthesis of Intermediate 83A

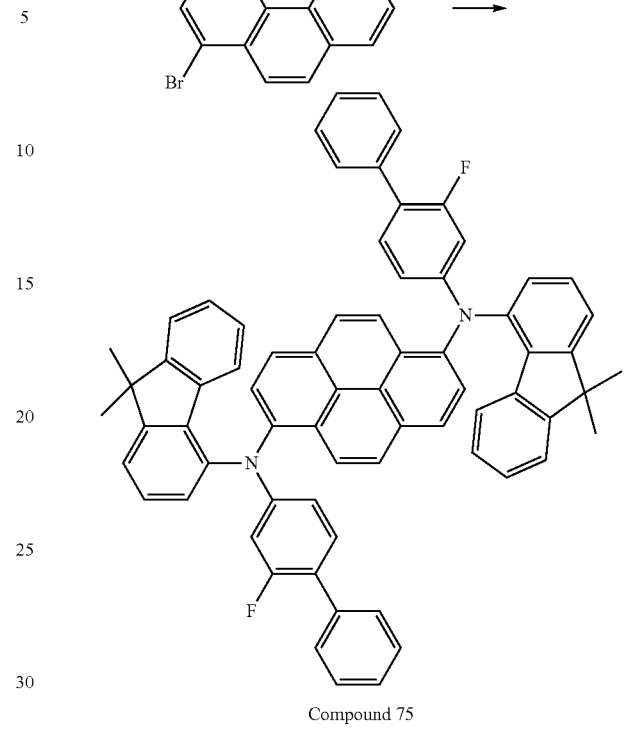

Intermediate 83B

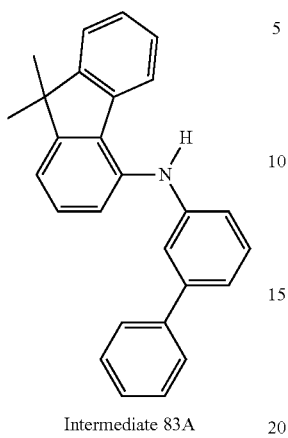

Intermediate 83A

Intermediate 83A was synthesized as in the synthetic method of Intermediate 2A of Synthesis Example 1, except that Intermediate 83B was used instead of 1-fluoro-aniline.

Synthesis of Compound 83

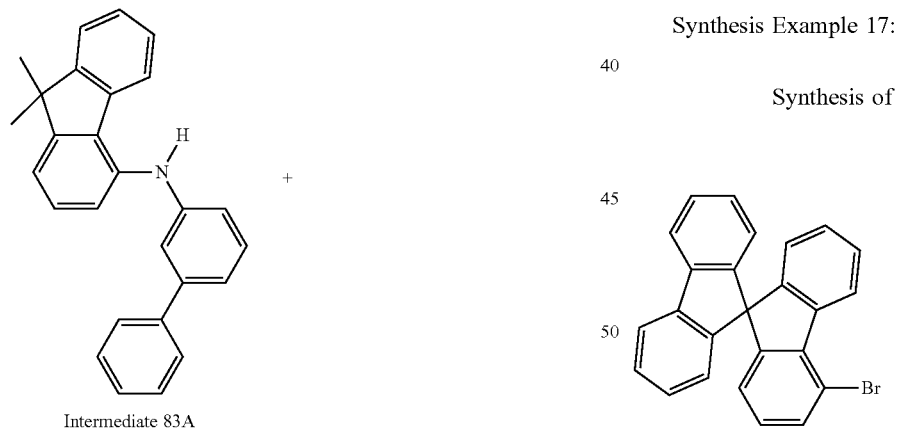

Compound 83

3.3 g of Compound 83 (Yield: 47%) was synthesized as in the synthetic method of Compound 2 of Synthesis Example 1, except that Intermediate 83A was used instead of Intermediate 2A. The obtained compound was identified by NMR and MS.

H-NMR CDCl$_3$, 300 MHz, ppm): 7.9-7.7 (m, 8H), 7.6-7.3 (m, 18H), 7.0-6.9 (m, 10H), 6.6-6.5 (m, 4H), 1.7 (s, 12H).

MS (MALDI-TOF) m/z: 920 [M]+.

Synthesis Example 17: Synthesis of Compound 93

Synthesis of Intermediate 93A

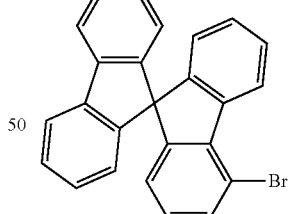

+

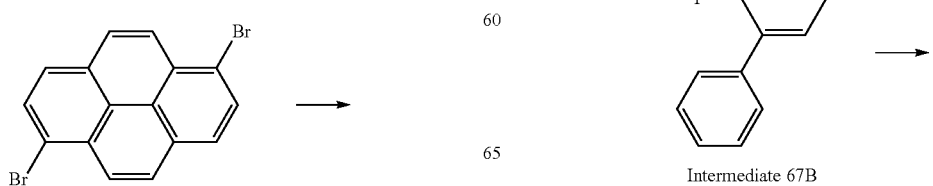

Intermediate 67B

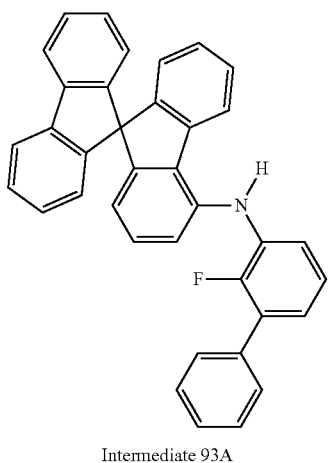

Intermediate 93A

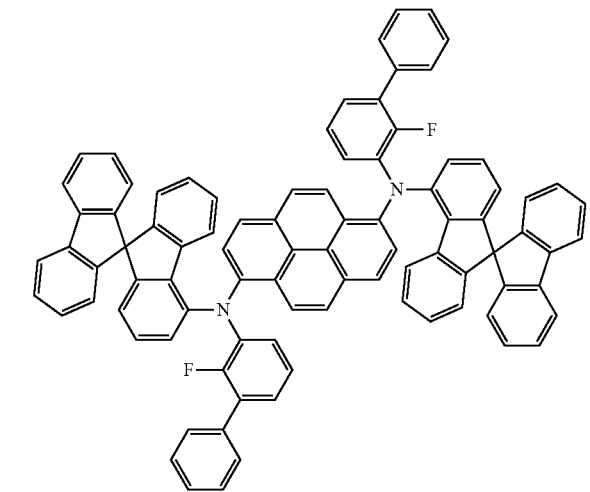

Compound 93

Intermediate 93A was synthesized as in the synthetic method of Intermediate 2A of Synthesis Example 1, except that 4-bromo-9,9′-spirobifluorene was used instead of 4-bromo-9,9-dimethyl-9H-fluorene, and Intermediate 67B was used instead of 1-fluoro-aniline.

Synthesis of Compound 93

3.2 g of Compound 93 (Yield: 47%) was synthesized as in the synthetic method of Compound 2 of Synthesis Example 1, except that Intermediate 93A was used instead of Intermediate 2A. The obtained compound was identified by NMR and MS.

H-NMR (CDCl$_3$, 300 MHz, ppm): 7.9-7.7 (m, 12H), 7.5-7.4 (m, 10H), 7.3-7.1 (m, 22H), 7.0-6.9 (m, 6H), 6.6-6.5 (m, 4H).

MS (MALDI-TOF) m/z: 1200 [M]+.

Synthesis Example 18: Synthesis of Compound 95

Synthesis of Intermediate 95A

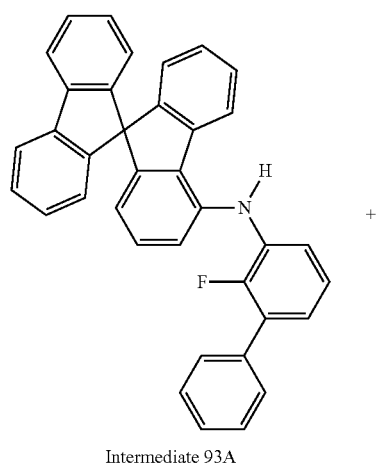

Intermediate 93A

+

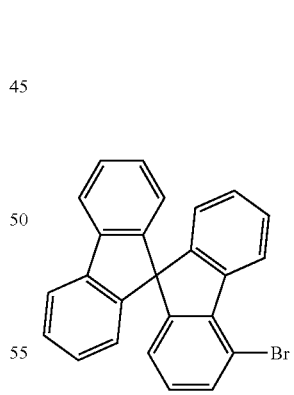

+

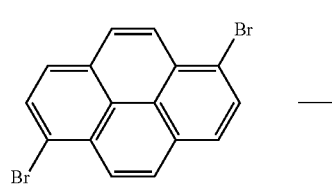

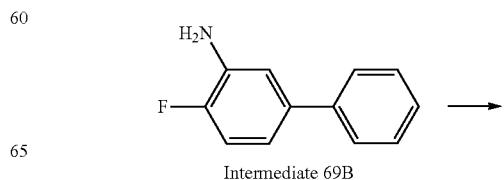

Intermediate 69B

H-NMR (CDCl₃, 300 MHz, ppm): 7.9-7.7 (m, 12H), 7.5-7.2 (m, 28H), 7.1-7.0 (m, 6H), 6.9-6.6 (m, 8H).
MS (MALDI-TOF) m/z: 1200 [M]+.

Synthesis Example 19: Synthesis of Compound 98

Synthesis of Intermediate 98A

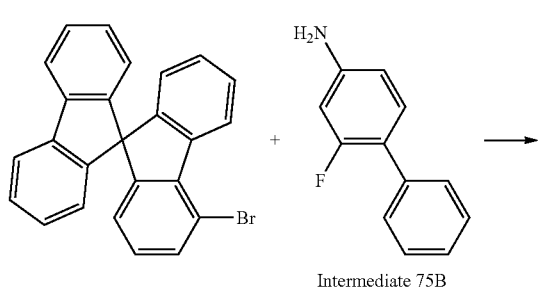

Intermediate 75B

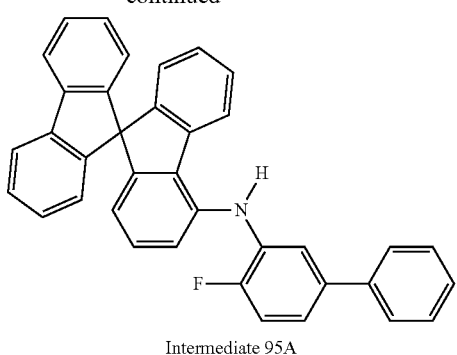

Intermediate 95A

Intermediate 95A was synthesized as in the synthetic method of Intermediate 2A of Synthesis Example 1, except that 4-bromo-9,9'-spirobifluorene was used instead of 4-bromo-9,9-dimethyl-9H-fluorene, and Intermediate 69B was used instead of 1-fluoro-aniline.

Synthesis of Compound 95

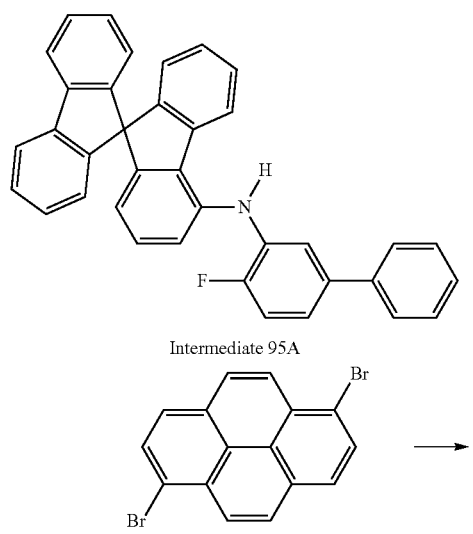

Intermediate 95A

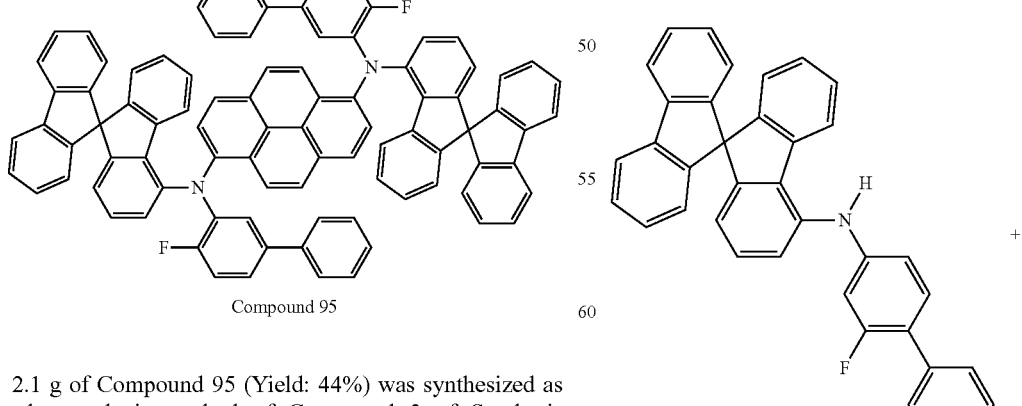

Compound 95

2.1 g of Compound 95 (Yield: 44%) was synthesized as in the synthetic method of Compound 2 of Synthesis Example 1, except that Intermediate 95A was used instead of Intermediate 2A. The obtained compound was confirmed by NMR and MS.

Intermediate 98A

Intermediate 98A was synthesized as in the synthetic method of Intermediate 2A of Synthesis Example 1, except that 4-bromo-9,9'-spirobifluorene was used instead of 4-bromo-9,9-dimethyl-9H-fluorene, and Intermediate 75B was used instead of 1-fluoro-aniline.

Synthesis of Compound 98

Intermediate 98A

-continued

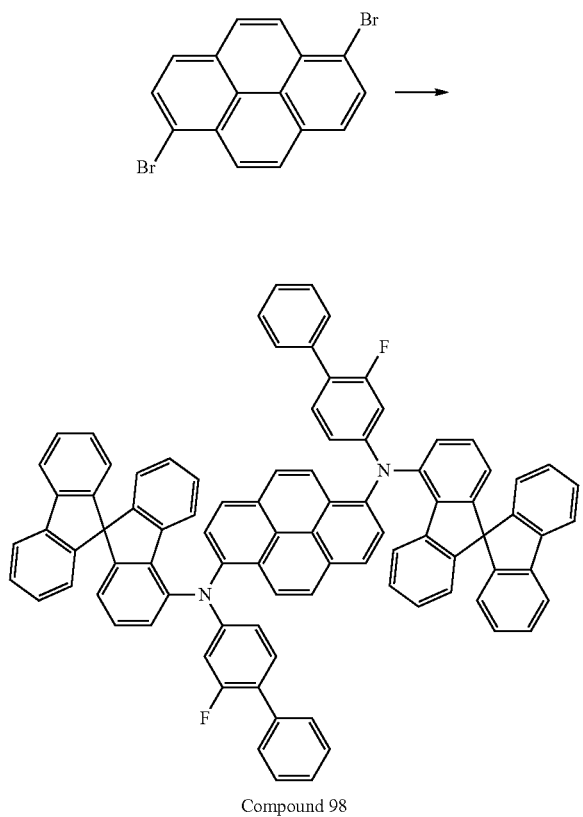

Compound 98

3.4 g of Compound 98 (Yield: 42%) was synthesized as in the synthetic method of Compound 2 of Synthesis Example 1, except that Intermediate 98A was used instead of Intermediate 2A. The obtained compound was identified by NMR and MS.

H-NMR (CDCl₃, 300 MHz, ppm): 7.9-7.7 (m, 12H), 7.5-7.2 (m, 30H), 7.1-7.0 (m, 6H), 6.6-6.5 (m, 6H).

MS (MALDI-TOF) m/z: 1200 [M]+.

Synthesis Example 20: Synthesis of Compound 104

Synthesis of Intermediate 104A

-continued

Intermediate 104A

Intermediate 104A was synthesized as in the synthetic method of Intermediate 2A of Synthesis Example 1, except that 4-bromo-9,9'-spirobifluorene was used instead of 4-bromo-9,9-dimethyl-9H-fluorene, and Intermediate 83B was used instead of 1-fluoro-aniline.

Synthesis of Compound 104

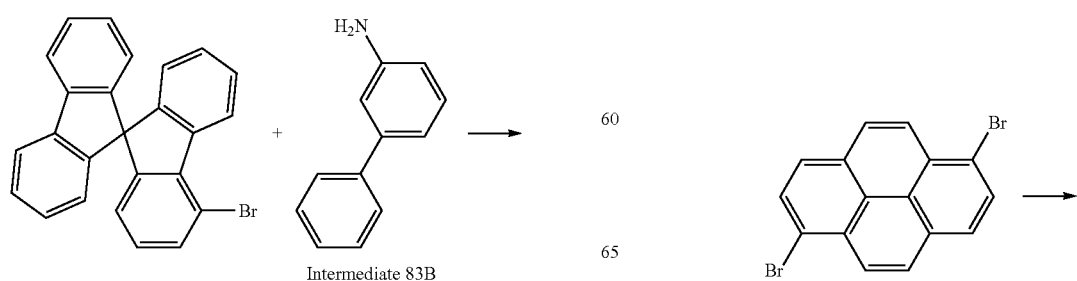

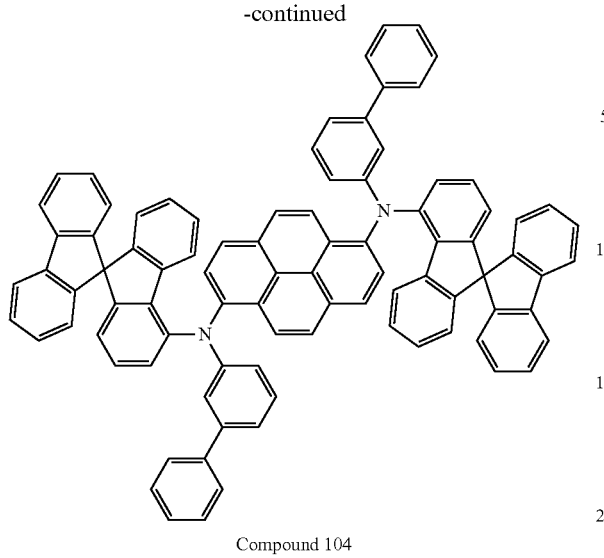

Compound 104

2.1 g of Compound 104 (Yield: 42%) was synthesized as in the synthetic method of Compound 2 of Synthesis Example 1, except that Intermediate 104A was used instead of Intermediate 2A. The obtained compound was confirmed by NMR and MS.

H-NMR (CDCl₃, 300 MHz, ppm): 7.9-7.7 (m, 12H), 7.5-7.4 (m, 12H), 7.3-7.1 (m, 18H), 7.0-6.9 (m, 10H), 6.6-6.5 (m, 4H).

MS (MALDI-TOF) m/z: 1164 [M]+.

Synthesis Example 21: Synthesis of Compound 110

Synthesis of Intermediate 110A

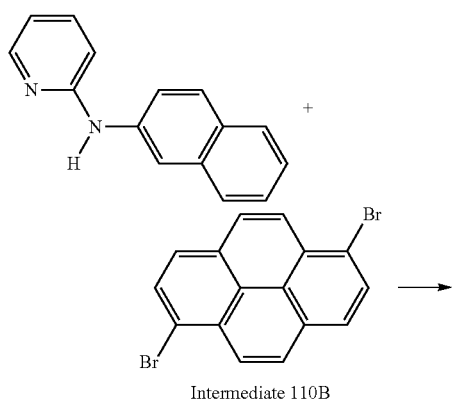

Intermediate 110B

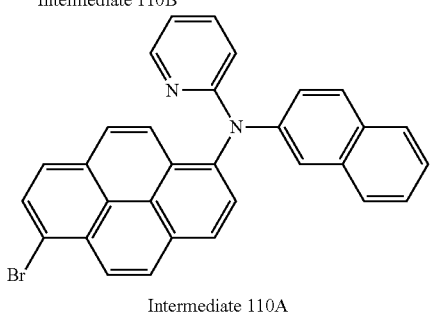

Intermediate 110A

Intermediate 110A was synthesized as in the synthetic method of Intermediate 18A of Synthesis Example 4, except that Intermediate 110B was used instead of Intermediate 18B.

Synthesis of Compound 110

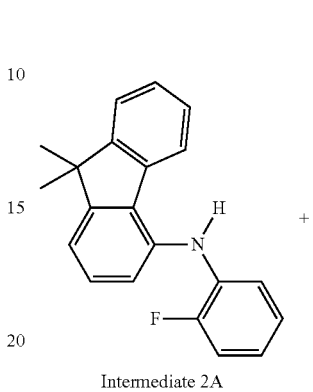

Intermediate 2A

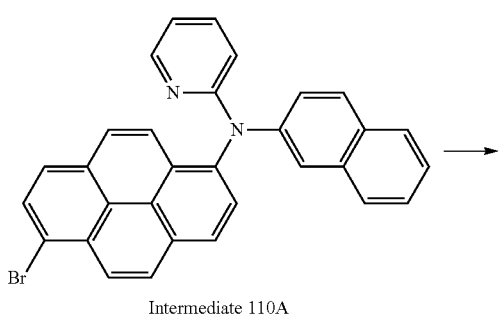

Intermediate 110A

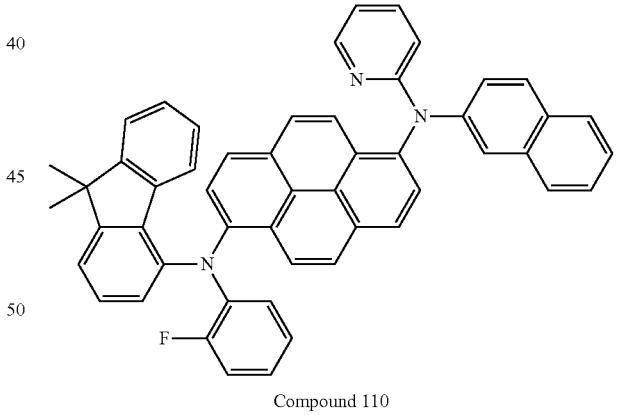

Compound 110

2.2 g of Compound 110 (Yield: 33%) was synthesized as in the synthetic method of Intermediate 18A of Synthesis Example 4, except that Intermediate 2A was used instead of Intermediate 18B, and Intermediate 110A was used instead of 1,6-dibromopyrene. The obtained compound was confirmed by NMR and MS.

H-NMR (CDCl₃, 300 MHz, ppm): 8.1-7.7 (m, 11H), 7.6-7.3 (m, 8H), 7.0-6.9 (m, 6H), 6.7-6.6 (m, 5H), 1.7 (s, 6H).

MS (MALDI-TOF) m/z: 721 [M]+.

Synthesis Example 22: Synthesis of Compound 113

Synthesis of Intermediate 113A

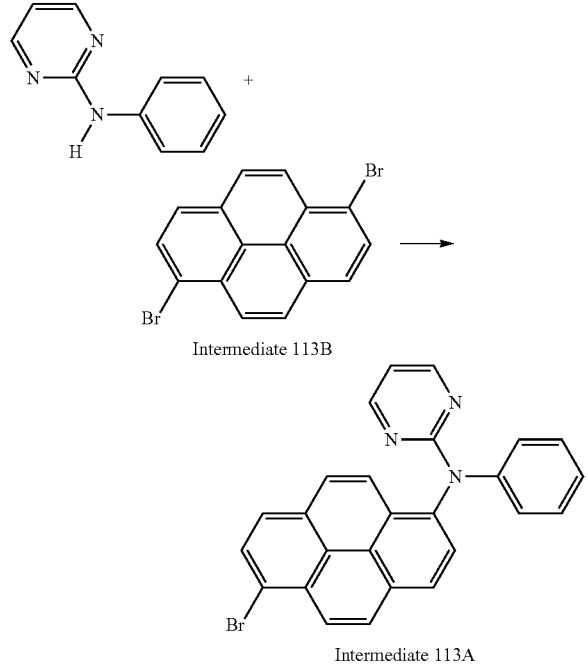

Intermediate 113A was synthesized as in the synthetic method of Intermediate 18A of Synthesis Example 4, except that Intermediate 113B was used instead of Intermediate 18B.

Synthesis of Compound 113

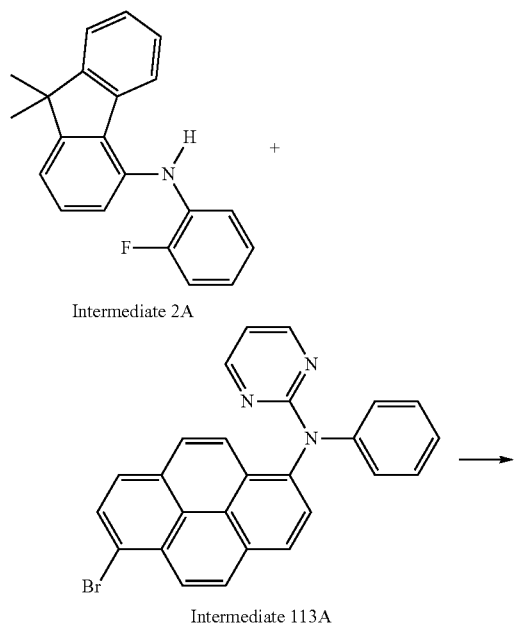

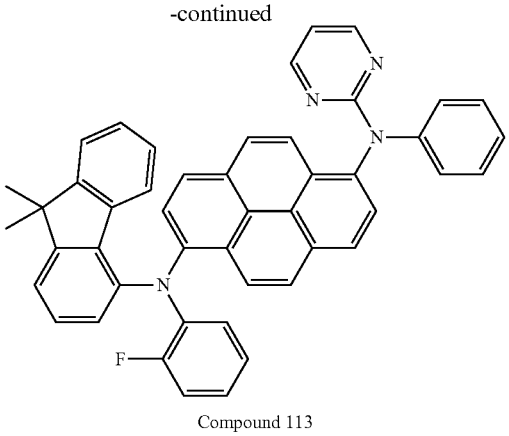

Compound 113

2.1 g of Compound 113 (Yield: 31%) was synthesized as in the synthetic method of Intermediate 18A of Synthesis Example 4, except that Intermediate 2A was used instead of Intermediate 18B, and Intermediate 113A was used instead of 1,6-dibromopyrene. The obtained compound was confirmed by NMR and MS.

H-NMR (CDCl$_3$, 300 MHz, ppm): 8.5 (m, 2H), 7.9-7.7 (m, 6H), 7.6-7.2 (m, 6H), 7.0-6.8 (m, 8H), 6.6-6.5 (m, 5H), 1.7 (s, 6H).

MS (MALDI-TOF) m/z: 672 [M]+.

Synthesis Example 23: Synthesis of Compound 174

Synthesis of Intermediate 174A

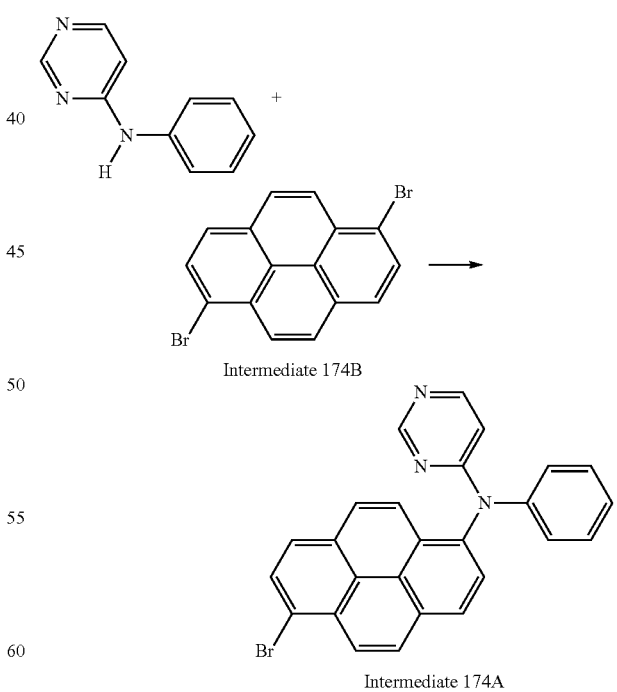

Intermediate 174A was synthesized as in the synthetic method of Intermediate 18A of Synthesis Example 4, except that Intermediate 174B was used instead of Intermediate 18B.

Synthesis of Compound 174

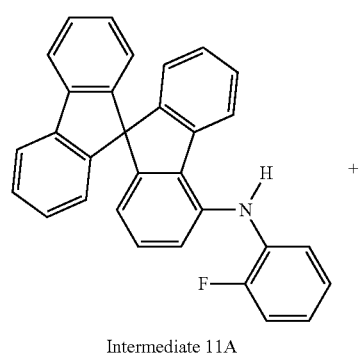
Intermediate 11A

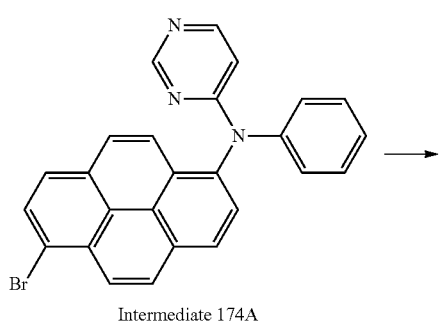
Intermediate 174A

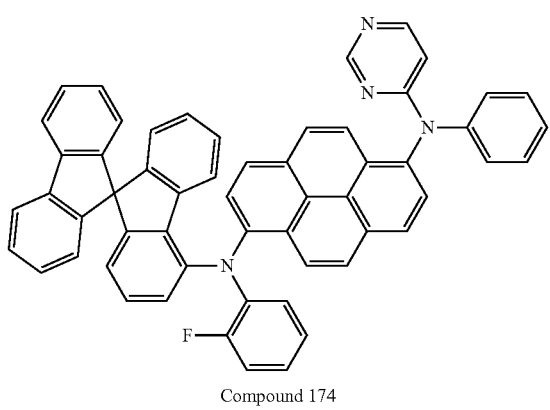
Compound 174

2.0 g of Compound 174 (Yield: 30%) was synthesized as in the synthetic method of Intermediate 18A of Synthesis Example 4, except that Intermediate 11A was used instead of Intermediate 18B, and Intermediate 174A was used instead of 1,6-dibromopyrene.

H-NMR (CDCl$_3$, 300 MHz, ppm): 8.4 (m, 2H), 7.9-7.6 (m, 10H), 7.3-7.2 (m, 10H), 7.0-6.8 (m, 7H), 6.6-6.4 (m, 6H).

MS (MALDI-TOF) m/z: 794 [M]+.

Synthesis Example 24: Synthesis of Compound 177

Synthesis of Intermediate 177A

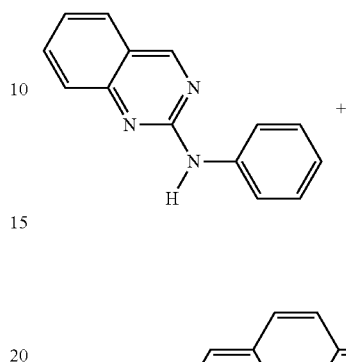

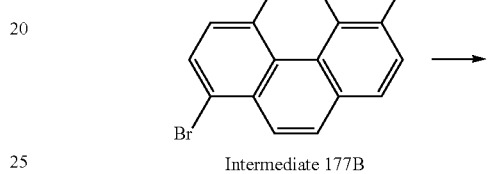
Intermediate 177B

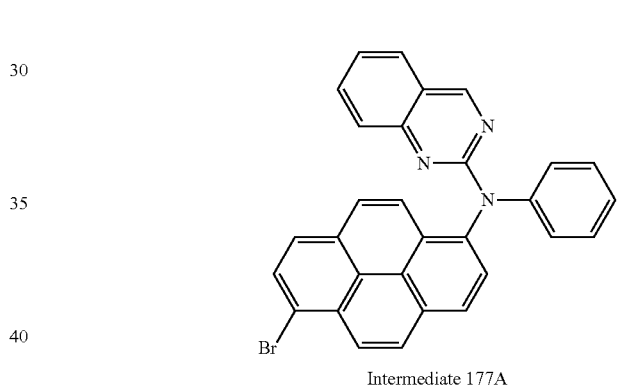
Intermediate 177A

Intermediate 177A was synthesized as in the synthetic method of Intermediate 18A of Synthesis Example 4, except that Intermediate 177B was used instead of Intermediate 18B.

Synthesis of Compound 177

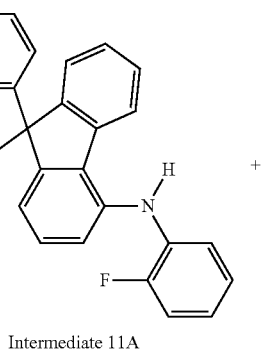
Intermediate 11A

-continued

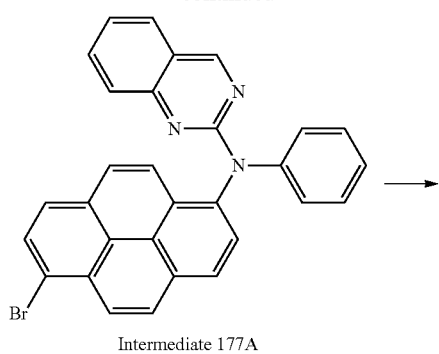
Intermediate 177A

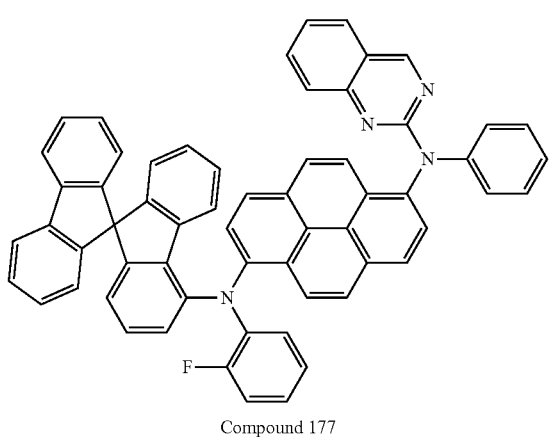
Compound 177

1.8 g of Compound 177 (Yield: 28%) was synthesized as in the synthetic method of Intermediate 18A of Synthesis Example 4, except that Intermediate 11A was used instead of Intermediate 18B, and Intermediate 177A was used instead of 1,6-dibromopyrene. The obtained compound was confirmed by NMR and MS.

H-NMR (CDCl$_3$, 300 MHz, ppm): 9.3 (s, 1H), 8.2-7.6 (m, 14H), 7.3-7.2 (m, 10H), 7.0-6.8 (m, 7H), 6.6-6.5 (5H).

MS (MALDI-TOF) m/z: 844 [M]+.

Synthesis Example 25: Synthesis of Compound 29

Synthesis of Compound 29

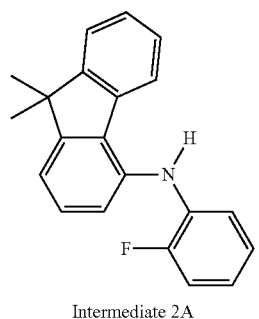
Intermediate 2A

-continued

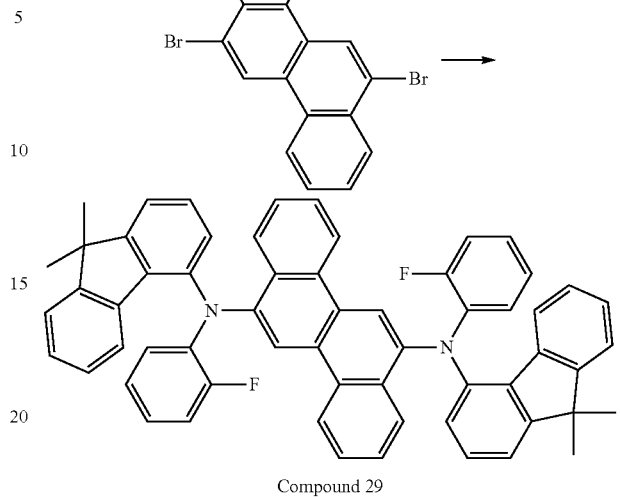
Compound 29

1.4 g of Compound 29 (Yield: 37%) was synthesized as in the synthetic method of Compound 2 of Synthesis Example 1, except that 6,12-dibromochrysene was used instead of 1,6-dibromopyrene. The obtained compound was identified by NMR and MS.

H-NMR (CDCl$_3$, 300 MHz, ppm): 8.9 (m, 2H), 8.1-7.8 (m, 8H), 7.6-7.3 (m, 8H), 7.0-6.9 (m, 8H), 6.6-6.5 (m, 6H), 1.7 (s, 12H).

MS (MALDI-TOF) m/z: 830 [M]+.

Synthesis Example 26: Synthesis of Compound 31

Synthesis of Compound 31

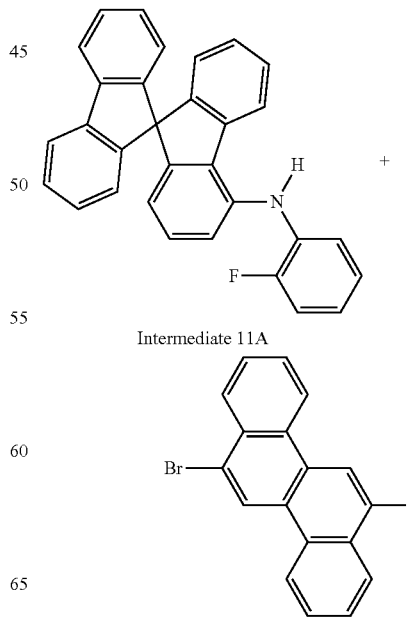
Intermediate 11A

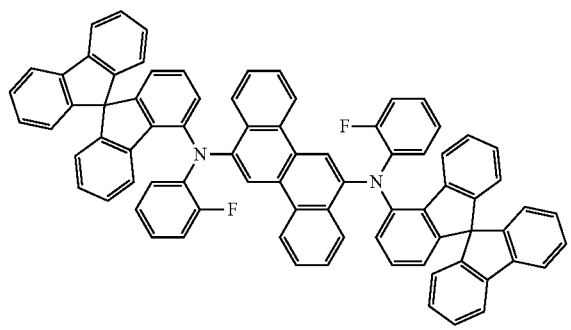

Compound 31

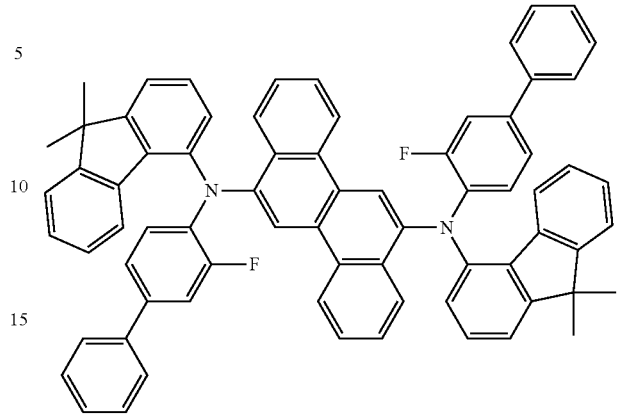

Compound 37

1.2 g of Compound 31 (Yield: 34%) was synthesized as in the synthetic method of Compound 2 of Synthesis Example 1, except that 6,12-dibromochrysene was used instead of 1,6-dibromopyrene and Intermediate 11A was used instead of Intermediate 2A. The obtained compound was identified by NMR and MS.

H-NMR (CDCl$_3$, 300 MHz, ppm): 8.9 (m, 2H), 8.1-7.8 (m, 12H), 7.6-7.5 (m, 4H), 7.4-7.2 (m, 16H), 7.0-6.9 (m, 8H), 6.7-6.6 (m, 6H).

MS (MALDI-TOF) m/z: 1074 [M]+.

Synthesis Example 27: Synthesis of Compound 37

Synthesis of Compound 37

1.1 g of Compound 37 (Yield: 31%) was synthesized as in the synthetic method of Compound 2 of Synthesis Example 1, except that 6,12-dibromochrysene was used instead of 1,6-dibromopyrene and Intermediate 37A was used instead of Intermediate 2A. The obtained compound was identified by NMR and MS.

H-NMR (CDCl$_3$, 300 MHz, ppm): 8.9 (m, 2H), 8.1-7.8 (m, 8H), 7.5-7.3 (m, 22H), 7.0-6.9 (m, 4H), 6.7-6.6 (m, 4H), 1.7 (s, 12H).

MS (MALDI-TOF) m/z: 982 [M]+.

Synthesis Example 28: Synthesis of Compound 188

Synthesis of Intermediate 118A

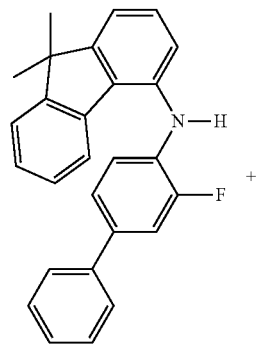

Intermediate 37A

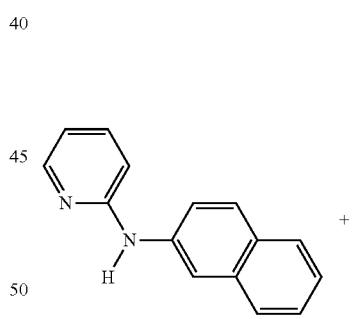

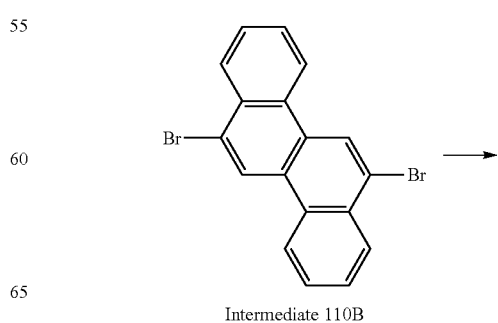

Intermediate 110B

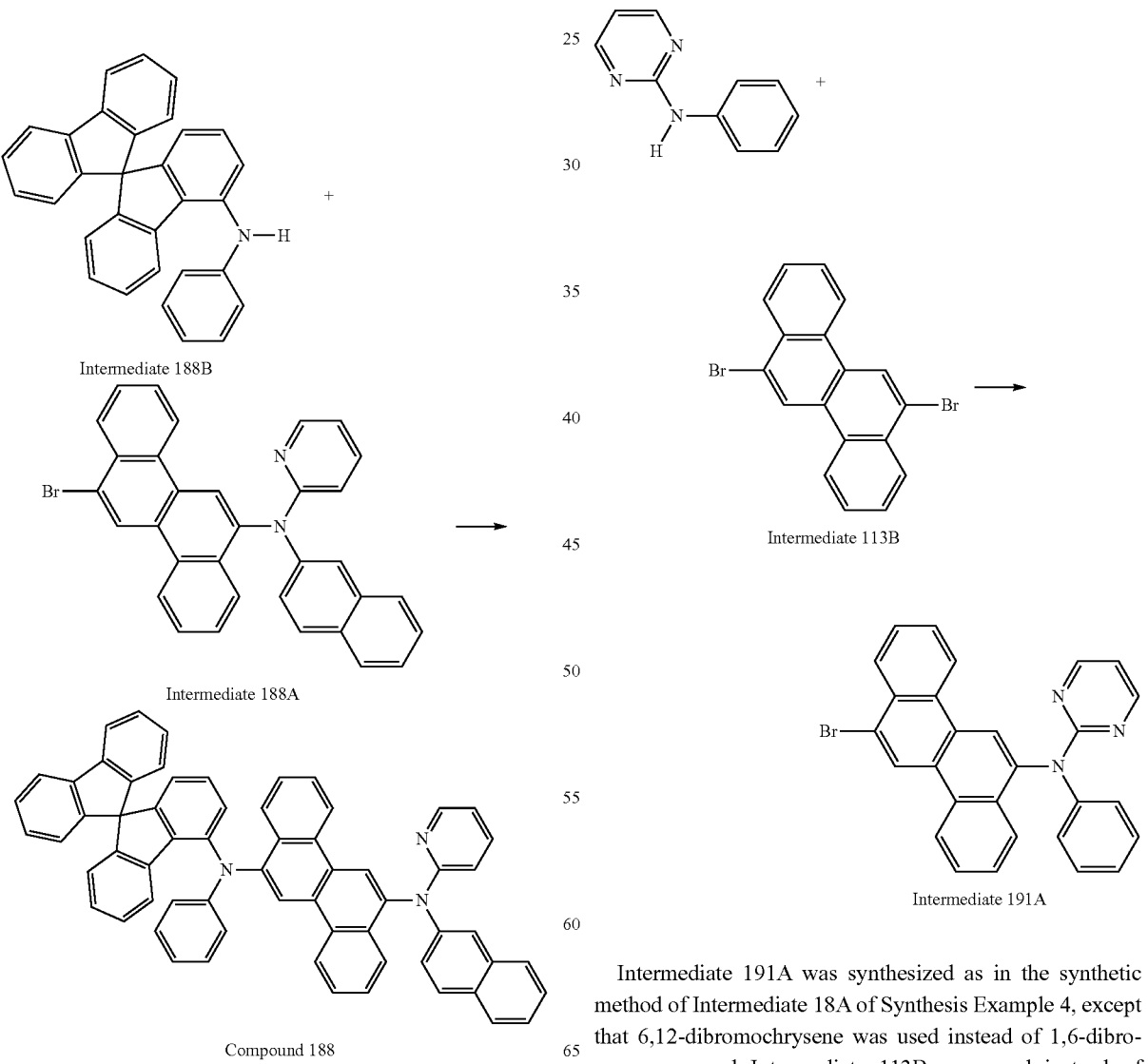

Intermediate 188A was synthesized as in the synthetic method of Intermediate 18A of Synthesis Example 4, except that 6,12-dibromochrysene was used instead of 1,6-dibromopyrene, and Intermediate 110B was used instead of Intermediate 18B.

Synthesis of Compound 188

1.0 g of Compound 188 (Yield: 17%) was synthesized as in the synthetic method of Intermediate 18A of Synthesis Example 4, except that Intermediate 188B was used instead of Intermediate 18B, and Intermediate 188A was used instead of 1,6-dibromopyrene. The obtained compound was confirmed by NMR and MS.

H-NMR (CDCl$_3$, 300 MHz, ppm): 8.9 (m, 2H), 8.1-7.7 (m, 15H), 7.6-7.5 (m, 4H), 7.4-7.2 (m, 11H), 7.0-6.6 (m, 9H).

MS (MALDI-TOF) m/z: 851 [M]+.

Synthesis Example 29: Synthesis of Compound 191

Synthesis of Intermediate 191A

Intermediate 191A was synthesized as in the synthetic method of Intermediate 18A of Synthesis Example 4, except that 6,12-dibromochrysene was used instead of 1,6-dibromopyrene, and Intermediate 113B was used instead of Intermediate 18B.

Synthesis of Compound 191

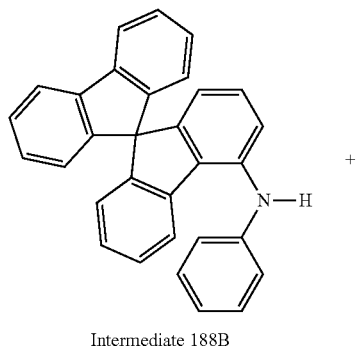

Intermediate 188B

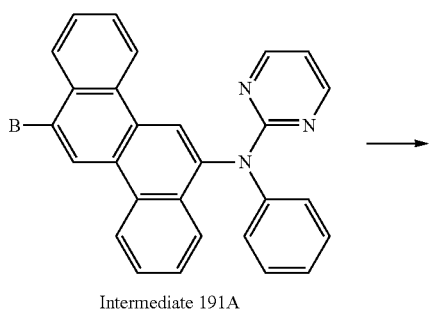

Intermediate 191A

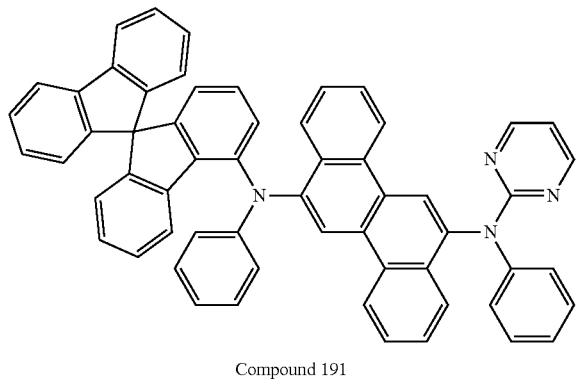

Compound 191

1.0 g of Compound 191 (Yield: 19%) was synthesized as in the synthetic method of Intermediate 18A of Synthesis Example 4, except that Intermediate 188B was used instead of Intermediate 18B, and Intermediate 191A was used instead of 1,6-dibromopyrene. The obtained compound was confirmed by NMR and MS.

H-NMR (CDCl$_3$, 300 MHz, ppm): 8.9 (m, 2H), 8.5-8.1 (m, 5H), 7.9-7.8 (m, 7H), 7.6-7.2 (m, 13H), 7.0-6.6 (m, 11H).

MS (MALDI-TOF) m/z: 802 [M]+.

Synthesis Example 30: Synthesis of Compound 40

Synthesis of Compound 40

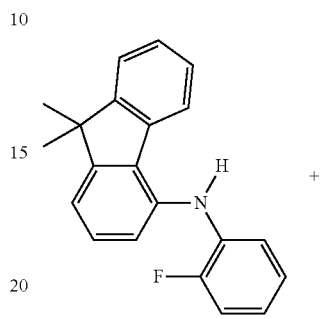

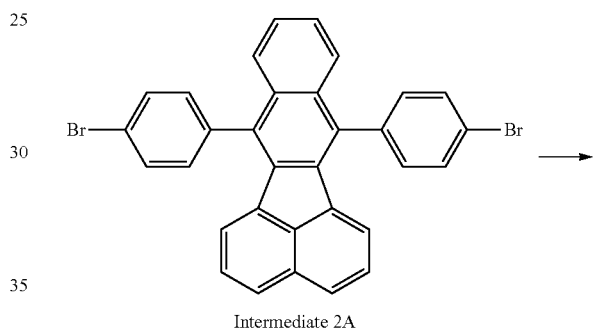

Intermediate 2A

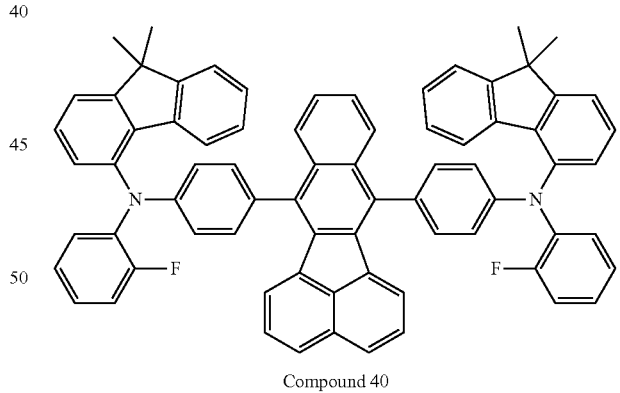

Compound 40

3.1 g of Compound 40 (Yield: 51%) was synthesized as in the synthetic method of Compound 2 of Synthesis Example 1, except that 7,12-bis(4-bromophenyl)benzo[k]fluoranthene was used instead of 1,6-dibromopyrene. The obtained compound was identified by NMR and MS.

H-NMR (CDCl$_3$, 300 MHz, ppm): 8.6 (m, 2H), 7.9-7.8 (m, 6H), 7.6-7.3 (m, 14H (, 7.0-6.9 (m, 8H), 6.7-6.6 (m, 10H), 1.7 (s, 12H).

MS (MALDI-TOF) m/z: 1006 [M]+.

Synthesis Example 31: Synthesis of Compound 43

Synthesis of Compound 43

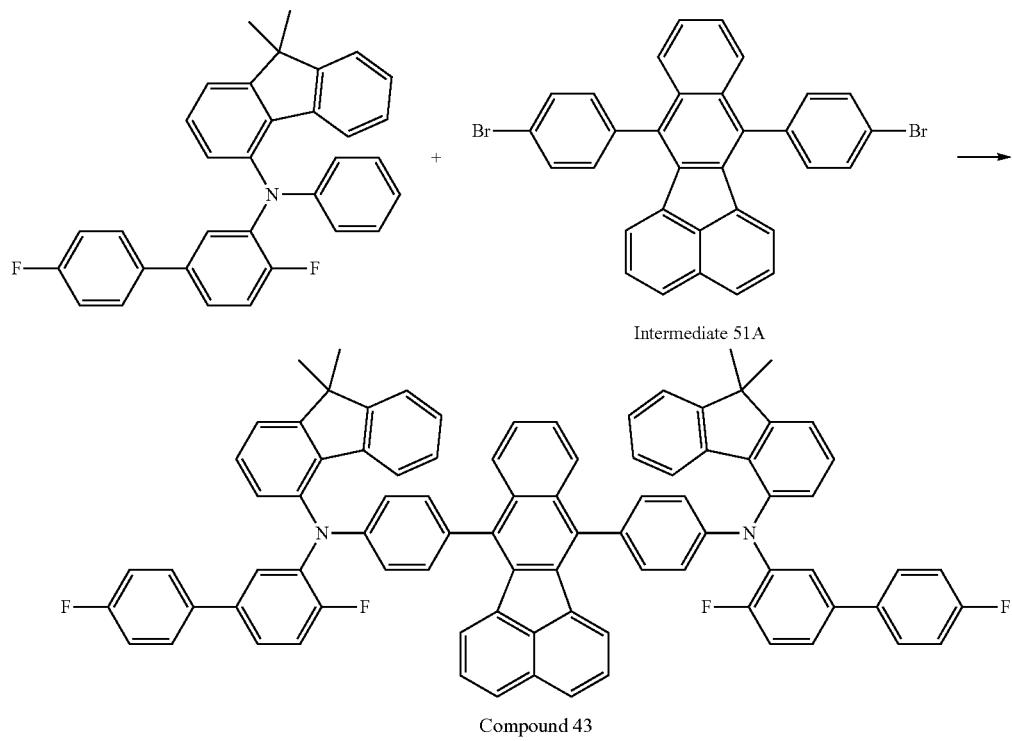

Intermediate 51A

Compound 43

3.4 g of Compound 43 (Yield: 48%) was synthesized as in the synthetic method of Compound 2 of Synthesis Example 1, except that 7,12-bis(4-bromophenyl)benzo[k]fluoranthene was used instead of 1,6-dibromopyrene and Intermediate 51A was used instead of Intermediate 2A. The obtained compound was identified by NMR and MS.

H-NMR (CDCl$_3$, 300 MHz, ppm): 8.6 (m, 2H), 7.9-7.8 (m, 6H), 7.6-7.3 (m, 22H), 7.0-6.9 (m, 8H), 6.8-6.6 (m, 8H), 1.7 (s, 12H).

MS (MALDI-TOF) m/z: 1194 [M]+.

Synthesis Example 32: Synthesis of Compound 46

Synthesis of Compound 46

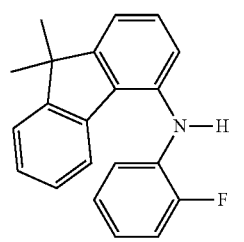

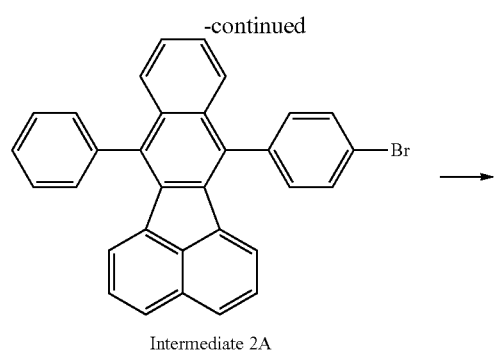

Intermediate 2A

-continued

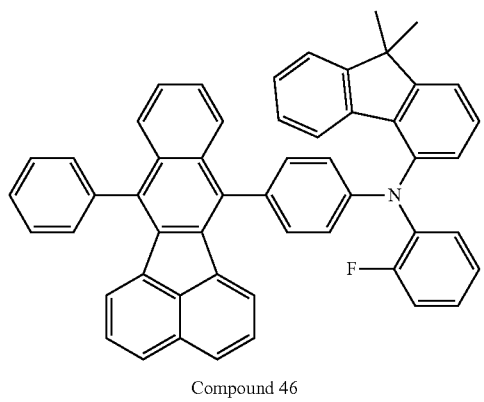

Compound 46

3.5 g of Compound 46 (Yield: 48%) was synthesized as in the synthetic method of Compound 2 of Synthesis Example 1, except that 7-(4-bromophenyl)-12-phenylbenzo[k]fluoranthene was used instead of 1,6-dibromopyrene and Intermediate 2A was used instead of Intermediate 18B. The obtained compound was identified by NMR and MS.

H-NMR (CDCl$_3$, 300 MHz, ppm): 8.6 (m, 2H), 7.9-7.8 (m, 5H), 7.6-7.3 (m, 14H), 7.0-6.9 (m, 4H), 6.7-6.6 (m, 5H), 1.7 (s, 6H).

MS (MALDI-TOF) m/z: 705 [M]+.

Synthesis Example 33: Synthesis of Compound 206

Synthesis of Intermediate 206A

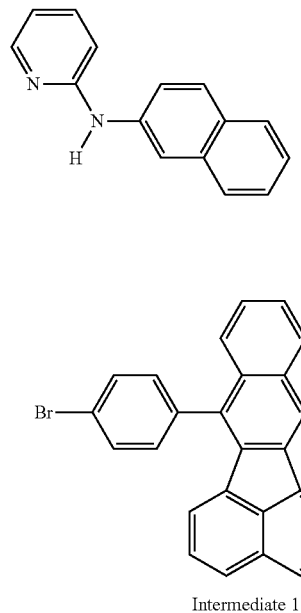

+

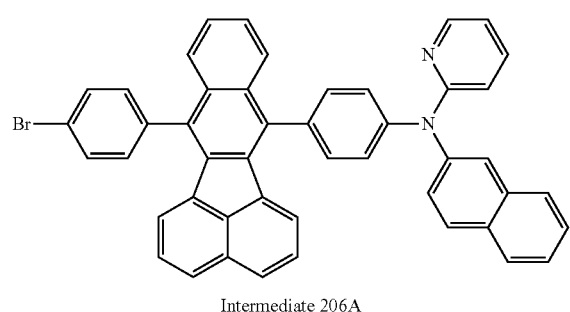

Intermediate 110B

→

Intermediate 206A

Intermediate 206A was synthesized as in the synthetic method of Intermediate 18A of Synthesis Example 4, except that Intermediate 110B was used instead of Intermediate 18B, and 7,12-bis(4-bromophenyl)benzo[k]fluoranthene was used instead of 1,6-dibromopyrene.

Synthesis of Compound 206

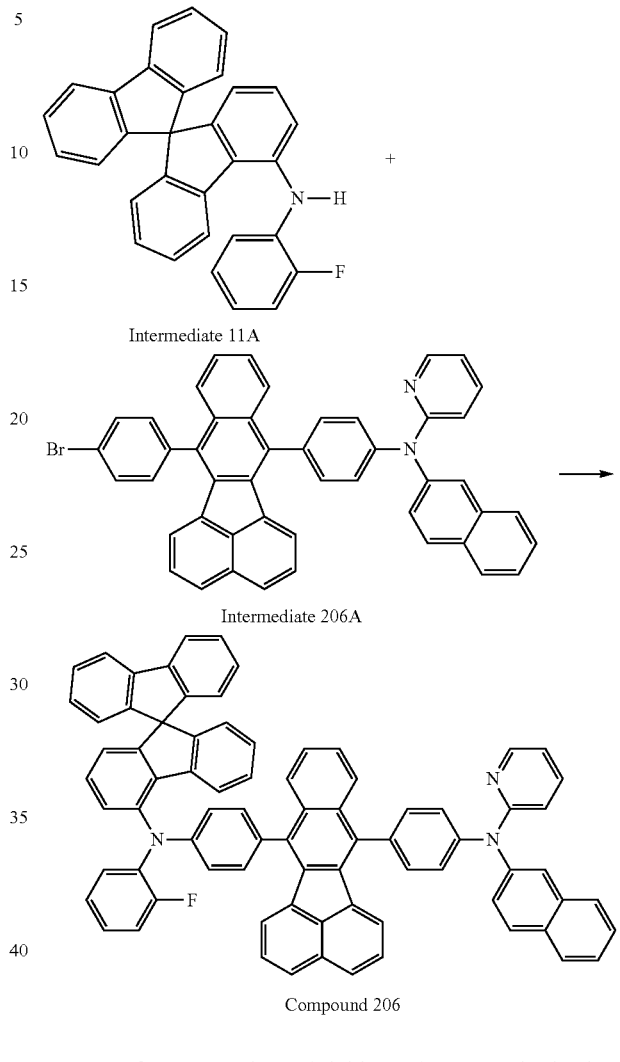

Intermediate 11A

+

Intermediate 206A

→

Compound 206

0.3 g of Compound 206 (Yield: 11%) was synthesized as in the synthetic method of Intermediate 18A of Synthesis Example 4, except that Intermediate 11A was used instead of Intermediate 18B, and Intermediate 206A was used instead of 1,6-dibromopyrene. The obtained compound was confirmed by NMR and MS.

H-NMR (CDCl$_3$, 300 MHz, ppm): 8.6 (m, 2H), 8.1-7.7 (m, 12H), 7.6-7.4 (m, 12H), 7.2-7.0 (m, 13H), 6.7-6.6 (m, 9H).

MS (MALDI-TOF) m/z: 1045 [M]+.

Synthesis Example 34: Synthesis of Compound 209

Synthesis of Intermediate 209A

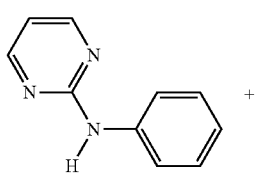

+

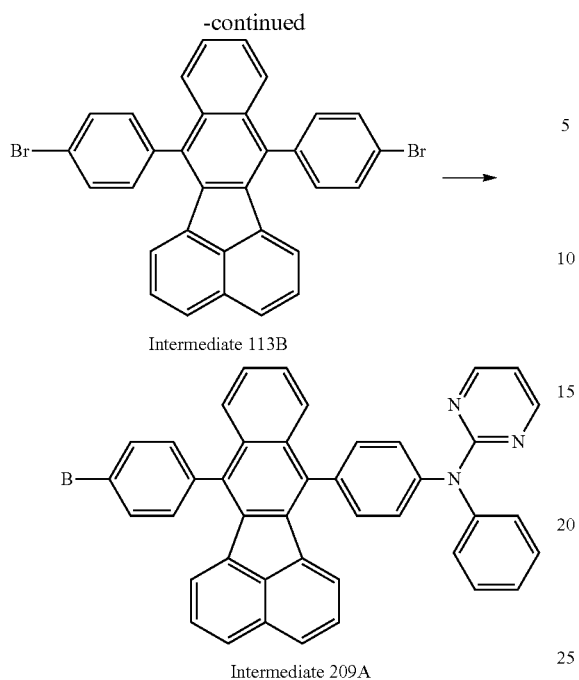

Intermediate 113B

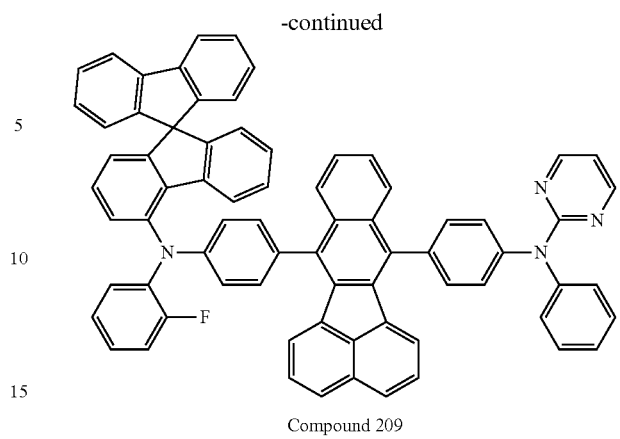

Compound 209

0.2 g of Compound 209 (Yield: 9%) was synthesized as in the synthetic method of Intermediate 18A of Synthesis Example 4, except that Intermediate 11A was used instead of Intermediate 18B, and Intermediate 209A was used instead of 1,6-dibromopyrene. The obtained compound was confirmed by NMR and MS.

H-NMR (CDCl$_3$, 300 MHz, ppm): 8.6-8.5 (m, 4H), 7.9-7.8 (m, 7H), 7.6-7.5 (m, 9H), 7.4-7.2 (m, 10H), 7.0-6.8 (m, 6H), 6.7-6.6 (m, 9H).

MS (MALDI-TOF) m/z: 996 [M]+.

Intermediate 209A was synthesized as in the synthetic method of Intermediate 18A of Synthesis Example 4, except that Intermediate 113B was used instead of Intermediate 18B, and 7,12-bis(4-bromophenyl)benzo[k]fluoranthene was used instead of 1,6-dibromopyrene.

Synthesis of Compound 209

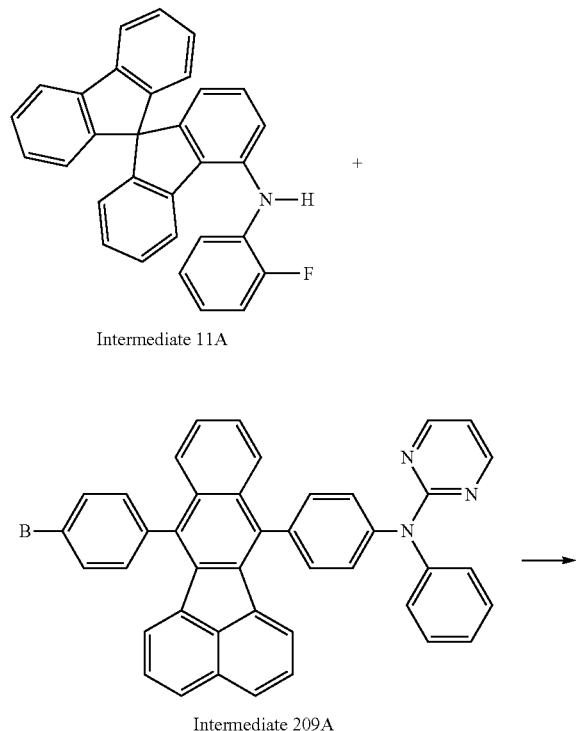

Example 1

A 15 Ω/cm$^2$ (1200 Å) ITO glass substrate manufactured by Corning Co., Ltd was cut to a size of 50 mm×50 mm×0.5 mm and sonicated with isopropyl alcohol and pure water each for 15 minutes, and then irradiated with ultraviolet light for 30 minutes, followed by exposure to ozone. Then, this glass substrate was installed in a vacuum deposition device.

m-MTDATA was deposited on an ITO layer functioning as an anode at a deposition rate of 1 Å/sec to form a hole injection layer having a thickness of 600 Å, and then alpha-NPD was deposited on the hole injection layer at a deposition rate of 1 Å/sec to form a hole transport layer having a thickness of 300 Å.

Then, Compound 2 (dopant) and 9,10-di-naphthalene-2-yl-anthracene (ADN, host) were co-deposited on the hole transport layer at deposition rates of 0.05 Å/sec and 1 Å/sec, respectively, to form an emission layer having a thickness of 200 Å.

Thereafter, Alq$_3$ was deposited on the emission layer to form an electron transport layer having a thickness of 300 Å, and LiF was deposited on the electron transport layer to form an electron injection layer having a thickness of 10 Å, and Al was deposited on the electron injection layer to form a cathode having a thickness of 2000 Å, thereby completing the manufacture of an organic light-emitting diode.

Example 2

An organic light-emitting diode was manufactured as in Example 1, except that as a dopant for use in the emission layer, Compound 3 was used instead of Compound 2.

Example 3

An organic light-emitting diode was manufactured as in Example 1, except that as a dopant for use in the emission layer, Compound 11 was used instead of Compound 2.

Example 4

An organic light-emitting diode was manufactured as in Example 1, except that as a dopant for use in the emission layer, Compound 18 was used instead of Compound 2.

Example 5

An organic light-emitting diode was manufactured as in Example 1, except that as a dopant for use in the emission layer, Compound 22 was used instead of Compound 2.

Example 6

An organic light-emitting diode was manufactured as in Example 1, except that as a dopant for use in the emission layer, Compound 25 was used instead of Compound 2.

Example 7

An organic light-emitting diode was manufactured as in Example 1, except that as a dopant for use in the emission layer, Compound 49 was used instead of Compound 2.

Example 8

An organic light-emitting diode was manufactured as in Example 1, except that as a dopant for use in the emission layer, Compound 50 was used instead of Compound 2.

Example 9

An organic light-emitting diode was manufactured as in Example 1, except that as a dopant for use in the emission layer, Compound 51 was used instead of Compound 2.

Example 10

An organic light-emitting diode was manufactured as in Example 1, except that as a dopant for use in the emission layer, Compound 53 was used instead of Compound 2.

Example 11

An organic light-emitting diode was manufactured as in Example 1, except that as a dopant for use in the emission layer, Compound 62 was used instead of Compound 2.

Example 12

An organic light-emitting diode was manufactured as in Example 1, except that as a dopant for use in the emission layer, Compound 63 was used instead of Compound 2.

Example 13

An organic light-emitting diode was manufactured as in Example 1, except that as a dopant for use in the emission layer, Compound 67 was used instead of Compound 2.

Example 14

An organic light-emitting diode was manufactured as in Example 1, except that as a dopant for use in the emission layer, Compound 69 was used instead of Compound 2.

Example 15

An organic light-emitting diode was manufactured as in Example 1, except that as a dopant for use in the emission layer, Compound 75 was used instead of Compound 2.

Example 16

An organic light-emitting diode was manufactured as in Example 1, except that as a dopant for use in the emission layer, Compound 83 was used instead of Compound 2.

Example 17

An organic light-emitting diode was manufactured as in Example 1, except that as a dopant for use in the emission layer, Compound 93 was used instead of Compound 2.

Example 18

An organic light-emitting diode was manufactured as in Example 1, except that as a dopant for use in the emission layer, Compound 95 was used instead of Compound 2.

Example 19

An organic light-emitting diode was manufactured as in Example 1, except that as a dopant for use in the emission layer, Compound 98 was used instead of Compound 2.

Example 20

An organic light-emitting diode was manufactured as in Example 1, except that as a dopant for use in the emission layer, Compound 104 was used instead of Compound 2.

Example 21

An organic light-emitting diode was manufactured as in Example 1, except that as a dopant for use in the emission layer, Compound 110 was used instead of Compound 2.

Example 22

An organic light-emitting diode was manufactured as in Example 1, except that as a dopant for use in the emission layer, Compound 113 was used instead of Compound 2.

Example 23

An organic light-emitting diode was manufactured as in Example 1, except that as a dopant for use in the emission layer, Compound 174 was used instead of Compound 2.

Example 24

An organic light-emitting diode was manufactured as in Example 1, except that as a dopant for use in the emission layer, Compound 177 was used instead of Compound 2.

Comparative Example 1

An organic light-emitting diode was manufactured as in Example 1, except that as a dopant for use in the emission layer, Compound A was used instead of Compound 2.

<Compound A>

Comparative Example 2

An organic light-emitting diode was manufactured as in Example 1, except that as a dopant for use in the emission layer, Compound B was used instead of Compound 2.

<Compound B>

Comparative Example 3

An organic light-emitting diode was manufactured as in Example 1, except that as a dopant for use in the emission layer, Compound C was used instead of Compound 2.

<Compound C>

Comparative Example 4

An organic light-emitting diode was manufactured as in Example 1, except that as a dopant for use in the emission layer, Compound D was used instead of Compound 2.

<Compound D>

Evaluation Example 1

The driving voltage, current density, brightness, and color coordinates of the organic light-emitting diodes manufactured according to Examples 1 to 24 and Comparative Examples 1 to 4 were evaluated using a PR650 Spectroscan Source Measurement Unit. (product of PhotoResearch Company). Results thereof are shown in Table 1.

TABLE 1

| Emission layer host | Emission layer dopant | Brightness (cd/m²) | Current density (mA/cm²) | Driving voltage (V) | Color coordinate (CIE) |
|---|---|---|---|---|---|
| Ex. 1 | ADN | Comp. 2 | 700 | 11 | 4.1 | (0.14, 0.075) |
| Ex. 2 | ADN | Comp. 3 | 700 | 13 | 4.2 | (0.14, 0.089) |
| Ex. 3 | ADN | Comp. 11 | 700 | 12 | 4.1 | (0.14, 0.079) |
| Ex. 4 | ADN | Comp. 18 | 700 | 12 | 4.2 | (0.14, 0.095) |
| Ex. 5 | ADN | Comp. 22 | 700 | 13 | 4.3 | (0.14, 0.095) |
| Ex. 6 | ADN | Comp. 25 | 700 | 14 | 4.4 | (0.14, 0.088) |
| Ex. 7 | ADN | Comp. 49 | 700 | 12 | 4.4 | (0.14, 0.083) |
| Ex. 8 | ADN | Comp. 50 | 700 | 13 | 4.3 | (0.14, 0.082) |
| Ex. 9 | ADN | Comp. 51 | 700 | 12 | 4.4 | (0.14, 0.084) |
| Ex. 10 | ADN | Comp. 53 | 700 | 14 | 4.4 | (0.14, 0.091) |
| Ex. 11 | ADN | Comp. 62 | 700 | 11 | 4.2 | (0.14, 0.085) |
| Ex. 12 | ADN | Comp. 63 | 700 | 12 | 4.2 | (0.14, 0.087) |
| Ex. 13 | ADN | Comp. 67 | 700 | 12 | 4.2 | (0.14, 0.077) |
| Ex. 14 | ADN | Comp. 69 | 700 | 13 | 4.3 | (0.14, 0.082) |
| Ex. 15 | ADN | Comp. 75 | 700 | 12 | 4.2 | (0.14, 0.084) |
| Ex. 16 | ADN | Comp. 83 | 700 | 13 | 4.3 | (0.14, 0.095) |
| Ex. 17 | ADN | Comp. 93 | 700 | 12 | 4.3 | (0.14, 0.077) |
| Ex. 18 | ADN | Comp. 95 | 700 | 12 | 4.2 | (0.14, 0.082) |
| Ex. 19 | ADN | Comp. 98 | 700 | 13 | 4.3 | (0.14, 0.083) |
| Ex. 20 | ADN | Comp. 104 | 700 | 13 | 4.2 | (0.14, 0.093) |
| Ex. 21 | ADN | Comp. 110 | 700 | 12 | 4.4 | (0.14, 0.078) |
| Ex. 22 | ADN | Comp. 113 | 700 | 14 | 4.5 | (0.14, 0.075) |
| Ex. 23 | ADN | Comp. 174 | 700 | 13 | 4.5 | (0.14, 0.077) |
| Ex. 24 | ADN | Comp. 177 | 700 | 14 | 4.4 | (0.14, 0.089) |
| Comp. Ex. 1 | ADN | Comp. A | 700 | 16 | 4.6 | (0.16, 0.20) |
| Comp. Ex. 2 | ADN | Comp. B | 700 | 15 | 4.5 | (0.15, 0.18) |
| Comp. Ex. 3 | ADN | Comp. C | 700 | 21 | 4.8 | (0.16, 0.21) |
| Comp. Ex. 4 | ADN | Comp. D | 700 | 18 | 4.7 | (0.14, 0.12) |

From Table 1, it was confirmed that the organic light-emitting diodes of Examples 1 to 24 have lower driving voltages, higher current densities, and better color purity characteristics than the organic light-emitting diodes of Comparative Examples 1 to 4.

Example 25

An organic light-emitting diode was manufactured as in Example 1, except that as a dopant for use in the emission layer, Compound 29 was used instead of Compound 2.

Example 26

An organic light-emitting diode was manufactured as in Example 1, except that as a dopant for use in the emission layer, Compound 31 was used instead of Compound 2.

Example 27

An organic light-emitting diode was manufactured as in Example 1, except that as a dopant for use in the emission layer, Compound 37 was used instead of Compound 2.

Example 28

An organic light-emitting diode was manufactured as in Example 1, except that as a dopant for use in the emission layer, Compound 188 was used instead of Compound 2.

Example 29

An organic light-emitting diode was manufactured as in Example 1, except that as a dopant for use in the emission layer, Compound 191 was used instead of Compound 2.

Comparative Example 5

An organic light-emitting diode was manufactured as in Example 1, except that as a dopant for use in the emission layer, Compound E was used instead of Compound 2.

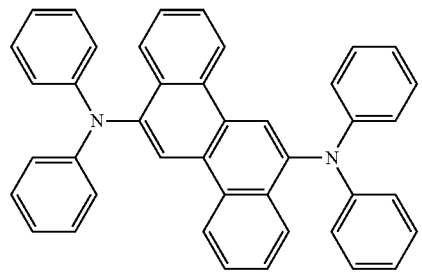

<Compound E>

Comparative Example 6

An organic light-emitting diode was manufactured as in Example 1, except that as a dopant for use in the emission layer, Compound F was used instead of Compound 2.

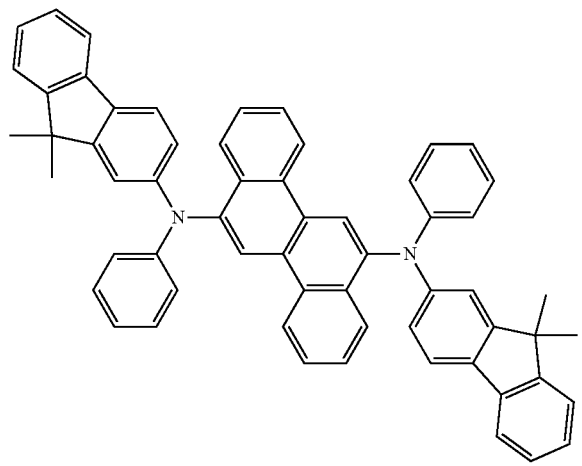

<Compound F>

Comparative Example 7

An organic light-emitting diode was manufactured as in Example 1, except that as a dopant for use in the emission layer, Compound G was used instead of Compound 2.

<Compound G>

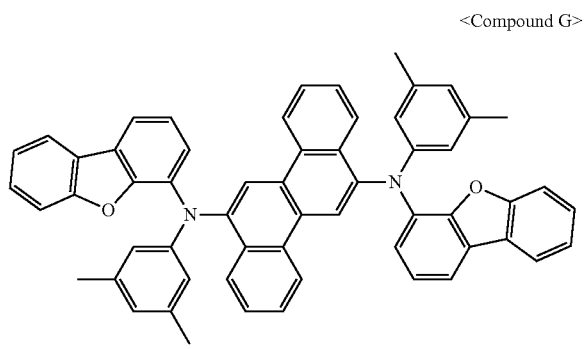 [SMILES: Cc1cc(C)cc(N(c2cc3c4ccccc4c(N(c4cc(C)cc(C)c4)c4cccc5c4oc4ccccc45)cc3c3ccccc23)c2cccc3c2oc2ccccc23)c1]

Comparative Example 8

An organic light-emitting diode was manufactured as in Example 1, except that as a dopant for use in the emission layer, Compound H was used instead of Compound 2.

<Compound H>

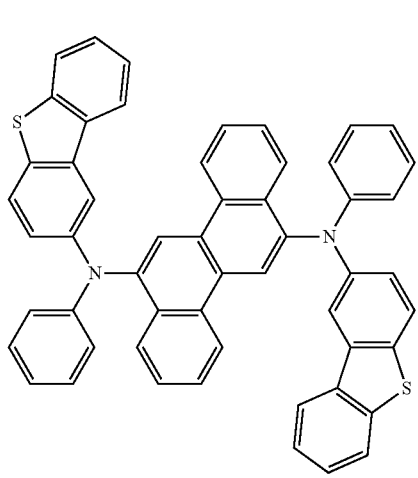

Evaluation Example 2

The driving voltage, current density, brightness, and color coordinate of the organic light-emitting diodes manufactured according to Examples 25 to 29 and Comparative Examples 5 to 8 were evaluated using a PR650 Spectroscan Source Measurement Unit. (product of PhotoResearch Company). Results thereof are shown in Table 2.

TABLE 2

| | E-mission layer host | Emission layer dopant | Brightness (cd/m$^2$) | Current density (mA/cm$^2$) | Driving voltage (V) | Color coordinate (CIE) |
|---|---|---|---|---|---|---|
| Ex. 25 | ADN | Comp. 29 | 700 | 13 | 4.4 | (0.14, 0.080) |
| Ex. 26 | ADN | Comp. 31 | 700 | 13 | 4.2 | (0.14, 0.085) |
| Ex. 27 | ADN | Comp. 37 | 700 | 15 | 4.3 | (0.14, 0.082) |
| Ex. 28 | ADN | Comp. 188 | 700 | 16 | 4.4 | (0.14, 0.077) |
| Ex. 29 | ADN | Comp. 191 | 700 | 16 | 4.5 | (0.14, 0.074) |
| Comp. Ex. 5 | ADN | Comp. E | 700 | 17 | 4.7 | (0.14, 0.16) |
| Comp. Ex. 6 | ADN | Comp. F | 700 | 16 | 4.6 | (0.15, 0.22) |
| Comp. Ex. 7 | ADN | Comp. G | 700 | 20 | 5.0 | (0.15, 0.28) |
| Comp. Ex. 8 | ADN | Comp. H | 700 | 21 | 5.2 | (0.15, 0.23) |

From Table 2, it was confirmed that the organic light-emitting diodes of Examples 25 to 29 have lower driving voltages, higher current density, and better color purity characteristics than the organic light-emitting diodes of Comparative Examples 5 to 8.

Example 30

An organic light-emitting diode was manufactured as in Example 1, except that as a dopant for use in the emission layer, Compound 40 was used instead of Compound 2.

Example 31

An organic light-emitting diode was manufactured as in Example 1, except that as a dopant for use in the emission layer, Compound 43 was used instead of Compound 2.

Example 31

An organic light-emitting diode was manufactured as in Example 1, except that as a dopant for use in the emission layer, Compound 46 was used instead of Compound 2.

Example 33

An organic light-emitting diode was manufactured as in Example 1, except that as a dopant for use in the emission layer, Compound 206 was used instead of Compound 2.

Example 34

An organic light-emitting diode was manufactured as in Example 1, except that as a dopant for use in the emission layer, Compound 209 was used instead of Compound 2.

Comparative Example 9

An organic light-emitting diode was manufactured as in Example 1, except that as a dopant for use in the emission layer, Compound I was used instead of Compound 2.

<Compound I>

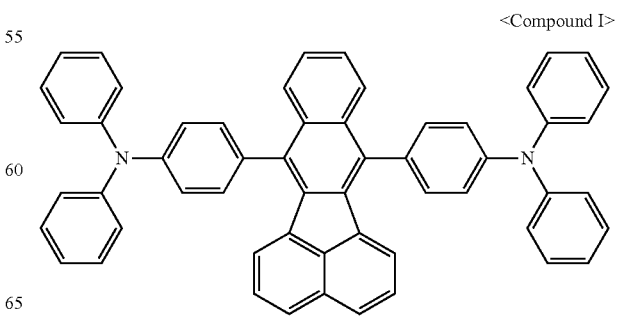

Comparative Example 10

An organic light-emitting diode was manufactured as in Example 1, except that as a dopant for use in the emission layer, Compound J was used instead of Compound 2.

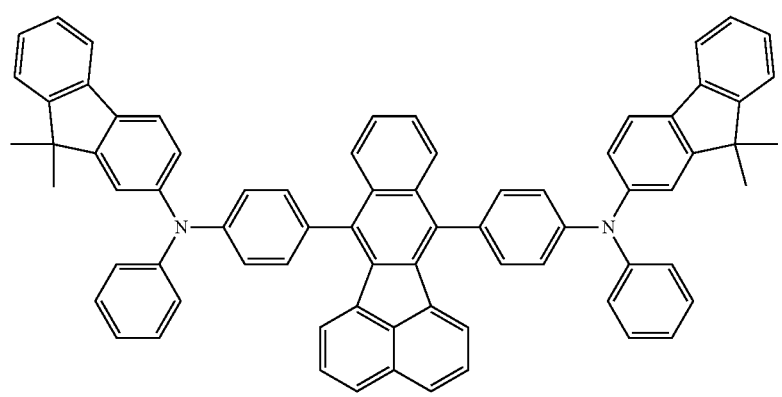

<Compound L>

Evaluation Example 3

The driving voltage, current density, brightness, and color coordinate of the organic light-emitting diodes manufactured according to Examples 30 to 34 and Comparative Examples 9 and 10 were evaluated using a PR650 Spectroscan Source Measurement Unit. (product of PhotoResearch Company). Results thereof are shown in Table 2.

TABLE 3

| | Emission layer host | Emission layer dopant | Brightness (cd/m$^2$) | Current density (mA/cm$^2$) | Driving voltage (V) | Color coordinate (CIE) |
|---|---|---|---|---|---|---|
| Ex. 30 | ADN | Comp. 40 | 700 | 19 | 4.4 | (0.14, 0.082) |
| Ex. 31 | ADN | Comp. 43 | 700 | 17 | 4.7 | (0.14, 0.084) |
| Ex. 32 | ADN | Comp. 46 | 700 | 18 | 4.6 | (0.14, 0.088) |
| Ex. 33 | ADN | Comp. 206 | 700 | 17 | 4.5 | (0.14, 0.084) |
| Ex. 34 | ADN | Comp. 209 | 700 | 19 | 4.6 | (0.14, 0.078) |
| Comp. Ex. 9 | ADN | Comp. I | 700 | 25 | 5.4 | (0.14, 0.19) |
| Comp. Ex. 10 | ADN | Comp. J | 700 | 27 | 5.5 | (0.15, 0.20) |

From Table 3, it was confirmed that the organic light-emitting diodes of Examples 30 to 34 have lower driving voltages, higher current density, and better color purity characteristics than the organic light-emitting diodes of Comparative Examples 9 and 10.

Organic light-emitting diodes and organic light-emitting apparatuses including the amine-based compounds described above have low driving voltages, high current densities, and good color purity characteristics.

While the present invention has been illustrated and described with reference to certain exemplary embodiments, it will be understood by those of ordinary skill in the art that various changes and modifications to the described embodiments may be made without departing from the spirit and scope of the present invention as defined by the following claims.

What is claimed is:

1. An amine-based compound represented by any one of Formulae 1A through 1D below:

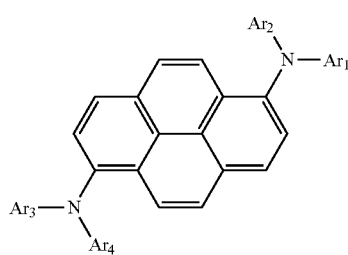

Formula 1A

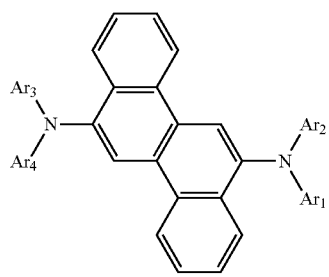

Formula 1B

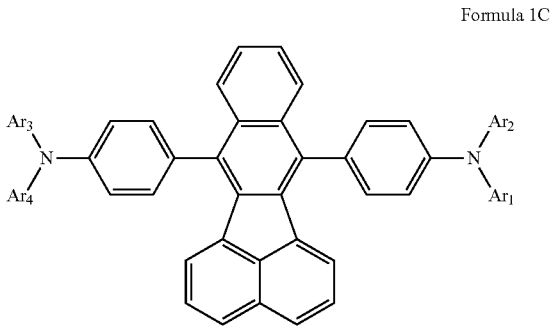

Formula 1C

-continued

Formula 1D

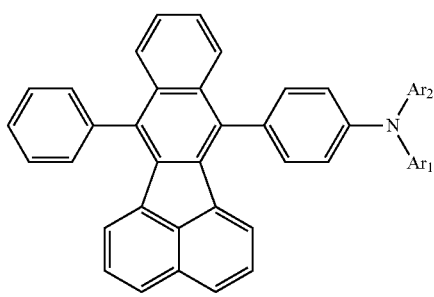

wherein in Formulae 1A through 1 D:
in Formulae 1B through 1D, $Ar_1$ to $Ar_4$ are each independently a substituted or unsubstituted $C_6$-$C_{60}$ aryl group, a substituted or unsubstituted $C_2$-$C_{60}$ heteroaryl group, a substituent represented by Formula 2A, or a substituent represented by Formula 2B, and in Formula 1A, $Ar_1$ to $Ar_4$ are each independently:
 a $C_2$-$C_{60}$ heteroaryl group, a substituent represented by Formula 2A, a substituent represented by Formula 2B, a phenyl group, a pentalenyl, an indenyl, an azulenyl, a heptalenyl, an indacenyl, an acenaphthyl group, a 9,9 dimethyl fluorenyl, a phenalenyl, a phenanthrenyl, an anthryl group, a fluoranthenyl group, a triphenylenyl group, a pyrenyl group, a chrysenyl group, a naphthacenyl group, a picenyl group, a perylenyl group, a pentaphenyl group, or a hexacenyl group; or
 a $C_2$-$C_{60}$ heteroaryl group, a substituent represented by Formula 2A, a substituent represented by Formula 2B, a phenyl group, a pentalenyl, an indenyl, an azulenyl, a heptalenyl, an indacenyl, an acenaphthyl group, a 9,9 dimethyl fluorenyl, a phenalenyl, a phenanthrenyl, an anthryl group, a fluoranthenyl group, a triphenylenyl group, a pyrenyl group, a chrysenyl group, a naphthacenyl group, a picenyl group, a perylenyl group, a pentaphenyl group, or a hexacenyl group substituted with:
 —F;
 —Cl;
 —Br;
 —I;
 —CN;
 a hydroxyl group;
 a nitro group;
 an amino group;
 an amidino group;
 a hydrazine;
 a hydrazone;
 a carboxylic acid group or salt thereof;
 a sulfonic acid group or salt thereof;
 a phosphoric acid group or salt thereof;
 a $C_1$-$C_{60}$ alkyl group;
 a $C_1$-$C_{60}$ alkoxy group;
 a $C_2$-$C_{60}$ alkenyl group;
 a $C_2$-$C_{60}$ alkynyl group;
 a $C_1$-$C_{60}$ alkyl group, $C_1$-$C_{60}$ alkoxy group, $C_2$-$C_{60}$ alkenyl group, or $C_2$-$C_{60}$ alkynyl group substituted with at least one selected from:
  —F,
  —Cl,
  —Br,
  —CN,
  a hydroxyl group,
  a nitro group,
  an amino group,
  an amidino group,
  a hydrazine,
  a hydrazone,
  a carboxylic acid group or salt thereof,
  a sulfonic acid group or salt thereof, or
  a phosphoric acid group or salt thereof;
 a $C_3$-$C_{60}$ cycloalkyl group;
 a $C_5$-$C_{60}$ aryl group;
 a $C_2$-$C_{60}$ heteroaryl group;
 a $C_5$-$C_{60}$ aralkyl group; a $C_5$-$C_{60}$ aryloxy group; or
 a $C_3$-$C_{60}$ cycloalkyl group, $C_5$-$C_{60}$ aryl group, $C_2$-$C_{60}$ heteroaryl group, $C_5$-$C_{60}$ aralkyl group, or $C_5$-$C_{60}$ aryloxy group substituted with at least one selected from:
  —F,
  —Cl,
  —Br,
  —CN,
  a hydroxyl group,
  a nitro group,
  an amino group,
  an amidino group,
  a hydrazine,
  a hydrazone,
  a carboxylic acid group or salt thereof,
  a sulfonic acid group or salt thereof,
  a phosphoric acid group or salt thereof,
  a $C_1$-$C_{60}$ alkyl group,
  a $C_1$-$C_{60}$ alkoxy group,
  a $C_2$-$C_{60}$ alkenyl group,
  a $C_2$-$C_{60}$ alkynyl group,
  a $C_5$-$C_{60}$ aryl group, or
  a $C_2$-$C_{60}$ heteroaryl group:
wherein at least one of $Ar_1$ to $Ar_4$ in Formula 1A through 1D is a substituent represented by Formula 2A or a substituent represented by Formula 2B:

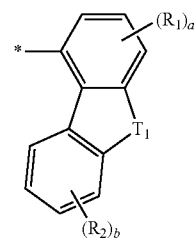

<Formula 2A>

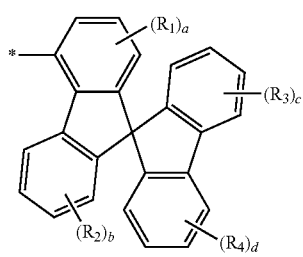

<Formula 2B> wherein:
 in Formula 2A, $T_1$ is O, S, $N(R_{11})$, $C(R_{12})(R_{13})$, or $Si(R_{14})(R_{15})$;

in Formula 2A and 2B, a is an integer of 0 to 3; b, c, and d are each independently an integer of 0 to 4; and * is a binding site to N of one of Formulas 1A to 1D;

wherein in Formula 2A and 2B, $R_1$ to $R_4$, $R_{11}$, $R_{14}$ and $R_{15}$ may be each independently one selected from the group consisting of:
—F;
—Cl;
—Br;
—I;
—CN;
a hydroxyl group;
a —NO$_2$ group;
an amino group;
an amidino group;
a hydrazine;
a hydrazone;
a carboxylic acid group or salt thereof;
a sulfonic acid group or salt thereof;
a phosphoric acid group or salt thereof;
a $C_1$-$C_{60}$ alkyl group;
a $C_1$-$C_{60}$ alkoxy group;
a $C_2$-$C_{60}$ alkenyl group;
a $C_2$-$C_{60}$ alkynyl group;
a $C_1$-$C_{60}$ alkyl group, $C_1$-$C_{60}$ alkoxy group, $C_2$-$C_{60}$ alkenyl group, or a $C_2$-$C_{60}$ alkynyl group substituted with at least one selected from the group consisting of:
—F,
—Cl,
—Br,
—CN,
a hydroxyl group,
a —NO$_2$ group,
an amino group,
an amidino group,
a hydrazine,
a hydrazone,
a carboxylic group or salt thereof,
a sulfonic acid group or salt thereof, and
a phosphoric acid group or salt thereof;
a $C_3$-$C_{60}$ cycloalkyl group;
a $C_3$-$C_{60}$ cycloalkenyl group;
a $C_6$-$C_{60}$ aryl group;
a $C_2$-$C_{60}$ heteroaryl group;
a $C_6$-$C_{60}$ aralkyl group;
a $C_6$-$C_{60}$ aryloxy group;
a $C_6$-$C_{60}$ arylthio group; and
a $C_3$-$C_{60}$ cycloalkyl group, $C_3$-$C_{60}$ cycloalkenyl group, $C_6$-$C_{60}$ aryl group, $C_2$-$C_{60}$ heteroaryl group, $C_6$-$C_{60}$ aralkyl group, $C_6$-$C_{60}$ aryloxy group, or $C_6$-$C_{60}$ arylthio group substituted with at least one selected from the group consisting of deuterium, —F, —Cl, —Br, —I, —CN, a hydroxyl group, a —NO$_2$ group, an amino group, an amidino group, a hydrazine, a hydrazone, a carboxylic acid group or salt thereof, a sulfonic acid group or salt thereof, a phosphoric acid group or salt thereof, a $C_1$-$C_{60}$ alkyl group, a $C_1$-$C_{60}$ alkyl group substituted with at least one —F, a $C_1$-$C_{60}$ alkoxy group, a $C_2$-$C_{60}$ alkenyl group, a $C_2$-$C_{60}$ alkynyl group, a $C_6$-$C_{60}$ aryl group, and a $C_2$-$C_{60}$ heteroaryl group;

wherein $R_{12}$ and $R_{13}$ may be each independently one selected from the group consisting of:
—F;
—Cl;
—Br;
—I;
—CN;
a hydroxyl group;
a —NO$_2$ group;
an amino group;
an amidino group;
a hydrazine;
a hydrazone;
a carboxylic acid group or salt thereof;
a sulfonic acid group or salt thereof;
a phosphoric acid group or salt thereof;
a methyl group;
a $C_1$-$C_{60}$ alkoxy group;
a $C_2$-$C_{60}$ alkenyl group;
a $C_2$-$C_{60}$ alkynyl group;
a methyl group, $C_1$-$C_{60}$ alkoxy group, $C_2$-$C_{60}$ alkenyl group, or a $C_2$-$C_{60}$ alkynyl group substituted with at least one selected from the group consisting of:
—F,
—Cl,
—Br,
—CN,
a hydroxyl group,
a —NO$_2$ group,
an amino group,
an amidino group,
a hydrazine,
a hydrazone,
a carboxylic group or salt thereof,
a sulfonic acid group or salt thereof, and
a phosphoric acid group or salt thereof;
a $C_3$-$C_{60}$ cycloalkyl group;
a $C_3$-$C_{60}$ cycloalkenyl group;
a $C_6$-$C_{60}$ aryl group;
a $C_2$-$C_{60}$ heteroaryl group;
a $C_6$-$C_{60}$ aralkyl group;
a $C_6$-$C_{60}$ aryloxy group;
a $C_6$-$C_{60}$ arylthio group; and
a $C_3$-$C_{60}$ cycloalkyl group, $C_3$-$C_{60}$ cycloalkenyl group, $C_6$-$C_{60}$ aryl group, $C_2$-$C_{60}$ heteroaryl group, $C_6$-$C_{60}$ aralkyl group, $C_6$-$C_{60}$ aryloxy group, or $C_6$-$C_{60}$ arylthio group substituted with at least one selected from the group consisting of deuterium, —F, —Cl, —Br, —I, —CN, a hydroxyl group, a —NO$_2$ group, an amino group, an amidino group, a hydrazine, a hydrazone, a carboxylic acid group or salt thereof, a sulfonic acid group or salt thereof, a phosphoric acid group or salt thereof, a $C_1$-$C_{60}$ alkyl group, a $C_1$-$C_{60}$ alkyl group substituted with at least one —F, a $C_1$-$C_{60}$ alkoxy group, a $C_2$-$C_{60}$ alkenyl group, a $C_2$-$C_{60}$ alkynyl group, a $C_6$-$C_{60}$ aryl group, and a $C_2$-$C_{60}$ heteroaryl group;

wherein at least one other of $Ar_1$ to $Ar_4$ in Formula 1A is:
a phenyl group, pentalenyl group, indenyl group, azulenyl group, heptalenyl group, indacenyl group, acenaphthyl group, 9,9 dimethyl fluorenyl group, phenalenyl group, phenanthrenyl group, anthryl group, fluoranthenyl group, triphenylenyl group, pyrenyl group, chrysenyl group, naphthacenyl group, picenyl group, perylenyl group, pentaphenyl group, or hexacenyl group substituted with at least one selected from the group consisting of:
—F,
—CN,
—NO$_2$, and a $C_1$-$C_{20}$ alkyl group substituted with at least one —F;
a pyridinyl group, a pyrazinyl group, a pyrimidinyl group, a triazinyl group, a quinolinyl group, an isoquinolinyl group a naphthyridinyl group, a quinazolinyl group, a quinoxalinyl group, or a cinnolinyl group;
a pyridinyl group, a pyrazinyl group, a pyrimidinyl group, a triazinyl group, a quinolinyl group, an isoquinolinyl group a naphthyridinyl group, a quinazolinyl group, a quinoxalinyl group, or a cinnolinyl group substituted with at least one selected from the group consisting of:
—F,
—CN,
—$NO_2$, and
a $C_1$-$C_{20}$ alkyl group substituted with at least one —F;
a substituent represented by Formula 2A in which either:
$T_1$ is O, S or $N(R_{11})$, or
at least one of $R_1$ and $R_2$ is selected from the group consisting of:
—F,
—CN,
—$NO_2$, and
a $C_1$-$C_{20}$ alkyl group substituted with at least one —F; and
a substituent represented by Formula 2B in which at least one of $R_1$ through $R_4$ is selected from the group consisting of:
—F,
—CN,
—$NO_2$, and
a $C_1$-$C_{20}$ alkyl group substituted with at least one —F;
wherein at least one other of $Ar_1$ to $Ar_4$ in Formula 1B through 1D is a $C_6$-$C_{60}$ aryl group substituted with at least one selected from the group consisting of:
—F,
—CN,
—$NO_2$, and
a $C_1$-$C_{20}$ alkyl group substituted with at least one —F;
a pyridinyl group, a pyrazinyl group, a pyrimidinyl group, a triazinyl group, a quinolinyl group, an isoquinolinyl group a naphthyridinyl group, a quinazolinyl group, a quinoxalinyl group, or a cinnolinyl group;
a pyridinyl group, a pyrazinyl group, a pyrimidinyl group, a triazinyl group, a quinolinyl group, an isoquinolinyl group a naphthyridinyl group, a quinazolinyl group, a quinoxalinyl group, or a cinnolinyl group substituted with at least one selected from the group consisting of:
—F,
—CN,
—$NO_2$, and
a $C_1$-$C_{20}$ alkyl group substituted with at least one —F; and
* and *' are binding sites with A.

2. The amine-based compound of claim 1, wherein in Formula 2A of the at least one of $Ar_1$ to $Ar_4$ in Formula 1A through 1D that is a substituent represented by Formula 2A or a substituent represented by Formula 2B:

$T_1$ is O, S, $N(R_{11})$, or $C(R_{12})(R_{13})$, wherein:
$R_{11}$ is one selected from the group consisting of:
a $C_6$-$C_{20}$ aryl group; and
a $C_6$-$C_{20}$ aryl group substituted with at least one selected from the group consisting of:
—F,
—Cl,
—Br,
—CN,
a hydroxyl group,
a —$NO_2$ group,
an amino group,
an amidino group,
a hydrazine,
a hydrazone,
a carboxylic acid group or salt thereof,
a sulfonic acid group or salt thereof,
a phosphoric acid group or salt thereof,
a $C_1$-$C_{20}$ alkyl group,
a $C_1$-$C_{20}$ alkyl group substituted with at least one —F, and
a $C_1$-$C_{20}$ alkoxy group, and
$R_{12}$ and $R_{13}$ are each independently one selected from the group consisting of:
a methyl group;
a methyl group substituted with at least one selected from the group consisting of:
—F,
—Cl,
—Br,
—CN,
a hydroxyl group,
a —$NO_2$ group,
an amino group,
an amidino group,
a hydrazine,
a hydrazone,
a carboxylic acid group or salt thereof,
a sulfonic acid group or salt thereof, and
a phosphoric acid group or salt thereof;
a $C_6$-$C_{20}$ aryl group; and
a $C_6$-$C_{20}$ aryl group substituted with at least one selected from the group consisting of:
—F,
—Cl,
—Br,
—CN,
a hydroxyl group,
a —$NO_2$ group,
an amino group,
an amidino group,
a hydrazine,
a hydrazone,
a carboxylic acid group or salt thereof,
a sulfonic acid group or salt thereof,
a phosphoric acid group or salt thereof,
a $C_1$-$C_{20}$ alkyl group, and
a $C_1$-$C_{20}$ alkyl group substituted with at least one F, and
a $C_1$-$C_{20}$ alkoxy group;
$R_1$ and $R_2$ are each independently one selected from the group consisting of:
—Cl;
—Br;
—I;
—CN;
a hydroxyl group;

a —NO$_2$ group;
an amino group;
an amidino group;
a hydrazine;
a hydrazone;
a carboxylic acid group or salt thereof;
a sulfonic acid group or salt thereof;
a phosphoric acid group or salt thereof;
a C$_1$-C$_{20}$ alkyl group;
a C$_1$-C$_{20}$ alkoxy group; and
a C$_1$-C$_{20}$ alkyl group or C$_1$-C$_{20}$ alkoxy group substituted with at least one selected from the group consisting of:
—F,
—Cl,
—Br,
—CN,
a hydroxyl group,
an —NO$_2$ group,
an amino group,
an amidino group,
a hydrazine,
a hydrazone,
a carboxylic acid group or salt thereof,
a sulfonic acid group or salt thereof, and
a phosphoric acid group or salt thereof; and
a and b are each independently 0, 1, or 2.

3. The amine-based compound of claim 1, wherein in Formula 2B:
R$_1$ to R$_4$ are each independently one selected from the group consisting of:
—F;
—Cl;
—Br;
—I;
—CN;
a hydroxyl group;
a —NO$_2$ group;
an amino group;
an amidino group;
a hydrazine;
a hydrazone;
a carboxylic acid group or salt thereof;
a sulfonic acid group or salt thereof;
a phosphoric acid group or salt thereof;
a C$_1$-C$_{20}$ alkyl group;
a C$_1$-C$_{20}$ alkoxy group; and
a C$_1$-C$_{20}$ alkyl group or C$_1$-C$_{20}$ alkoxy group substituted with at least one selected from the group consisting of:
—F,
—Cl,
—Br,
—CN,
a hydroxyl group,
a —NO$_2$ group,
an amino group,
an amidino group,
a hydrazine,
a hydrazone,
a carboxylic acid group or salt thereof,
a sulfonic acid group or salt thereof, and
a phosphoric acid group or salt thereof; and
a to d are each independently 0, 1, or 2.

4. The amine-based compound of claim 1, wherein Ar$_1$ to Ar$_4$ in Formula 1B through 1D are each independently a substituted or unsubstituted phenyl group, a substituted or unsubstituted pentalenyl, a substituted or unsubstituted indenyl, a substituted or unsubstituted naphthyl group, a substituted or unsubstituted azulenyl, a substituted or unsubstituted heptalenyl, a substituted or unsubstituted indacenyl, a substituted or unsubstituted acenaphthyl group, a substituted or unsubstituted 9,9 dimethyl fluorenyl, a substituted or unsubstituted phenalenyl, a substituted or unsubstituted phenanthrenyl, a substituted or unsubstituted anthryl group, a substituted or unsubstituted fluoranthenyl group, a substituted or unsubstituted triphenylenyl group, a substituted or unsubstituted pyrenyl group, a substituted or unsubstituted chrysenyl group, a substituted or unsubstituted naphthacenyl group, a substituted or unsubstituted picenyl group, a substituted or unsubstituted perylenyl group, a substituted or unsubstituted pentaphenyl group, a substituted or unsubstituted hexacenyl group, a substituted or unsubstituted pyrrolyl group, a substituted or unsubstituted pyrazolyl group, a substituted or unsubstituted imidazolyl group, a substituted or unsubstituted imidazolinyl group, a substituted or unsubstituted imidazopyridinyl group, a substituted or unsubstituted imidazopyrimidinyl group, a substituted or unsubstituted pyridinyl group, a substituted or unsubstituted pyrazinyl, a substituted or unsubstituted pyrimidinyl group, a substituted or unsubstituted benzoimidazolyl group, a substituted or unsubstituted indolyl group, a substituted or unsubstituted purinyl group, a substituted or unsubstituted quinolinyl group, a substituted or unsubstituted isoquinolinyl group, a substituted or unsubstituted phthalazinyl group, a substituted or unsubstituted indolizinyl group, a substituted or unsubstituted naphthyridinyl group, a substituted or unsubstituted quinazolinyl group, a substituted or unsubstituted quinoxalinyl group, a substituted or unsubstituted cinnolinyl group, a substituted or unsubstituted indazolyl group, a substituted or unsubstituted carbazolyl group, a substituted or unsubstituted phenazinyl group, a substituted or unsubstituted phenanthridinyl group, a substituted or unsubstituted pyranyl group, a substituted or unsubstituted chromenyl group, a substituted or unsubstituted furanyl group, a substituted or unsubstituted benzofuranyl group, a substituted or unsubstituted thiophenyl group, a substituted or unsubstituted benzothiophenyl group, a substituted or unsubstituted isothiazolyl group, a substituted or unsubstituted benzoimidazolyl group, a substituted or unsubstituted isoxazolyl group, a substituted or unsubstituted dibenzothiophenyl group, a substituted or unsubstituted dibenzofuranyl group, a substituted or unsubstituted triazinyl group, a substituted or unsubstituted oxadiazolyl group, a substituted or unsubstituted pyridazinyl group, a substituted or unsubstituted triazolyl group, a substituted or unsubstituted tetrazolyl group, a substituted or unsubstituted phenanthrolinyl group, a substituent represented by Formula 2A, or a substituent represented by Formula 2B, Ar$_1$ to Ar$_4$ in Formula 1A are each independently:
a phenyl group, a pentalenyl, an indenyl, an azulenyl, a heptalenyl, an indacenyl, an acenaphthyl group, a 9,9 dimethyl fluorenyl, a phenalenyl, a phenanthrenyl, an anthryl group, a fluoranthenyl group, a triphenylenyl group, a pyrenyl group, a chrysenyl group, a naphthacenyl group, a picenyl group, a perylenyl group, a pentaphenyl group, a hexacenyl group, a pyrrolyl group, a pyrazolyl group, an imidazolyl group, an imidazolinyl group, an imidazopyridinyl group, an imidazopyrimidinyl group, a pyridinyl group, a pyrazinyl, a pyrimidinyl group, a benzoimidazolyl group, an indolyl group, a purinyl group, a quinolinyl group, an isoquinolinyl group, a phthalazinyl group, an indolizinyl group, a naphthyridinyl group, a quinazolinyl group, a quinoxalinyl group, a cinnolinyl group, an indazolyl group, a carbazolyl group, a phenazinyl group, a phenanthridinyl group, a pyranyl group, a chromenyl group, a furanyl group, a benzofuranyl group, a thiophenyl group, a benzothiophenyl group, a isothiazolyl group, a benzoimidazolyl group, an isoxazolyl group, a dibenzothiophenyl group, a dibenzofuranyl group, a triazinyl group, an oxadiazolyl group, a pyridazinyl group, a triazolyl group, a tetrazolyl group, a phenanthrolinyl group, a substituent represented by Formula 2A, or a substituent represented by Formula 2B; or a phenyl group, a pentalenyl, an indenyl, an azulenyl, a heptalenyl, an indacenyl, an acenaphthyl group, a 9,9 dimethyl fluorenyl, a phenalenyl, a phenanthrenyl, an anthryl group, a fluoranthenyl group, a triphenylenyl group, a pyrenyl group, a chrysenyl group, a naphthacenyl group, a picenyl group, a perylenyl group, a pentaphenyl group, a hexacenyl group, a pyrrolyl group, a pyrazolyl group, an imidazolyl group, an imidazolinyl group, an imidazopyridinyl group, an imidazopyrimidinyl group, a pyridinyl group, a pyrazinyl, a pyrimidinyl group, a benzoimidazolyl group, an indolyl group, a purinyl group, a quinolinyl group, an isoquinolinyl group, a phthalazinyl group, an indolizinyl group, a naphthyridinyl group, a quinazolinyl group, a quinoxalinyl group, a cinnolinyl group, an indazolyl group, a carbazolyl group, a phenazinyl group, a phenanthridinyl group, a pyranyl group, a chromenyl group, a furanyl group, a benzofuranyl group, a thiophenyl group, a benzothiophenyl group, a isothiazolyl group, a benzoimidazolyl group, an isoxazolyl group, a dibenzothiophenyl group, a dibenzofuranyl group, a triazinyl group, an oxadiazolyl group, a pyridazinyl group, a triazolyl group, a tetrazolyl group, a phenanthrolinyl group, a substituent represented by Formula 2A, or a substituent represented by Formula 2B substituted with:
—F;
—Cl;
—Br;
—I;
—CN;
a hydroxyl group;
a nitro group;
an amino group;
an amidino group;
a hydrazine;
a hydrazone;
a carboxylic acid group or salt thereof;
a sulfonic acid group or salt thereof;
a phosphoric acid group or salt thereof;
a $C_1$-$C_{60}$ alkyl group;
a $C_1$-$C_{60}$ alkoxy group;
a $C_2$-$C_{60}$ alkenyl group;
a $C_2$-$C_{60}$ alkynyl group;
a $C_1$-$C_{60}$ alkyl group, $C_1$-$C_{60}$ alkoxy group, $C_2$-$C_{60}$ alkenyl group, or $C_2$-$C_{60}$ alkynyl group substituted with at least one selected from:
—F,
—Cl,
—Br,
—CN,
a hydroxyl group,
a nitro group,
an amino group,
an amidino group,
a hydrazine,
a hydrazone,
a carboxylic acid group or salt thereof,
a sulfonic acid group or salt thereof, or
a phosphoric acid group or salt thereof;
a $C_3$-$C_{60}$ cycloalkyl group;
a $C_5$-$C_{60}$ aryl group;
a $C_2$-$C_{60}$ heteroaryl group;
a $C_5$-$C_{60}$ aralkyl group; a $C_5$-$C_{60}$ aryloxy group; or
a $C_3$-$C_{60}$ cycloalkyl group, $C_5$-$C_{60}$ aryl group, $C_2$-$C_{60}$ heteroaryl group, $C_5$-$C_{60}$ aralkyl group, or $C_5$-$C_{60}$ aryloxy group substituted with at least one selected from:
—F,
—Cl,
—Br,
—CN,
a hydroxyl group,
a nitro group,
an amino group,
an amidino group,
a hydrazine,
a hydrazone,
a carboxylic acid group or salt thereof,
a sulfonic acid group or salt thereof,
a phosphoric acid group or salt thereof,
a $C_1$-$C_{60}$ alkyl group,
a $C_1$-$C_{60}$ alkoxy group,
a $C_2$-$C_{60}$ alkenyl group,
a $C_2$-$C_{60}$ alkynyl group,
a $C_5$-$C_{60}$ aryl group, or
a $C_2$-$C_{60}$ heteroaryl group; and
wherein at least one of $Ar_1$ to $Ar_4$ in Formula 1A through 1D is a substituent represented by Formula 2A or a substituent represented by Formula 2B, and
wherein the at least one other of $Ar_1$ to $Ar_4$ in Formulae 1A is:
a phenyl group, pentalenyl group, indenyl group, azulenyl group, heptalenyl group, indacenyl group, acenaphthyl group, 9,9 dimethyl fluorenyl group, phenalenyl group, phenanthrenyl group, anthryl group, fluoranthenyl group, triphenylenyl group, pyrenyl group, chrysenyl group, naphthacenyl group, picenyl group, perylenyl group, pentaphenyl group, or hexacenyl group substituted with at least one selected from the group consisting of:
—F,
—CN,
—NO$_2$, and
a $C_1$-$C_{20}$ alkyl group substituted with at least one —F;
a pyridinyl group, a pyrazinyl group, a pyrimidinyl group, a triazinyl group, a quinolinyl group, an isoquinolinyl group a naphthyridinyl group, a quinazolinyl group, a quinoxalinyl group, or a cinnolinyl group;
a pyridinyl group, a pyrazinyl group, a pyrimidinyl group, a triazinyl group, a quinolinyl group, an isoquinolinyl group a naphthyridinyl group, a quinazolinyl group, a quinoxalinyl group, or a cinnolinyl group substituted with at least one selected from the group consisting of:
—F,
—CN,
—NO$_2$, and
a C$_1$-C$_{20}$ alkyl group substituted with at least one —F;
a substituent represented by Formula 2A in which either:
T$_1$ is O, S or N(R$_{11}$), or
at least one of R$_1$ and R$_2$ is selected from the group consisting of:
—F,
—CN,
—NO$_2$, and
a C$_1$-C$_{20}$ alkyl group substituted with at least one —F; and
a substituent represented by Formula 2B in which at least one of R$_1$ through R$_4$ is selected from the group consisting of:
—F,
—CN,
—NO$_2$, and
a C$_1$-C$_{20}$ alkyl group substituted with at least one —F;
wherein the at least one other of Ar$_1$ to Ar$_4$ in Formula 1B through 1D is a C$_6$-C$_{60}$ aryl group substituted with at least one selected from the group consisting of:
—F,
—CN,
—NO$_2$, and
a C$_1$-C$_{20}$ alkyl group substituted with at least one —F;
a pyridinyl group, a pyrazinyl group, a pyrimidinyl group, a triazinyl group, a quinolinyl group, an isoquinolinyl group a naphthyridinyl group, a quinazolinyl group, a quinoxalinyl group, or a cinnolinyl group;
a pyridinyl group, a pyrazinyl group, a pyrimidinyl group, a triazinyl group, a quinolinyl group, an isoquinolinyl group a naphthyridinyl group, a quinazolinyl group, a quinoxalinyl group, or a cinnolinyl group substituted with at least one selected from the group consisting of:
—F,
—CN,
—NO$_2$, and
a C$_1$-C$_{20}$ alkyl group substituted with at least one —F.

5. The amine-based compound of claim 1, wherein:
Ar$_1$ to Ar$_4$ in Formula 1A are each independently:
a phenyl group, pentalenyl group, indenyl group, azulenyl group, heptalenyl group, indacenyl group, acenaphthyl group, 9,9 dimethyl fluorenyl group, phenalenyl group, phenanthrenyl group, anthryl group, fluoranthenyl group, triphenylenyl group, pyrenyl group, chrysenyl group, naphthacenyl group, picenyl group, perylenyl group, pentaphenyl group, or hexacenyl group substituted with at least one selected from the group consisting of:
—F,
—CN,
—NO$_2$, and
a C$_1$-C$_{20}$ alkyl group substituted with at least one —F;
a unsubstituted C$_2$-C$_{60}$ heteroaryl group;
a C$_2$-C$_{60}$ heteroaryl group substituted with at least one selected from the group consisting of:
—F,
—CN,
—NO$_2$, and
a C$_1$-C$_{20}$ alkyl group substituted with at least one —F;
a substituent represented by Formula 2A; and
a substituent represented by Formula 2B;
Ar$_1$ to Ar$_4$ in Formula 1B through 1D are each independently:
a C$_6$-C$_{60}$ aryl group substituted with at least one selected from the group consisting of:
—F,
—CN,
—NO$_2$, and
a C$_1$-C$_{20}$ alkyl group substituted with at least one —F;
a unsubstituted C$_2$-C$_{60}$ heteroaryl group;
a C$_2$-C$_{60}$ heteroaryl group substituted with at least one selected from the group consisting of:
—F,
—CN,
—NO$_2$, and
a C$_1$-C$_{20}$ alkyl group substituted with at least one —F;
a substituent represented by Formula 2A; and
a substituent represented by Formula 2B;
wherein at least one of Ar$_1$ to Ar$_4$ in Formulae 1A through 1D is a substituent represented by Formula 2A or a substituent represented by Formula 2B, and
wherein the at least one other of Ar$_1$ to Ar$_4$ in Formulae 1A is a phenyl group, pentalenyl group, indenyl group, azulenyl group, heptalenyl group, indacenyl group, acenaphthyl group, 9,9 dimethyl fluorenyl group, phenalenyl group, phenanthrenyl group, anthryl group, fluoranthenyl group, triphenylenyl group, pyrenyl group, chrysenyl group, naphthacenyl group, picenyl group, perylenyl group, pentaphenyl group, or hexacenyl group substituted with at least one selected from the group consisting of:
—F,
—CN,
—NO$_2$, and
a C$_1$-C$_{20}$ alkyl group substituted with at least one —F;
a pyridinyl group, a pyrazinyl group, a pyrimidinyl group, a triazinyl group, a quinolinyl group, an isoquinolinyl group a naphthyridinyl group, a quinazolinyl group, a quinoxalinyl group, or a cinnolinyl group;
a pyridinyl group, a pyrazinyl group, a pyrimidinyl group, a triazinyl group, a quinolinyl group, an isoquinolinyl group a naphthyridinyl group, a quinazolinyl group, a quinoxalinyl group, or a cinnolinyl group substituted with at least one selected from the group consisting of:
—F,
—CN,
—NO$_2$, and
a C$_1$-C$_{20}$ alkyl group substituted with at least one —F;
a substituent represented by Formula 2A in which either:
T$_1$ is O, S or N(R$_{11}$), or
at least one of R$_1$ and R$_2$ is selected from the group consisting of:
—F,
—CN,
—NO$_2$, and
a C$_1$-C$_{20}$ alkyl group substituted with at least one —F; and
a substituent represented by Formula 2B in which at least one of R$_1$ through R$_4$ is selected from the group consisting of:

—F,
—CN,
—NO$_2$, and
a C$_1$-C$_{20}$ alkyl group substituted with at least one —F;
wherein the at least one other of Ar$_1$ to Ar$_4$ in Formula 1B through 1D is a C$_6$-C$_{60}$ aryl group substituted with at least one selected from the group consisting of:
—F,
—CN,
—NO$_2$, and
a C$_1$-C$_{20}$ alkyl group substituted with at least one —F;
a pyridinyl group, a pyrazinyl group, a pyrimidinyl group, a triazinyl group, a quinolinyl group, an isoquinolinyl group a naphthyridinyl group, a quinazolinyl group, a quinoxalinyl group, or a cinnolinyl group;
a pyridinyl group, a pyrazinyl group, a pyrimidinyl group, a triazinyl group, a quinolinyl group, an isoquinolinyl group a naphthyridinyl group, a quinazolinyl group, a quinoxalinyl group, or a cinnolinyl group substituted with at least one selected from the group consisting of:
—F,
—CN,
—NO$_2$, and
a C$_1$-C$_{20}$ alkyl group substituted with at least one —F.

6. The amine-based compound of claim 1, wherein
Ar$_1$ to Ar$_4$ in Formula 1B through 1D are each independently a substituent selected from the group consisting of substituents represented by Formula 3(1) to Formula 3(25), a substituent represented by Formula 2A, and a substituent represented by Formula 2B, wherein at least one of Ar$_1$ to Ar$_4$ is a substituent represented by Formula 2A or a substituent represented by Formula 2B, and
Ar$_1$ to Ar$_4$ in Formula 1A are each independently a substituent selected from the group consisting of substituents represented by Formula 3(1) and 3(4) to Formula 3(25), a substituent represented by Formula 2A, and a substituent represented by Formula 2B,
wherein at least one of Ar$_1$ to Ar$_4$ in Formula 1A through 1D is a substituent represented by Formula 2A or a substituent represented by Formula 2B:

Formula 3(1)

*—⟨phenyl⟩—(R$_{21}$)$_{aa}$

Formula 3(2)

*—⟨naphthyl⟩—(R$_{21}$)$_{ac}$

Formula 3(3)

⟨naphthyl⟩—(R$_{21}$)$_{ab}$
*

Formula 3(4)

⟨phenanthrenyl⟩—(R$_{21}$)$_{ab}$
*

Formula 3(5)

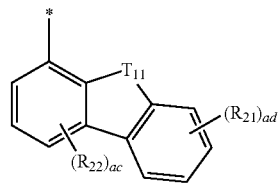

Formula 3(6)

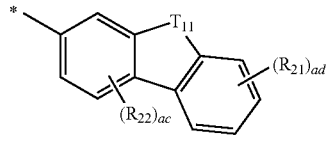

Formula 3(7)

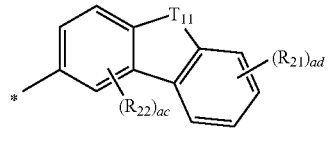

Formula 3(8)

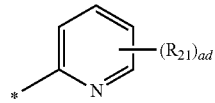

Formula 3(9)

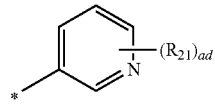

Formula 3(10)

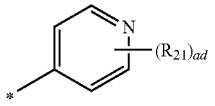

Formula 3(11)

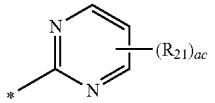

Formula 3(12)

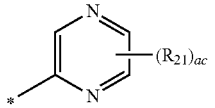

Formula 3(13)

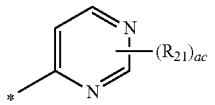

Formula 3(14)

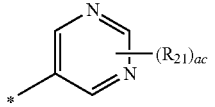

Formula 3(15)

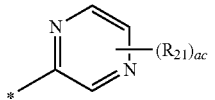

-continued

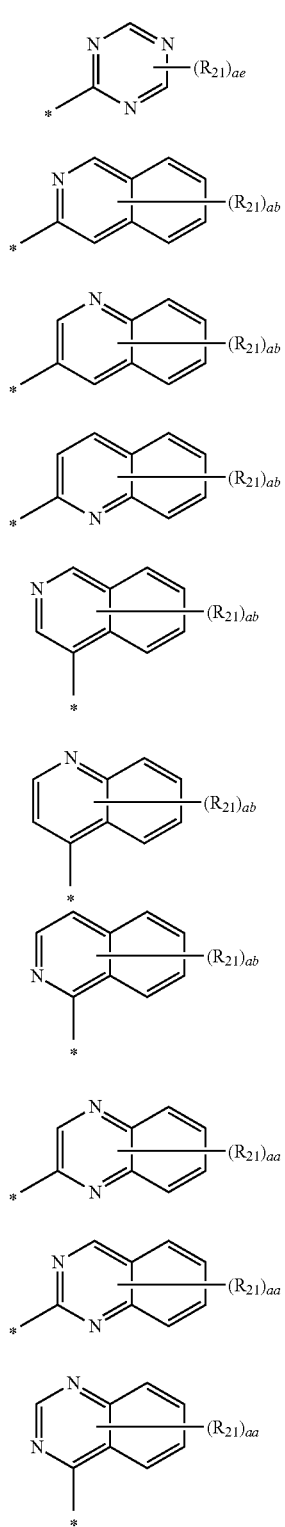

Formula 3(16)
Formula 3(17)
Formula 3(18)
Formula 3(19)
Formula 3(20)
Formula 3(21)
Formula 3(22)
Formula 3(23)
Formula 3(24)
Formula 3(25)

wherein in Formulae 3(1) to 3(25):
$T_{11}$ is O, S, $N(R_{31})$, or $C(R_{32})(R_{33})$, wherein:
 $R_{31}$ is one selected from the group consisting of
  a $C_6$-$C_{20}$ aryl group; and
  a $C_6$-$C_{20}$ aryl group substituted with at least one selected from the group consisting of:
   —F,
   —Cl,
   —Br,
   —I;
   —CN,
   a hydroxyl group,
   a —$NO_2$ group,
   an amino group,
   an amidino group,
   a hydrazine,
   a hydrazone,
   a carboxylic acid group or salt thereof,
   a sulfonic acid group or salt thereof,
   a phosphoric acid group or salt thereof,
   a $C_1$-$C_{20}$ alkyl group,
   a $C_1$-$C_{20}$ alkyl group substituted with at least one F, and
   a $C_1$-$C_{20}$ alkoxy group, and
 $R_{32}$ and $R_{33}$ are each independently one selected from the group consisting of:
  a $C_1$-$C_{20}$ alkyl group;
  a $C_1$-$C_{20}$ alkyl group substituted with at least one selected from the group consisting of:
   —F,
   —Cl,
   —Br,
   —CN,
   a hydroxyl group,
   a —$NO_2$ group,
   an amino group,
   an amidino group,
   a hydrazine,
   a hydrazone,
   a carboxylic acid group or salt thereof,
   a sulfonic acid group or salt thereof, and
   a phosphoric acid group or salt thereof;
  a $C_6$-$C_{20}$ aryl group; and
  a $C_6$-$C_{20}$ aryl group substituted with at least one selected from the group consisting of:
   —F,
   —Cl,
   —Br,
   —CN,
   a hydroxyl group,
   a —$NO_2$ group,
   an amino group,
   an amidino group,
   a hydrazine,
   a hydrazone,
   a carboxylic acid group or salt thereof,
   a sulfonic acid group or salt thereof,
   a phosphoric acid group or salt thereof,
   a $C_1$-$C_{20}$ alkyl group,
   a $C_1$-$C_{20}$ alkyl group substituted with at least one —F, and
   a $C_1$-$C_{20}$ alkoxy group;
$R_{21}$ are $R_{22}$ are each independently one selected from the group consisting of:
 —F;
 —Cl;
 —Br;
 —I;
 —CN;
 a hydroxyl group;
 a —$NO_2$ group;

an amino group;
an amidino group;
a hydrazine;
a hydrazone;
a carboxylic acid group or salt thereof;
a sulfonic acid group or salt thereof;
a phosphoric acid group or salt thereof;
a $C_1$-$C_{20}$ alkyl group;
a $C_1$-$C_{20}$ alkoxy group;
a $C_1$-$C_{20}$ alkyl group or $C_1$-$C_{20}$ alkoxy group substituted with at least one selected from the group consisting of:
  —F,
  —Cl,
  —Br,
  —CN,
  a hydroxyl group,
  a —$NO_2$ group,
  an amino group,
  an amidino group,
  a hydrazine,
  a hydrazone,
  a carboxylic acid group or salt thereof,
  a sulfonic acid group or salt thereof, and
  a phosphoric acid group or salt thereof;
a $C_6$-$C_{20}$ aryl group;
a $C_2$-$C_{20}$ heteroaryl group; and
a $C_2$-$C_{60}$ aryl group or a $C_2$-$C_{20}$ heteroaryl group substituted with at least one selected from the group consisting of:
  —F,
  —Cl,
  —Br,
  —CN,
  a hydroxyl group,
  a —$NO_2$ group,
  an amino group,
  an amidino group,
  a hydrazine,
  a hydrazone,
  a carboxylic acid group or salt thereof,
  a sulfonic acid group or salt thereof,
  a phosphoric acid group or salt thereof,
  a $C_1$-$C_{20}$ alkyl group,
  a $C_1$-$C_{20}$ alkyl group substituted with at least one —F, and
  a $C_1$-$C_{20}$ alkoxy group;
aa is an integer of 0 to 5;
ab is an integer of 0 to 6;
ac is an integer of 0 to 3;
ad is an integer of 0 to 4;
ae is an integer of 0 to 2; and
* is a binding site with N in one of Formulas 1A to 1D, and
wherein the at least one other of $Ar_1$ to $Ar_4$ in Formulae 1A is:
  a phenyl group, pentalenyl group, indenyl group, azulenyl group, heptalenyl group, indacenyl group, acenaphthyl group, 9,9 dimethyl fluorenyl group, phenalenyl group, phenanthrenyl group, anthryl group, fluoranthenyl group, triphenylenyl group, pyrenyl group, chrysenyl group, naphthacenyl group, picenyl group, perylenyl group, pentaphenyl group, or hexacenyl group substituted with at least one selected from the group consisting of:
    —F,
    —CN,
    —$NO_2$, and
    a $C_1$-$C_{20}$ alkyl group substituted with at least one —F;
  a pyridinyl group, a pyrazinyl group, a pyrimidinyl group, a triazinyl group, a quinolinyl group, an isoquinolinyl group a naphthyridinyl group, a quinazolinyl group, a quinoxalinyl group, or a cinnolinyl group;
  a pyridinyl group, a pyrazinyl group, a pyrimidinyl group, a triazinyl group, a quinolinyl group, an isoquinolinyl group a naphthyridinyl group, a quinazolinyl group, a quinoxalinyl group, or a cinnolinyl group substituted with at least one selected from the group consisting of:
    —F,
    —CN,
    —$NO_2$, and
    a $C_1$-$C_{20}$ alkyl group substituted with at least one —F;
  a substituent represented by Formula 2A in which either:
    $T_1$ is O, S or $N(R_{11})$, or
    at least one of $R_1$ and $R_2$ is selected from the group consisting of:
      —F,
      —CN,
      —$NO_2$, and
      a $C_1$-$C_{20}$ alkyl group substituted with at least one —F; and
  a substituent represented by Formula 2B in which at least one of $R_1$ through $R_4$ is selected from the group consisting of:
    —F,
    —CN,
    —$NO_2$, and
    a $C_1$-$C_{20}$ alkyl group substituted with at least one —F;
wherein the at least one other of $Ar_1$ to $Ar_4$ in Formula 1B through 1D is a $C_6$-$C_{60}$ aryl group substituted with at least one selected from the group consisting of:
  —F,
  —CN,
  —$NO_2$, and
  a $C_1$-$C_{20}$ alkyl group substituted with at least one —F;
a pyridinyl group, a pyrazinyl group, a pyrimidinyl group, a triazinyl group, a quinolinyl group, an isoquinolinyl group a naphthyridinyl group, a quinazolinyl group, a quinoxalinyl group, or a cinnolinyl group;
a pyridinyl group, a pyrazinyl group, a pyrimidinyl group, a triazinyl group, a quinolinyl group, an isoquinolinyl group a naphthyridinyl group, a quinazolinyl group, a quinoxalinyl group, or a cinnolinyl group substituted with at least one selected from the group consisting of:
  —F,
  —CN,
  —$NO_2$, and
  a $C_1$-$C_{20}$ alkyl group substituted with at least one —F.

7. The amine-based compound of claim 6, wherein $R_{21}$ and $R_{22}$ are each independently one selected from the group consisting of:
  —F;
  —CN;
  a —$NO_2$ group;
  a $C_1$-$C_{20}$ alkyl group or a $C_1$-$C_{20}$ alkoxy group substituted with at least one selected from the group consisting of:

—F,
—CN, and
a —NO₂ group;
a phenyl group;
a naphthyl group;
a pyridinyl group;
a pyrimidinyl group;
a pyrazinyl group;
a quinolinyl group;
an isoquinolinyl group;
a quinazolinyl group;
a quinoxalinyl group; and
a phenyl group, naphthyl group, pyridinyl group, pyrimidinyl group, pyrazinyl group, quinolinyl group, isoquinolinyl group, quinazolinyl group, or a quinoxalinyl group substituted with at least one selected from the group consisting of:
—F,
—CN, and
—NO₂.

8. The amine-based compound of claim 1, wherein in Formula 1A, 1B, or 1C,

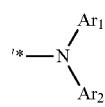

is a first diarylamino group and is identical to

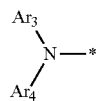

which is a second diarylamino group.

9. The amine-based compound of claim 1, wherein in Formula 1A, 1B or 1C

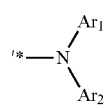

is a first diarylamino group and is different from

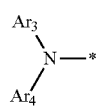

which is a second diarylamino group.

10. The amine-based compound of claim 6, wherein
the amine-based compound is represented by one of Formulae 1A to 1C, and
Ar₁ and Ar₃ in Formulae 1A to 1C are each independently a substituent represented by Formula 2A or a substituent represented by Formula 2B,
Ar₂ and Ar₄ in Formula 1A are each independently a substituent represented by one of Formula 3(1) and 3(4) to Formula 3(25), and
Ar₂ and Ar₄ in Formula 1B and 1C are each independently a substituent represented by one of Formula 3(1) to Formula 3(25):

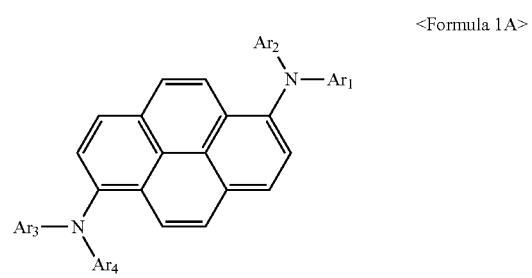
<Formula 1A>

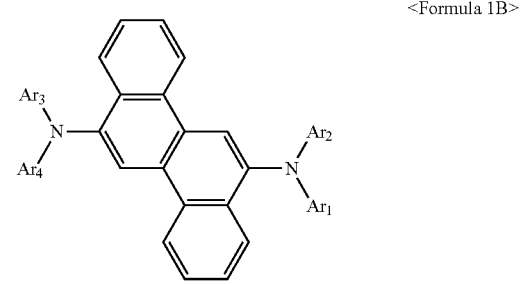
<Formula 1B>

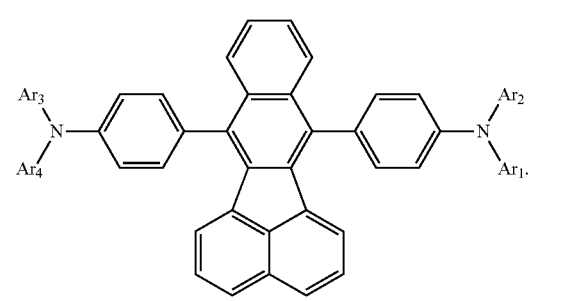
<Formula 1C>

11. The amine-based compound of claim 6, wherein
the amine-based compound is represented by one of Formulae 1A to 1C, and
Ar₃ in Formulae 1A to 1C is a substituent represented by Formula 2A or a substituent represented by Formula 2B,
Ar₁, Ar₂ and Ar₄ in Formula 1A are each independently a substituent represented by one of Formula 3(1) and 3(4) to Formula 3(25), and
Ar₁, Ar₂ and Ar₄ in Formula 1B and 1C are each independently a substituent represented by one of Formula 3(1) to Formula 3(25):

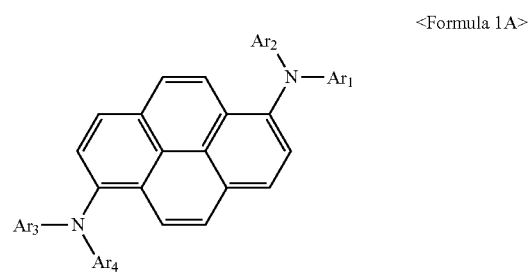
<Formula 1A>

-continued

<Formula 1B>

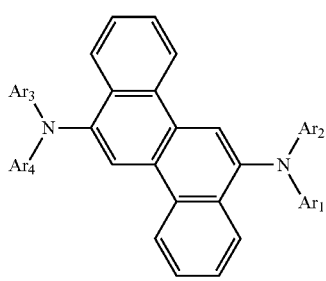

<Formula 1C>

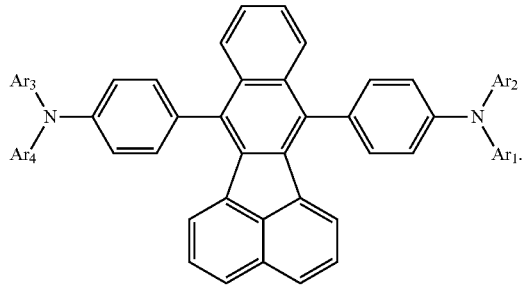

12. The amine-based compound of claim 6, wherein
the amine-based compound is represented by Formula 1D, and
Ar$_3$ in Formula 1D is a substituent represented by Formula 2A or a substituent represented by Formula 2B, and
Ar$_1$ in Formula 1D is a substituent represented by one of Formula 3(1) to Formula 3(25):

<Formula 1D>

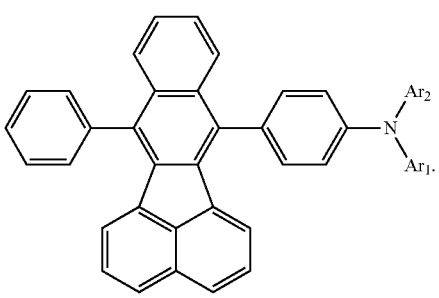

13. An organic light-emitting diode comprising: a first electrode; a second electrode facing the first electrode; and an organic layer between the first electrode and the second electrode, wherein the organic layer comprises the amine-based compound of claim 1.

14. The organic light-emitting diode of claim 13, wherein the organic layer comprises at least one layer selected from a hole injection layer, a hole transport layer, a functional layer having hole injection and hole transport functions, a buffer layer, an electron blocking layer, an emission layer, a hole blocking layer, an electron transport layer, an electron injection layer, or a functional layer having electron injection and electron transport functions.

15. The organic light-emitting diode of claim 14, wherein the organic layer comprises an emission layer, and the emission layer comprises the amine-based compound.

16. The organic light-emitting diode of claim 15, wherein the amine-based compound included in the emission layer functions as a dopant, and the emission layer further comprises a host.

17. The organic light-emitting diode of claim 16, wherein the host comprises at least one selected from the group consisting of an anthracene-based compound represented by Formula 400 and an anthracene-based compound represented by Formula 401:

<Formula 400>

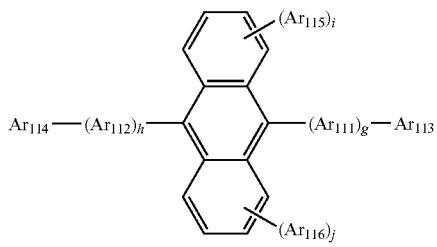

<Formula 401>

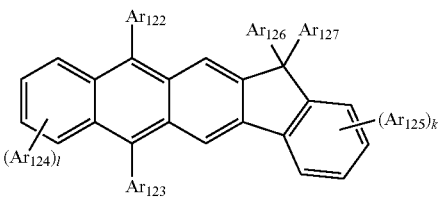

wherein in Formulae 400 and 401:
Ar$_{111}$ and Ar$_{112}$ are each independently a substituted or unsubstituted C$_6$-C$_{60}$ arylene group;
Ar$_{113}$ to Ar$_{116}$ and Ar$_{122}$ to Ar$_{125}$ are each independently a substituted or unsubstituted C$_1$-C$_{10}$ alkyl group, or a substituted or unsubstituted C$_6$-C$_{60}$ aryl group;
Ar$_{126}$ and Ar$_{127}$ are each independently a C$_1$-C$_{10}$ alkyl group; and
g, h, i, j, k, and l are each independently an integer of 0 to 4.

18. An organic light-emitting apparatus, comprising:
a substrate comprising a first sub-pixel, a second sub-pixel, and a third sub-pixel;
a first electrode in each of the first sub-pixel, the second sub-pixel, and the third sub-pixel;
a second electrode facing the first electrodes, the second electrode being a common electrode shared by the first sub-pixel, the second sub-pixel, and the third sub-pixel;
a first emission layer between the first electrode of the first sub-pixel and the second electrode, the first emission layer being configured to emit a first color light;
a second emission layer between the first electrode of the second sub-pixel and the second electrode, the second emission layer being configured to emit a second color light; and
a third emission layer between the first electrode of the third sub-pixel and the second electrode, the third emission layer being configured to emit a third color light,
wherein:
the first emission layer comprises the amine-based compound of claim 1,
the first electrode is a transparent electrode or a semi-transparent electrode, and the second electrode is a reflective electrode, or the first electrode is a reflective electrode, and the second electrode is a transparent electrode or a semi-transparent electrode, and a mixed light comprising the first color light, the second color light, and the third color light is white light, and the first color light is blue light.
19. An amine-based compound represented by one of Compounds 2-7, 11, 13-27, 29, 31, 33, 35, 37, 39-81, 87-102 and 108-222:
2
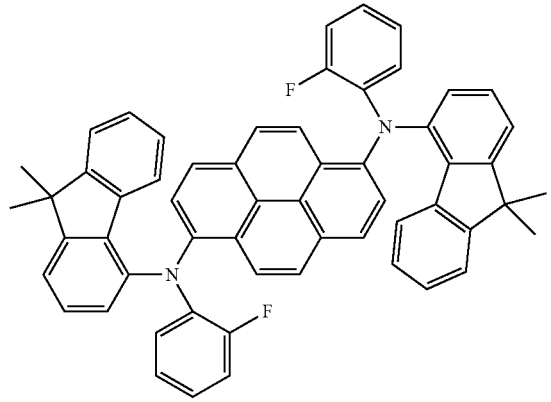
3
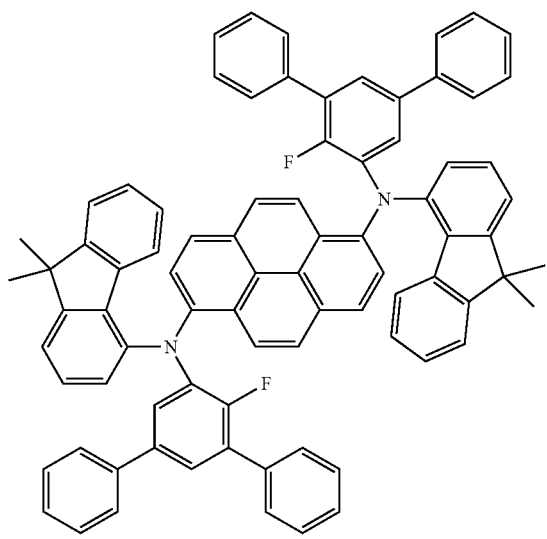
4
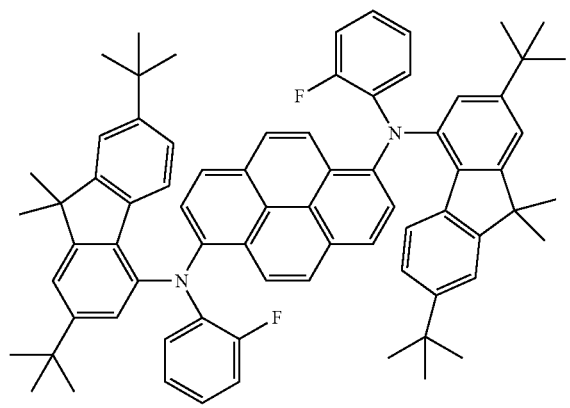
5
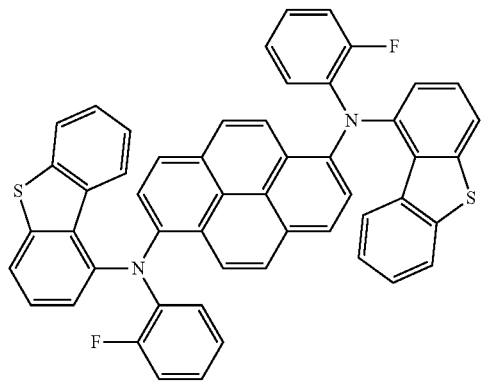
6
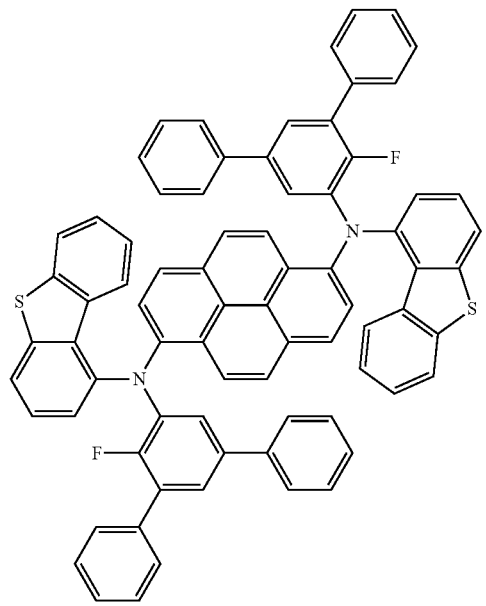

-continued
7
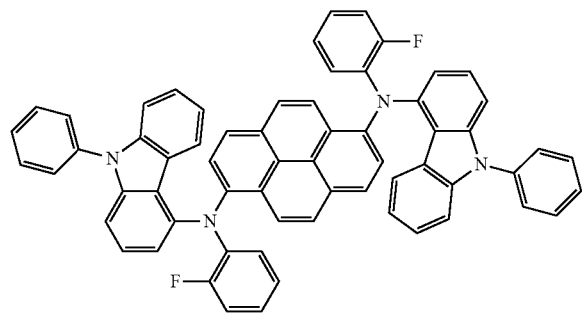
11
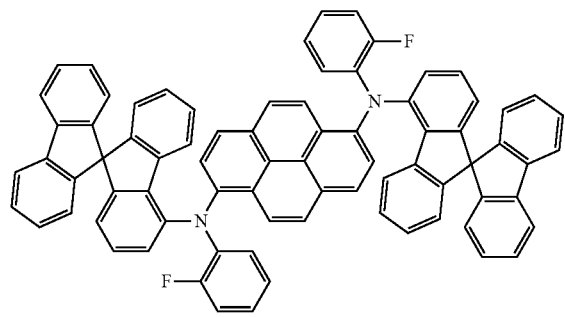
13
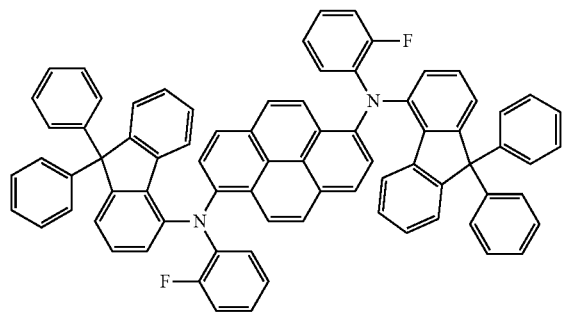
14
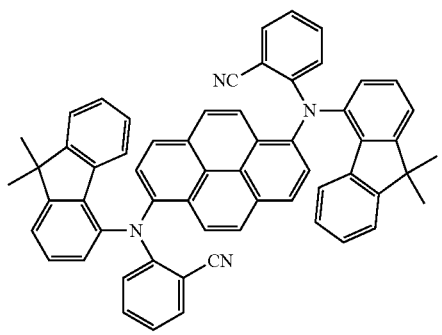
15
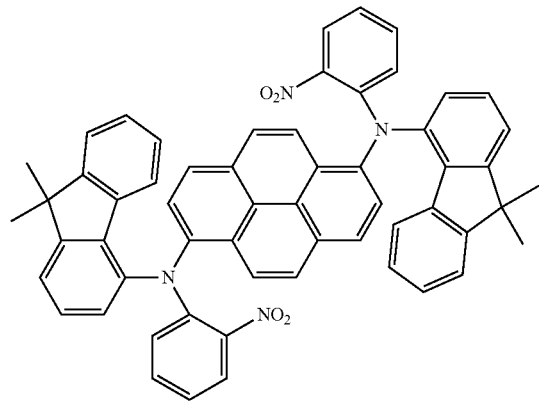
16
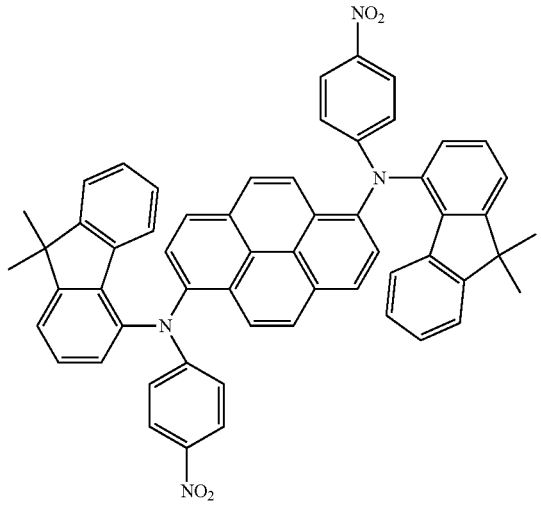

-continued
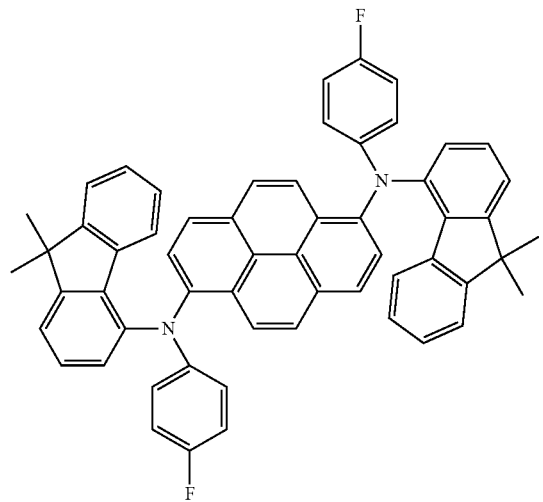
17
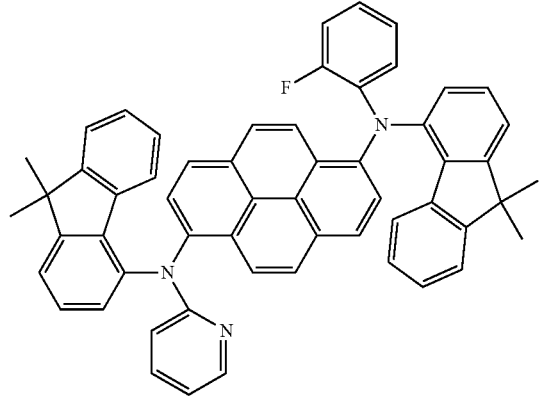
18
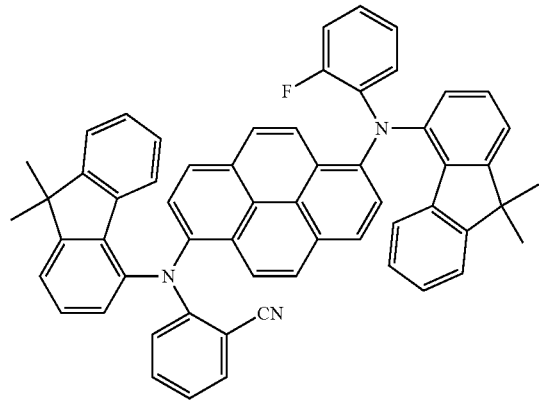
19
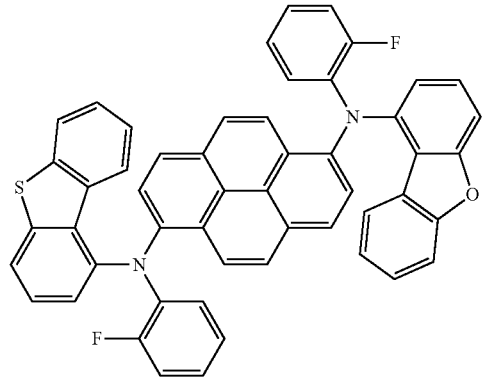
20
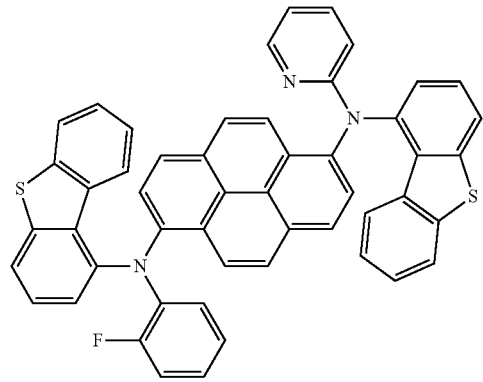
21
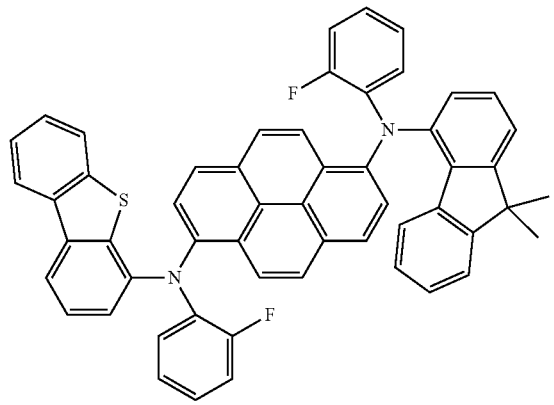
22

-continued
23
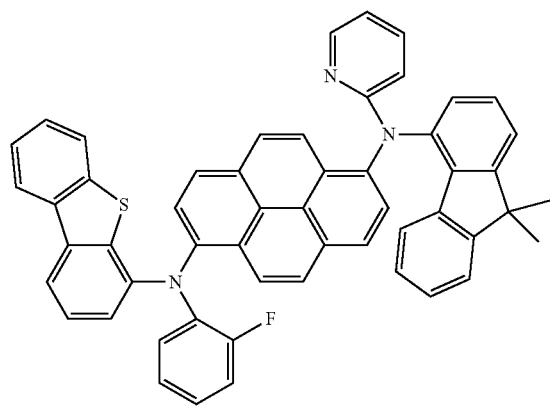
24
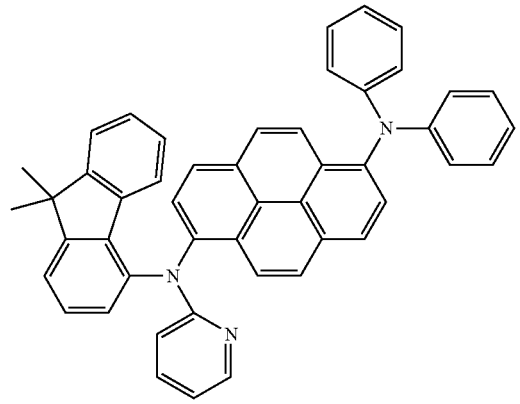
25
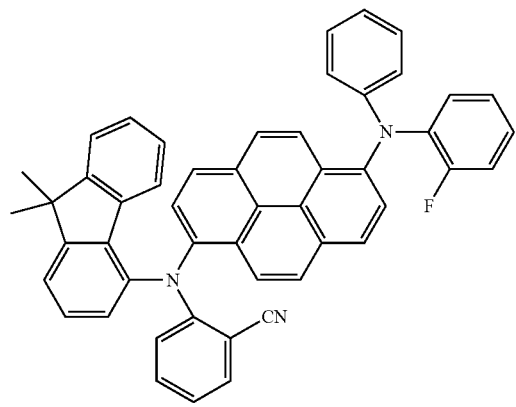
26
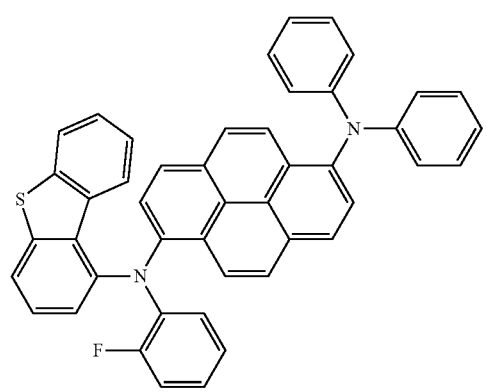
27
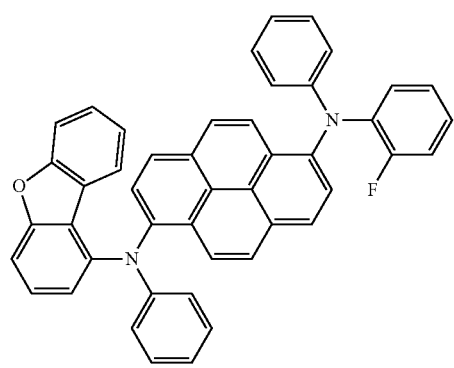
29
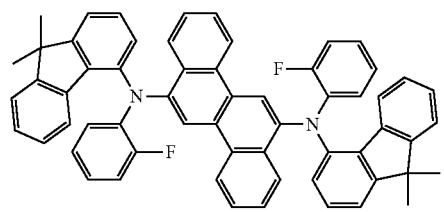

-continued
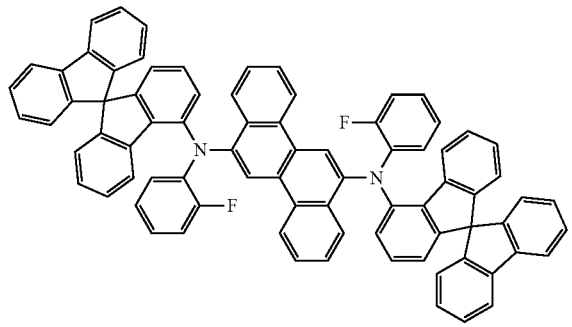
31
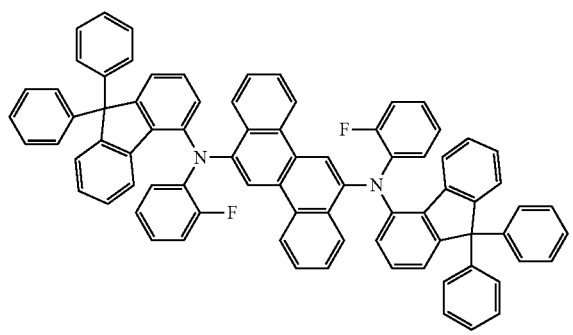
33
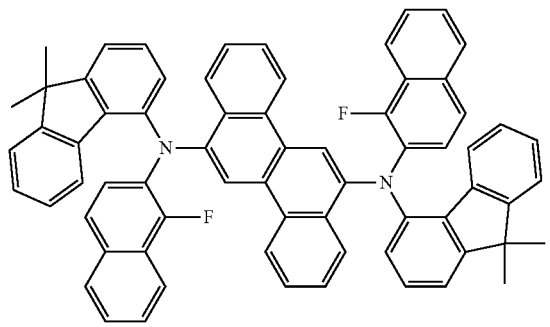
35
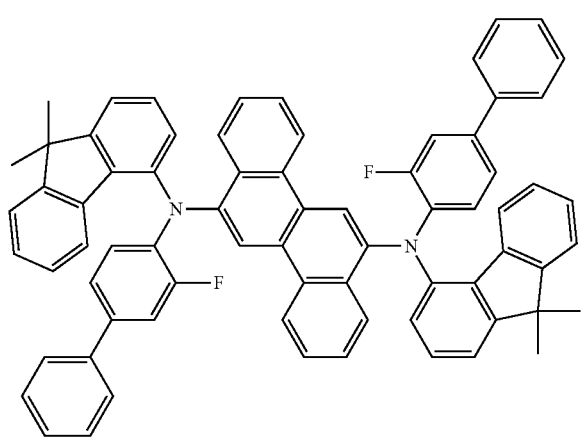
37

-continued
39
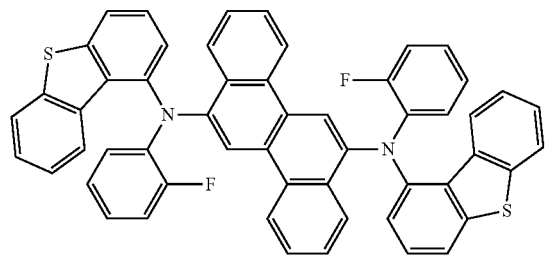
40
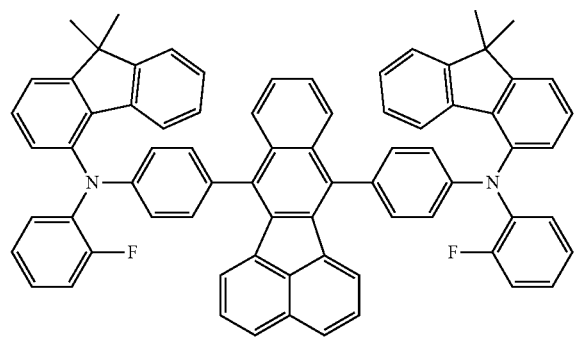
41
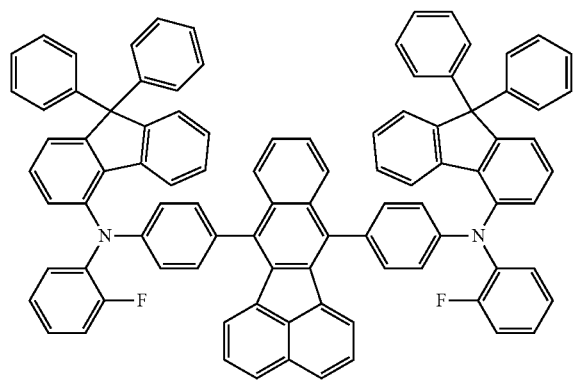
42
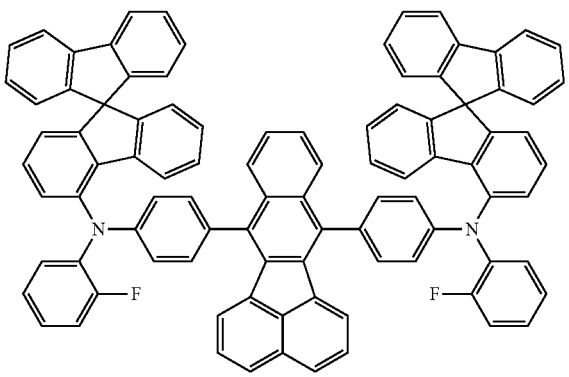
43
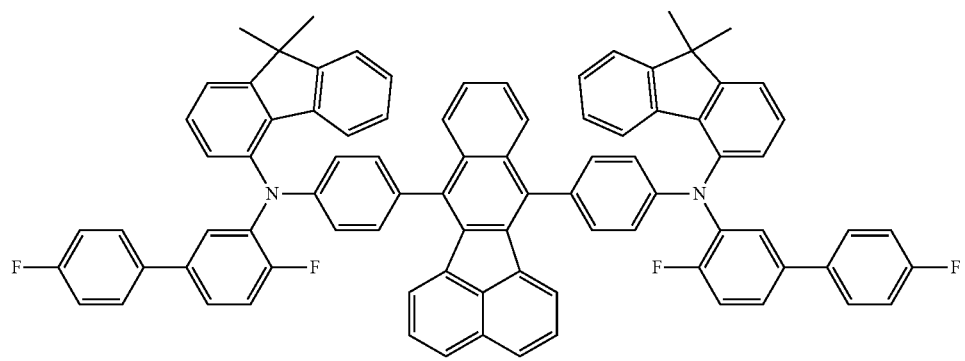
44
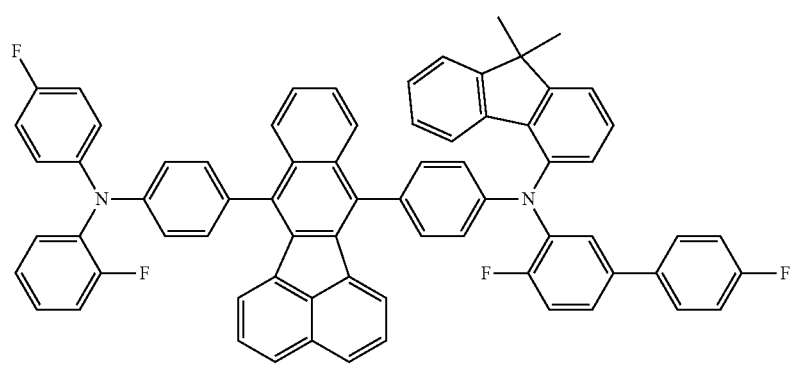

-continued
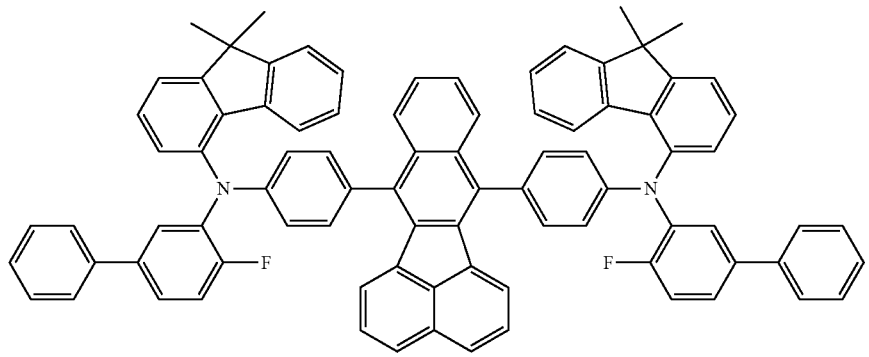
45
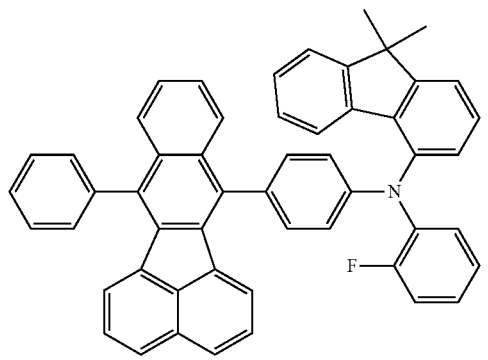
46
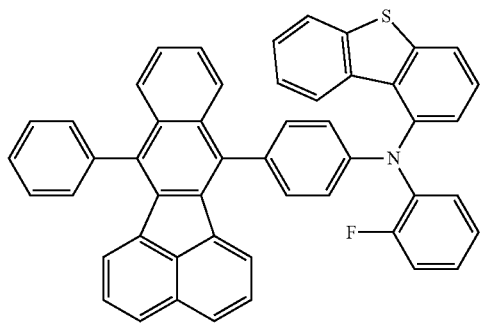
47
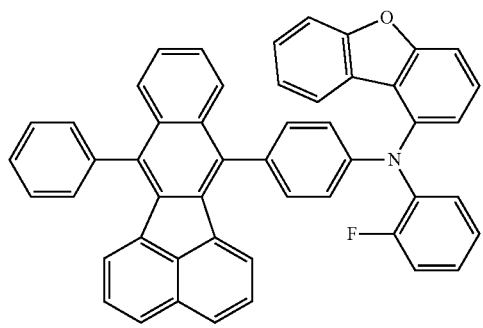
48
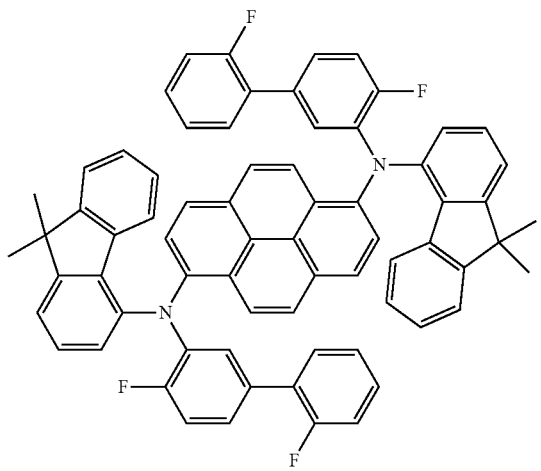
49
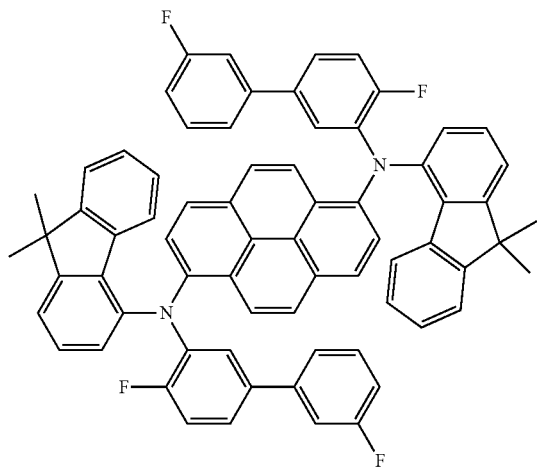
50
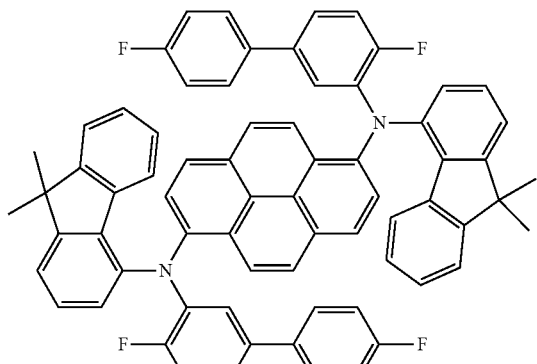
51

-continued
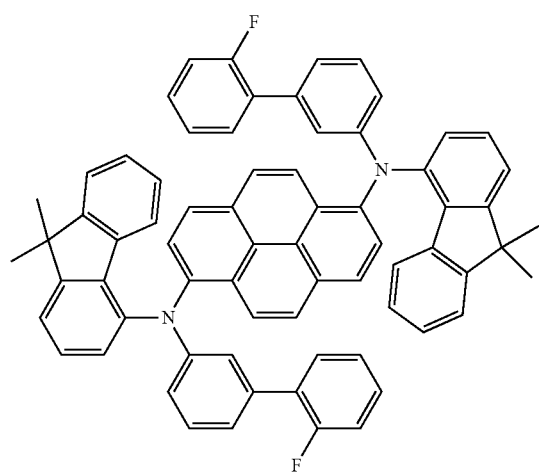
52
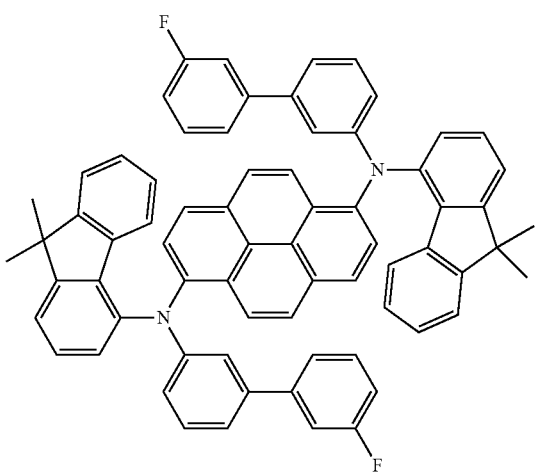
53
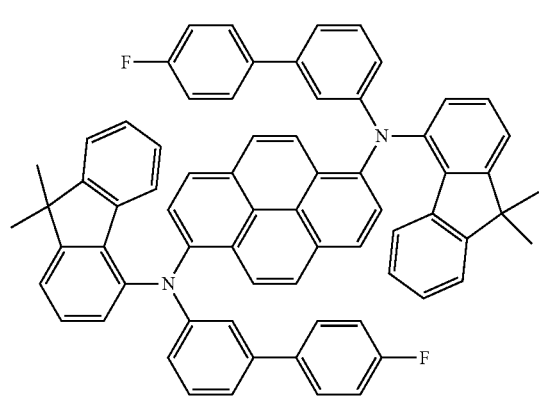
54
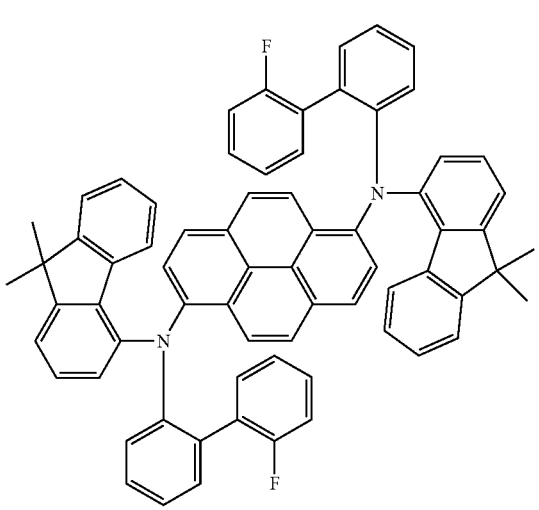
55
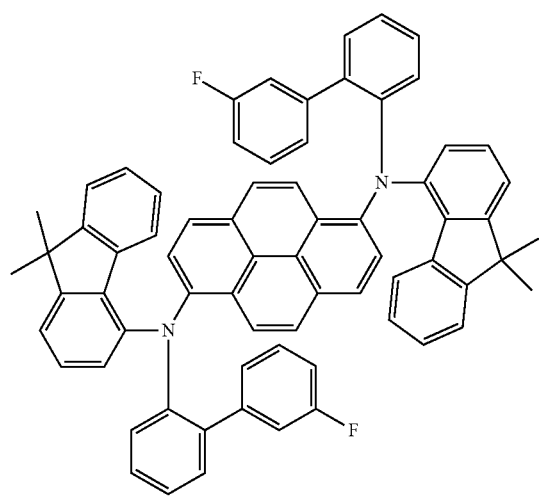
56
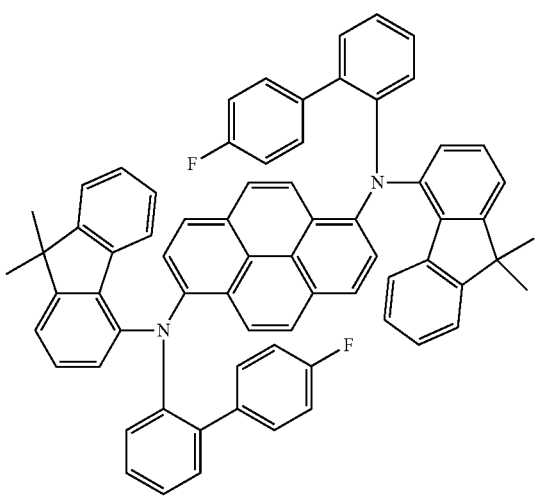
57

58
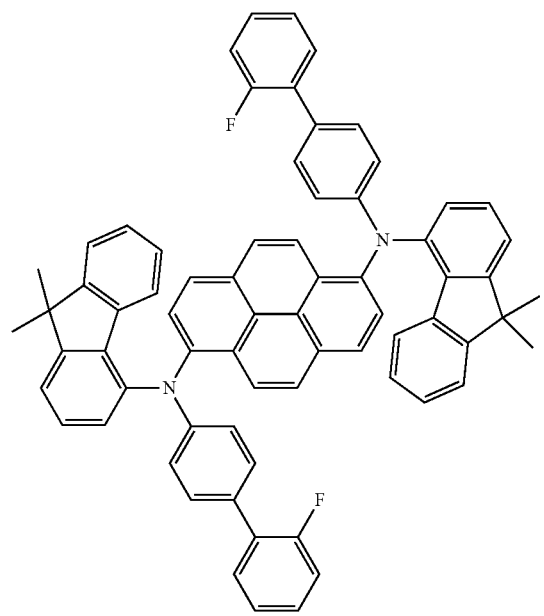
59
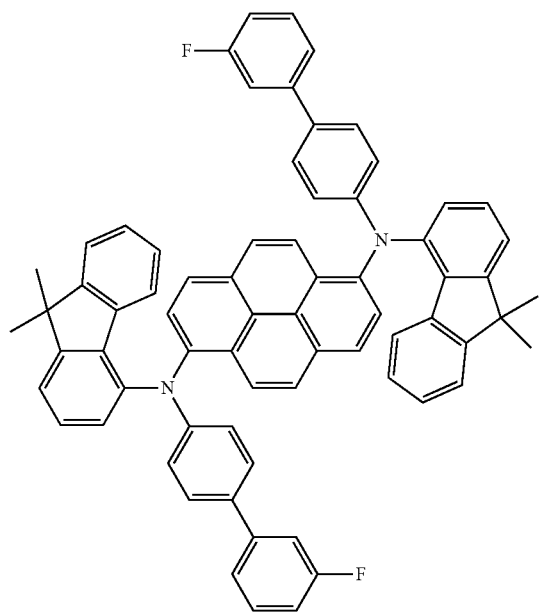
60
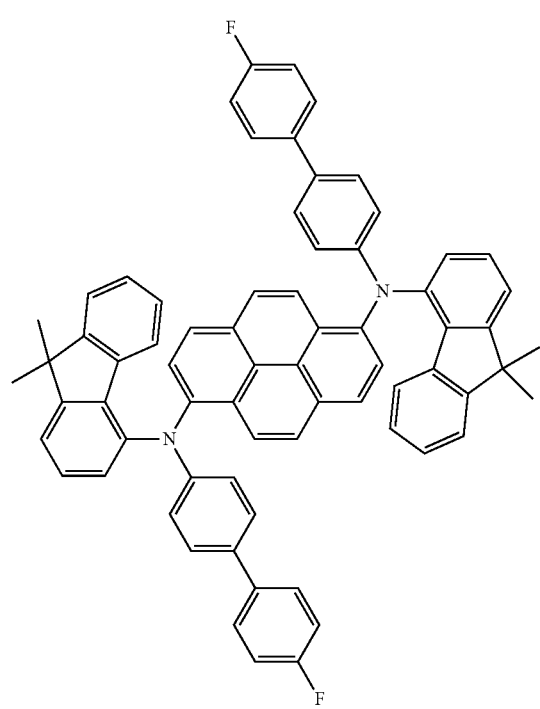
61
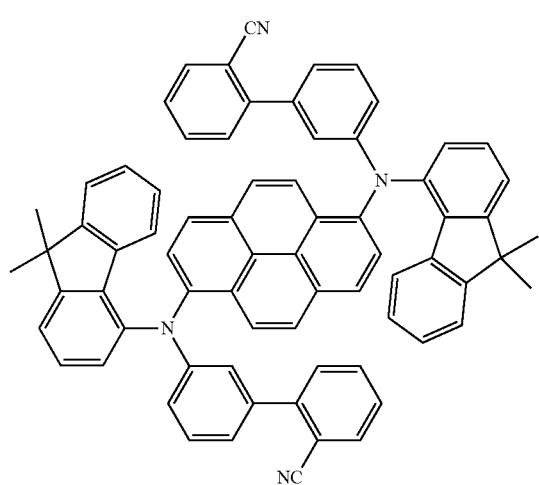

-continued
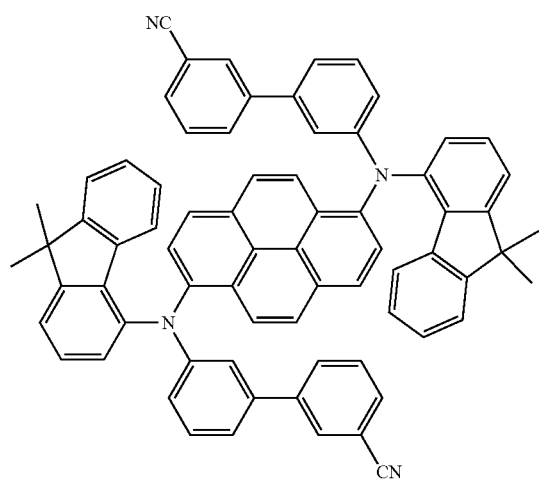
62
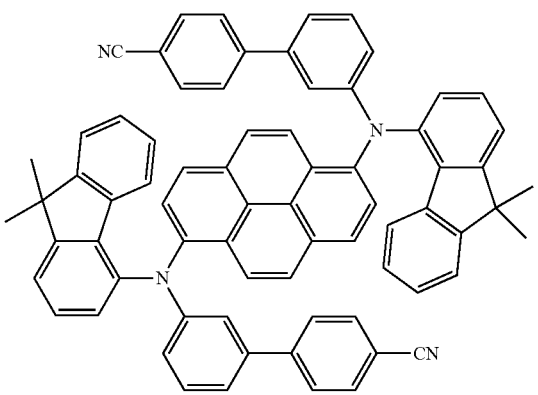
63
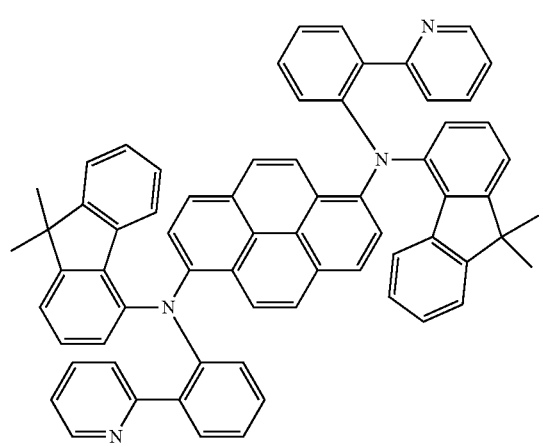
64
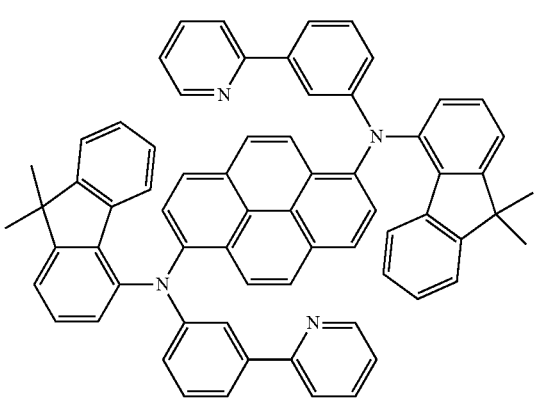
65
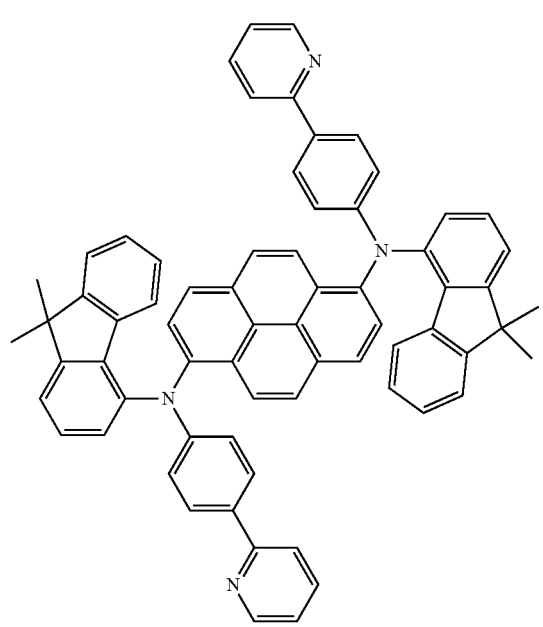
66
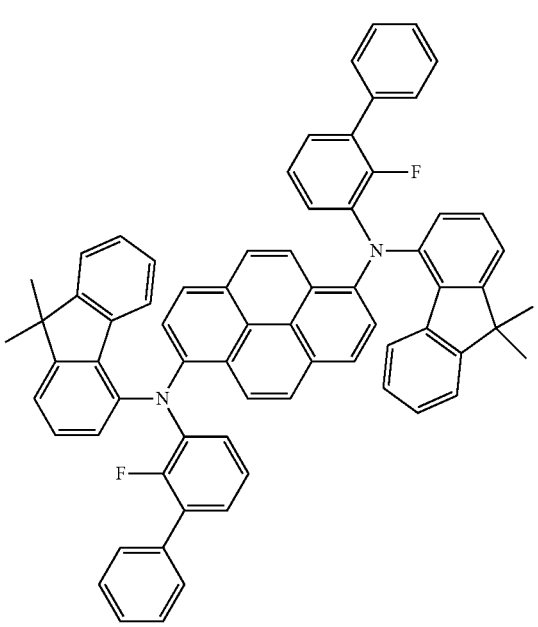
67

-continued
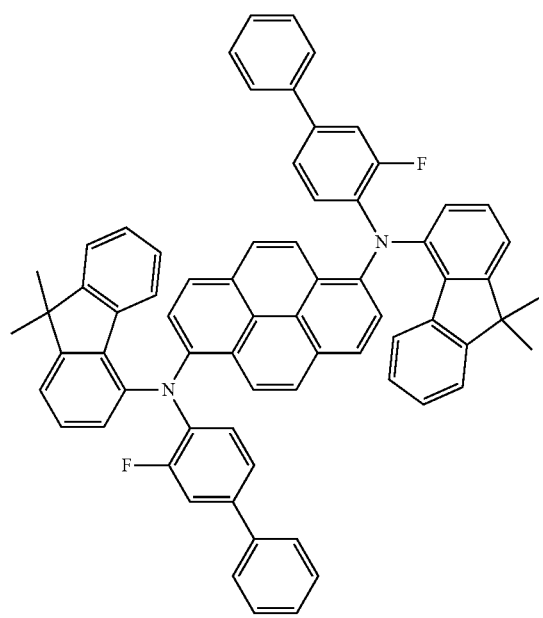
68
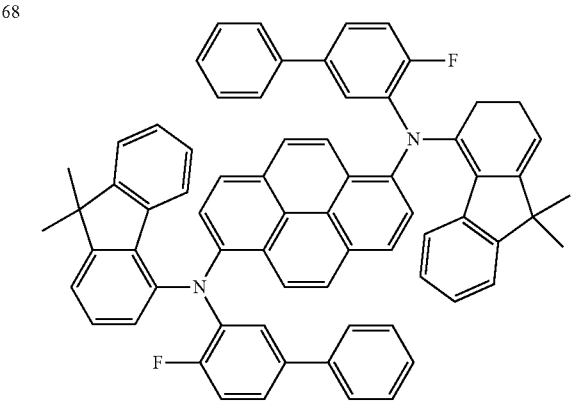
69
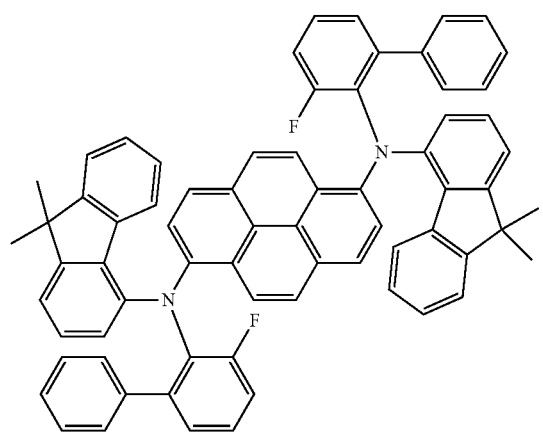
70
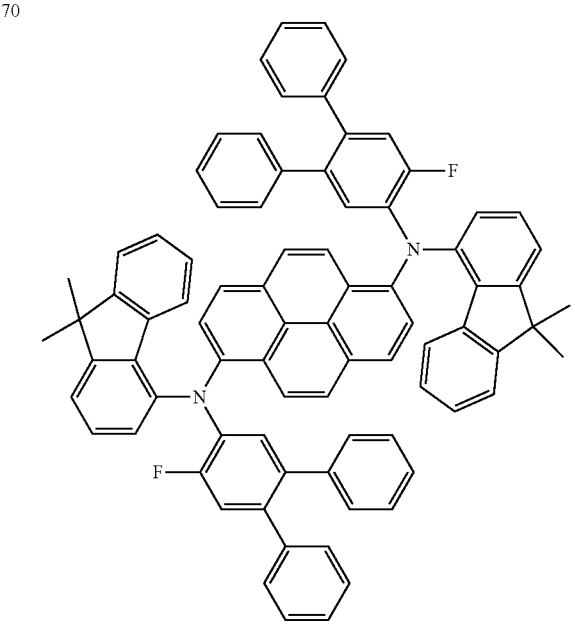
71

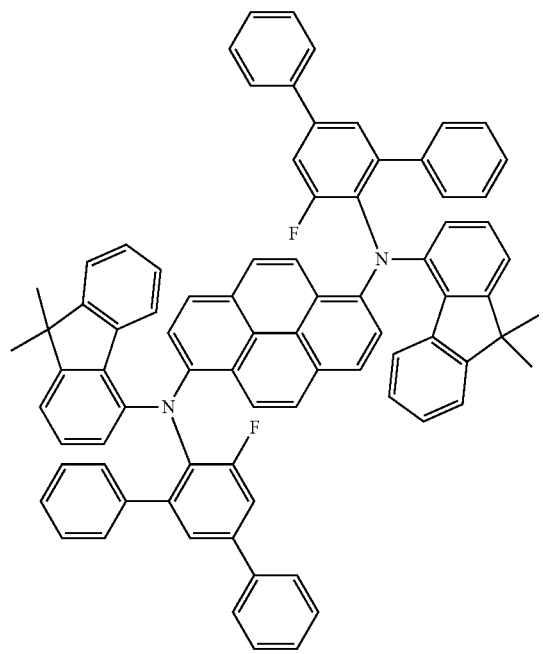
72
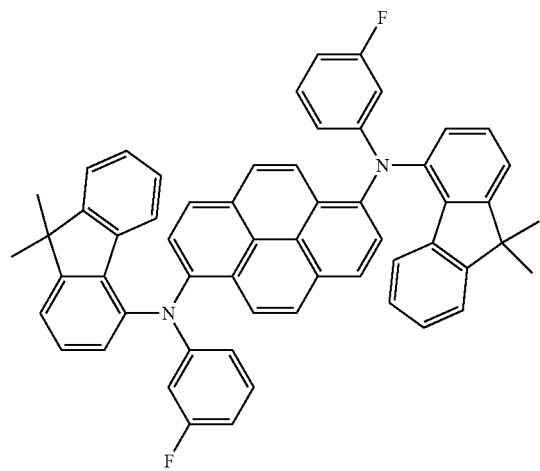
73
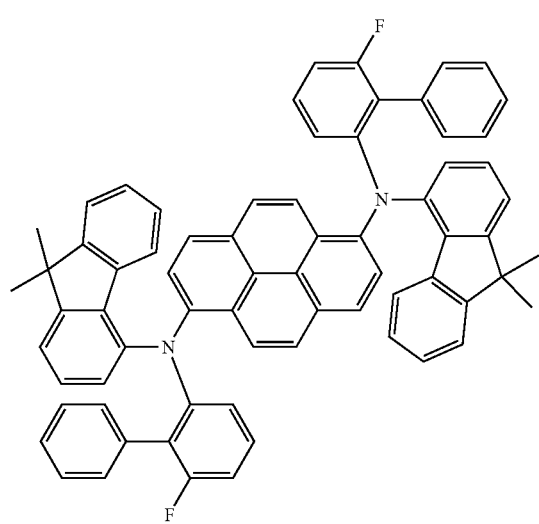
74
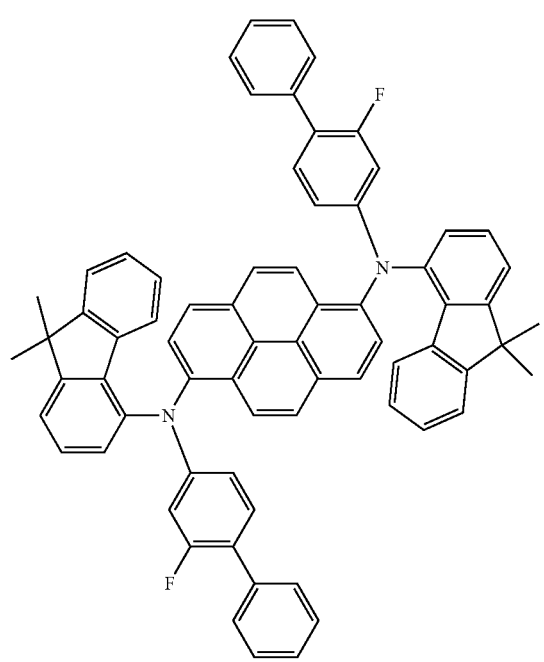
75

-continued
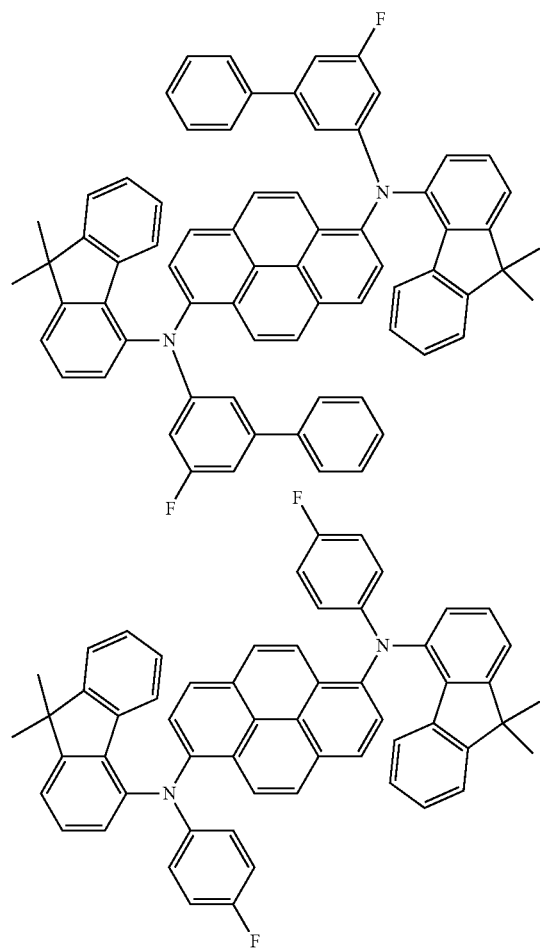
76
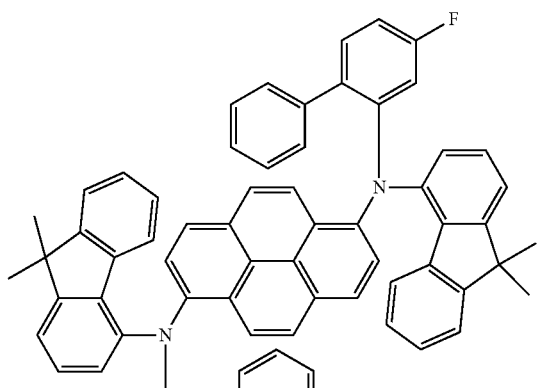
77
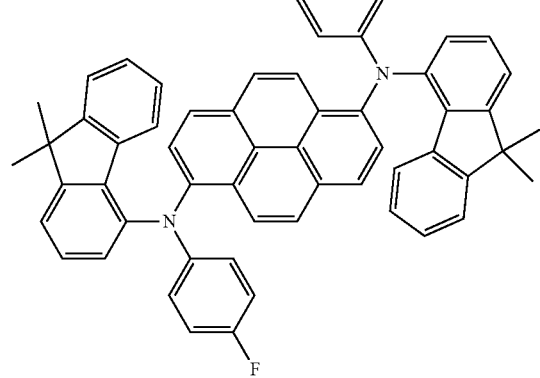
78
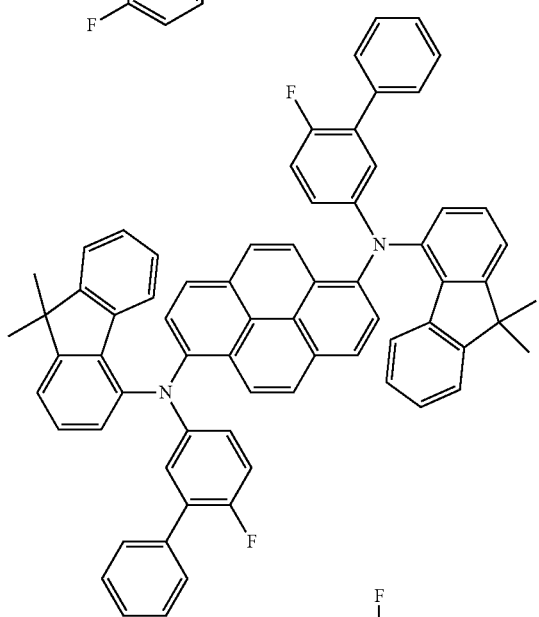
79
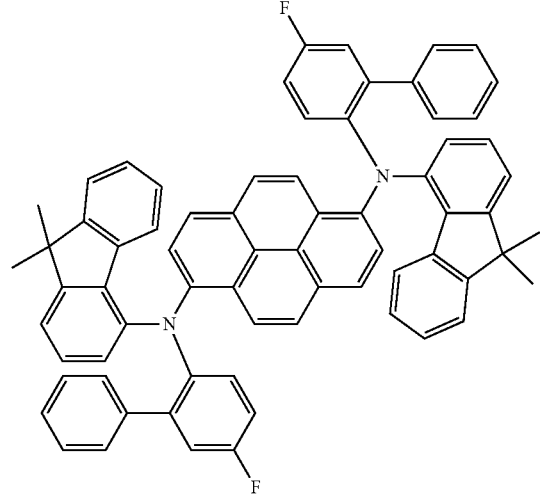
80
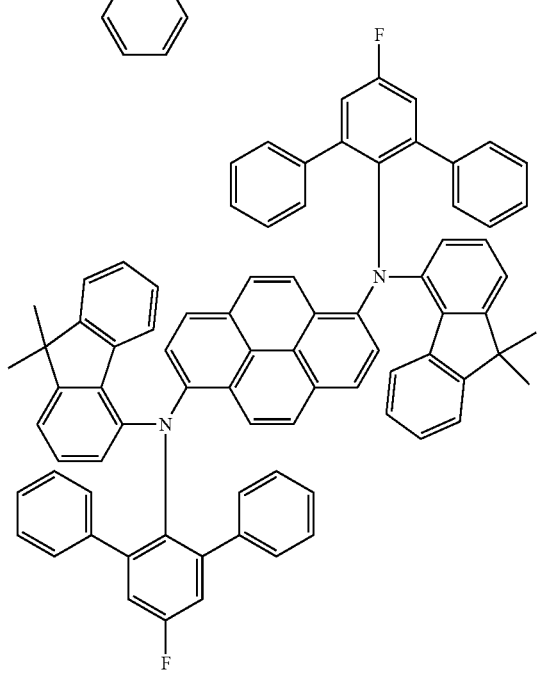
81

-continued
87
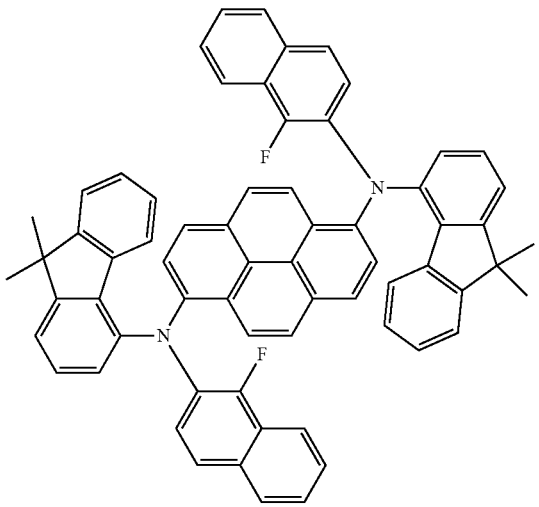
88
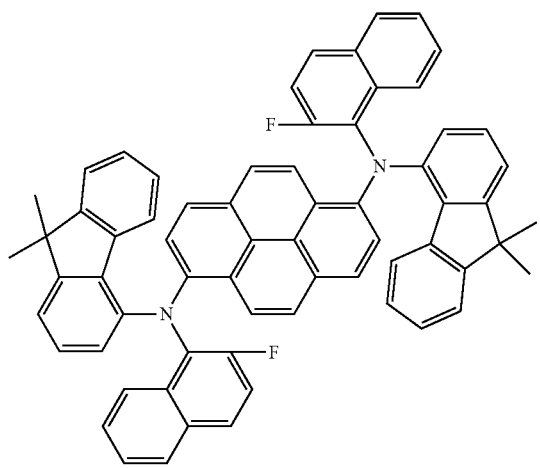
89
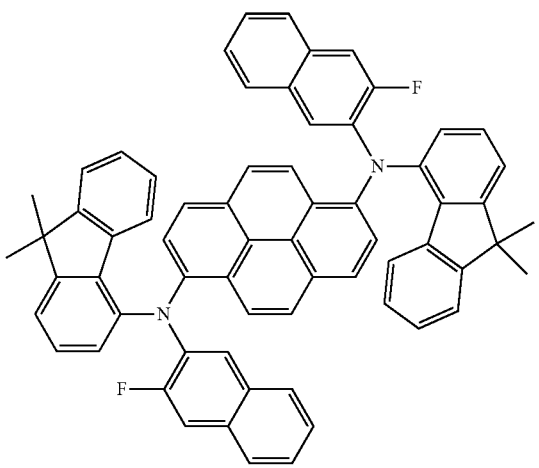
90
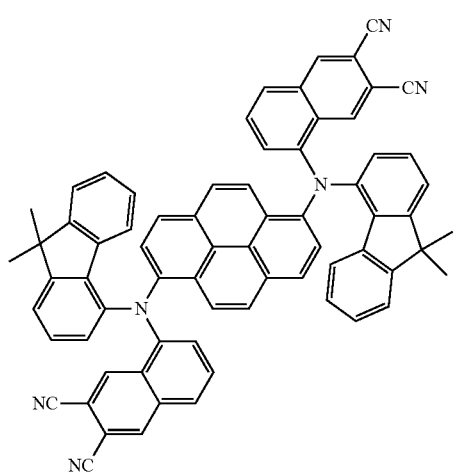
91
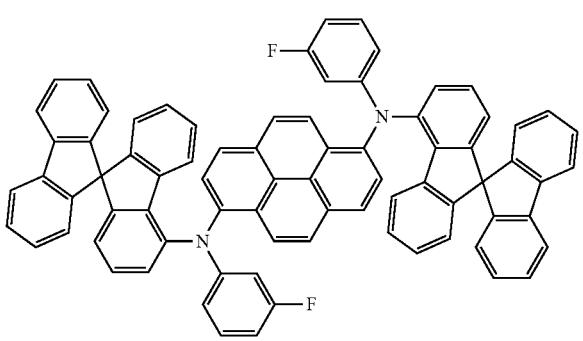

-continued
92
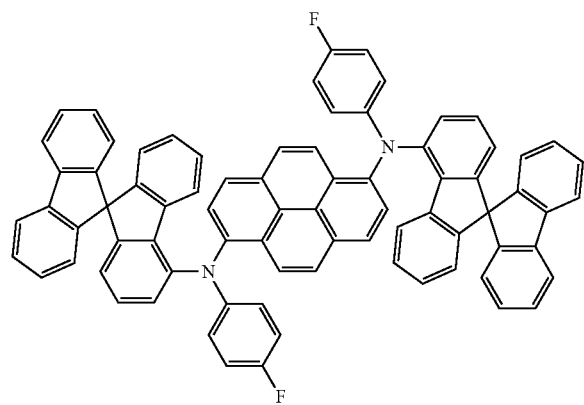
93
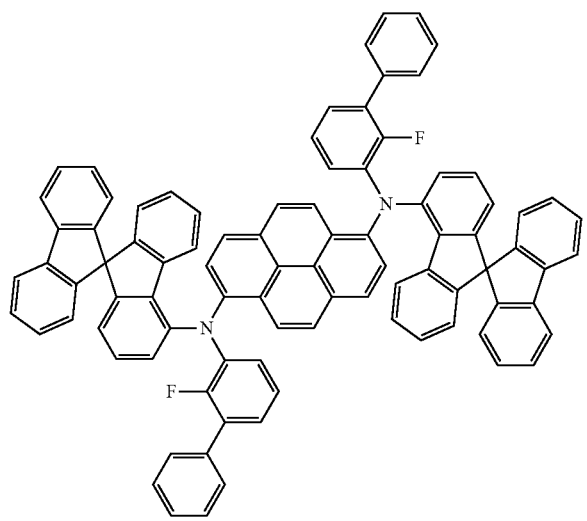
94
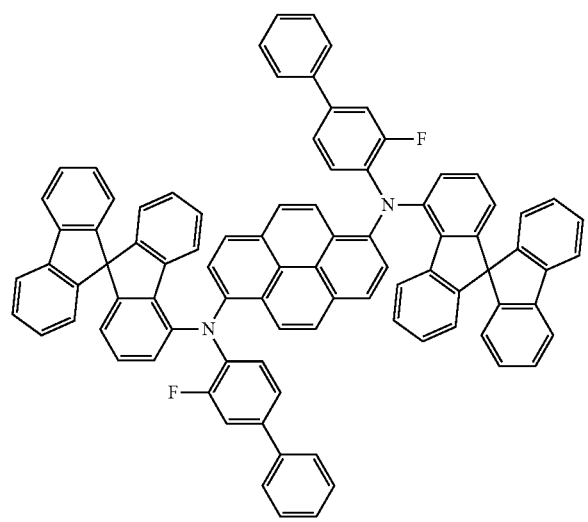
95
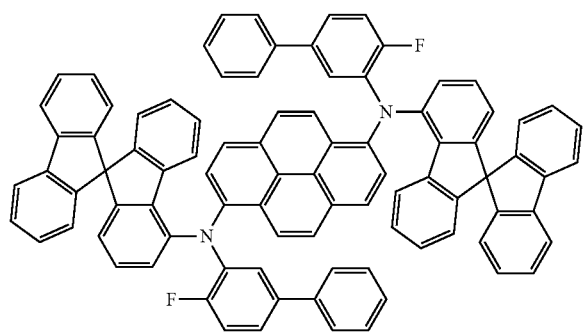
96
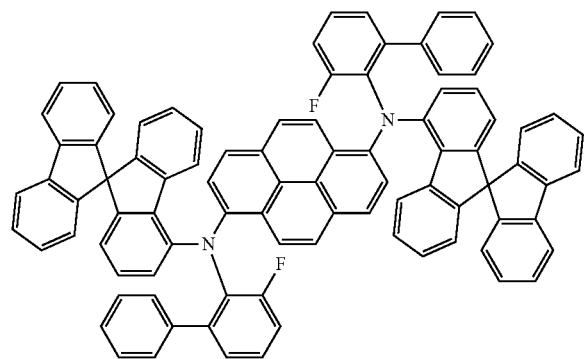
97
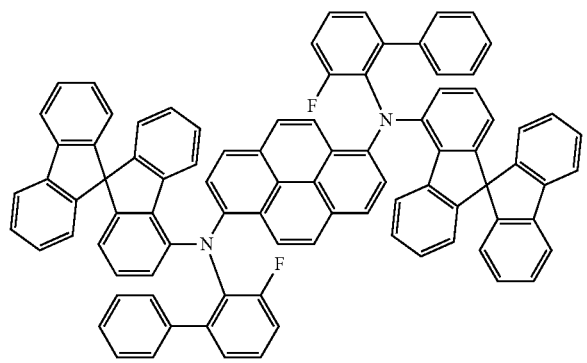

-continued
98
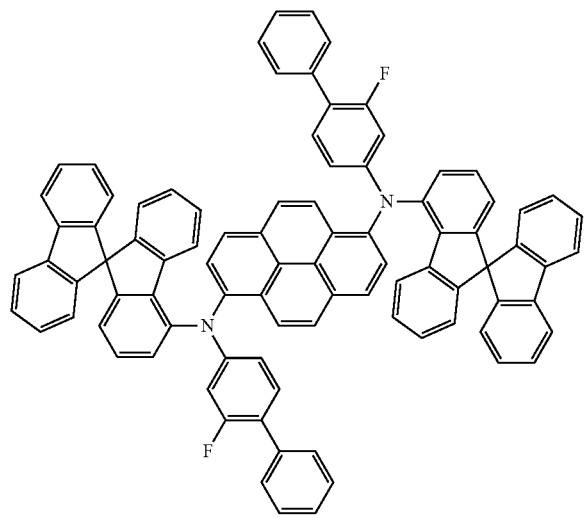
99
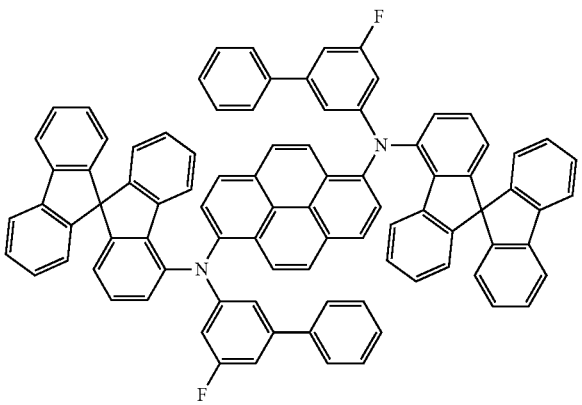
100
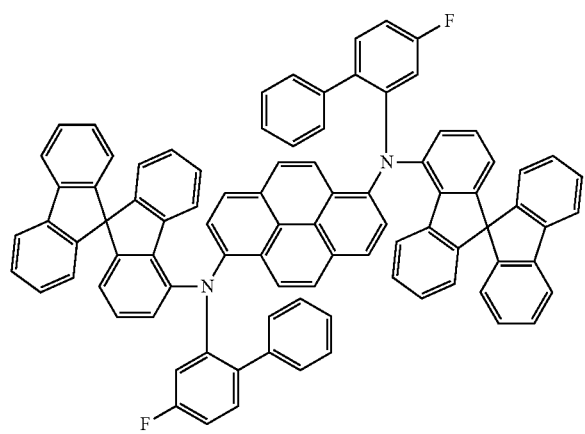
101
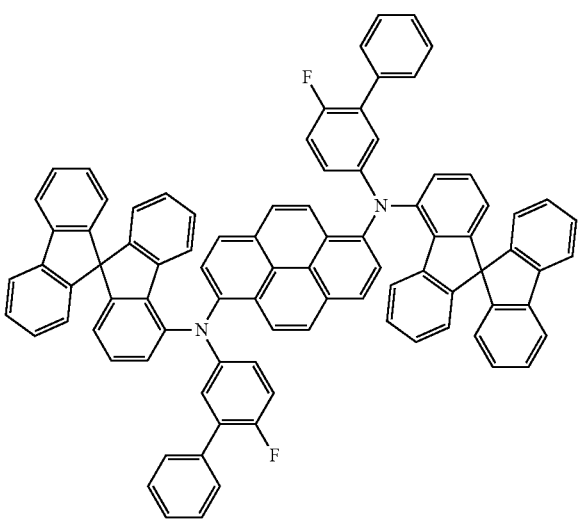
102
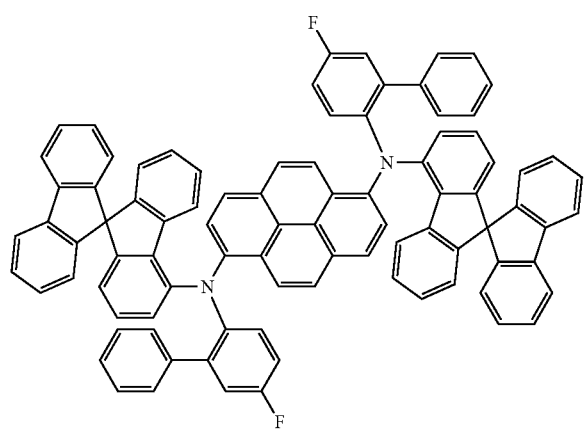

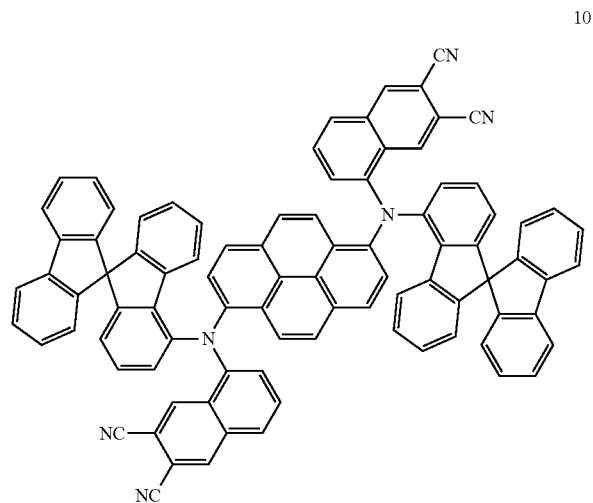
108
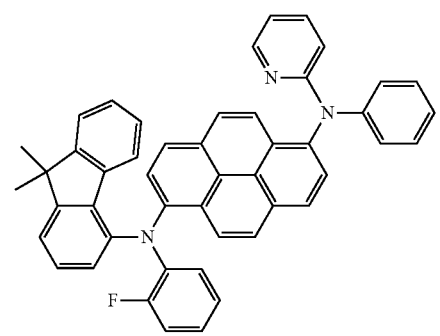
109
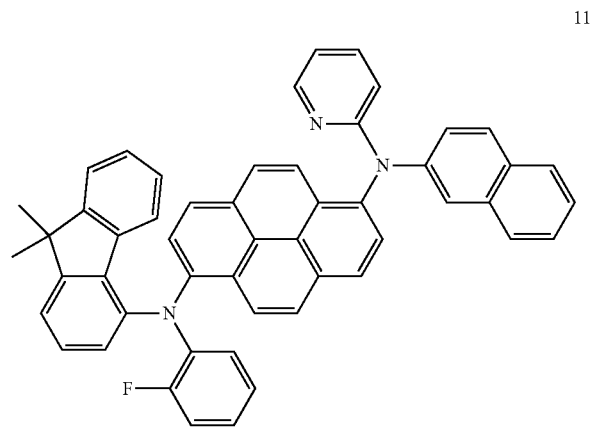
110
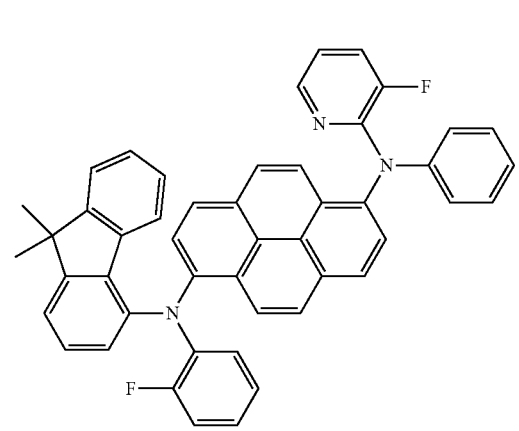
111
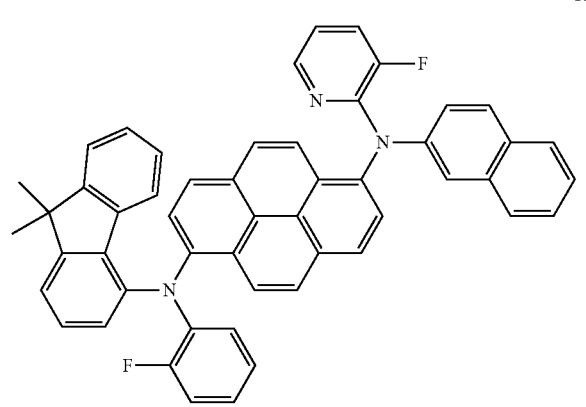
112
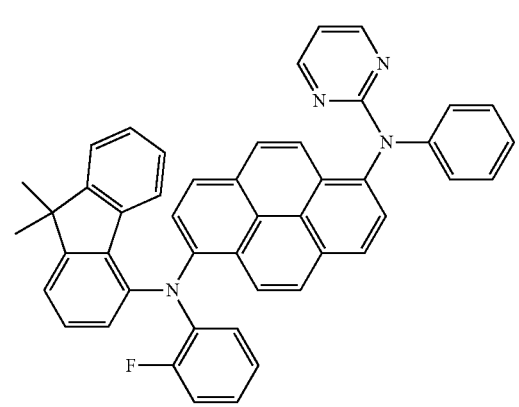
113

-continued
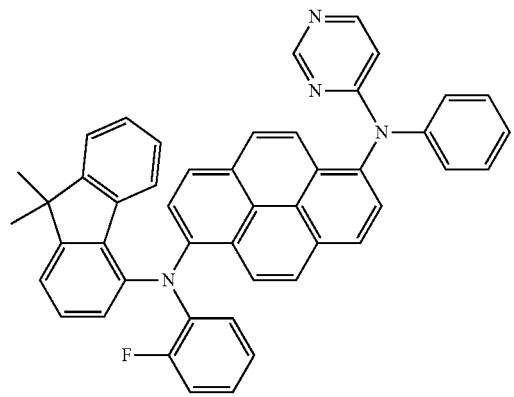
114
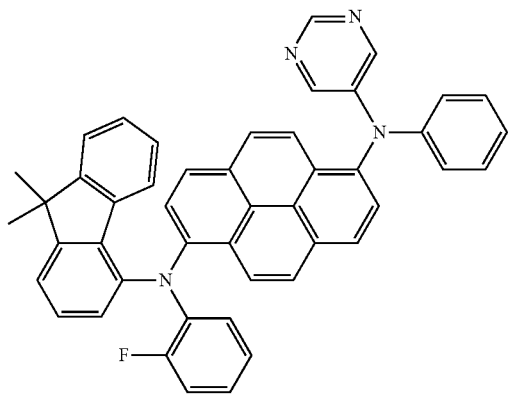
115
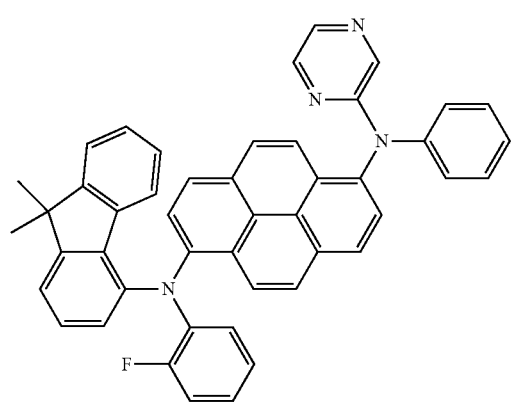
116
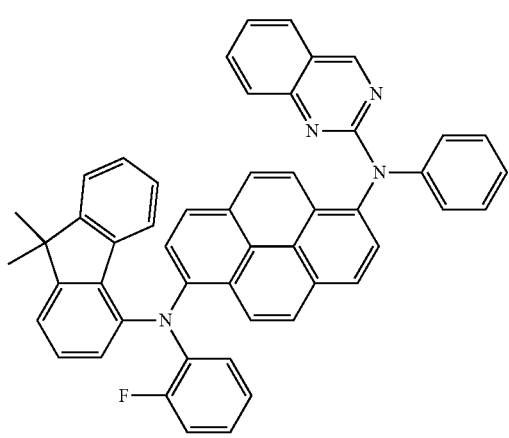
117
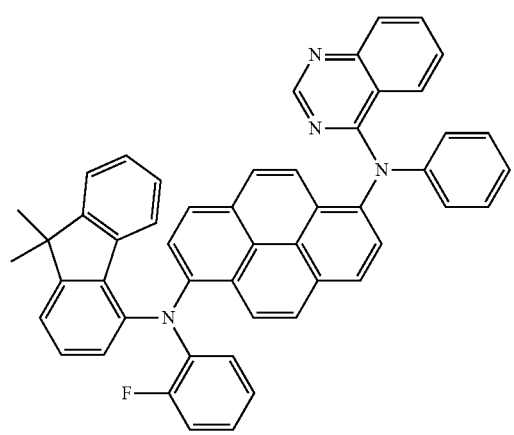
118
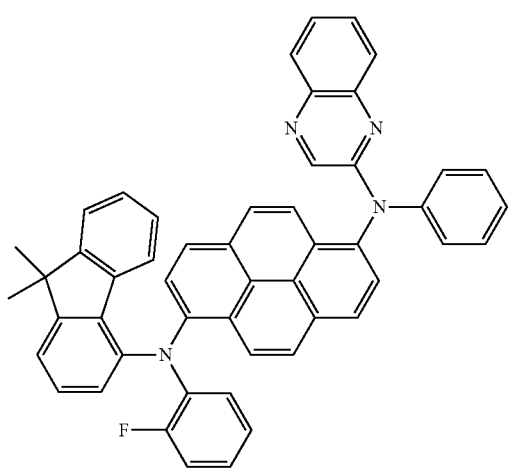
119

-continued
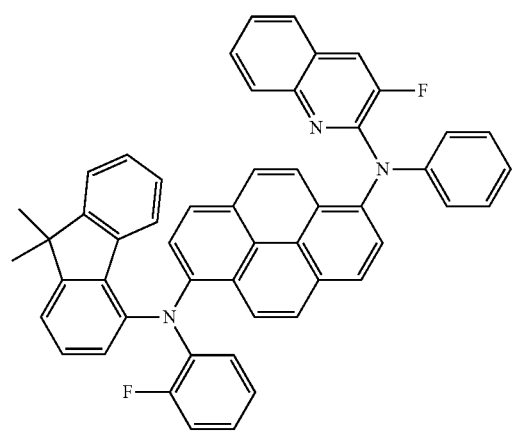
120
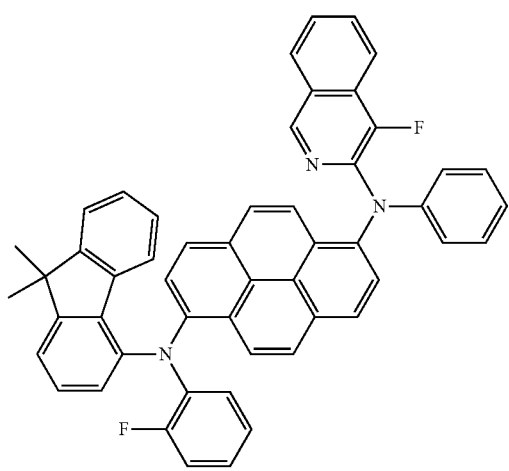
121
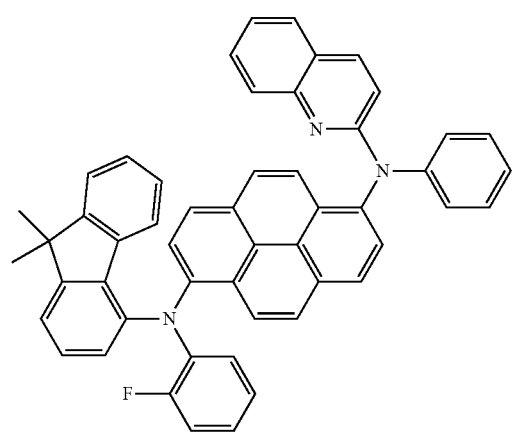
122
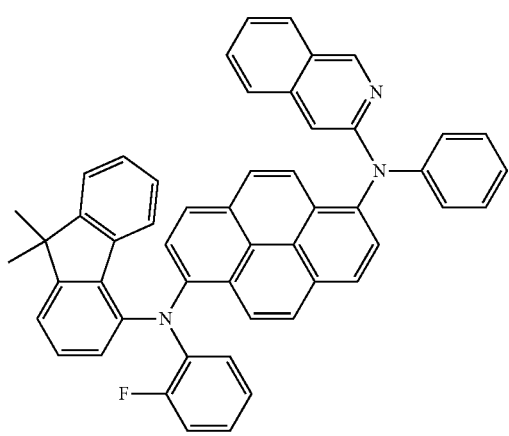
123
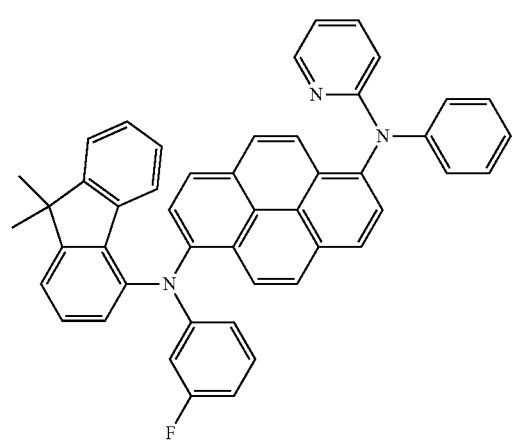
124
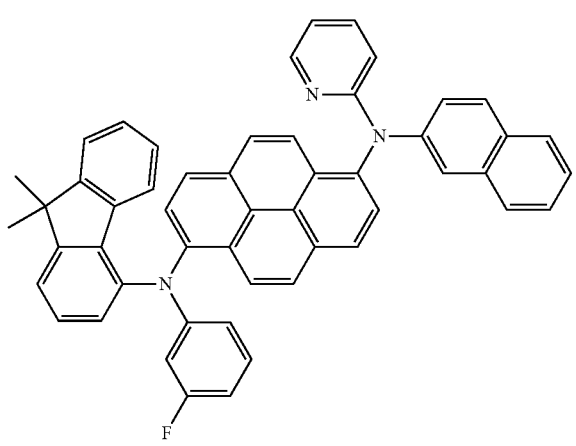
125

-continued
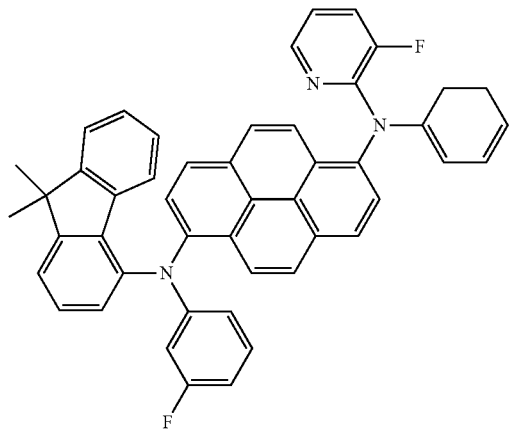
126
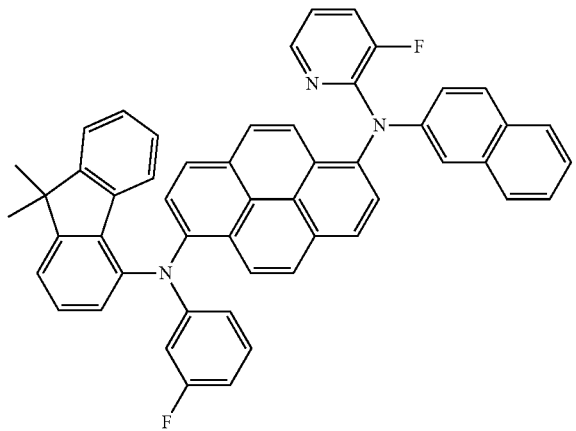
127
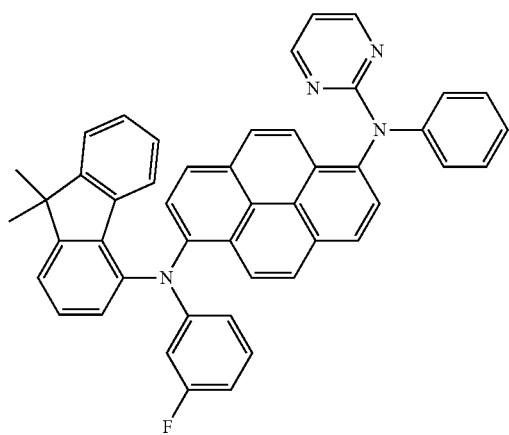
128
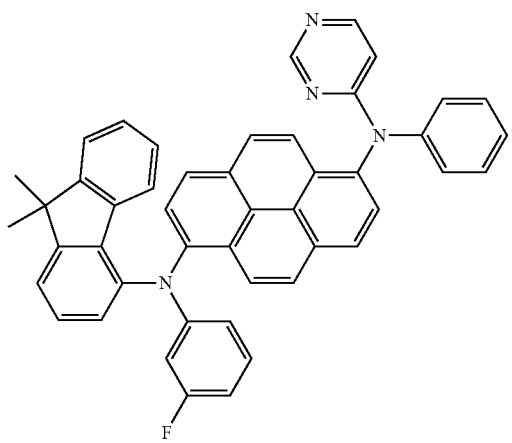
129
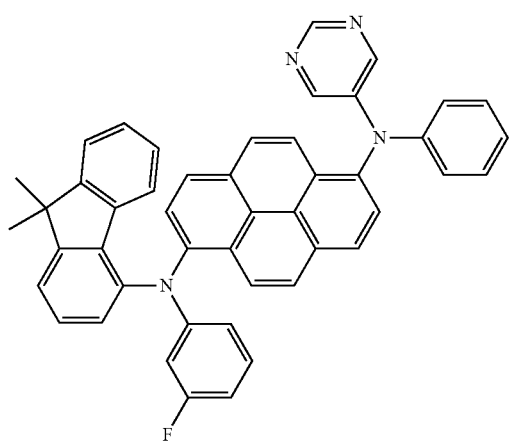
130
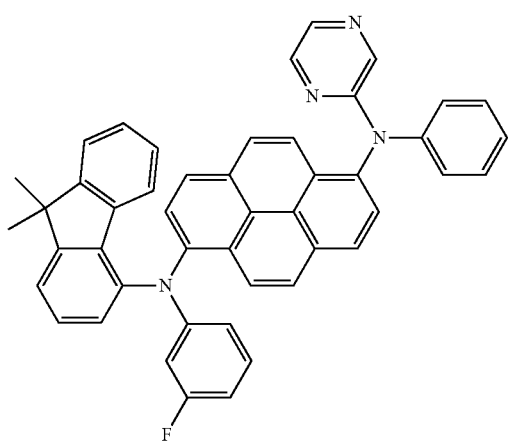
131

-continued
132
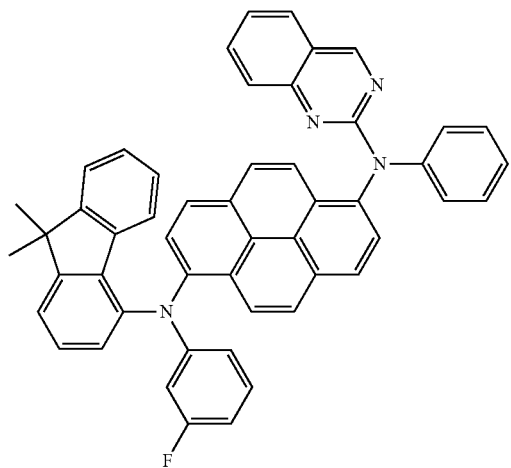
133
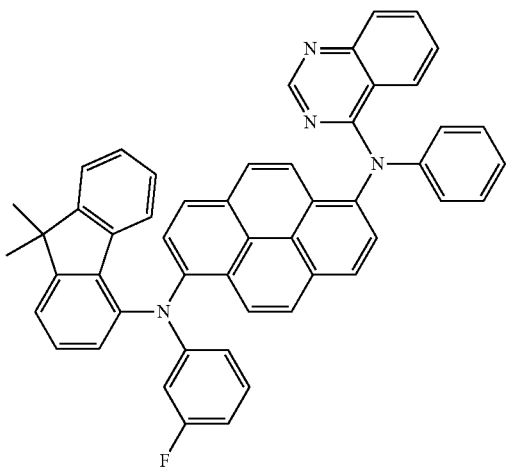
134
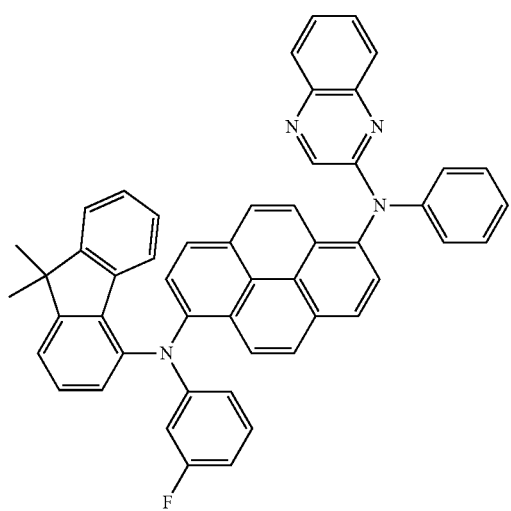
135
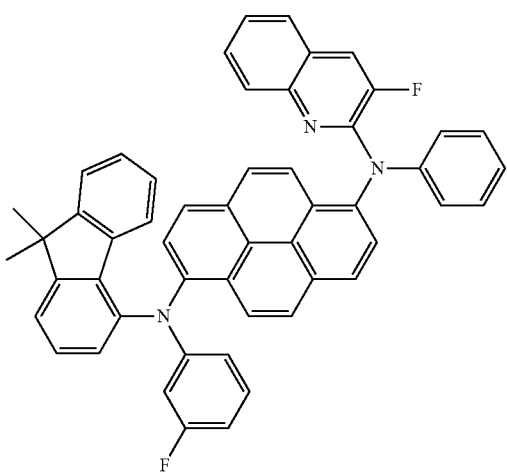
136
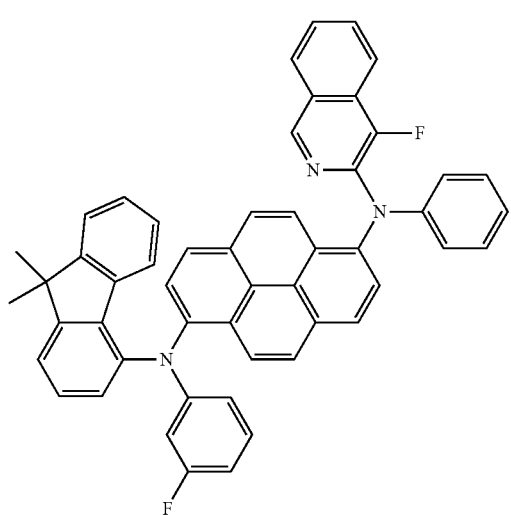
137
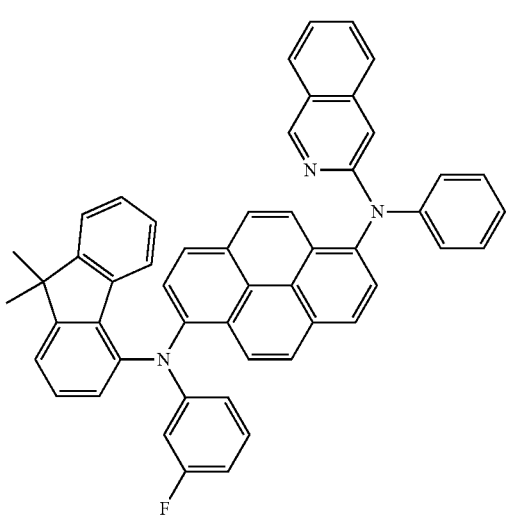

-continued
138
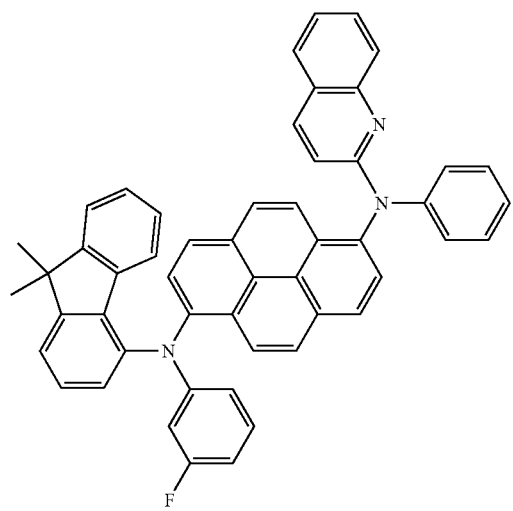
139
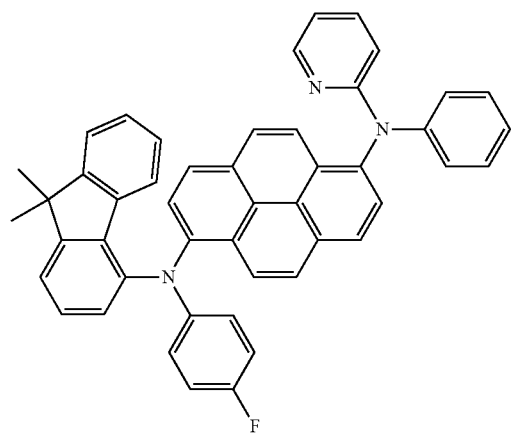
140
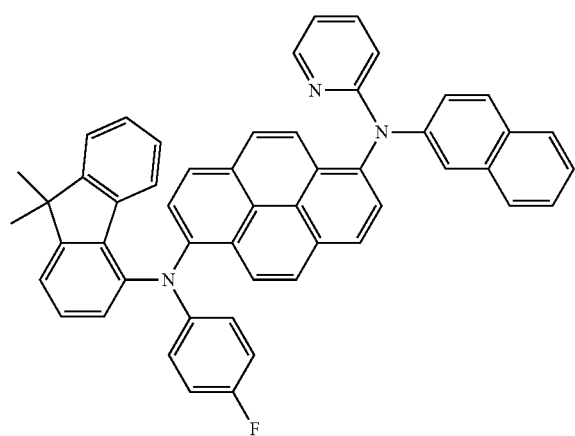
141
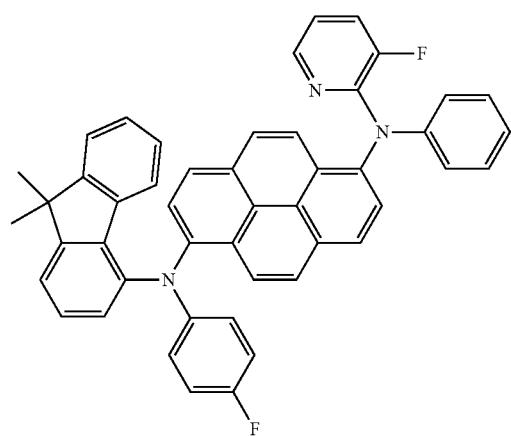
142
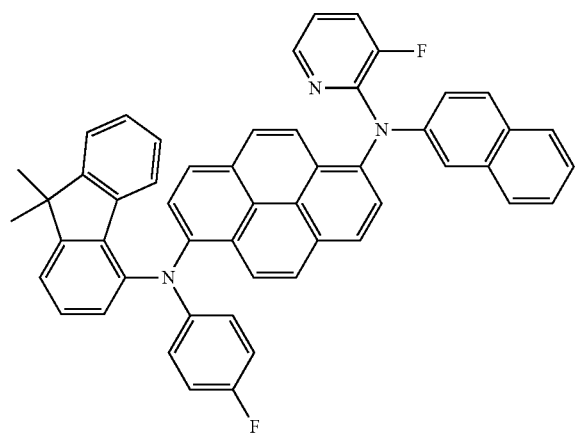
143
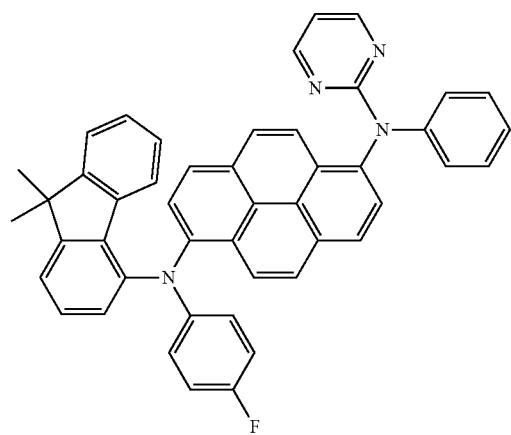

-continued
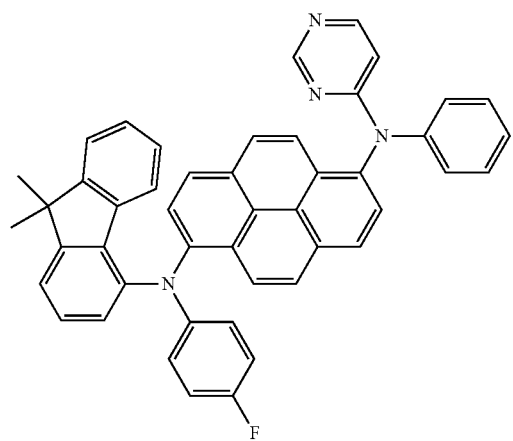
144
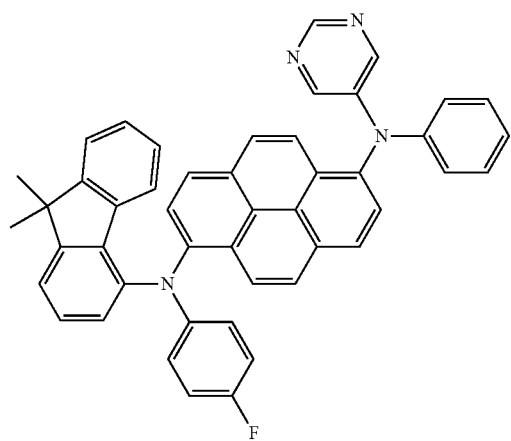
145
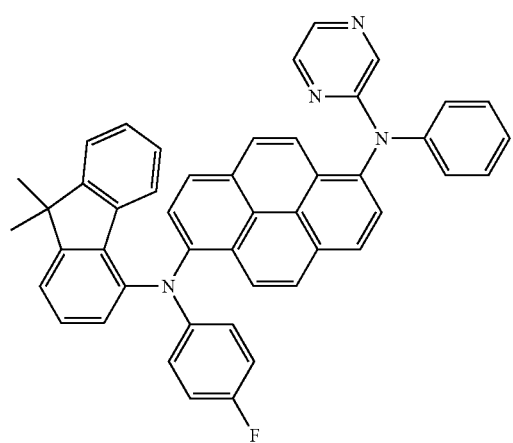
146
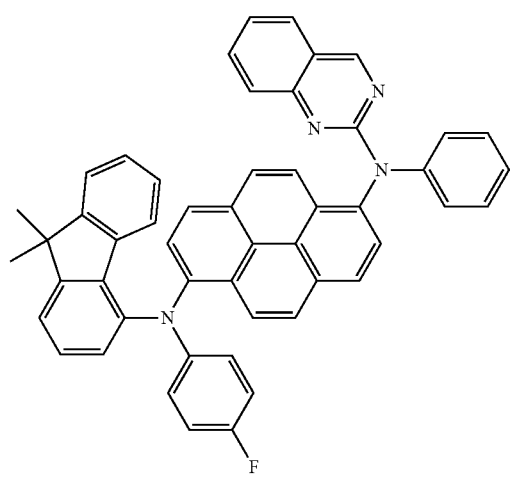
147
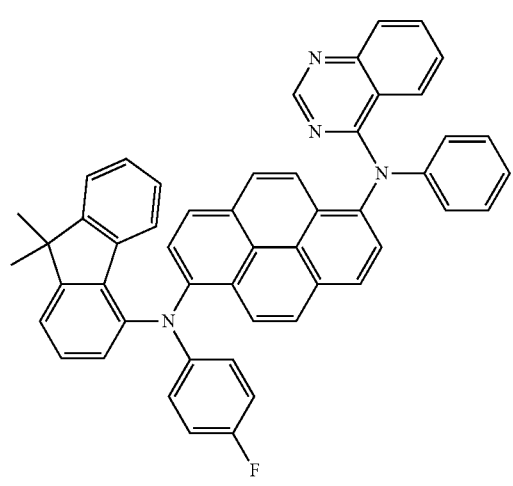
148
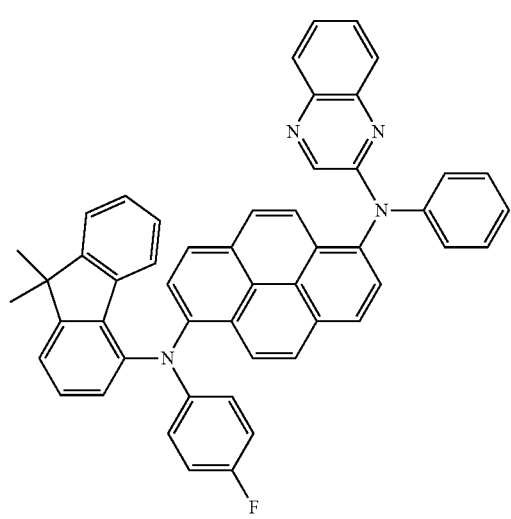
149

-continued
150
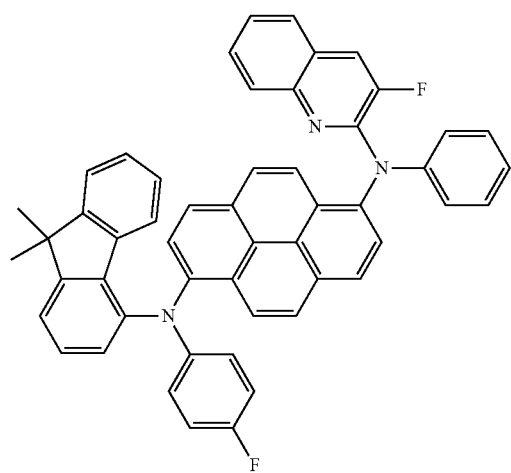
151
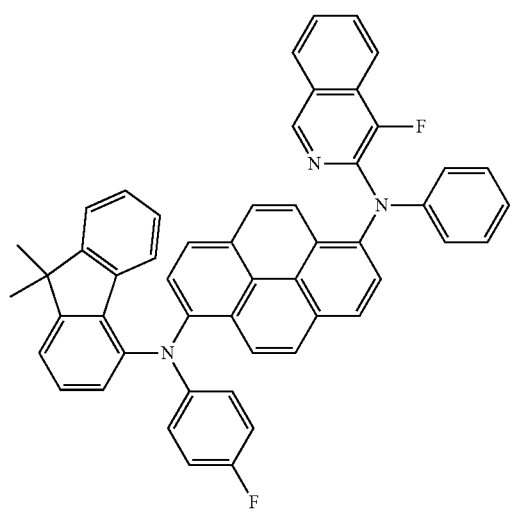
152
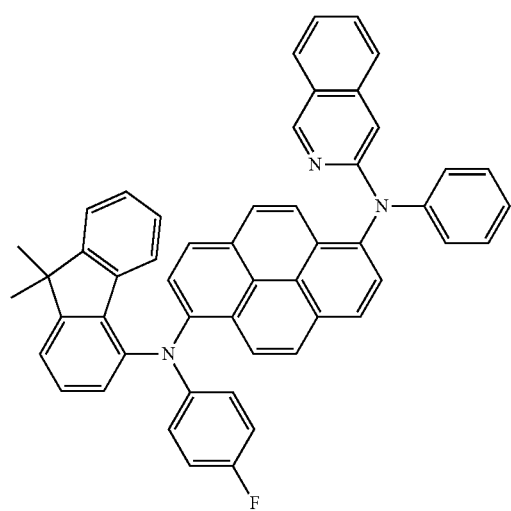
153
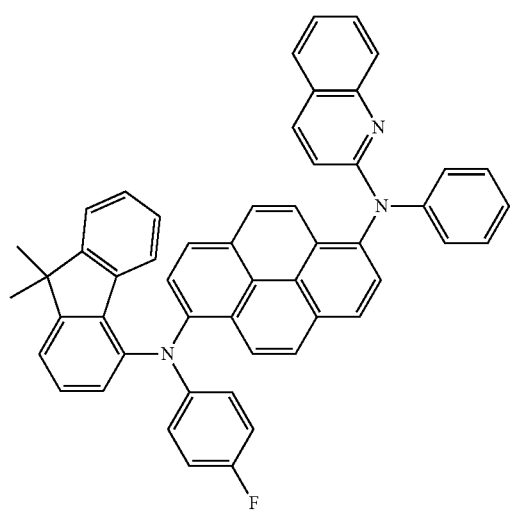
154
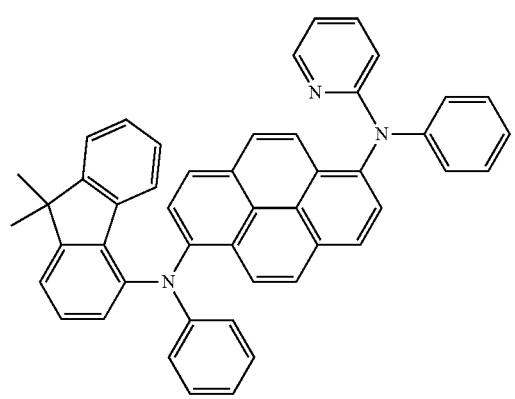
155
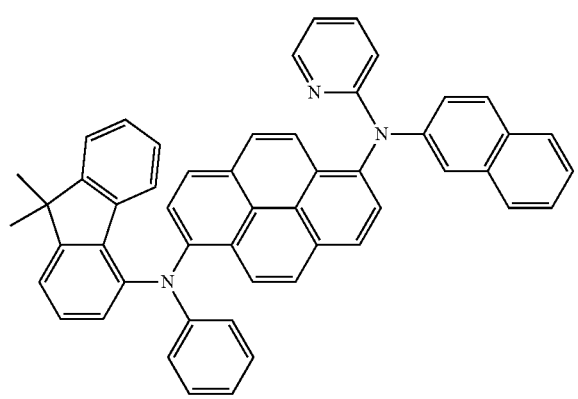

-continued
156
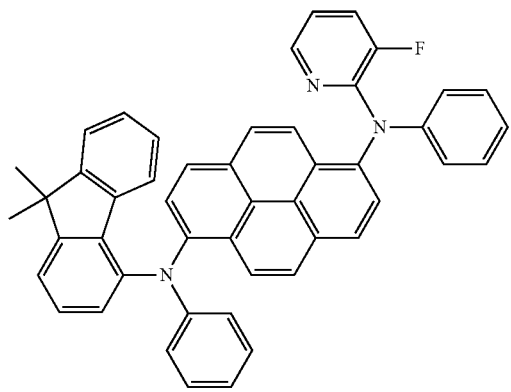
157
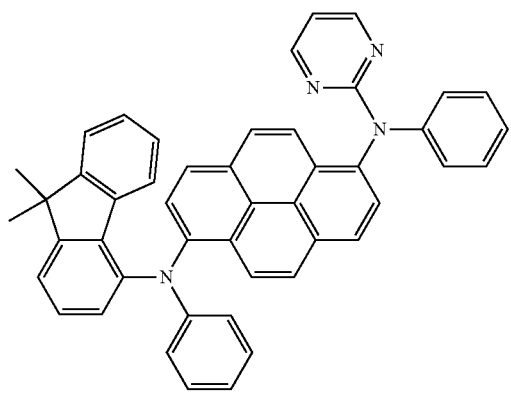
158
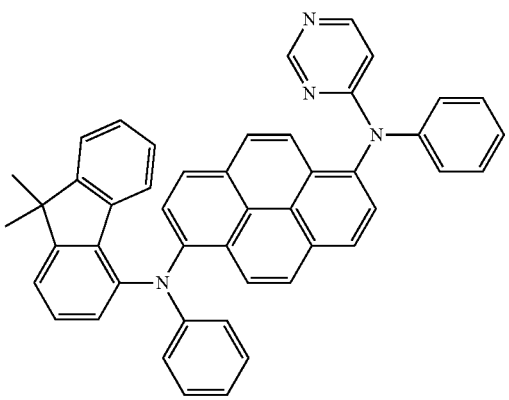
159
160
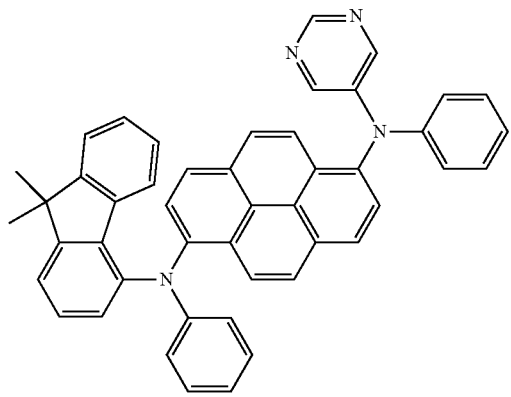
161
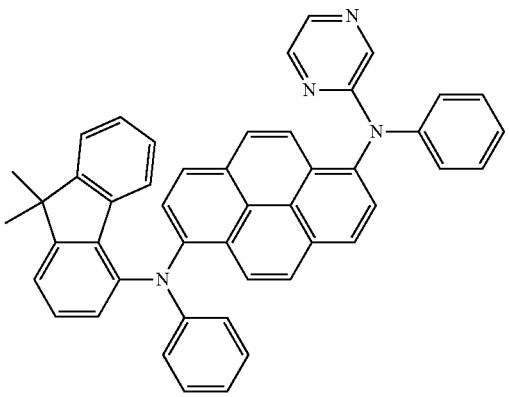
162
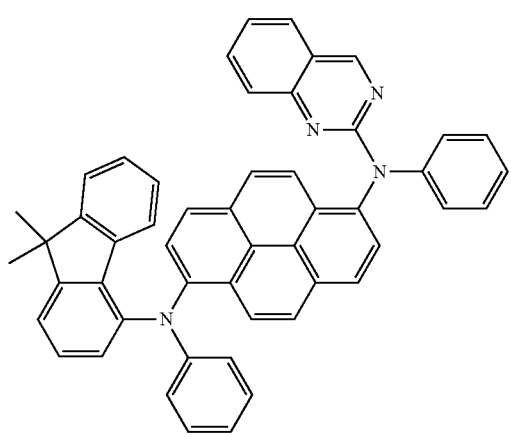
163
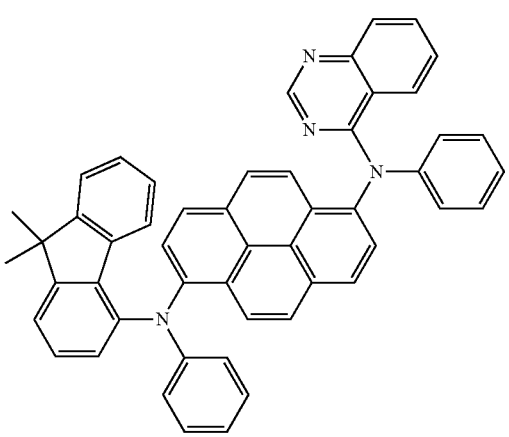

-continued
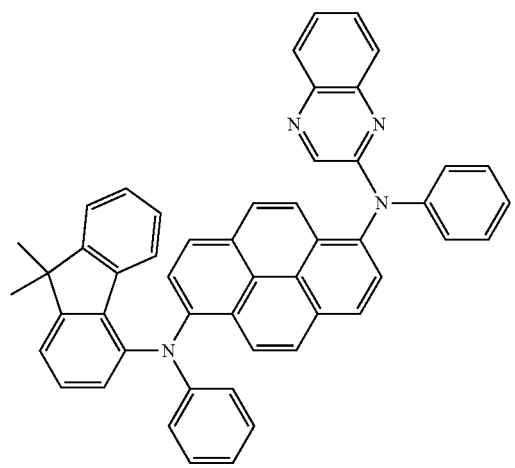
164
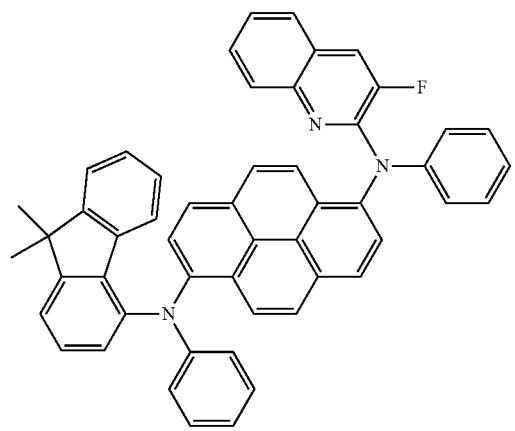
165
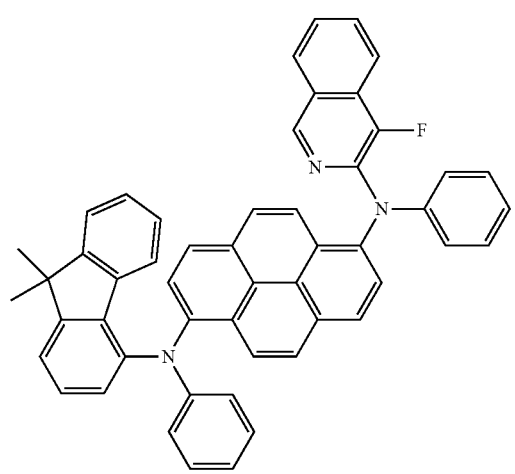
166
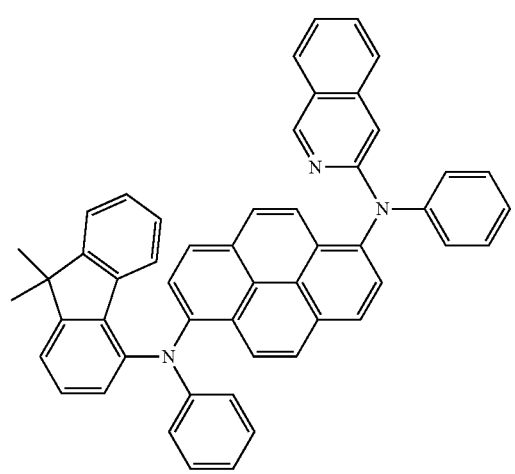
167
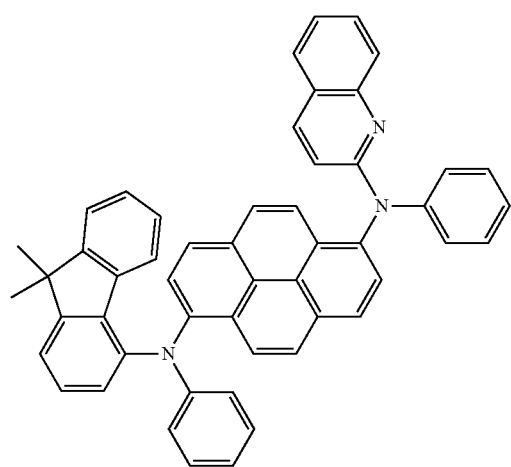
168
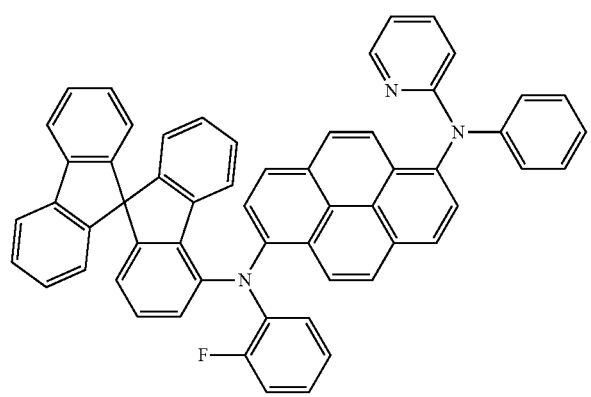
169

-continued
170
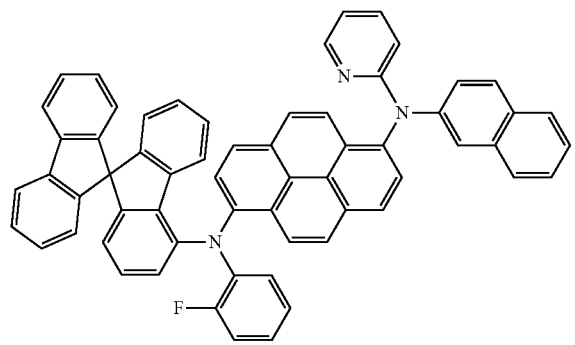
171
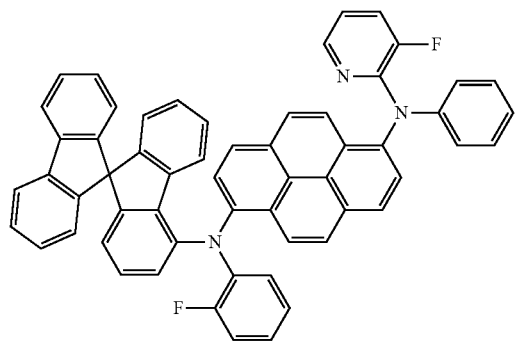
172
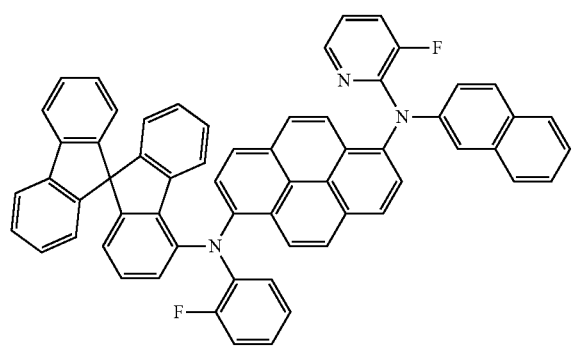
173
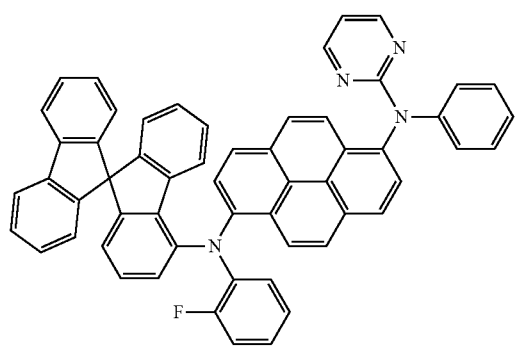
174
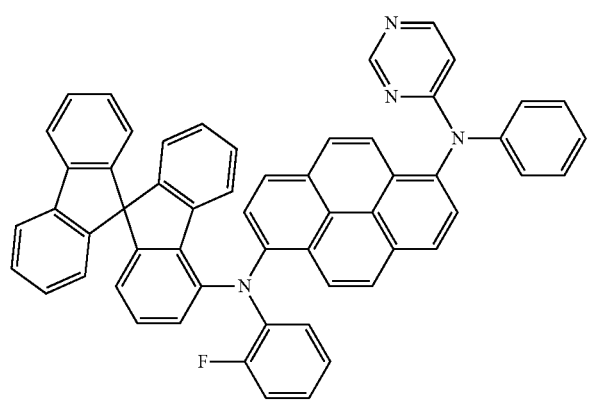
175
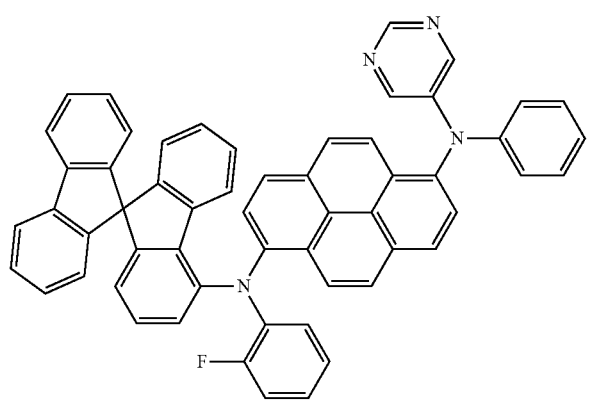
176
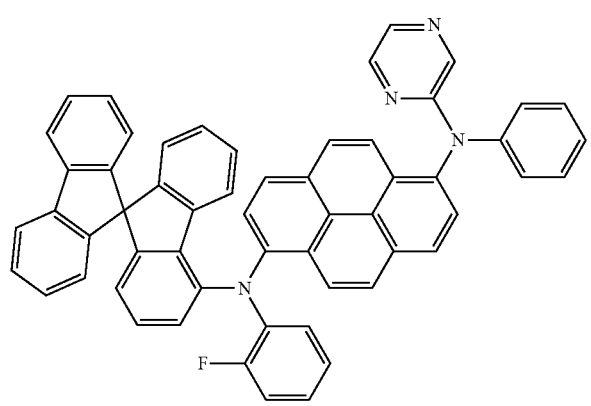
177
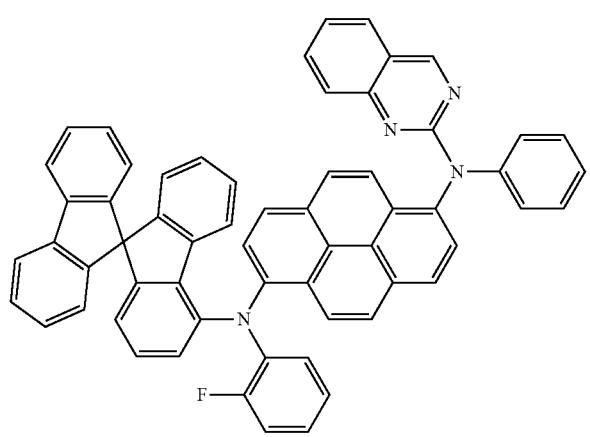

-continued
178
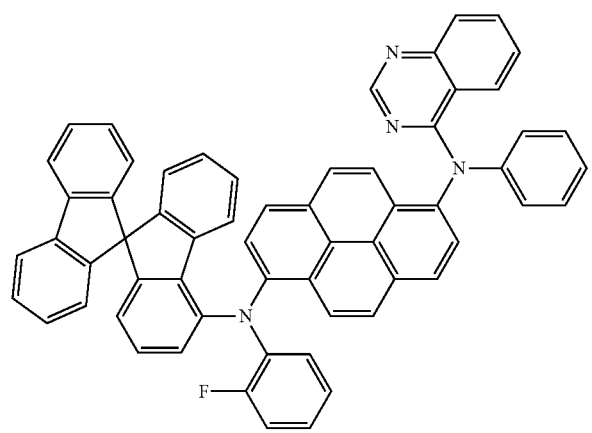
179
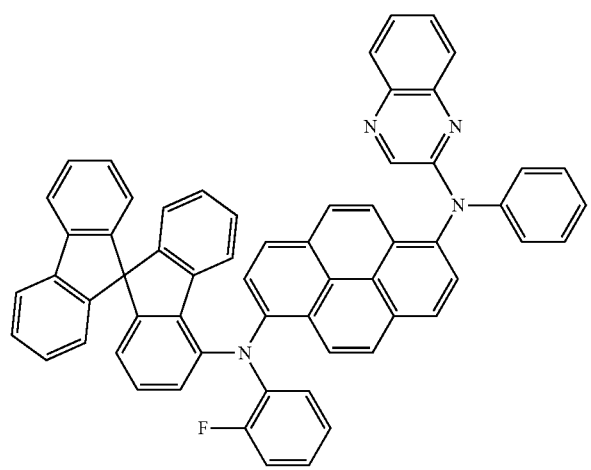
180
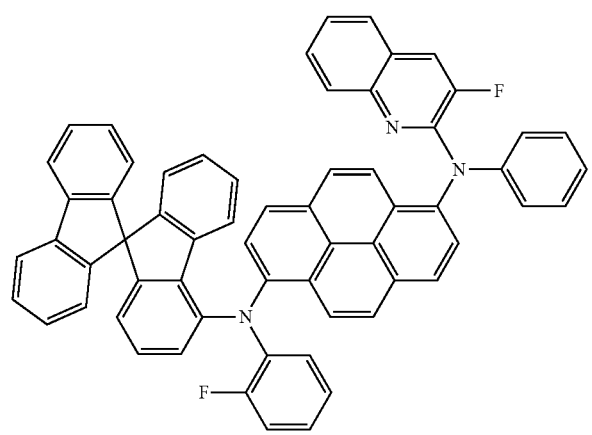
181
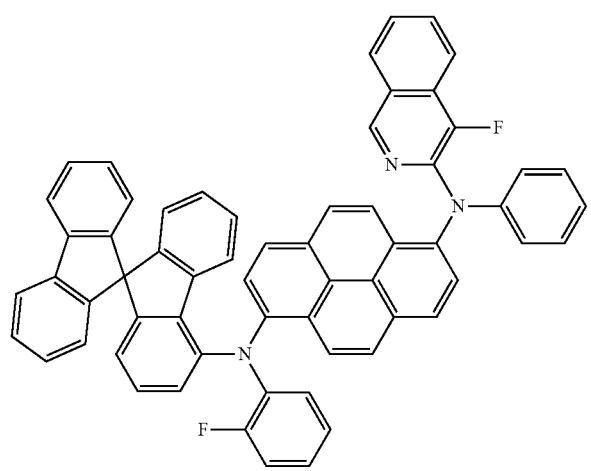
182
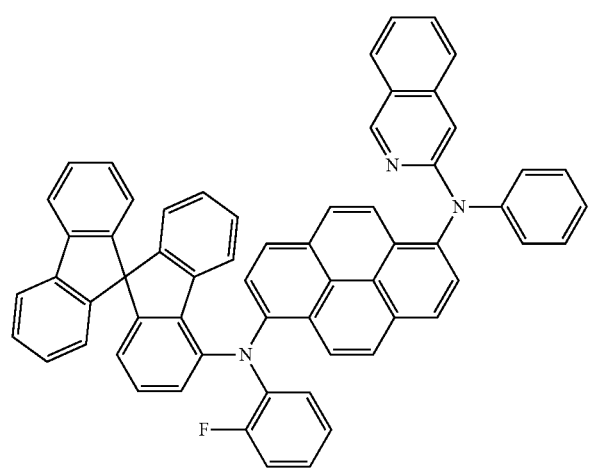
183
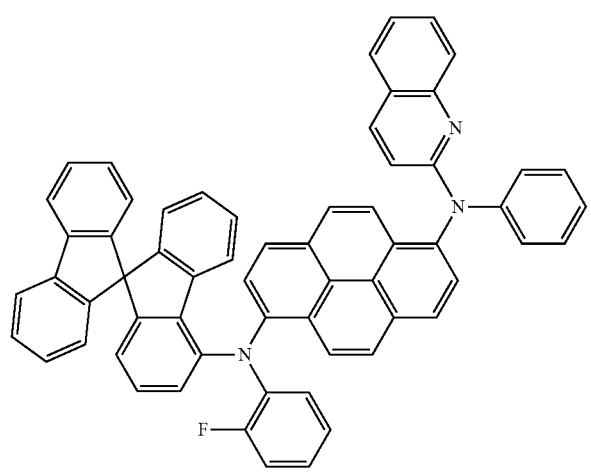

-continued
184
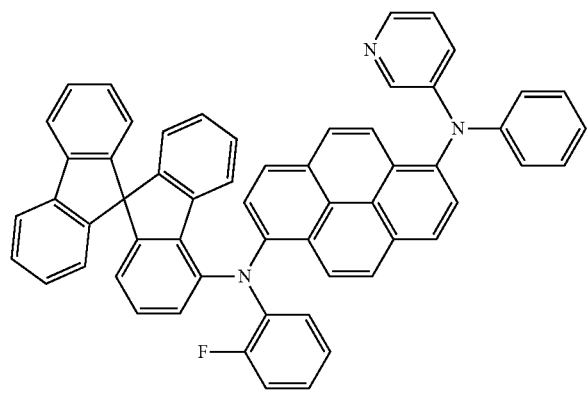
185
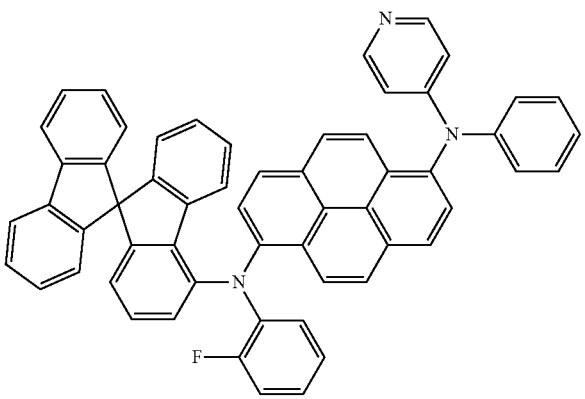
186
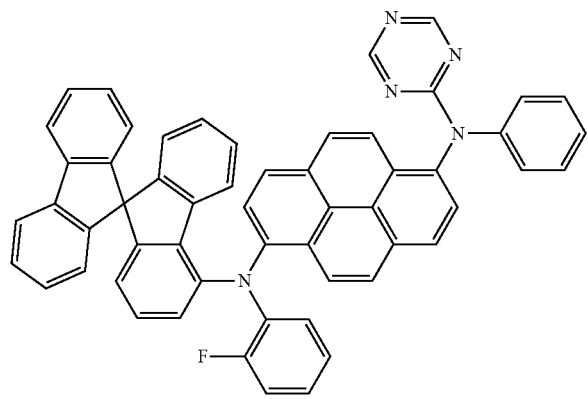
187
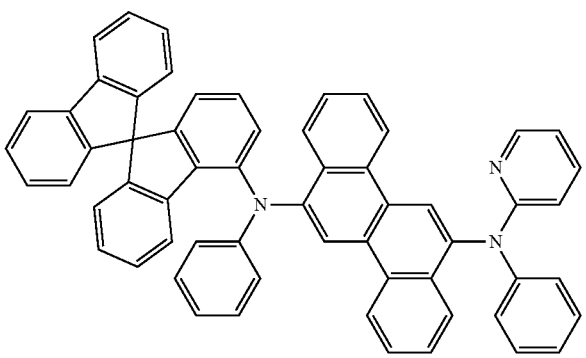
188
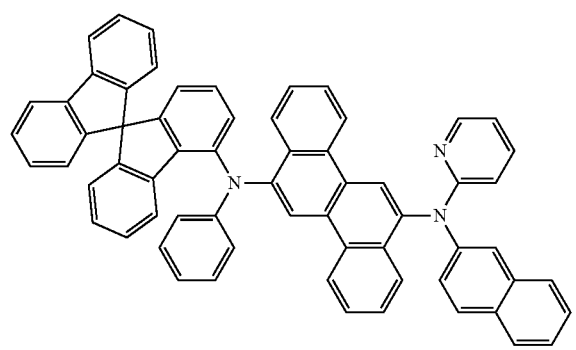
189
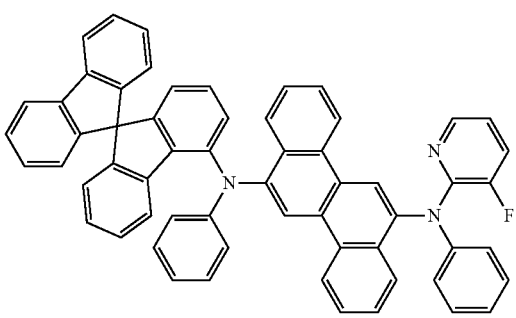
190
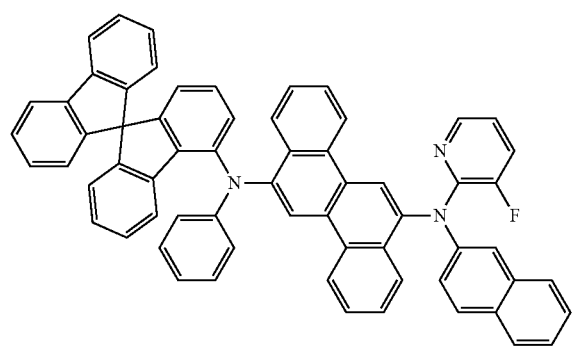
191
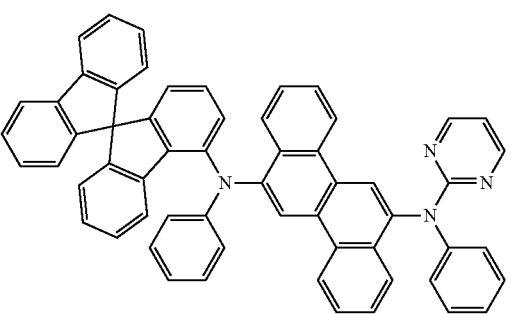

-continued
192
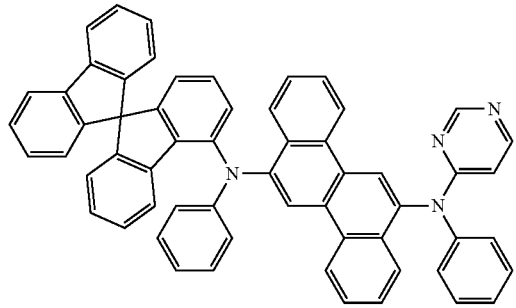
193
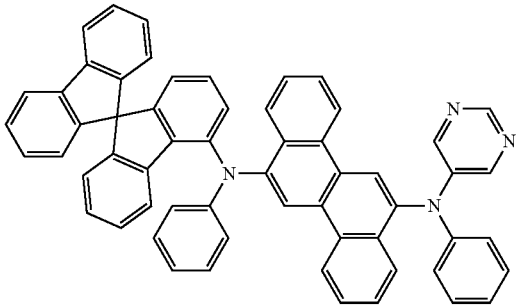
194
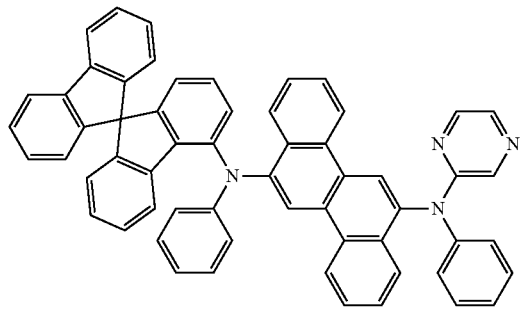
195
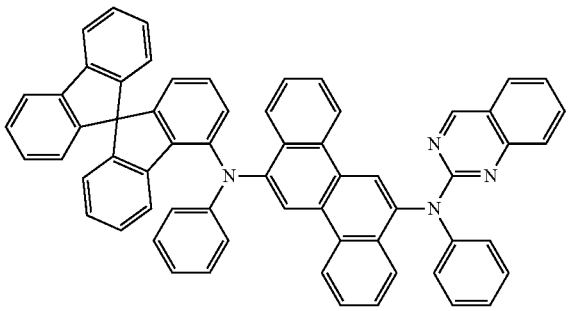
196
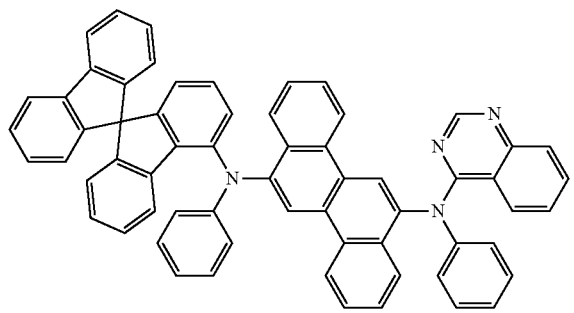
197
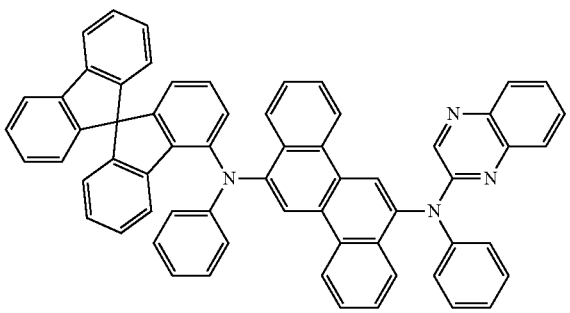
198
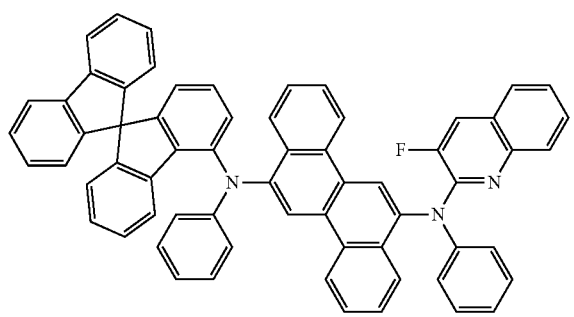
199
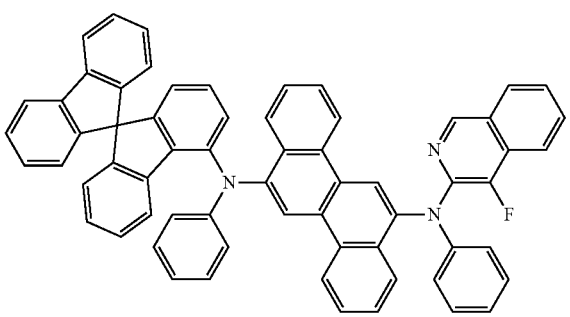
200
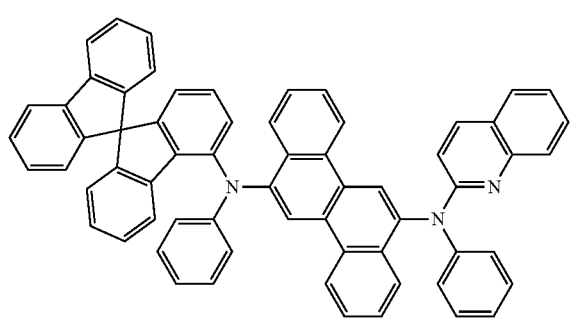
201
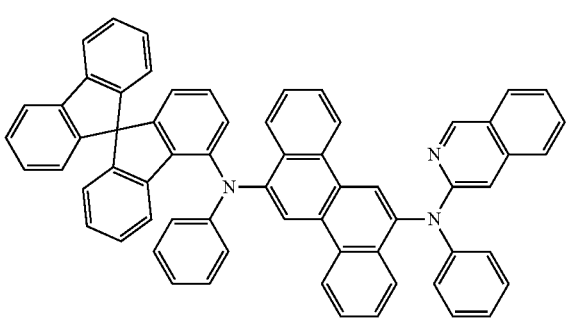

-continued
287
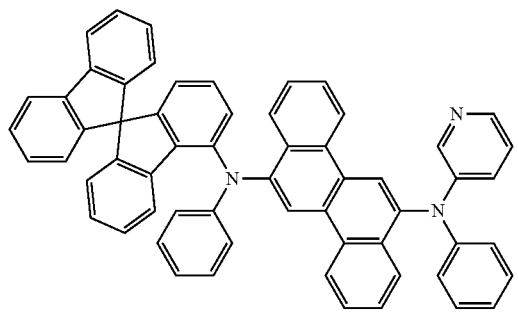
202
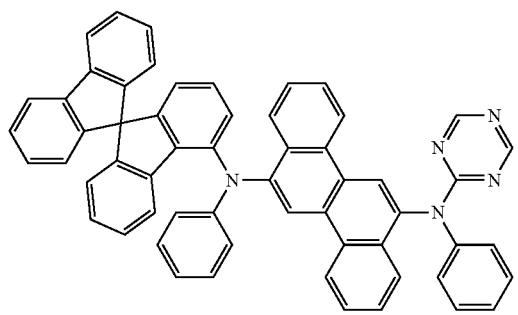
204
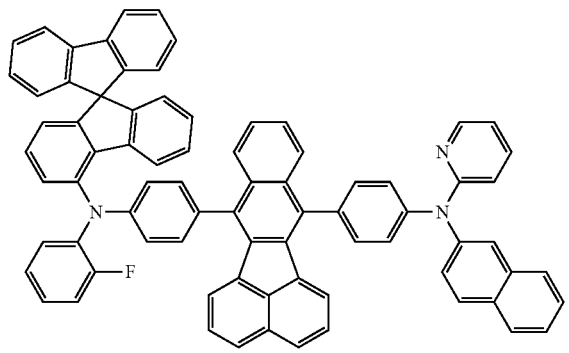
206
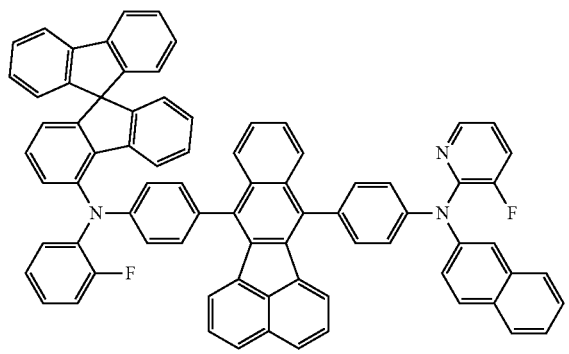
208
288
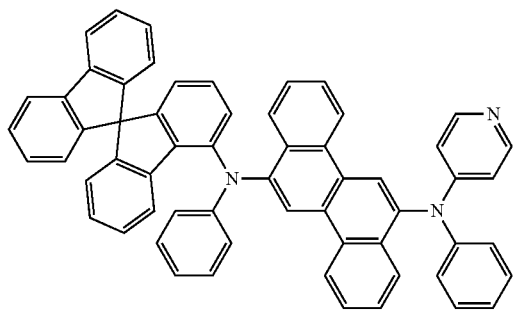
203
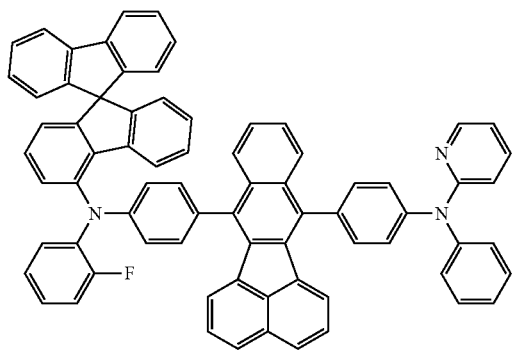
205
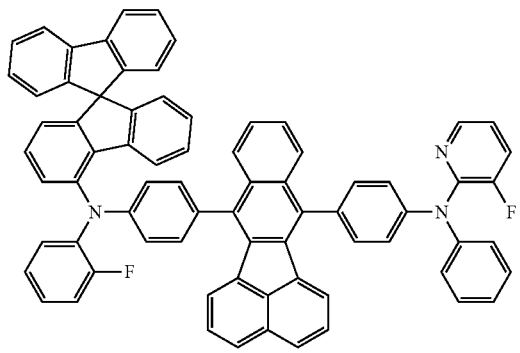
207
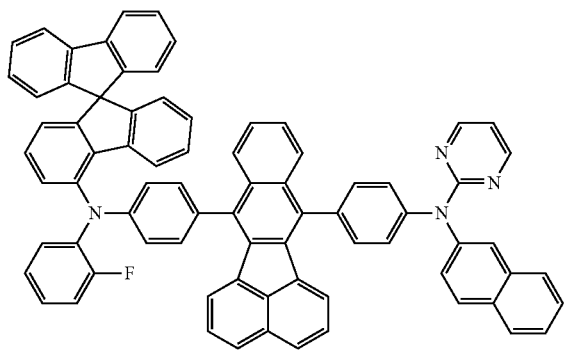
209

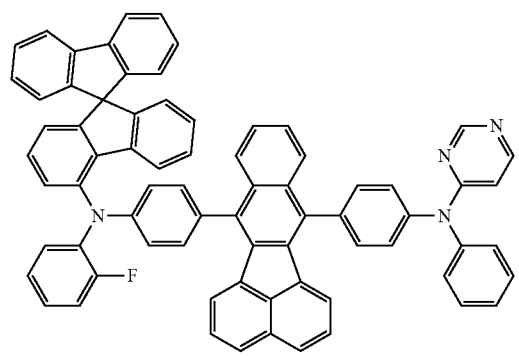
210
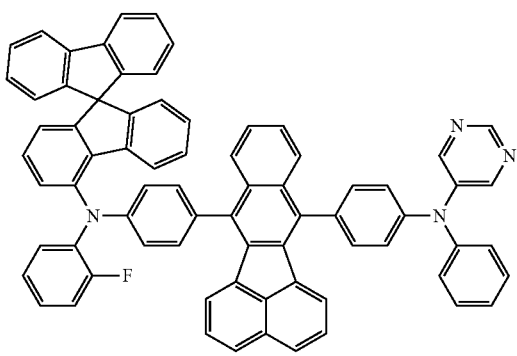
211
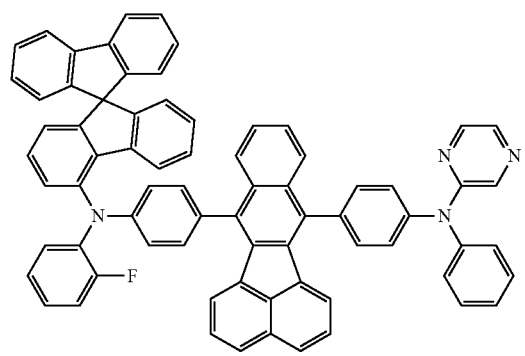
212
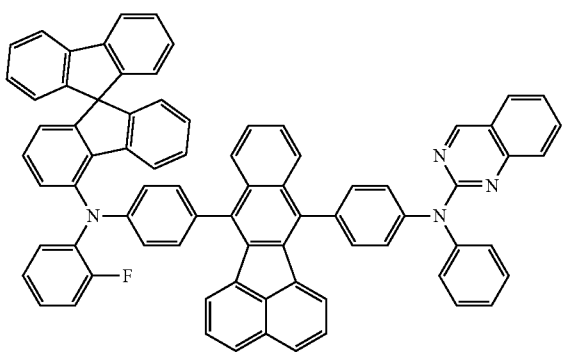
213
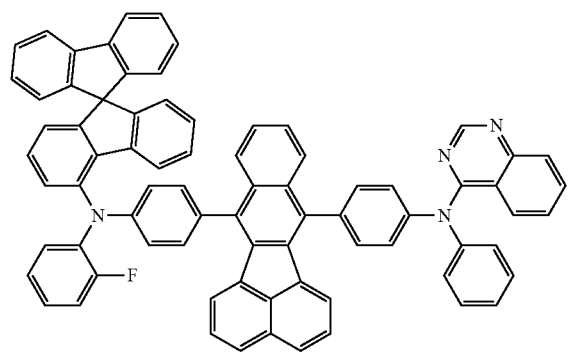
214
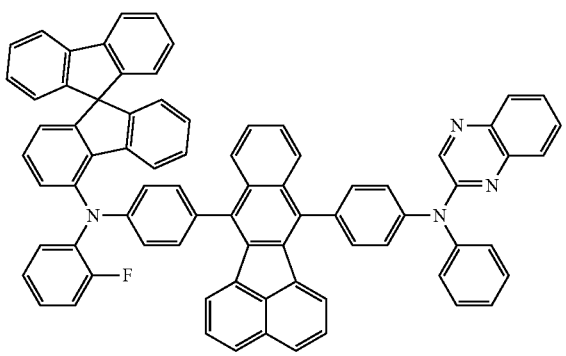
215
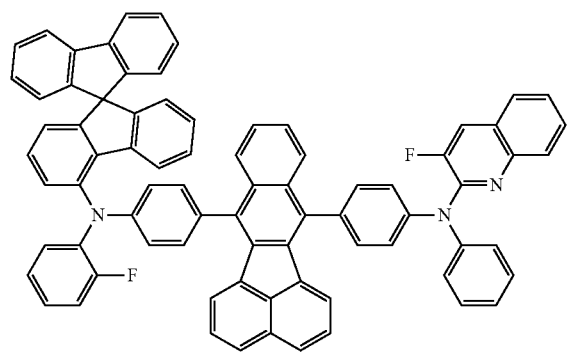
216
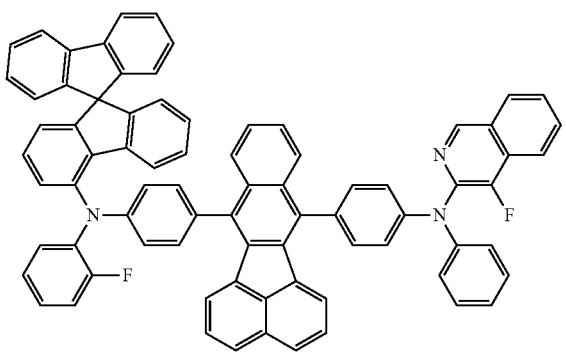
217

-continued
218
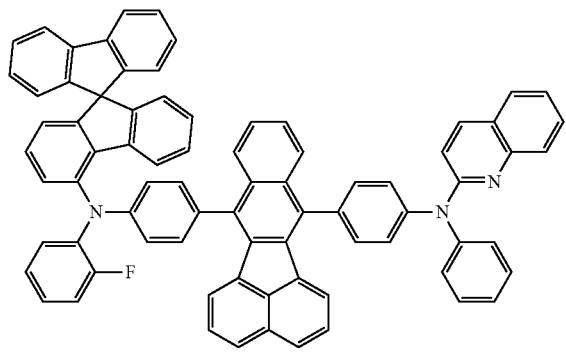
219
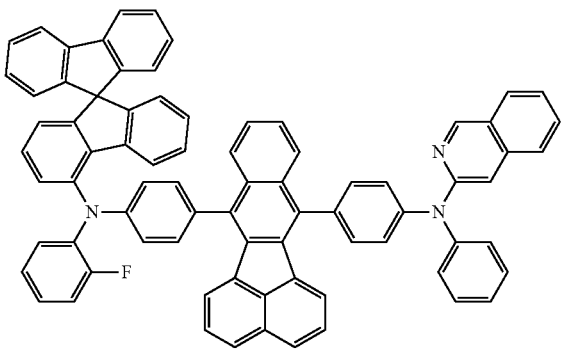
220
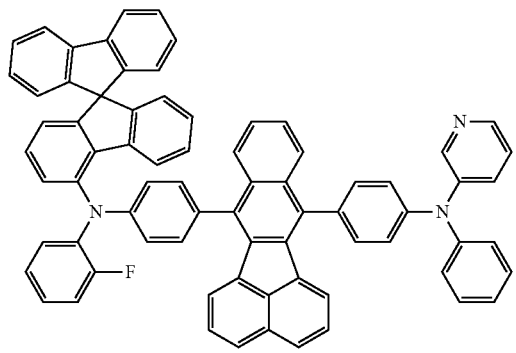
221
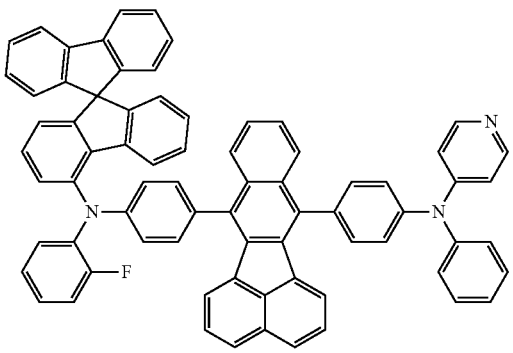
222
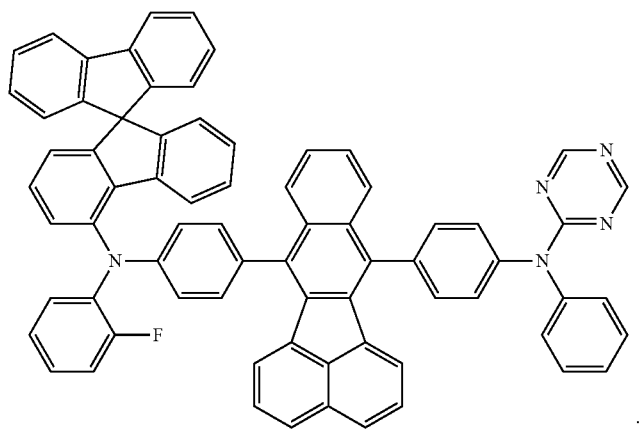
\* \* \* \* \*